(12) United States Patent
Yan et al.

(10) Patent No.: US 11,820,805 B2
(45) Date of Patent: Nov. 21, 2023

(54) CONJUGATE BASED SYSTEMS FOR CONTROLLED INSULIN DELIVERY

(71) Applicants: Merck Sharp & Dohme Corp., Rahway, NJ (US); Lin Yan, East Brunswick, NJ (US); Pei Huo, Millburn, NJ (US); Ahmet Kekec, Hoboken, NJ (US); Danqing D. Feng, Green Brook, NJ (US); Yuping Zhu, Basking Ridge, NJ (US); Dmitri Pissarnitski, Scotch Plains, NJ (US); Chris Moyes, Westfiled, NJ (US); Songnian Lin, Holmdel, NJ (US)

(72) Inventors: Lin Yan, East Brunswick, NJ (US); Pei Huo, Millburn, NJ (US); Ahmet Kekec, Hoboken, NJ (US); Danqing D. Feng, Green Brook, NJ (US); Yuping Zhu, Basking Ridge, NJ (US); Dmitri Pissarnitski, Scotch Plains, NJ (US); Chris Moyes, Westfiled, NJ (US); Songnian Lin, Holmdel, NJ (US)

(73) Assignee: MERCK SHARP & DOHME LLC, Rahway, NJ (US)

( * ) Notice: Subject to any disclaimer, the term of this patent is extended or adjusted under 35 U.S.C. 154(b) by 344 days.

(21) Appl. No.: 16/771,818

(22) PCT Filed: Dec. 13, 2018

(86) PCT No.: PCT/US2018/065318
§ 371 (c)(1),
(2) Date: Jun. 11, 2020

(87) PCT Pub. No.: WO2019/125878
PCT Pub. Date: Jun. 27, 2019

(65) Prior Publication Data
US 2021/0198339 A1    Jul. 1, 2021

Related U.S. Application Data

(60) Provisional application No. 62/625,476, filed on Feb. 2, 2018, provisional application No. 62/599,970, filed on Dec. 18, 2017.

(51) Int. Cl.
| | |
|---|---|
| *C07K 14/62* | (2006.01) |
| *A61K 47/61* | (2017.01) |
| *A61K 47/54* | (2017.01) |
| *A61K 38/00* | (2006.01) |

(52) U.S. Cl.
CPC ............ *C07K 14/62* (2013.01); *A61K 47/549* (2017.08); *A61K 47/61* (2017.08); *A61K 38/00* (2013.01)

(58) Field of Classification Search
CPC ...... A61K 38/00; A61K 47/549; A61K 47/61; C07K 14/62; A61P 25/18; A61P 5/48
See application file for complete search history.

(56) References Cited

U.S. PATENT DOCUMENTS

| | | |
|---|---|---|
| 4,348,387 A | 9/1982 | Brownlee et al. |
| 4,421,685 A | 12/1983 | Chance et al. |
| 5,461,031 A | 10/1995 | De Felippis |
| 5,474,978 A | 12/1995 | Bakaysa et al. |
| 5,504,188 A | 4/1996 | Baker et al. |
| 5,547,929 A | 8/1996 | Anderson, Jr. et al. |
| 5,650,486 A | 7/1997 | De Felippis |
| 5,693,609 A | 12/1997 | Baker et al. |
| 5,747,642 A | 5/1998 | De Felippis |
| 5,750,497 A | 5/1998 | Havelund et al. |
| 5,830,506 A | 11/1998 | Taylor |
| 5,866,538 A | 2/1999 | Norup et al. |

(Continued)

FOREIGN PATENT DOCUMENTS

| | | | | |
|---|---|---|---|---|
| CN | 102365025 | * | 1/2010 | ............. A61K 38/28 |
| WO | 1999019297 A1 | | 4/1999 | |

(Continued)

OTHER PUBLICATIONS

US 5,691,198 A, 11/1997, Jin et al. (withdrawn)
Abdel-Rahman, Hamdy M. et al., HIV Protease Inhibitors: Peptidomimetic Drugs and Future Perspectives, Current Medicinal Chemistry, 2002, 1905-1922, 9.
Abraira, Carlos et al., Veterans Affairs Cooperative Study on Glycemic Control and Complications in Type II Diabetes (VA CSDM), Diabetes Care, 1995, 1113-1123, 18(8).
Adam, Gregory C. et al., Chemical Strategies for Functional Proteomics, Molecular & Cellular Proteomics, 2002, 781-790, 1.
Adamczyk, Maciej et al., Synthesis of 5- and 6-Hydroxymethylfluorescein Phosphoramidites, J. Org. Chem., 2000, 596-601, 65.

(Continued)

*Primary Examiner* — Marcela M Cordero Garcia
(74) *Attorney, Agent, or Firm* — Julie M. Lake; Catherine D. Fitch

(57) ABSTRACT

The present disclosure provides conjugates that comprise an insulin molecule conjugated via a conjugate framework to two or more separate ligands that each include a saccharide, wherein the framework, ligand, saccharide and insulin molecule optionally comprise a fatty chain (e.g., a C8-30 fatty chain), wherein when said insulin molecule is conjugated both to a C8-30 fatty chain and one or more separate ligands that each include a saccharide, said C8-30 fatty chain is linked to insulin molecule only, and wherein when the framework or ligand comprises a fatty chain the insulin molecule is conjugated to two or more separate ligands. In certain embodiments, a conjugate is characterized in that, when the conjugate is administered to a mammal, at least one pharmacokinetic (PK) and/or pharmacodynamic (PD) property of the conjugate is sensitive to serum concentration of a second saccharide. In certain embodiments, a conjugate is also characterized by having a protracted PK profile. Exemplary conjugates and sustained release formulations are provided in addition to methods of use and preparation.

3 Claims, 3 Drawing Sheets
Specification includes a Sequence Listing.

(56) References Cited

U.S. PATENT DOCUMENTS

| | | | |
|---|---|---|---|
| 5,902,603 | A | 5/1999 | Chen et al. |
| 5,922,675 | A | 7/1999 | Baker et al. |
| 5,952,297 | A | 9/1999 | De Felippis et al. |
| 6,011,007 | A | 1/2000 | Havelund et al. |
| 6,034,054 | A | 3/2000 | DeFelippis et al. |
| 6,051,551 | A | 4/2000 | Hughes et al. |
| 6,174,856 | B1 | 1/2001 | Langballe et al. |
| 6,268,335 | B1 | 7/2001 | Brader |
| 6,335,316 | B1 | 1/2002 | Hughes et al. |
| 6,410,053 | B1 | 6/2002 | Taylor |
| 6,444,641 | B1 | 9/2002 | Flora |
| 6,465,426 | B2 | 10/2002 | Brader |
| 6,551,992 | B1 | 4/2003 | DeFelippis et al. |
| 6,869,930 | B1 | 3/2005 | Havelund et al. |
| 6,906,028 | B2 | 6/2005 | DeFelippis et al. |
| 7,387,996 | B2 | 6/2008 | Langkjaer |
| 8,106,007 | B2 | 1/2012 | Bos et al. |
| 8,906,850 | B2 | 12/2014 | Zion et al. |
| 11,041,009 | B2 * | 6/2021 | Feng .................... A61P 3/10 |
| 11,413,352 | B2 * | 8/2022 | Moyes ................ A61K 47/542 |
| 2003/0135050 | A1 | 7/2003 | Kolb et al. |
| 2003/0153728 | A1 | 8/2003 | Kolb et al. |
| 2003/0153771 | A1 | 8/2003 | Kolb et al. |
| 2004/0202719 | A1 | 10/2004 | Zion et al. |
| 2011/0281791 | A1 * | 11/2011 | Zion ................... A61K 47/549 |
| | | | 604/151 |
| 2012/0010134 | A1 | 1/2012 | Zion et al. |
| 2012/0046223 | A1 | 2/2012 | Zion et al. |
| 2014/0274888 | A1 | 9/2014 | Zion et al. |
| 2015/0105317 | A1 | 4/2015 | Lin et al. |
| 2017/0254798 | A1 | 9/2017 | Mu et al. |
| 2021/0177981 | A1 * | 6/2021 | Yan ........................ A61P 3/10 |

FOREIGN PATENT DOCUMENTS

| | | |
|---|---|---|
| WO | 2000063161 A1 | 10/2000 |
| WO | 2007083146 A2 | 7/2007 |
| WO | 2012015692 A2 | 2/2012 |
| WO | 2015051052 A2 | 4/2015 |
| WO | 2016164288 A1 | 10/2016 |

OTHER PUBLICATIONS

Adolfsson, Hans et al., Comparison of Amine Additives Most Effective in the New Methyltrioxorhenium-Catalyzed Epoxidation Process, Tetrahedron Letters, 1999, 3991-3994, 40.

Agard, Nicholas J. et al., A Strain-Promoted [3+2] Azide-Alkyne Cycloaddition for Covalent Modification of Biomolecules in Living Systems, J. Am. Chem. Soc., 2004, 15046-15047, 126.

Ahren, B. et al., Glucagon secretory response to hypoglycaemia, adrenaline and carbachol in streptozotocindiabetic rats, Acta Physiol Scand, 1995, 215-221, 155.

Akram, J. et al., Insulin lispro (Lys(B28), Pro(B29) in the treatment of diabetes during the fasting month of Ramadan, Diabetic Medicine, 1999, 861-866, 16.

Alessandro Dondoni, Triazole: The Keystone in Glycosylated Molecular Architectures Constructed by a Click Reaction, Chem Asian J., 2007, 700-708, 2.

Anderson, James H. et al., Improved Mealtime Treatment of Diabetes Mellitus Using an Insulin Analogue, Clinical Therapeutics, 1997, 62-72, 19(1).

Anderson, James H. et al., Mealtime Treatment With Insulin Analog Improves Postprandial Hyperglycemia and Hypoglycemia in Patients With Non-Insulin-Dependent Diabetes Mellitus, Arch Intern Med., 1997, 1249-1255, 157.

Anderson, James H. et al., Reduction of Postprandial Hyperglycemia and Frequency of Hypoglycemia in IDDM Patients on Insulin-Analog treatment, Diabetes, 1997, 265-270, 46.

Asada, Hiroyuki et al., Absorption Characteristics of Chemical l y Modif ied-I nsu li n Derivatives with Various Fatty Acids in the Small and Large Intestine, Journal of Pharmaceutical Sciences, 1995, 682-687, 84(6).

Asada, Hiroyuki et al., Stability of Acyl Derivatives of Insulin in the Small Intestine: Relative Importance of Insulin Association Characteristics in Aqueous Solution, Pharmaceutical Research, 1994, 1115-1120, 11(8).

Barnett, Anthony H. et al., Insulin analogues, Lancet, 1997, 47-51, 349.

Beau, Jean-Marie et al., Nucleophilic C-Glycosyl Donors for C-Glycoside Synthesis, Top. Curr. Chem., 1997, 1-54, 187.

Bemis, Guy W. et al., The Properties of Known Drugs. 1. Molecular Frameworks, J. Med. Chem., 1996, 2887-2893, 39.

Bertozzi, Carolyn R. et al., Chemical Glycobiology, Science, 2001, 2357-2364, 291.

Bezouska, Karel et al., Design, functional evaluation and biomedical applications of carbohydrate dendrimers (glycodendrimers), Reviews in Molecular Biotechnology, 2002, 269-290, 90.

Billing, Johan F. et al., C2-Symmetric Macrocyclic Carbohydrate/ Amino Acid Hybrids through Copper(I)-Catalyzed Formation of 1,2,3-Triazoles, J. Org. Chem., 2005, 4847-4850, 70.

Binder, C. et al., Insulin Pharmacokinetics, Diabetes Care, 1984, 188-199, 7.

Blundell, Tom et al., Insulin: The Structure in the Crystal and its Reflection in Chemistry and Biology, Adv. Protein Chem., 1972, 279-402, 26.

Bock, Victoria D. et al., CuI-Catalyzed Alkyne-Azide "Click" Cycloadditions from a Mechanistic and Synthetic Perspective, Eur. J. Org. Chem., 2006, 51-68, N/A.

Bodine, Kyle D. et al., Highly Convergent Synthesis of C3- or C2-Symmetric Carbohydrate Macrocycles, Organic Letters, 2005, 4479-4482, 7(20).

Bodine, Kyle D. et al., Synthesis of Readily Modifiable Cyclodextrin Analogues via Cyclodimerization of an Alkynyl-Azido Trisaccharide, J. Am. Chem. Soc., 2004, 1638-1639, 126.

Bohacek, Regine S. et al., The Art and Practice of Structure-Based Drug Design: A Molecular Modeling Perspective, Medicinal Research Reviews, 1996, 3-50, 16(1).

Bolli, G.B. et al., Insulin analogues and their potential in the management of diabetes mellitus, Diabetologia, 1999, 1151-1167, 42.

Bolli, G.B., Hypoglycaemia Unawareness, Diabetes & Metabolism, 1997, 29-35, 23 (Suppl 3).

Bolli, G.B., Physiological insulin replacement in type 1 diabetes mellitus, Exp Clin Endocrinol Diabetes, 2001, S317-S332, 109 (Suppl 2).

Bolli, Geremia B. et al., Insulin glargine, Lancet, 2000, 443-445, 356.

Bourne, Yves et al., Structural insights into ligand interactions at the acetylcholinesterase peripheral anionic site, The EMBO Journal, 2003, 1-12, 22(1).

Bradbury, J. Howard et al., Nuclear-Magnetic-Resonance—Spectroscopic Studies of the Amino Groups of Insulin, Eur J. Biochem., 1977, 573-582, 76.

Brase, Stefan et al., Organic Azides: An Exploding Diversity of a Unique Class of Compounds, Angew. Chem. Int. Ed., 2005, 5188-5240, 44.

Brase, Stefan et al., Organische Azide—explodierende Vielfalt bei einer einzigartigen Substanzklasse, Angew. Chem., 2005, 5320-5374, 117.

Breinbauer, Rolf et al., Azide—Alkyne Coupling: A Powerful Reaction for Bioconjugate Chemistry, ChemBioChem, 2003, 1147-1149, 4.

Brems, David et al., Altering the Association Properties of Insulin by Amino Acid Replacement, Protein Engineering, 1992, 527-533, 5.

Brunelle, Rocco et al., Meta-Analysis of the Effect of Insulin Lispro on Severe Hypoglycemia in Patients With Type I Diabetes, Diabetes Care, 1998, 1726-1731, 21.

Bundle, David R. et al., Thiooligosaccharide Conjugate Vaccines Evoke Antibodies Specific for Native Antigens, Angew. Chem, 2005, 7903-7907, 117.

Bundle, David R. et al., Thiooligosaccharide Conjugate Vaccines Evoke Antibodies Specific for Native Antigens, Angew. Chem. Int. Ed., 2005, 7725-7729, 44.

(56) References Cited

OTHER PUBLICATIONS

Burge, Mark R. et al., Meal Composition is a Determinant of Lispro-Induced Hypoglycemia in IDDM, Diabetes Care, 1997, 152-155, 20.
Cao, Hongzhi et al., Synthesis of a S-linked heparan sulfate trisaccharide as the substrate mimic of heparanase, Tetrahedron Letters, 2005, 4337-4340, 46.
Cefalu, William T. et al., Inhaled Human Insulin Treatment in Patients with Type 2 Diabetes Mellitus, Annals of Internal Medicine, 2001, 203-207, 134(3).
Changeux, Jean-Pierre, Responses of acetylcholinesterase from Torpedo marmorata to salts and curarizing agents, Mol. Pharmacol., 1966, 369-392, 2.
Chehab, Farid F. et al., Detection of specific DNA sequences by fluorescence amplification: a color complementation assay, Proc. Natl. Acad. Sci. U. S. A., 1989, 9178-9182, 86.
Chen, Qi et al., Synthesis of a C3-symmetric (1-6)-N-acetyl-beta-D-glucosamine octadecasaccharide using click chemistry, Carbohydrate Research, 2005, 2476-2482, 340.
Cheshev, Pavel et al., First synthesis of 1,2,3-triazolo-linked (1,6)-alpha-D-oligomannoses (triazolomannoses) by iterative Cu(I)-catalyzed alkyne-azide cycloaddition, Org. Biomol. Chem., 2006, 3225-3227, 4.
Chittaboina, Srinivas et al., One-pot synthesis of triazole-linked glycoconjugates, Tetrahedron Letters, 2005, 2331-2336, 46.
Choi, Wonjae E. et al., Spectroscopic Evidence for Preexisting T- and R-State Insulin Hexamer Conformations, Proteins Structure, Function, and Genetics, 1996, 377-390, 26.
Click Chemistry: Diverse Chemical Function from a few Good Reactions, Agnew Chem. Int. Ed., 2001, pp. 2004-2021, 40.
Colombel, A. et al., Improvement of blood glucose control in Type 1 diabetic patients treated with lispro and multiple NPH injections, Diabet. Med., 1999, 319-324, 16.
Compain, Philippe et al., Carbohydrate Mimetics-Based Glycosyltransferase Inhibitors, Bioorganic & Medicinal Chemistry, 2001, 3077-3092, 9.
Cumpstey, Ian et al., C2-Symmetrical Thiodigalactoside Bis-Benzamido Derivatives as High-Affinity Inhibitors of Galectin-3: Efficient Lectin Inhibition through Double Arginine-Arene Interactions, Angew. Chem, 2005, 5240-5242, 117.
Cumpstey, Ian et al., C2-Symmetrical Thiodigalactoside Bis-Benzamido Derivatives as High-Affinity Inhibitors of Galectin-3: Efficient Lectin Inhibition through Double Arginine-Arene Interactions, Angew. Chem. Int. Ed., 2005, 5110-5112, 44.
Dale, H.H., The action of certain esters of choline and their relation to muscarine, J. Pharmacol. Exp. Ther., 1914, 147-190, 6.
Dalvie, Deepak K. et al., Biotransformation Reactions of Five-Membered Aromatic Heterocyclic Rings, Chemical Research in Toxicology, 2002, 269-299, 15.
Danishefsky, Samuel J. et al., From the Laboratory to the Clinic: A Retrospective on Fully Synthetic Carbohydrate-Based Anticancer Vaccines, Angew. Chem. Int. Ed., 2000, 836-863, 39.
Danishefsky, Samuel J. et al., Vom Labor zur Klinik: vollsynthetische Antitumor-Impfstoffe auf Kohlenhydratbasis, Angew. Chem., 2000, 882-911, 112.
Dedola, Simone et al., Recent applications of the CuI-catalysed Huisgen azide-alkyne 1,3-dipolar cycloaddition reaction in carbohydrate chemistry, Org. Biomol. Chem., 2007, 1006-1017, 5.
Deiters, Alexander et al., Adding Amino Acids with Novel Reactivity to the Genetic Code of Saccharomyces cerevisiae, J. Am. Chem. Soc., 2003, 11782-11783, 125.
Del Sindaco, P. et al., Use of the Short-acting Insulin Analogue Lispro in Intensive Treatment of Type 1 Diabetes Mellitus: Importance of Appropriate Replacement of Basal Insulin and Time-interval Injection-meal, Diabetic Medicine, 1998, 592-600, 15.
Dimarchi, R.D. et al., Preparation of an Insulin with Improved Pharmacokinetics Relative to Human Insulin through Consideration of Structural Homology with Insulin-Like Growth Factor I, Horm Res, 1994, 93-96, 41(Suppl 2).
Dimitriadis, George D. et al., Importance of Timing of Preprandial Subcutaneous Insulin Administration in the Management of Diabetes Mellitus, Diabetes Care, 1983, 374-377, 6(4).
Dondoni, Alessandro et al., Assembling Heterocycle-Tethered C-Glycosyl and alpha-Amino Acid Residues via 1,3-Dipolar Cycloaddition Reactions, Organic Letters, 2004, 2929-2932, 6(17).
Dondoni, Alessandro et al., C-Glycoside Clustering on Calix[4]arene, Adamantane, and Benzene Scaffolds through 1,2,3-Triazole Linkers, J. Org. Chem, 2006, 7546-7557, 71.
Dondoni, Alessandro et al., Methods for Anomeric Carbon-Linked and Fused Sugar Amino Acid Synthesis: The Gateway to Artificial Glycopeptides, Chem. Rev., 2000, 4395-4421, 100.
Dorner, Simon et al., A short route for the synthesis of "sweet" macrocycles via a click-dimerization-ring-closing metathesis approach, Chem. Commun., 2005, 2852-2854, N/A.
Driguez, Hugues, Thiooligosaccharides as Tools for Structural Biology, ChemBioChem, 2001, 311-318, 2.
Dwek, Raymond A., Glycobiology: Toward Understanding the Function of Sugars, Chem. Rev., 1996, 683-720, 96.
Ebeling, Pertti et al., Strategies Toward Improved Control During Insulin Lispro Therapy in IDDM, Diabetes Care, 1997, 1287-1289, 20.
Elliott, R.B. et al., Parenteral absorption of insulin from the lung in diabetic children, Aust. Paediatr. J., 1987, 293-297, 23.
Fazio, Fabio et al., Synthesis of Sugar Arrays in Microtiter Plate, J. Am. Chem. Soc., 2002, 14397-14402, 124.
Fernandez-Megia, Eduardo et al., A Click Approach to Unprotected Glycodendrimers, Macromolecules, 2006, 2113-2120, 39.
Furstner, Alois et al., Efficient Total Syntheses of Resin Glycosides and Analogues by Ring-Closing Olefin Metathesis, J. Am. Chem. Soc., 1999, 7814-7821, 121.
Furstner, Alois et al., Metathesis Route to Resin Glycosides: Formal Total Synthesis of Tricolorin A, J. Org. Chem., 1998, 424-425, 63.
Garg, S.K. et al., Long-term efficacy of HumalogR in subjects with Type 1 diabetes mellitus, Diabetic Medicine, 1999, 384-387, 16.
Geng, Xudong et al., In Pursuit of Carbohydrate-Based HIV Vaccines, Part 2: The Total Synthesis of High-Mannose—Type gp120 Fragments—Evaluation of Strategies Directed to Maximal Convergence, Angew. Chem., 2004, 2616-2619, 116.
Geng, Xudong et al., In Pursuit of Carbohydrate-Based HIV Vaccines, Part 2: The Total Synthesis of High-Mannose—Type gp120 Fragments—Evaluation of Strategies Directed to Maximal Convergence, Angew. Chem. Int. Ed., 2004, 2562-2565, 43.
Gerber, Robert A. et al., Treatment Satisfaction With Inhaled Insulin in Patients With Type 1 Diabetes, Diabetes Care, 2001, 1556-1559, 24.
Gholami, M.R. et al., Hydrophobic effects in 1,3-dipolar cycloaddition of C,N-diphenylnitrone with Dibutyl fumarate in aqueous solutions, J. Chem. Res., 1999, 226-227, 3.
Gierlich, Johannes et al., Click Chemistry as a Reliable Method for the High-Density Postsynthetic Functionalization of Alkyne-Modified DNA, Organic Letters, 2006, 3639-3642, 8(17).
Girish, C. et al., Newer Insulin Analogues and Inhaled Insulin, Indian J Med Sci, 2006, 117-123, 60.
Gontcharov, Alexander V. et al., tert-Butylsulfonamide. A New Nitrogen Source for Catalytic Aminohydroxylation and Aziridination of Olefins, Organic Letters, 1999, 783-786, 1(5).
Guerci, Bruno et al., Comparison of Metabolic Deterioration between Insulin Analog and Regular Insulin after a 5-Hour Interruption of a Continuous Subcutaneous Insulin Infusion in Type 1 Diabetic Patients, The Journal of Clinical Endocrinology & Metabolism, 1999, 2673-2678, 84.
H.B.F. Dixon et al., Reversible Blocking of Amino Groups with Citraconic Anhydride, Biochem J., 1968, 312-314, 109.
Harel, M. et al., Quaternary ligand binding to aromatic residues in the active-site gorge of acetylcholinesterase, Proc. Natl. Acad. Sci. USA, 1993, 9031-9035, 90.
Harju, Kirsi et al., Solid-Phase Synthesis of 1,2,3-Triazoles via 1,3-Dipolar Cycloaddition, J. Comb. Chem., 2003, 826-833, 5.
Hartmuth C. Kolb et al., The Growing Impact of Click Chemistry on Drug Discovery, Drug Discovery Today, 2003, 1128-1137, 8.

(56) References Cited

OTHER PUBLICATIONS

Hashimoto, Muneaki et al., Synthesis of Palmitoyl Derivatives of Insulin and Their Biological Activities, Pharmaceutical Research, 1989, 171-176, 6.

Hedman, CA et al., Direct Comparison of Insulin Lispro and Aspart Shows Small Differences in Plasma Insulin Profiles After Subcutaneous Injection in Type 1 Diabetes, Diabetes Care, 2001, 1120-1121, 24.

Heinemann, L. et al., Time-action profile of the long-acting insulin analog insulin glargine (HOE901) in comparison with those of NPH insulin and placebo, Diabetes Care, 2000, 644-649, 23.

Heinemann, L. et al., Time-action profile of the soluble, fatty acid acylated, long-acting insulin analogue NN304, Diabetic Medicine, 1999, 332-338, 16.

Heinemann, L. et al., Time-action Profile of Inhaled Insulin, Diabetic Medicine, 1997, 63-72, 14.

Heinemann, Lutz et al., Clinical Pharmacology of Human Insulin, Diabetes Care, 1993, 90-100, 16 (Suppl 3).

Heise, Tim et al., Lower Within-Subject Variability of Insulin Detemir in Comparison to NPH Insulin and Insulin Glargine in People With Type 1 Diabetes, Diabetes, 2004, 1614-1620, 53.

Heise, Tim, Rapid and Long-Acting Analogues as an Approach to Improve Insulin Therapy: An Evidence-Based Medicine Assessment, Current Pharmaceutical Design, 2001, 1303-1325, 7.

Henry, Robert R. et al., Inhaled Insulin Using the AERx Insulin Diabetes Management System in Healthy and Asthmatic Subjects, Diabetes Care, 2003, 764-769, 26.

Hermansen, Kjeld et al., Comparison of the Soluble Basal Insulin Analog Insulin Detemir With NPH Insulin, Diabetes Care, 2001, 296-301, 24.

Hirsch, Irl B., Insulin Analogues, N Engl J Med, 2005, 174-183, 352.

Home, P.D. et al., Comparative Pharmacokinetics and pharmacodynamics of the novel rapid-acting insulin analogue, insulin aspart, in healthy volunteers, Eur J Clin Pharmacol, 1999, 199-203, 55.

Home, P.D. et al., Insulin aspart vs. human insulin in the management of long-term blood glucose control in type 1 diabetes mellitus: a randomized controlled trial, Diabetic Medicine, 2000, 762-771, 17.

Home, Philip D. et al., Improved Glycemic Control With Insulin Aspart, Diabetes Care, 1998, 1904-1909, 21.

Hong Mei et al., NB1-C16-Insulin: Site-Specific Synthesis, Purification, and Biological Activity, Pharmaceutical Research, 1999, 1680-1686, vol. 16 No. 11.

Hoogenboom, Richard et al., Synthesis of star-shaped poly(e-caprolactone) via 'click' chemistry and 'supramolecular click' chemistry, Chem. Commun., 2006, 4010-4012, N/A.

Horne, W. Seth et al., Heterocyclic Peptide Backbone Modifications in an alpha-Helical Coiled Coil, J. Am. Chem. Soc., 2004, 15366-15367, 126.

Huisgen, R., Kinetics and Mechanism of 1,3-Dipolar Cycloadditions, Angewandte Chemie Internatinal Edition, 1963, 633-645, 2(11).

Huisgen, R., Kinetik und Mechanismus 1.3-Dipolarer Cycloadditionen, Angew. Chem., 1963, 742-754, 75(16/17).

Huisgen, Rolf, 1,3-Dipolar Cycloadditions, Past and Future, Angewandte Chemie International Edition, 1963, 565-598, 2(10).

Huisgen, Rolf, 1.3-Dipolare Cycloadditionen, Rüickschau und Ausblick, Angew. Chem., 1963, 604-637, 75(13).

Imperiali, Barbara, Protein Glycosylation: The Clash of the Titans, Acc. Chem. Res., 1997, 452-459, 30.

John E. Gerich M.D., Novel Insulins: Expanding Options in Diabetes Management, The American Journal of Medicine, 2002, 308-316, vol. 113.

Joosten, John A. F. et al., High-Yielding Microwave-Assisted Synthesis of Triazole-Linked Glycodendrimers by Copper-Catalyzed [3+2] Cycloaddition, Eur. J. Org. Chem, 2005, 3182-3185, N/A.

Jorgensen, Karl Anker, Catalytic asymmetric hetero-Diels-Alder reactions of carbonyl compounds and imines, Angew. Chem. Int. Ed., 2000, 3558-3588, 39.

Kang, Steven et al., Comparison of subcutaneous soluble human insulin and insulin analogues (AspB9, GluB27; AspB10; AspB28) on meal-related plasma glucose excursions in type I diabetic subjects, Diabetes Care, 1991, 571-577, 14.

Kim, Sungwon et al., Insulinotropic activity of sulfonylurea/pullulan conjugate in rat islet microcapsule, Biomaterials, 2003, 4843-4851, 24.

Kinstler, Olaf B. et al., Characterization and Stability of N-terminally PEGylated rhG-CSF, Pharmaceutical Research, 1996, 996-1002, 13(7).

Kohn, Maja et al., Die Staudinger-Ligation—ein Geschenk fur die Chemische Biologie, Angew. Chem., 2004, 3168-3178, 116.

Kohn, Maja et al., The Staudinger Ligation—A Gift to Chemical Biology, Angew. Chem. Int. Ed., 2004, 3106-3116, 43.

Kolb, H.C., Application of Click Chemistry to the generation of new chemical libraries for drug discovery, 221st Am. Chem. Soc. Meeting, Abstracts of Papers, ORGN-434, 2001, 1-2, Part 2.

Kolb, Hartmuth C. et al., Catalytic Asymmetric Dihydroxylation, Chem. Rev., 1994, 2483-2547, 94.

Kolb, Hartmuth C. et al., Click-Chemie: diverse chemische Funktionalität mit einer Handvoll guter Reaktionen, Angew. Chem., 2001, 2056-2075, 113.

Kuberan, Balagurunathan et al., Synthesis of a C-Glycoside Analogue of sTn: An HIV- and Tumor-Associated Antigen, Angew Chem Int Ed Engl, 2003, 2073-2075, 42(18).

Kuberan, Balagurunathan et al., Synthesis of a C-Glycoside Analogue of sTn: An HIV- and Tumor-Associated Antigen, Angew. Chem., 2003, 2119-2121, 115.

Kuhle, Engelbert, One-hundred years of sulfenic acid chemistry. IIa. Oxidation, reduction, and addition reactions of sulfenyl halides, Synthesis (Mass.), 1970, 563-586, 11.

Kuijpers, Brian H. M. et al., Expedient Synthesis of Triazole-Linked Glycosyl Amino Acids and Peptides, Organic Letters, 2004, 3123-3126, 6(18).

Kurtaran, Amir et al., Technetium-99m-Galactosyl-Neoglyco albumin Combined with Iodine-123-Tyr-(A14)-Insulin Visualizes Human Hepatocellular Carcinomas, J. Nucl. Med., 1995, 1875-1881, 36.

Kurtzhals, Peter et al., Albumin binding of insulins acylated with fatty acids: characterization of the ligand-protein interaction and correlation between binding affinity and timing of the insulin effect in vivo, Biochem. J., 1995, 725-731, 312.

Ladmiral, Vincent et al., Synthesis of Neoglycopolymers by a Combination of "Click Chemistry" and Living Radical Polymerization, J. Am. Chem. Soc., 2006, 4823-4830, 128.

Lalli, Carlo et al., Long-Term Intensive Treatment of Type 1 Diabetes With the Short-Acting Insulin Analog Lispro in Variable Combination With NPH Insulin at Mealtime, Diabetes Care, 1999, 468-477, 22.

Laube, Beth L. et al., Preliminary Study of the Efficacy of Insulin Aerosol Delivered by Oral Inhalation in Diabetic Patients, JAMA, 1993, 2106-2109, 269.

Lee, Lac V. et al., A Potent and Highly Selective Inhibitor of Human alpha-1,3-Fucosyltransferase via Click Chemistry, J. Am. Chem. Soc., 2003, 9588-9589, 125.

Lehle, Ludwig et al., Protein Glycosylation, Conserved from Yeast to Man: A Model Organism Helps Elucidate Congenital Human Diseases, Angew. Chem. Int. Ed., 2006, 6802-6818, 45.

Lehle, Ludwig et al., Proteinglycosylierung, konserviert von der Bckerhefe bis zum Menschen: Ein Modellorganismus hilft bei der Aufklrung menschlicher Erbkrankheiten, Angew. Chem., 2006, 6956-6972, 118.

Lehn, Jean-Marie et al., Dynamic Combinatorial Chemistry, Science, 2001, 2331-2332, 291.

Lepore, Mauro et al., Pharmacokinetics and pharmacodynamics of subcutaneous injection of long-acting human insulin analog glargine, NPH insulin, and ultralente human insulin and continuous subcutaneous infusion of insulin lispro, Diabetes, 2000, 2142-2148, 49.

Levinson, Paul D. et al., Eighty Years of Insulin Therapy: 1922-2002, Rhode Island: Med. and Health, 2003, 101-106, 86.

Lewis, Warren G. et al., Click Chemistry In Situ: Acetylcholinesterase as a Reaction Vessel for the Selective Assembly of a Femtomolar Inhibitor from an Array of Building Blocks, Angew. Chem. Int. Ed. Engl., 2002, 1053-1057, 41.

(56) References Cited

OTHER PUBLICATIONS

Lindholm, Anders et al., Improved Postprandial Glycemic Control With Insulin Aspart, Diabetes Care, 1999, 801-805, 22.
Lindsay, D.G. et al., The Acetylation of Insulin, Biochem. J., 1971, 737-745, 121.
Link, A. James et al., Cell Surface Labeling of *Escherichia coli* via Copper(I)-Catalyzed [3+2] Cycloaddition, J. Am. Chem. Soc., 2003, 11164-11165, 125.
Lober, Stefan et al., Click Linker: Efficient and High-Yielding Synthesis of a New Family of SPOS Resins by 1,3-Dipolar Cycloaddition, Organic Letters, 2003, 1753-1755, 5(10).
Lundquist, Joseph J. et al., The Cluster Glycoside Effect, Chem. Rev., 2002, 555-578, 102.
Lwowski, Walter, 1,3-Dipolar Cycloaddition Chemistry, Azides and Nitrous Oxide, 1984, 559-645, 1.
Lyttle, Matthew H. et al., New Reagents and Methods for the Synthesis of Internal and 3'-Labeled DNA, Bioconjugate Chem., 2002, 1146-1154, 13.
Mahal, Lara K. et al., Engineering Chemical Reactivity on Cell Surfaces Through Oligosaccharide Biosynthesis, Science, 1997, 1125-1128, 276.
Mammen, Mathai et al., Polyvalent Interactions in Biological Systems: Implications for Design and Use of Multivalent Ligands and Inhibitors, Angew. Chem. Int. Ed., 1998, 2754-2794, 37.
Mammen, Mathai et al., Polyvalente Wechselwirkungen in biologischen Systemen: Auswirkungen auf das Design und die Verwendung multivalenter Liganden und Inhibitoren, Angew. Chem., 1998, 2908-2953, 110.
Mandal, Mihirbaran et al., In Pursuit of Carbohydrate-Based HIV Vaccines, Part 1: The Total Synthesis of Hybrid-Type gp120 Fragments, Angew. Chem. Int. Ed., 2004, 2557-2561, 43.
Mandal, Mihirbaran et al., In Pursuit of Carbohydrate-Based HIV Vaccines, Part 1: The Total Synthesis of Hybrid-Type gp120 Fragments, Angew. Chem., 2004, 2611-2615, 116.
Mandal, Tarun K., Inhaled insulin for diabetes mellitus, Am J Health Syst Pharm, 2005, 1359-1364, 62.
Markussen, J. et al., Soluble, fatty acid acylated insulins bind to albumin and show protracted action in pigs, Diabetologia, 1996, 281-288, 39.
Melki, Vincent et al., Improvement of HbA1C and blood glucose stability in IDDM patients treated with lispro insulin analog in external pumps, Diabetes Care, 1998, 977-982, 21.
Miller, Veronica, Resistance to Protease Inhibitors, J. Acquir. Immune Defic. Syndr., 2001, S34-S50, 26 (Suppl 1).
Miroslav Baudys et al., Extending Insulin Action in vivo by Conjugation to Carboxymethyl Dextran, Bioconjugate Chem., 1998, 176-183, 9.
Mitchell, Michael L. et al., Synthesis and Evaluation of Transition-State Analogue Inhibitors of alpha-1,3-Fucosyltransferase, Angew. Chem. Int. Ed. Engl., 2002, 3041-3044, 41.
Mocharla, Vani P. et al., In Situ Click Chemistry: Enzyme-Generated Inhibitors of Carbonic Anhydrase II, Angew. Chem., 2005, 118-122, 117.
Mocharla, Vani P.et al., In Situ Click Chemistry: Enzyme-Generated Inhibitors of Carbonic Anhydrase II, Angew. Chem. Int. Ed., 2005, 116-120, 44.
Mock, W.L. et al., Cycloaddition Induced by Cucurbituril. A Case of Pauling Principle Catalysis, J. Org. Chem., 1983, 3619-3620, 48.
Mock, William L. et al., Catalysis by Cucurbituril. The Significance of Bound-Substrate Destabilization for Induced Triazole Formation, J. Org. Chem., 1989, 5302-5308, 54.
Mock, William L., Cucurbituril, Top. Curr. Chem., 1995, 1-24, 175.
Myers, Sharon R. et al., Acylation of Human Insulin With Palmitic Acid Extends the Time Action of Human Insulin in Diabetic Dogs, Diabetes, 1997, 637-642, 46.
Newman, David J. et al., Natural Products as Sources of New Drugs over the Period 1981-2002, J. Nat. Prod., 2003, 1022-1037, 66.
Nguyen, Regis et al., Using an Enzyme's Active Site to Template Inhibitors, Angew. Chem. Int. Ed. Engl., 2001, 1774-1776, 40.

Ohkubo, Yasuo et al., Intensive insulin therapy prevents the progression of diabetic microvascular complications in Japanese patients with non-insulin-dependent diabetes mellitus: a randomized prospective 6-year study, Diabetes Research and Clinical Practice, 1995, 103-117, 28.
Owens, D. R. et al., Alternative routes of insulin delivery, Diabet. Med., 2003, 886-898, 20.
Owens, David R. et al., Pharmacokinetics of 125I-labeled insulin glargine (HOE 901) in healthy men: comparison with NPH insulin and the influence of different subcutaneous injection sites, Diabetes Care, 2000, 813-819, 23.
Palmieri, Richard et al., 1H Fourier Transform NMR Studies of Insulin: Coordination of Ca2+ to the Glu(B13) Site Drives Hexamer Assembly and Induces a Conformation Change, Biochemistry, 1988, 3387-3397, 27.
Patrick, A. W. et al., The Importance of the Time Interval Between InsulinInjection and Breakfast in Determining Postprandial Glycaemic Control—A Comparison Between Human and Porcine Insulin, Diabetic Medicine, 1988, 32-35, 5.
Patton, John S. et al., Inhaled insulin, Advanced Drug Delivery Reviews, 1999, 235-247, 35.
Patton, John S., Mechanisms of macromolecule absorption by the lungs, Advanced Drug Delivery Reviews, 1996, 3-36, 19.
Perez-Balderas, Francisco et al., Multivalent Neoglycoconjugates by Regiospecific Cycloaddition of Alkynes and Azides Using Organic-Soluble Copper Catalysts, Organic Letters, 2003, 1951-1954, 5(11).
Pfutzner, P et al., Intensive insulin therapy with insulin lispro in patients with type 1 diabetes reduces the frequency of hypoglycemic episodes, Exp Clin Endocrinol, 1996, 25-30, 104.
Pieber, Thomas R. et al., Efficacy and Safety of HOE 901 Versus NPH Insulin in Patients With Type 1 Diabetes, Diabetes Care, 2000, 157-162, 23.
Prescher, Jennifer A. et al., Chemical remodelling of cell surfaces in living animals, Nature, 2004, 873-877, 430.
Purcell, William P. et al., Electronic and molecular structure of selected unsubstituted and dimethyl amides from measurements of electric moments and nuclear magnetic resonance, J. Phys. Chem., 1967, 4316-4319, 71.
Quattrin, Teresa et al., Efficacy and Safety of Inhaled Insulin (Exubera) Compared With Subcutaneous Insulin Therapy in Patients With Type 1 Diabetes, Diabetes Care, 2004, 2622-2627, 27.
Quesenberry, Michael S. et al., Difference in the Binding Mode of Two Mannose-Binding Proteins: Demonstration of a Selective Minicluster Effect, Biochemistry, 1997, 2724-2732, 36.
Radziuk, Basal activity profiles of NPH and Ne Palmitoyl Lys B29 Human Insulins in Subjects wtih IDDM, Diabetologia, 1998, pp. 116-120, 41.
Radziuk, Jerry M. et al., Bioavailability and Bioeffectiveness of Subcutaneous Human Insulin and Two of its Analogs-LysB28ProB29-Human Insulin and AspB10LysB28ProB29-Human Insulin-Assessed in a Conscious Pig Model, Diabetes, 1997, 548-556, 46.
Raskin, Philip et al., A 16-Week Comparison of the Novel Insulin Analog Insulin Glargine (HOE 901) and NPH Human Insulin Used With Insulin Lispro in Patients With Type 1 Diabetes, Diabetes Care, 2000, 1666-1671, 23.
Ratner, Robert E. et al., Less hypoglycemia with insulin glargine in intensive insulin therapy for type 1 diabetes, Diabetes Care, 2000, 639-643, 23.
Reichard, Per et al., The effect of long-term intensified insulin treatment on the development of microvascular complications of diabetes mellitus, The New England Journal of Medicine, 1993, 304-309, 329.
Ress, Dino K. et al., Synthesis of Double C-Glycoside Analogue of sTn, J. Org. Chem., 2005, 8197-8200, 70.
Rich, Jamie R. et al., Glycosyltransferase-Catalyzed Synthesis of Thiooligosaccharides, Angew. Chem. Int. Ed., 2004, 613-615, 43.
Rich, Jamie R. et al., Glycosyltransferase-Catalyzed Synthesis of Thiooligosaccharides, Angew. Chem., 2004, 623-625, 116.
Rich, Jamie R. et al., S-Linked Ganglioside Analogues for Use in Conjugate Vaccines, Organic Letters, 2004, 897-900, 6(6).
Rideout, Darryl et al., Synergism Through Direct Covalent Bonding Between Agents: A Strategy for Rational Design of Chemotherapeutic Combinations, Biopolymers, 1990, 247-262, 29.

(56) References Cited

OTHER PUBLICATIONS

Rideout, Darryl, Self-Assembling Cytotoxins, Science, 1986, 561-563, 233.
Rizza, Robert A. et al., Control of blood sugar in insulin-dependent diabetes: comparison of an artificial endocrine pancreas, continuous subcutaneous insulin infusion, and intensified conventional insulin therapy, The New England Journal of Medicine, 1980, 1313-1318, 303(23).
Robertson, D. Argyll, The Calabar bean as a new agent in ophthalmic practice, Edinburgh Med. J., 1863, 815-820, 8.
Rodionov, Valentin O. et al., Mechanism of the Ligand-Free CuI-Catalyzed Azide-Alkyne Cycloaddition Reaction, Angew. Chem. Int. Ed., 2005, 2210-2215, 44.
Rodionov, Valentin O. et al., Mechanism of the Ligand-Free CuI-Catalyzed Azide-Alkyne Cycloaddition Reaction, Angewandte Chemie, 2005, 2250-2255, 117.
Rosenstock, Julio et al., Inhaled Insulin Improves Glycemic Control When Substituted for or Added to Oral Combination Therapy in Type 2 Diabetes, Annals of Internal Medicine, 2005, 549-558, 143.
Rostovtsev, Vsevolod V. et al., A Stepwise Huisgen Cycloaddition Process: Copper(I)-Catalyzed Regioselective "Ligation" of Azides and Terminal Alkynes, Angew. Chem. Int. Ed., 2002, 2596-2599, 41(14).
Rostovtsev, Vsevolod V. et al., A Stepwise Huisgen Cycloaddition Process: Copper(I)-Catalyzed Regioselective "Ligation" of Azides and Terminal Alkynes, Angew. Chem., 2002, 2708-2711, 114(14).
Roy, Melinda et al., Spectroscopic Signatures of the T to R Conformational Transition in the Insulin Hexam, J. Biol. Chem., 1989, 19081-19085, 264.
Rutledge, K. Suchari et al., Effectiveness of Postprandial Humalog in Toddlers With Diabetes, Pediatrics, 1997, 968-972, 100.
Sanger, F. et a l., DNA sequencing with chain-terminating inhibitors, Proc. Natl. Acad. Sci. U. S. A., 1977, 5463-5467, 74.
Saxon, Eliana et al., Investigating Cellular Metabolism of Synthetic Azidosugars with the Staudinger Ligation, J. Am. Chem. Soc., 2002, 14893-14902, 124.
Schuttler, Achim et al., Darstellung von N,N-Bis(methylsulfonylethoxycarbonyl)insulinen, Hoppe Seyler's Z. Physiol. Chem., 1979, 1721-1725, 360.
Schuttler, Achim et al., Preparation of N,N-Bis (methylsulfonylethoxycarbonyl) insulins, Hoppe-Seyler's Z., Physiol. Chem., 1979, 1721-1725, 360.
Sears, P. et al., Enzyme action in glycoprotein synthesis, Cell. Mol. Life Sci., 1998, 223-252, 54.
Sears, Pamela et al., Carbohydrate Mimetics: A New Strategy for Tackling the Problem of Carbohydrate-Mediated Biological Recognition, Angew. Chem. Int. Ed., 1999, 2300-2324, 38.
Sears, Pamela et al., Kohlenhydratmimetika: ein neuer Lösungsansatz für das Problem der kohlenhydratvermittelten biologischen Erkennung, Angew. Chem., 1999, 2446-2471, 111.
Seitz, Oliver, Glycopeptide Synthesis and the Effects of Glycosylation on Protein Structure and Activity, ChemBioChem, 2000, 214-246, 1.
Seo, Tae Seok et al., Click Chemistry to Construct Fluorescent Oligonucleotides for DNA Sequencing, J. Org. Chem., 2003, 609-612, 68.
Shu, Yue-Zhong, Recent Natural Products Based Drug Development: A Pharmaceutical Industry Perspective, J. Nat. Prod., 1998, 1053-1071, 61.
Skyler, Jay S. et al., Efficacy of inhaled human insulin in type 1 diabetes mellitus: a randomised proof-of-concept study, Lancet, 2001, 331-335, 357.
Slieker, L. J. et al., Modifications in the B10 and B26-30 regions of the B chain of human insulin alter affinity for the human IGF-I receptor more than for the insulin receptor, Diabetologia, 1997, S54-S61, 40.
Speers, Anna E. et al., Activity-Based Protein Profiling in Vivo Using a Copper(I)-Catalyzed Azide-Alkyne [3+2] Cycloaddition, J. Am. Chem. Soc., 2003, 4686-4687, 125.
Srinivasachari, Sathya et al., Trehalose Click Polymers Inhibit Nanoparticle Aggregation and Promote pDNA Delivery in Serum, J. Am. Chem. Soc., 2006, 8176-8184, 128.
Stephen Crotty et al., The New Insulins, Pediatric Emergency Care, 2007, 903-908, 23(12).
Sun, Xue-Long et al., Carbohydrate and Protein Immobilization onto Solid Surfaces by Sequential Diels-Alder and Azide-Alkyne Cycloadditions, Bioconjugate Chem., 2006, 52-57, 17.
Sussman, Joel L. et al., Atomic Structure of Acetylcholinesterase from Torpedo californica: A Prototypic Acetylcholine-Binding Protein, Science, 1991, 872-879, 253.
Taylor, Palmer et al., Interaction of Fluorescence Probes with Acetylcholinesterase. The Site and Specificity of Propidium Binding!, Biochemistry, 1975, 1989-1997, 14.
Ter Braak, Edit et al., Injection site effects on the pharmacokinetics and glucodynamics of insulin lispro and regular insulin, Diabetes Care, 1996, 1437-1440, 19.
The Diabetes Control and Complications Trial Research Group, The effect of intensive treatment of diabetes on the development and progression of long-term complicatins in unsulin-dependent diabetes mellitus, The New England Journal of Medicine, 1993, 977-986, 3329(14).
Theisen, Pete et al., Fluorescent Dye Phosphoramidite Labelling of Oligonucleotides, Tetrahedron Letters, 1992, 5033-5036, 33(35).
Thoma, Gebhard et al., Versatile Functionalization of Polylysine: Synthesis, Characterization, and Use of Neoglycoconjugates, J. Am. Chem. Soc., 1999, 5919-5929, 121.
Tietze, Lutz F. et al., Hetero Diels-Alder Reactions in Organic Chemistry, Top. Curr. Chem., 1997, 1-120, 189.
Tornoe, Christian W. et al., Peptidotriazoles on Solid Phase: [1,2,3]-Triazoles by Regiospecific Copper(I)-Catalyzed 1,3-Dipolar Cycloadditions of Terminal Alkynes to Azides, J. Org. Chem., 2002, 3057-3064, 67.
Touitou, E. et al., Prevention of Molecular Self-Association by Sodium Salicylate: Effect on Insulin and 6-Carboxyfluorescein, J. Pharm. Sci., 1987, 791-793, 76.
Tung, R.D. et al., Design and Synthesis of Amprenavir, A Novel HIV Protease Inhibitor, Infectious Diseasae and Therapy, 2002, 101-118, 25.
Vague, Philippe et al., Insulin Detemir is Associated With More Predictable Glycemic Control and Reduced Risk of Hypoglycemia Than NPH Insulin in Patients With Type 1 Diabetes on a Basal-Bolus Regimen With Premeal Insulin Aspart, Diabetes Care, 2003, 590-596, 26.
Van Maarseveen, Jan H. et al., Engineering des genetischen Codes: Molekularbiologie und Organische Chemie kombiniert, Angew. Chem., 2003, 6106-6108, 115.
Van Maarseveen, Jan H. et al., Re-Engineering the Genetic Code: Combining Molecular Biology and Organic Chemistry, Angew. Chem. Int. Ed., 2003, 5926-5928, 42.
Vocadlo, David J. et al., A chemical approach for identifying O-GlcNAc-modified proteins in cells, Proc. Natl. Acad. Sci. U.S.A., 2003, 9116-9121, 100.
Vázquez-Carrera, M. et al., Insulin Analogues in the Management of Diabetes, Methods Find Exp Clin Pharmacol, 2004, 445-461, 26(6).
Wamhoff, H., 1,2,3-Triazoles and their Benzo Derivatives, Comprehensive Heterocyclic Chemistry, 1984, 669-732, 5.
Wan, Qian et al., A Potentially Valuable Advance in the Synthesis of Carbohydrate-Based Anticancer Vaccines through Extended Cycloaddition Chemistry, J. Org. Chem., 2006, 8244-8249, 71.
Wang, Qian et al., Bioconjugation by Copper(I)-Catalyzed Azide-Alkyne [3+2] Cycloaddition, J. Am. Chem. Soc., 2003, 3192-3193, 125.
Watt, Jacinta A. et al., Rapid, iterative assembly of octyl alpha-1,6-oligomannosides and their 6-deoxy equivalents, Org. Biomol. Chem., 2005, 1982-1992, 3.
Waxman, Kenneth et al., Absorption of Insulin in the Peritoneal Cavity in a Diabetic Animal Model, Artificial Organs, 1993, 925-928, 17(11).
Werz, Daniel B. et al., Total Synthesis of Antigen Bacillus Anthracis Tetrasaccharide—Creation of an Anthrax Vaccine Candidate, Angew. Chem. Int. Ed., 2005, 6315-6318, 44.

(56) References Cited

OTHER PUBLICATIONS

Werz, Daniel B. et al., Totalsynthese eines Tetrasaccharid-Antigens von Bacillus anthracis—Basis fur einen lmpfstoff gegen Anthrax, Angew. Chem., 2005, 6474-6476, 117.

White, John R. Jr. et al., Insulin analogues: New agents for improving glycemic control, Postgrad. Med., 1997, 58-70, 101.

Whittingham, Jean L. et al., Crystal Structure of a Prolonged-Acting Insulin with Albumin-Binding Properties, Biochemistry, 1997, 2826-2831, 36.

Wong, Chi-Huey, Protein Glycosylation: New Challenges and Opportunities, J. Org. Chem., 2005, 4219-4225, 70(11).

Woodward, R. B.et al., The Conservation of Orbital Symmetry, Angewandte Chemie International Edition, 1969, 781-853, 8(11).

Woodward, Von R. B. et al., Die Erhaltung der Orbitalsymmetrie, Angewandte Chemie, 1969, 797-869, 81(21).

Wu, Peng et al., Multivalent, bifunctional dendrimers prepared by click chemistry, Chem. Commun., 2005, 5775-5777, N/A.

Wu, Xiangyang et al., Synthesis of Glycoconjugate Vaccines for Candida albicans Using Novel Linker Methodology, J. Org. Chem., 2005, 7381-7388, 70.

Yali J. Tsai et al., Synthesis and Purification of NB1-Palmitoyl Insulin, Pharm. Sci., 1997, 1264-1268, vol. 86, No. 11.

Yip, Vivian L. Y. et al., Family 4 Glycosidases Carry Out Efficient Hydrolysis of Thioglycosides by an alpha,beta-Elimination Mechanism, Angew. Chem. Int. Ed., 2006, 6179-6182, 45.

Yip, Vivian L. Y. et al., Family 4 Glycosidases Carry Out Efficient Hydrolysis of Thioglycosides by an alpha,beta-Elimination Mechanism, Angew. Chem., 2006, 6325-6328, 118.

Yki-Jarvinen, H. et al., Less nocturnal hypoglycemia and better post-dinner glucose control with bedtime insulin glargine compared with bedtime NPH insulin during insulin combination therapy in type 2 diabetes, Diabetes Care, 2000, 1130-1136, 23.

Yuan, Xuejun et al., Recent Advances in the Synthesis of C-oligosaccharides, Curr Top Med Chem, 2005, 1393-1430, 5(14).

Zinman, Bernard et al., Insulin lispro in CSII: results of a double-blind crossover study, Diabetes, 1997, 440-443, 46.

\* cited by examiner

CONJUGATE BASED SYSTEMS FOR CONTROLLED INSULIN DELIVERY

CROSS-REFERENCE TO RELATED APPLICATIONS

This application is a National Stage application of International Patent Application No. PCT/US2018/065318, filed Dec. 13, 2018, which claims priority to U.S. Provisional Patent Application No. 62/625,476, filed Feb. 2, 2018, and to U.S. Provisional Patent Application No. 62/599,970, filed Dec. 18, 2017.

FIELD OF THE INVENTION

The present disclosure provides conjugates that comprise an insulin molecule conjugated via a conjugate framework to two or more separate ligands that each include a saccharide, wherein the framework, ligand, saccharide and insulin molecule optionally comprise a fatty chain (e.g., a C8-30 fatty chain), wherein when said insulin molecule is conjugated both to a C8-30 fatty chain and one or more separate ligands that each include a saccharide, said C8-30 fatty chain is linked to insulin molecule only, and wherein when the framework or ligand comprises a fatty chain the insulin molecule is conjugated to two or more separate ligands.

REFERENCE TO SEQUENCE LISTING SUBMITTED ELECTRONICALLY

The sequence listing of the present application is submitted electronically via EFS-Web as an ASCII formatted sequence listing with a file name "24558USPCT-SEQLIST-ST25.txt", creation date of Oct. 30, 2020, and a size of 6 KB. This sequence listing submitted via EFS-Web is part of the specification and is herein incorporated by reference in its entirety.

BACKGROUND OF THE INVENTION

The majority of "controlled-release" drug delivery systems known in the prior art (e.g., U.S. Pat. No. 4,145,410 which describes drug release from capsules which are enzymatically labile) are incapable of providing drugs to a patient at intervals and concentrations which are in direct proportion to the amount of a molecular indicator (e.g., a metabolite) present in the human body. The drugs in these prior art systems are thus not literally "controlled," but simply provided in a slow release format which is independent of external or internal factors.

The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

Each of these systems relies on the combination of a multivalent glucose binding molecule (e.g., the lectin Con A) and a sugar based component that is reversibly bound by the multivalent glucose binding molecule. Unfortunately, Con A and many of the other readily available lectins have the potential to stimulate lymphocyte proliferation. By binding to carbohydrate receptors on the surfaces of certain types of lymphocytes, these so-called "mitogenic" lectins can potentially induce the mitosis of lymphocytes and thereby cause them to proliferate. Most mitogenic lectins including Con A are selective T-cell mitogens. A few lectins are less selective and stimulate both T-cells and B-cells. Local or systemic in vivo exposure to mitogenic lectins can result in inflammation, cytotoxicity, macrophage digestion, and allergic reactions including anaphylaxis. In addition, plant lectins are known to be particularly immunogenic, giving rise to the production of high titers of anti-lectin specific antibodies. It will be appreciated that mitogenic lectins cannot therefore be used in their native form for in vivo methods and devices unless great care is taken to prevent their release. For example, in U.S. Pat. No. 5,830,506, Taylor highlights the toxic risks that are involved in using Con A and emphasizes the importance and difficulty of containing Con A within a drug delivery device that also requires glucose and insulin molecules to diffuse freely in and out of the device.

The risks and difficulties that are involved with these and other in vivo uses of lectins could be significantly diminished if an alternative controlled drug delivery system could be provided that did not require lectins.

SUMMARY OF THE INVENTION

The present disclosure provides conjugates that comprise an insulin molecule conjugated via a conjugate framework to one or more separate ligands that each include a saccharide, wherein the framework, ligand, or insulin molecule optionally comprise a fatty chain (e.g., a $C_{8-30}$ fatty chain). An aspect of this invention is realized when said insulin molecule is conjugated to a $C_{8-30}$ fatty chain and conjugated to one or more separate ligands that each include a saccharide. Another aspect of this invention is realized when the conjugate framework comprises an insulin molecule separately conjugated to two or more separate ligands and one of the ligand comprises a fatty chain that is not directly linked to the insulin molecule. An aspect of this invention is realized when the insulin molecule is conjugated to a $C_{8-30}$ fatty chain and a first ligand, which first ligand itself may comprise one or more additional ligands. Another aspect of this invention is realized when the insulin molecule is conjugated to a first and second ligand, each of which may comprise one or more additional ligands and a saccharide on one of the ligands has a $C_{8-30}$ fatty chain. Another aspect of this invention is realized when the insulin molecule is conjugated to a $C_{8-30}$ fatty chain, a first ligand and a second ligand, each of said ligands may comprise one or more additional ligands. Another aspect of this invention is realized when the insulin molecule is conjugated to a first and a second ligand, each of which may comprise one or more additional ligands and a $C_{8-30}$ fatty chain is linked to the framework of one of the ligands. In certain embodiments, a conjugate is characterized in that, when the conjugate is administered to a mammal, at least one pharmacokinetic (PK) and/or pharmacodynamic (PD) property of the conjugate is sensitive to serum concentration of a saccharide. In certain embodiments, a conjugate is also characterized by having a protracted PK profile. Exemplary conjugates and sustained release formulations are provided in addition to methods of use and preparation.

BRIEF DESCRIPTION OF THE DRAWINGS

FIG. 1. shows relative changes in plasma glucose in non-diabetic male Yucatan minipigs equipped with two Jugular vein vascular access ports (n=2-3 per study) following i.v. injection of conjugate IOC-5 at 0.69 nmol/kg under conditions of PBS infusion (●) or i.v. aMM infusion (□).

DETAILED DESCRIPTION OF THE INVENTION

Figure 1:
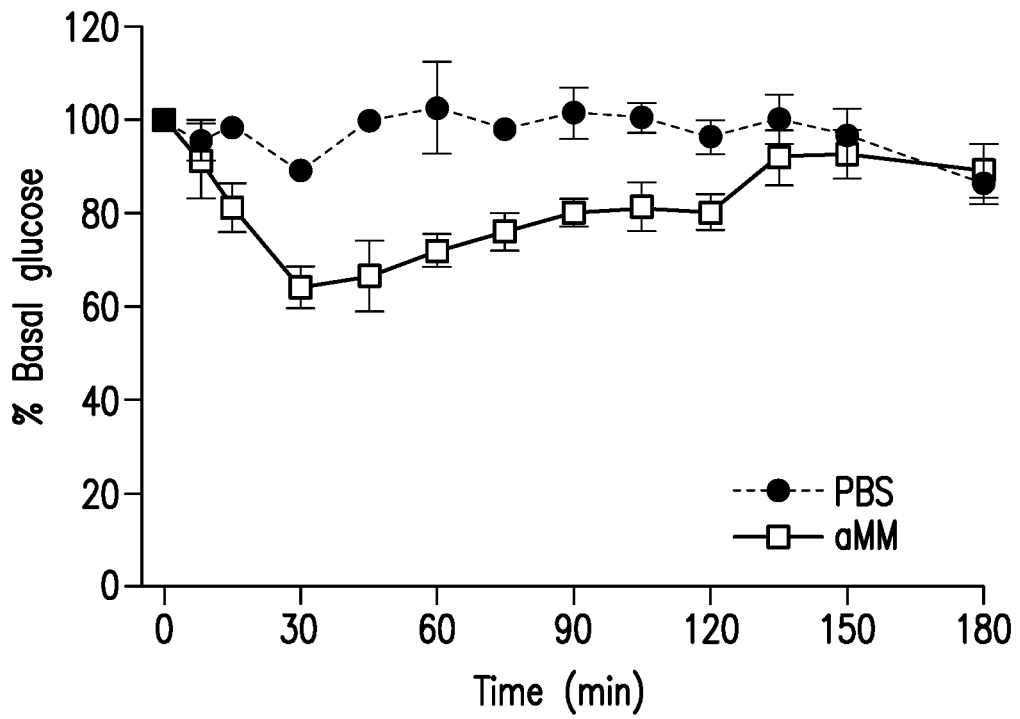
FIG. 1.
Figure 2:
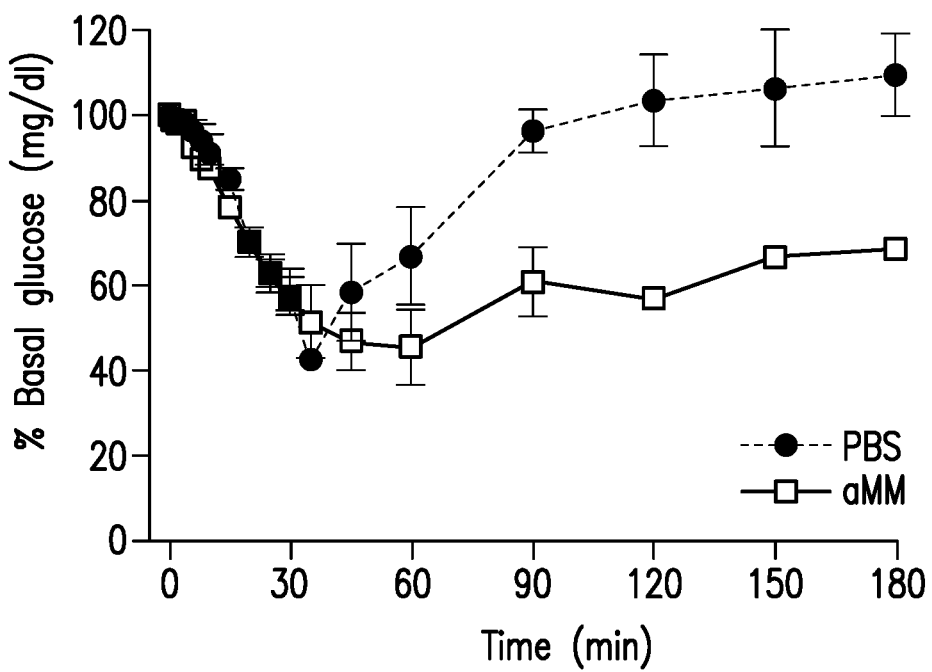
FIG. 2: shows relative changes in plasma glucose in non-diabetic male Yucatan minipigs equipped with two Jugular vein vascular access ports (n=3 per study) following i.v. injection of conjugate IOC-16 at 0.69 nmol/kg under conditions of PBS infusion (●) or i.v. aMM infusion (□).
Figure 3:
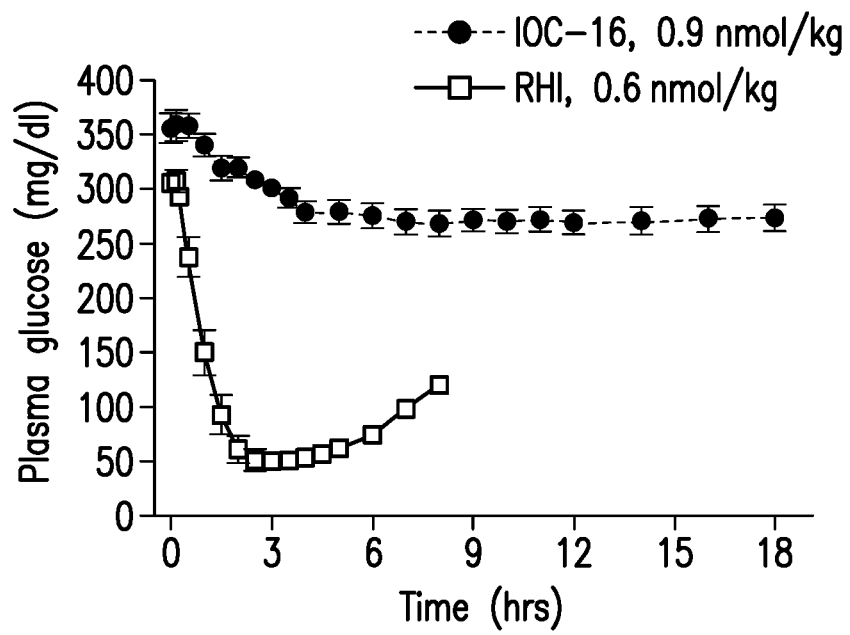
FIG. 3: shows plasma glucose depression curves in diabetic male Yucatan minipigs equipped with two Jugular vein vascular access ports (n=6-20 per study) following subcutaneous injection of conjugate IOC-16 at 0.9 nmol/kg (●) in comparison to subcutaneous injection of RHI at 0.6 nmol/kg (□).
Figure 4:
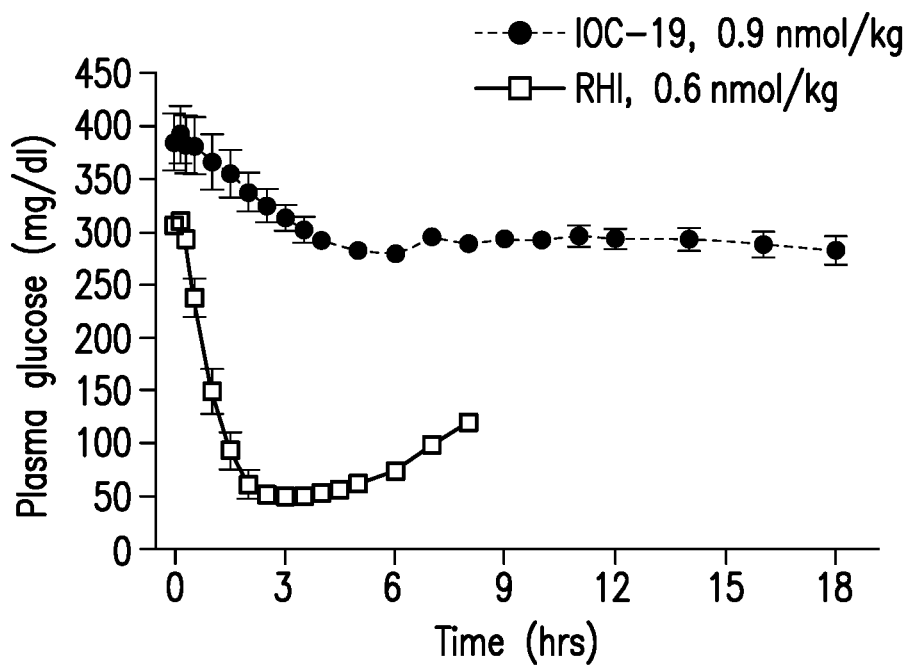
FIG. 4: shows plasma glucose depression curves in diabetic male Yucatan minipigs equipped with two Jugular vein vascular access ports (n=6-20 per study) following subcutaneous injection of conjugate IOC-19 at 0.9 nmol/kg (●) in comparison to subcutaneous injection of RHI at 0.6 nmol/kg (□).
Figure 5:
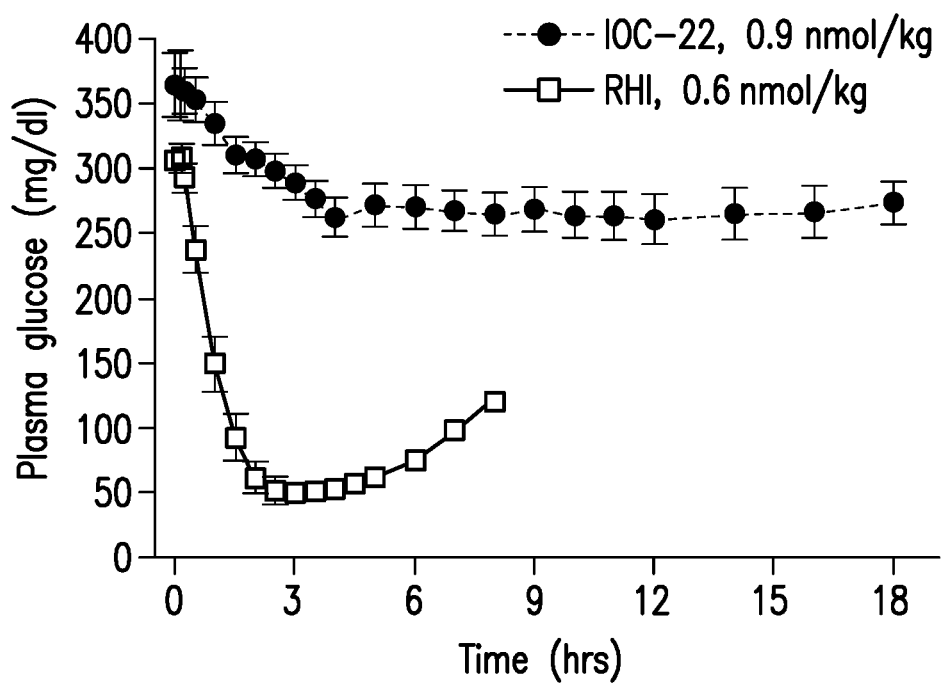
FIG. 5: shows plasma glucose depression curves in diabetic male Yucatan minipigs equipped with two Jugular vein vascular access ports (n=6-20 per study) following subcutaneous injection of conjugate IOC-22 at 0.9 nmol/kg (●) in comparison to subcutaneous injection of RHI at 0.6 nmol/kg (□).

This application refers to a number of documents including patent and non-patent documents. The entirety of each of these documents is incorporated herein by reference.

Conjugates

In one aspect, the disclosure provides conjugates that comprise an insulin molecule conjugated via a conjugate framework to two or more separate ligands that each include a saccharide, wherein the framework, ligand, and insulin molecule optionally comprise a fatty chain (e.g., a C8-30 fatty chain), wherein when said insulin molecule is conjugated both to a $C_{8-30}$ fatty chain and one or more separate ligands that each include a saccharide, said $C_{8-30}$ fatty chain is linked to insulin molecule only.

Conjugate Frameworks

This section describes some exemplary conjugate frameworks. In various embodiments, a conjugate or a pharmaceutically acceptable salt thereof of the present disclosure may be selected from the group consisting of general formulas (I), (II), (III), and (IVa):

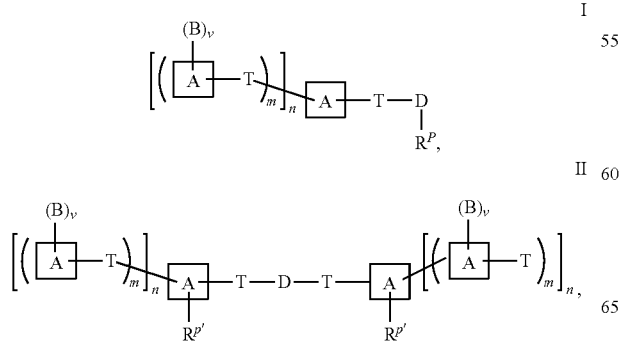

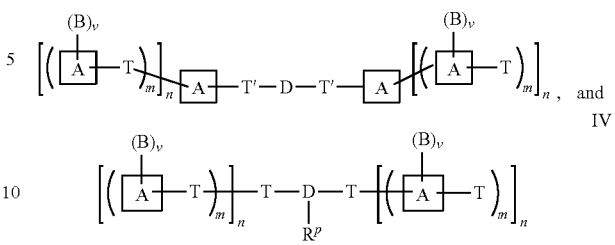

wherein
each occurrence of

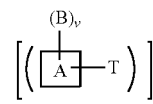

represents a potential branch within the conjugate;
each occurrence of

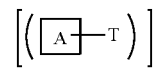

represents a potential repeat within a branch of the conjugate;

each occurrence of [A] is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of T' is independently selected from hydrogen, a bond, T, and $R^P$;

each occurrence of R is independently hydrogen, a suitable protecting group, or an acyl moiety, arylalkyl moiety, aliphatic moiety, aryl moiety, heteroaryl moiety, or heteroaliphatic moiety, said moieties, where possible, optionally substituted with 1 to 3 groups of OH or COOH or interrupted with a —CO— or —CONH— group;

$R^P$ is a straight or branched, saturated or unsaturated, optionally substituted $C_{10-40}$ hydrocarbon chain wherein one or more methylene units of $R^P$ are optionally and independently substituted or replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group, wherein the hydrocarbon chain comprises a $C_{8-30}$ fatty chain that is uninterrupted by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

R$^{P1}$ is independently selected from hydrogen and R$^P$;

—B is -T-L$^B$-X;

each occurrence of X is independently a ligand that includes a saccharide;

each occurrence of L$^B$ is independently a covalent bond or a group derived from the covalent conjugation of a T with an X;

-D is -T-L$^D$-W$^I$;

each occurrence of W$^I$ is independently an insulin molecule;

each occurrence of L$^D$ is independently a covalent bond or a group derived from the covalent conjugation of a T with a W$^I$;

n is an integer from 0 to 5, inclusive, as valency permits, wherein when n is 0 B is present and linked to T or D;

each occurrence of m is independently an integer from 1 to 5, inclusive; and each occurrence of v is independently an integer from 1 to 5, inclusive, as valency permits.

In various embodiments, a conjugate of the present disclosure may have the general formula (I):

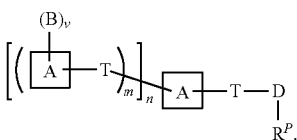

III

In various embodiments, a conjugate of the present disclosure may have the general formula (II):

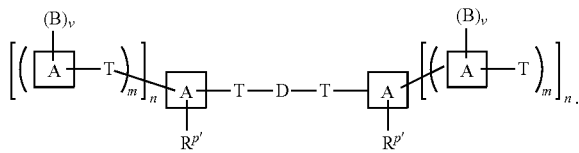

III

In various embodiments, a conjugate of the present disclosure may have the general formula (III):

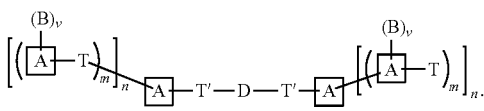

III

In various embodiments, a conjugate of the present disclosure may have the general formula (IV):

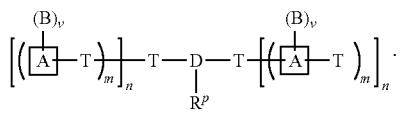

IV

A subembodiment of the invention of formula IV is realized and represented by structural formula IV-a:

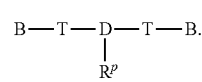

IV-a

It is to be understood that general formulae (I), (II), (III), (IV) and (IV-a) (and other formulae herein) do not expressly list every hydrogen. For example, if a central [A] is a C$_6$ aryl group and n+q≤6 it will be appreciated that the open position(s) on the C$_6$ aryl ring include a hydrogen.

In general, it will be appreciated that each occurrence of [A] represents a potential branching node and that the number of branches at each node are determined by the values of n for the central [A] and n for non-central occurrences of [A]. One of ordinary skill will appreciate that because each occurrence of n may be an integer from 0 to 5, the present disclosure contemplates linear, branched, and hyperbranched (e.g., dendrimer-like) embodiments of these conjugates.

Definitions

Definitions of specific functional groups, chemical terms, and general terms used throughout the specification are described in more detail below. Examples of conjugates of the invention can be found throughout the specification.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds and valency permits.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, and $^{36}$Cl, $^{123}$I and $^{125}$I. It will be appreciated that other isotopes may be incorporated by know means also.

Certain isotopically-labeled compounds of the invention (e.g., those labeled with $^3$H, $^{11}$C and $^{14}$C) are recognized as being particularly useful in compound and/or substrate tissue distribution assays using a variety of known techniques. Tritiated (i.e., $^3$H) and carbon-14 (i.e., $^{14}$C) isotopes are particularly preferred for their ease of preparation and detection. Further, substitution of a naturally abundant isotope with a heavier isotope, for example, substitution of protium with deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts".

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts".

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates), undecanoates, and the like.

Acyl—As used herein, the term "acyl," refers to $R^{X1}$—C(O)—, where $R^{X1}$ is hydrogen, or linear-, branched-, or cyclic-alkyl; linear-, branched-, or cyclic-alkenyl; or linear-, branched-, or cyclic-alkynyl moiety, wherein the acyl substituent is bonded through the carbonyl carbon to the substrate of which it is a substituent, or —NH—SO$_2$—$R^{X1}$, where —$R^{X1}$ is as previously defined; non-limiting examples of suitable acyl groups include formyl, acetyl, propanoyl, 2-methylpropanoyl, butanoyl and cyclohexanoyl. Exemplary acyl groups have the general formula —C(=O)$R^{X1}$, —C(=O)O$R^{X1}$, —C(=O)—O—C(=O) $R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$.

Aliphatic—As used herein, the term "aliphatic" or "aliphatic group" denotes a hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes a monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. Alkenyl groups include, for example, ethenyl, propenyl, butenyl, 1-methyl-2-buten-1-yl, and the like.

Alkyl—As used herein, the term "alkyl" refers to saturated, straight- or branched-chain hydrocarbon radicals derived from an aliphatic moiety containing between 1-6 carbon atoms by removal of a single hydrogen atom. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to a substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., —(CH$_2$)$_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below.

Fatty chain—As used herein, the term "fatty chain" refers to a $C_{8-30}$ aliphatic chain. A fatty chain may be completely saturated or may contain one or more units of unsaturation. A fatty chain may be substituted with functional groups such as, for example carboxlic acid.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. Suitable heteroaliphatic groups include, but are not limited to, linear or branched, heteroalkyl, heteroalkenyl, and heteroalkynyl groups.

Heteroaryl—As used herein, the term "heteroaryl" used alone or as part of a larger moiety, e.g., "heteroaralkyl", or "heteroaralkoxy", refers to a group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic".

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable 5- to 7-membered monocyclic or 7- to 11-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that from one to four, preferably from one to three, more preferably one or two, hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Suitable protecting group—As used herein, the term "suitable protecting group," refers to amino protecting groups or hydroxyl protecting groups depending on its location within the compound and includes, but not limited to, those described in detail in *Protecting Groups in Organic Synthesis*, T. W. Greene and P. G. M. Wuts, 3$^{rd}$ edition, John Wiley & Sons, 1999.

Exogenous—As used herein, an "exogenous" molecule is one which is not present at significant levels in a patient unless administered to the patient. In certain embodiments the patient is a mammal, e.g., a human, a dog, a cat, a rat, a minipig, etc. As used herein, a molecule is not present at significant levels in a patient if normal serum for that type of patient includes less than 0.1 mM of the molecule. In certain embodiments normal serum for the patient may include less than 0.08 mM, less than 0.06 mM, or less than 0.04 mM of the molecule.

Hyperbranched—As used herein, a "hyperbranched" structure is a covalent structure that includes at least one branched branch (e.g., a dendrimeric structure). A hyperbranched structure may include polymeric and/or non-polymeric substructures.

Normal serum—As used herein, "normal serum" is serum obtained by pooling approximately equal amounts of the liquid portion of coagulated whole blood from five or more non-diabetic patients. A non-diabetic human patient is a randomly selected 18-30 year old who presents with no diabetic symptoms at the time blood is drawn.

Polysaccharide—As used herein, a "polysaccharide" is a polymer of saccharides. The terms "polysaccharide", and "carbohydrate" may be used interchangeably. The polymer may include natural saccharides (e.g., arabinose, lyxose, ribose, xylose, ribulose, xylulose, allose, altrose, galactose, glucose, gulose, idose, mannose, talose, fructose, fucose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

The invention also encompasses pharmaceutical compositions containing a conjugates of formulas I through IV and methods for treating hyperglycemia using conjugates of formulas I through IV.

Description of Exemplary Groups
Ligand(s)

In general, the conjugates include at least one ligand. In certain embodiments, the conjugates include a single ligand. In certain embodiments, the conjugates include at least two separate ligands, e.g., 2, 3, 4, 5 or more ligands. When more than one ligand is present the ligands may have the same or different chemical structures. In certain embodiments, the conjugates include at least two separate ligands wherein the insulin molecule is conjugated to a first ligand, said first ligand optionally comprising one or more additional ligands.

In certain embodiments, the ligands are capable of competing with a saccharide (e.g., glucose or mannose) for binding to an endogenous saccharide-binding molecule (e.g., without limitation surfactant proteins A and D or members of the selectin family). In certain embodiments, the ligands are capable of competing with a saccharide (e.g., glucose or mannose) for binding to cell-surface sugar receptor (e.g., without limitation macrophage mannose receptor, glucose transporter ligands, endothelial cell sugar receptors, or hepatocyte sugar receptors). In certain embodiments, the ligands are capable of competing with glucose or mannose for binding to an endogenous glucose-binding molecule (e.g., without limitation surfactant proteins A and D or members of the selectin family). In certain embodiments, the ligands are capable of competing with a saccharide for binding to a non-human lectin (e.g., Con A). In certain embodiments, the ligands are capable of competing with glucose or mannose for binding to a non-human lectin (e.g., Con A). Exemplary glucose-binding lectins include calnexin, calreticulin, N-acetylglucosamine receptor, selectin, asialoglycoprotein receptor, collectin (mannose-binding lectin), mannose receptor, aggrecan, versican, *Pisum sativum* agglutinin (PSA), *Vicia faba* lectin, *Lens culinaris* lectin, soybean lectin, peanut lectin, *Lathyrus ochrus* lectin, sainfoin lectin, *Sophora japonica* lectin, *Bowringia milbraedii* lectin, concanavalin A (Con A), and pokeweed mitogen.

In certain embodiments, the ligand is of formula (IIIa) or (IIIb):

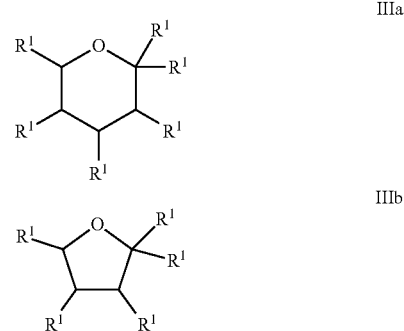

wherein:
each $R^1$ is independently hydrogen, $-OR^y$, $-N(R^y)_2$, $-SR^y$, $-O-Y$, -G-Z, or $-CH_2R$;
each $R^x$ is independently hydrogen, $-OR^y$, $-N(R^y)_2$, $-SR^y$, or $-O-Y$;
each $R^y$ is independently $-R^2$, $-SO_2R^2$, $-S(O)R^2$, $-P(O)(OR^2)_2$, $-C(O)R^2$, $-CO_2R^2$, or $-C(O)N(R^2)_2$;
each Y is independently a monosaccharide, disaccharide, or trisaccharide;
each G is independently a covalent bond or an optionally substituted $C_{1-9}$ alkylene, wherein one or more methylene units of G is optionally replaced by $-O-$, $-S-$, $-N(R^2)-$, $-C(O)-$, $-OC(O)-$, $-C(O)O-$, $-C(O)N(R^2)-$, $-N(R^2)C(O)-$, $-N(R^2)C(O)N(R^2)-$, $-SO_2-$, $-SO_2N(R^2)-$, $-N(R^2)SO_2-$, or $-N(R^2)SO_2N(R^2)-$;
each Z is independently halogen, $-N(R^2)_2$, $-OR^2$, $-SR^2$, $-N_3$, $-C\equiv CR^2$, $-CO_2R^2$, $-C(O)R^2$, or $-OSO_2R^2$; and
each $R^2$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the ligand of formula (IIIa) or (IIIb) is a monosaccharide. In certain embodiments, the ligand is a disaccharide. In certain embodiments, the ligand is a trisaccharide. In certain embodiments, the ligand is a tetrasaccharide. In certain embodiments, the ligand comprises no more than a total of four monosaccharide moieties.

As defined generally above, each $R^1$ is independently hydrogen, $-OR^y$, $-N(R^y)_2$, $-SR^y$, $-O-Y$, -G-Z, or $-CH_2R^x$. In certain embodiments, $R^1$ is hydrogen. In certain embodiments, $R^1$ is $-OH$. In other embodiments, $R^1$ is $-NHC(O)CH_3$. In certain embodiments, $R^1$ is $-O-Y$. In certain other embodiments, $R^1$ is -G-Z. In some embodiments, $R^1$ is $-CH_2OH$. In other embodiments, $R^1$ is $-CH_2-Y$. In yet other embodiments, $R^1$ is $-NH_2$. One of ordinary skill in the art will appreciate that each $R^1$ substituent in formula (IIIa) or (IIIb) may be of (R) or (S) stereochemistry.

As defined generally above, each $R^x$ is independently hydrogen, $-OR^y$, $-N(R^y)_2$, $-SR^y$, or $-O-Y$. In some embodiments, $R^x$ is hydrogen. In certain embodiments, $R^x$ is $-OH$. In other embodiments, $R^x$ is $-O-Y$.

As defined generally above, each $R^y$ is independently $-R^2$, $-SO_2R^2$, $-S(O)R^2$, $-P(O)(OR^2)_2$, $-C(O)R^2$, $-CO_2R^2$, or $-C(O)N(R^2)_2$. In some embodiments, $R^y$ is hydrogen. In other embodiments, $R^y$ is $-R^2$. In some embodiments, $R^y$ is $-C(O)R^2$. In certain embodiments, $R^y$ is acetyl. In other embodiments, $R^y$ is $-SO_2R^2$, $-S(O)R^2$, $-P(O)(OR^2)_2$, $-CO_2R^2$, or $-C(O)N(R^2)_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of $-O-Y$ through anomeric carbon to form a glycosidic bond. The glycosidic bond may be of an alpha or beta configuration.

As defined generally above, each G is independently a covalent bond or an optionally substituted $C_{1-9}$ alkylene, wherein one or more methylene units of G is optionally replaced by $-O-$, $-S-$, $-N(R^2)-$, $-C(O)-$, $-OC(O)-$, $-C(O)O-$, $-C(O)N(R^2)-$, $-N(R^2)C(O)-$, $-N(R^2)C(O)N(R^2)-$, $-SO_2-$, $-SO_2N(R^2)-$, $-N(R^2)SO_2-$, or $-N(R^2)SO_2N(R^2)-$. In some embodiments, G is a covalent bond. In certain embodiments, G is $-O-C_{1-8}$ alkylene. In certain embodiments, G is $-OCH_2CH_2-$.

As defined generally above, each Z is independently halogen, $-N(R^2)_2$, $-OR^2$, $-SR^2$, $-N_3$, $-C{\equiv}CR^2$, $-CO_2R^2$, $-C(O)R^2$, or $-OSO_2R^2$. In some embodiments, Z is a halogen or $-OSO_2R^2$. In other embodiments, Z is $-N_3$ or $-C{\equiv}CR^2$. In certain embodiments, Z is $-N(R^2)_2$, $-OR^2$, or $-SR^2$. In certain embodiments, Z is $-SH$. In certain embodiments, Z is $-NH_2$. In certain embodiments, -G-Z is $-OCH_2CH_2NH_2$.

In some embodiments, the $R^1$ substituent on the C1 carbon of formula (IIIa) is -G-Z to give a compound of formula (IIIa-i):

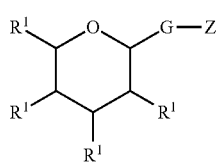

IIIa-i wherein $R^1$, G, and Z are as defined and described herein.

In some embodiments, the ligand is of formula (IIIa-ii):

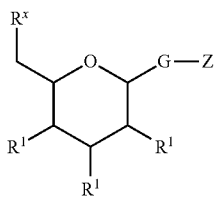

IIIa-ii wherein $R^1$, $R^x$, G, and Z are as defined and described herein.

In certain embodiments, the ligand(s) may have the same chemical structure as glucose or may be a chemically related species of glucose. In various embodiments it may be advantageous for the ligand(s) to have a different chemical structure from glucose, e.g., in order to fine tune the glucose response of the conjugate. For example, in certain embodiments, one might use a ligand that includes mannose, L-fucose, maltose, cellobiose, galactose, lactose or derivatives of these (e.g., alpha-L-fucopyranoside, mannosamine, beta-linked N-acetyl mannosamine, methylglucose, methylmannose, ethylglucose, ethylmannose, propylglucose, propylmannose, etc.) and/or higher order combinations of these (e.g., a bimannose, linear and/or branched trimannose, etc.).

In certain embodiments, the ligand includes a monosaccharide. In certain embodiments, the ligand includes a disaccharide. In certain embodiments, the ligand is includes a trisaccharide. In some embodiments, the ligand comprises a saccharide and one or more amine groups. In certain embodiments the saccharide and amine group are separated by a $C_1$-$C_6$ alkyl group, e.g., a $C_1$-$C_3$ alkyl group.

In some embodiments, the ligand is 2-aminoethyl α-D-glucopyranoside (AEG). In some embodiments, the ligand is 2-aminoethyl α-D-mannopyranoside (AEM). In some embodiments, the ligand is 2-aminoethyl α-D-mannopyranosyl-(1→2)-α-D-mannopyranoside (AEBM). In some embodiments, the ligand is 2-aminoethyl α-D-mannopyranosyl-(1→3)-[α-D-mannopyranosyl-(1→6)]-α-D-mannopyranoside (AETM). In certain embodiments, the ligand is 2-aminoethyl 2-acetamido-2-deoxy-β-D-glucopyranoside (AEGA).

In certain embodiments, a saccharide ligand is of the "D" configuration. In other embodiments, a saccharide ligand is of the "L" configuration.

Below we show the structures of these exemplary ligands. Other exemplary ligands will be recognized by those skilled in the art.

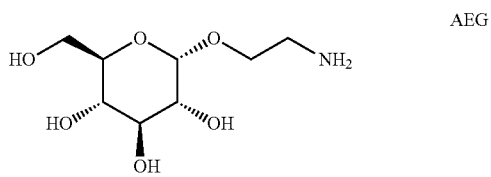

AEG

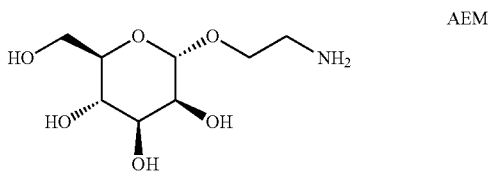

AEM

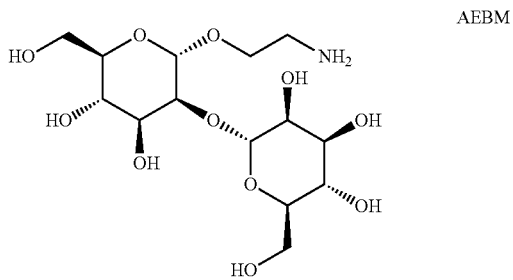

AEBM

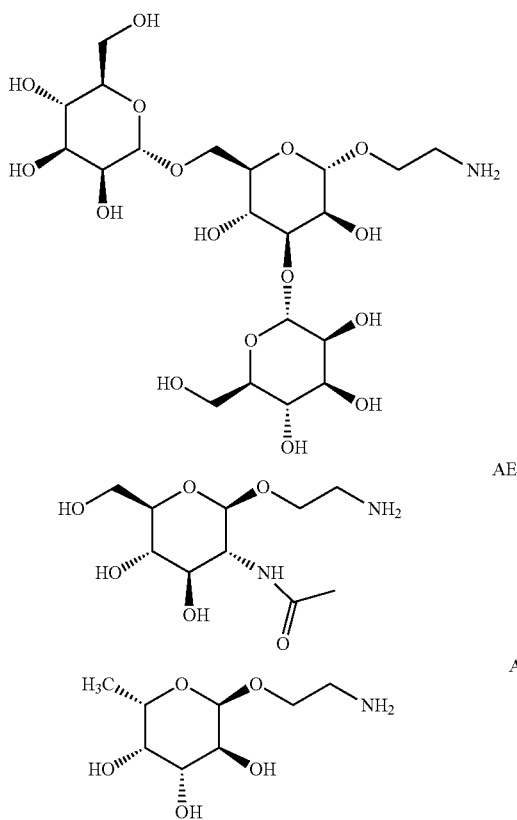

AETM

AEGA

AEF

As discussed in more detail below, in certain embodiments, the amine group on these exemplary ligands may react to form an amide bond when conjugated to a framework. Certain conjugate formulae that are used herein denote the junction between a ligand and framework as: X—NHJ-. It is to be understood that in these situations, the ligand (X) portions of the compounds shown above would lack the terminal amine group (since the amide bond is shown explicitly in the formulae). For example if AEM were to form an amide bond with a framework and X-NJ- were used to denote the junction between a ligand and framework then X in this formula would have structure below:

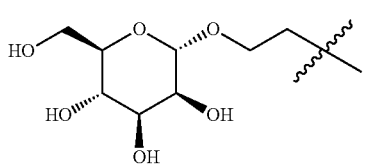

EM

In general, ligands may be directly or indirectly conjugated (i.e., via a linker or framework) to the insulin molecule. As discussed in more detail below, the ligands may be naturally present within a conjugate framework (e.g., as part of a polymer backbone or as a side group of a monomer). Alternatively (or additionally) ligands may be artificially incorporated into a conjugate framework (e.g., in the form of a chemical group that is synthetically added to a conjugate framework). In certain embodiments, a conjugate may include a framework which comprises 5 or more, 10 or more, or 20 or more ligands. In certain embodiments, a conjugate may comprise as few as 1, 2, 3, 4 or 5 separate ligands.

In certain embodiments, at least two separate ligands are conjugated to a single conjugate framework that is also conjugated to the insulin molecule. In some embodiments, at least one ligand, selected from the group consisting of AETM, AEG, AEM, AEBM, AEGA, and AEF is conjugated to one insulin molecule. In certain embodiments, at least one AETM ligand is conjugated to one insulin molecule. In certain embodiments, at least one AEG ligand is conjugated to one insulin molecule. In certain embodiments, at least one AEM ligand is conjugated to one insulin molecule. In certain embodiments, at least one AEBM ligand is conjugated to one insulin molecule. In certain embodiments, at least one AEF ligand is conjugated to one insulin molecule. In certain embodiments, at least one AEGA ligand is conjugated to one insulin molecule. In some embodiments, at least two ligands, such as AETM, AEG, AEM, AEBM, AEGA, or AEF are conjugated to one insulin molecule through a single conjugate framework. In certain embodiments, the at least two ligands are not the same ligand. In certain embodiments, the at least two ligands are the same ligand. In certain embodiments, at least two AETM ligands are conjugated to one insulin molecule. In certain embodiments, at least two AEG ligands are conjugated to one insulin molecule. In certain embodiments, at least two AEM ligands are conjugated to one insulin molecule. In certain embodiments, at least two AEBM ligands are conjugated to one insulin molecule.

As discussed in more detail below in the context of certain exemplary conjugate frameworks, in certain embodiments the separate ligands and insulin molecule may each be located on a separate branch of a branched conjugate framework. For example, the ligands and insulin molecule may be located on termini of these branches. In certain embodiments a hyperbranched conjugate framework may be used. Both polymeric and non-polymeric conjugate frameworks are encompassed.

Methods for conjugating ligands to a conjugate framework are discussed in more detail below. In certain embodiments, the saccharide within the one or more ligands is conjugated (directly or indirectly by way of a linker) via the C1, C2, C4 or C6 position. In certain embodiments, the conjugation involves the C1 position. The C1 position of a saccharide is also referred to as the anomeric carbon and may be connected to the insulin molecule or conjugate framework in the alpha or beta configuration. In certain embodiments, the C1 position is configured as the alpha anomer. In other embodiments, the C1 position is configured as the beta anomer.

Insulin Molecule

The conjugate of the invention herein includes an insulin molecule. As used herein, the term "insulin" or "insulin molecule" encompasses all salt and non-salt forms of the insulin molecule. It will be appreciated that the salt form may be anionic or cationic depending on the insulin molecule. By "insulin" or "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.).

The wild-type sequence of human insulin comprises an amino acid sequence of NO:1 (A-peptide) and an amino acid sequence of SEQ ID NO:2 (B-peptide) and three disulfide bridges as shown below:

A-Peptide (SEQ ID NO:1)

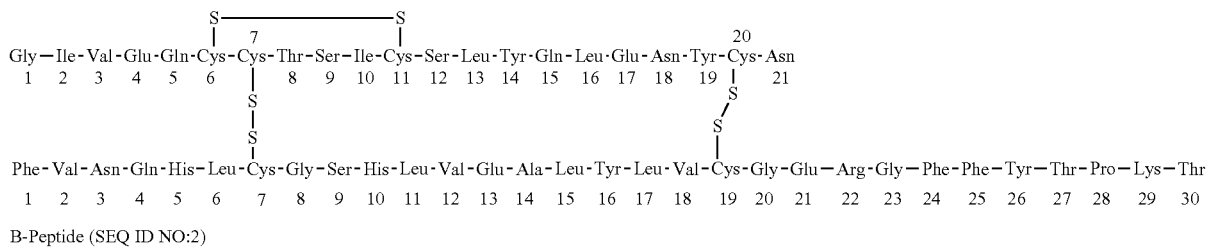

B-Peptide (SEQ ID NO:2)

The present disclosure is not limited to human insulin molecules (i.e., human proinsulin or bioactive human insulin molecules). In general, the present disclosure encompasses any human or non-human insulin that retains insulin-like bioactivity (i.e., is capable of causing a detectable reduction in glucose when administered to a suitable species at an appropriate dose in vivo). For example, as discussed below, the present disclosure also encompasses modified porcine insulin, bovine insulin, rabbit insulin, sheep insulin, etc.

It is to be understood that an insulin molecule of the present disclosure may include chemical modifications and/or mutations that are not present in a wild-type insulin. A variety of modified insulins are known in the art (e.g., see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of amino acids).

In certain embodiments, an insulin molecule of the present disclosure will differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1) amino acid substitutions, additions and/or deletions. In certain embodiments, an insulin molecule of the present disclosure will differ from a wild-type insulin by amino acid substitutions only. In certain embodiments, an insulin molecule of the present disclosure will differ from a wild-type insulin by amino acid additions only. In certain embodiments, an insulin molecule of the present disclosure will differ from a wild-type insulin by both amino acid substitutions and additions. In certain embodiments, an insulin molecule of the present disclosure will differ from a wild-type insulin by both amino acid substitutions and deletions.

In certain embodiments, amino acid substitutions may be made on the basis of similarity in polarity, charge, solubility, hydrophobicity, hydrophilicity, and/or the amphipathic nature of the residues involved. In certain embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In certain embodiments, the hydrophobic index of amino acids may be considered in choosing suitable mutations. The importance of the hydrophobic amino acid index in conferring interactive biological function on a polypeptide is generally understood in the art. Alternatively, the substitution of like amino acids can be made effectively on the basis of hydrophilicity. The importance of hydrophilicity in conferring interactive biological function of a polypeptide is generally understood in the art. The use of the hydrophobic index or hydrophilicity in designing polypeptides is further discussed in U.S. Pat. No. 5,691,198.

In certain embodiments, an insulin molecule of the present disclosure comprises an amino acid sequence of SEQ ID NO:3 (A-peptide) and an amino acid sequence of SEQ ID NO:4 (B-peptide) and three disulfide bridges as shown in formula $X^I$:

$$(X^I)$$

A-Peptide (SEQ ID NO:3)

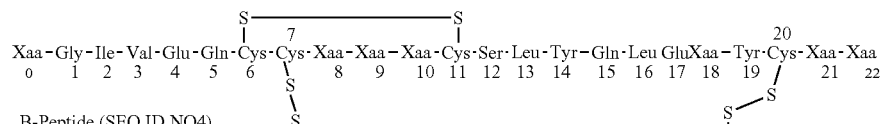

B-Peptide (SEQ ID NO4)

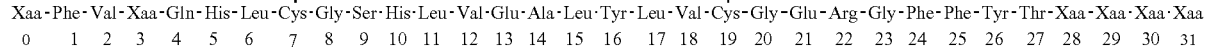

where Xaa at each of positions A0, A22, B0 and B31 is independently a codable amino acid, a sequence of codable amino acids, or missing; Xaa at each of positions A8, A9, A10, A18, and A21 is independently a codable amino acid; and Xaa at each of positions B3, B28, B29, and B30 is independently a codable amino acid or missing.

As used herein, a "codable amino acid" is any one of the 20 amino acids that are directly encoded for polypeptide synthesis by the standard genetic code.

In some embodiments, Xaa at each of positions A0, A22, B0 and B31 is independently a codable amino acid, a sequence of 2-50, 2-25, 2-10, 2-9, 2-8, 2-7, 2-6, 2-5, 2-4, 2-3, or 2 codable amino acids, or missing.

In some embodiments, Xaa at each of positions A0, A22, B0 and B31 is missing.

In some embodiments, Xaa at each of positions A0, A22 and B31 is missing.

In some embodiments, Xaa at each of positions A22, B0 and B31 is missing.

In some embodiments, Xaa at each of positions A22 and B31 is missing.

In certain embodiments, Xaa at one or more of the positions of the A- and B-peptides in formula $X^I$ is selected from the choices that are set forth in Table 1 and 2 below.

TABLE 1

A-peptide

| Position | Amino Acid Identity |
| --- | --- |
| A0 | Any codable amino acid, sequence of codable amino acids, or missing |
| A8 | Thr or Ala |
| A9 | Ser or Gly |
| A10 | Ile or Val |
| A18 | Asn, Asp or Glu |
| A21 | Asn, Asp, Glu, Gly or Ala |
| A22 | Any codable amino acid, sequence of codable amino acids, or missing |

TABLE 2

B-peptide

| Position | Amino Acid Identity |
| --- | --- |
| B0 | Any codable amino acid, sequence of codable amino acids, or missing |
| B3 | Asn, Lys, Asp or Glu, or missing |
| B28 | Pro, Ala, Lys, Leu, Val, or Asp, or missing |
| B29 | Lys, Pro, or Glu, or missing |
| B30 | Thr, Ala, Lys, Glu, Ser or Arg, or missing |
| B31 | Any codable amino acid, sequence of codable amino acids, Arg-Arg, or missing |

In some embodiments, an insulin molecule of formula $X^I$ comprises amino acids at positions A8, A9, A10, and B30 selected from those shown in Table 3 below. In some embodiments, an insulin molecule of formula $X^I$ comprises amino acids at positions A8, A9, A10, and B30 selected from those shown in Table 3 below for a single species (e.g., from the human sequence or Thr at A8, Ser at A9, Ile at A10 and Thr at B30).

TABLE 3

| | Amino Acid Position | | | |
| --- | --- | --- | --- | --- |
| Species | A8 | A9 | A10 | B30 |
| Human | Thr | Ser | Ile | Thr |
| Rabbit | Thr | Ser | Ile | Ser |
| Porcine | Thr | Ser | Ile | Ala |
| Bovine | Ala | Ser | Val | Ala |
| Sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B2}$-human insulin). This mutant also prevents the formation of multimers. In some embodiments, mutation at positions B28 and/or B29 is accompanied by one or more mutations elsewhere in the insulin molecule. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin molecules include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, an insulin molecule of the present disclosure may include one or more deletions. For example, in certain embodiments, a B-peptide sequence of an insulin molecule of the present disclosure is missing B1, B2, B3, B26, B27, B28 and/or B29.

In various embodiments, an insulin molecule of the present disclosure may be truncated. For example, the B-peptide sequence may be missing residues B(1-2), B(1→3), B30, B(29-30) or B(28-30). In some embodiments, these deletions and/or truncations apply to any of the aforementioned insulin molecules (e.g., without limitation to produce des(B30) insulin lispro, des(B30) insulin aspart, des(B30) insulin glulisine, des(B30) insulin glargine, etc.).

In some embodiments, an insulin molecule contains additional amino acid residues on the N- or C-terminus of the A or B-peptide sequences. In some embodiments, one or more amino acid residues are located at positions A0, A22, n0, and/or B31. In some embodiments, one or more amino acid residues are located at position A0. In some embodiments, one or more amino acid residues are located at position A22. In some embodiments, one or more amino acid residues are located at position B0. In some embodiments, one or more amino acid residues are located at position B31. In certain embodiments, an insulin molecule does not include any additional amino acid residues at positions A0, A22, B0, or B31.

In certain embodiments, an insulin molecule of the present disclosure may have mutations wherein one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$, or $Asn^{B3}$, or any combination of those residues, may be replaced by aspartic acid or glutamic acid. $Gln^{A15}$ or $Gln^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid ($His^{B10} \rightarrow Asp^{B10}$); replacement of the phenylalanine residue at position B1 with aspartic acid ($Phe^{B1} \rightarrow Asp^{B1}$); replacement of the threonine residue at position B30 with alanine ($Thr^{B30} \rightarrow AlaB^{30}$); replacement of the tyrosine residue at position B26 with alanine ($Tyr^{B26} \rightarrow Ala^{B26}$); and replacement of the serine residue at position B9 with aspartic acid ($Ser^{B9} \rightarrow Asp^{B9}$).

In certain embodiments, an insulin molecule of the present disclosure comprises the mutations of one of the following insulin molecules: $Lys^{B28}Pro^{B29}$-human insulin (insulin lispro), $Asp^{B28}$-human insulin (insulin aspart), $Lys^{B3}Glu^{B29}$-human insulin (insulin glulisine), $Arg^{B31}Arg^{B32}$-human insulin (insulin glargine), $Ala^{B26}$-human insulin, $Asp^{B1}$-human insulin, $Arg^{A0}$-human insulin, $Asp^{B1}Glu^{B13}$-human insulin, $Gly^{A21}$-human insulin, $Gly^{A21}Arg^{B31}Arg^{B32}$-human insulin, $Arg^{A0}Arg^{B31}Arg^{B32}$-human insulin, $Arg^{A0}Gly^{A21}Arg^{B31}Arg^{B32}$-human insulin, des(B30)-human insulin, des(B27)-human insulin, des(B28-B30)-human insulin, des(B1)-human insulin, des(B1-B3)-human insulin.

The present disclosure also encompasses modified forms of non-human insulins (e.g., porcine insulin, bovine insulin, rabbit insulin, sheep insulin, etc.) that comprise any one of the aforementioned mutations modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497.

In some embodiments, an insulin molecule is modified and/or mutated to reduce its affinity for the insulin receptor (e.g., human insulin receptor). Without wishing to be bound to a particular theory, it is believed that attenuating the receptor affinity of an insulin molecule through modification (e.g., acylation) or mutation may decrease the rate at which the insulin molecule is eliminated from serum. In some embodiments, a decreased insulin receptor affinity in vitro translates into a superior in vivo activity for an insulin conjugate. In certain embodiments, an insulin molecule is mutated such that the site of mutation is used as a conjugation point, and conjugation at the mutated site reduces binding to the insulin receptor (e.g., $Lys^{A3}$). In certain other embodiments, conjugation at an existing wild-type amino acid or terminus reduces binding to the insulin receptor (e.g., $Gly^{A1}$). In some embodiments, an insulin molecule is conjugated at position A4, A5, A8, A9, or B30. In certain embodiments, the conjugation at position A4, A5, A8, A9, or B30 takes place via a wild-type amino acid side chain (e.g., $Glu^{A4}$). In certain other embodiments, an insulin molecule is mutated at position A4, A5, A8, A9, or B30 to provide a site for conjugation (e.g., $Lys^{A4}$, $Lys^{A5}$, $Lys^{A8}$, $Lys^{A9}$, or $Lys^{B30}$).

Methods for conjugating insulin molecules are described herein. In certain embodiments, an insulin molecule is conjugated via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In certain embodiments, an insulin molecule is conjugated via the B1 amino acid residue. In certain embodiments the B1 amino acid residue is phenylalanine. It is to be understood however, that the present disclosure is not limited to N-terminal conjugation and that in certain embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue. In the case of insulin glulisine, conjugation to the at least one ligand via the B3 lysine residue may be employed. It will be appreciated that different conjugation positions on the B-chain may lead to different reductions in insulin activity.

Exemplary Insulin Conjugates

The conjugates of the present invention comprise an insulin molecule conjugated via a conjugate framework to a first ligand, wherein said first ligand optionally comprises one or more additional separate ligands, and wherein the conjugate framework comprises a $C_{8-30}$ fatty chain. In certain embodiments, the one or more separate ligands of such conjugate is selected from one or more ligands that are independently selected from the group consisting of aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF). In certain embodiments, the one or more separate ligands of such a conjugate are aminoethylglucose (AEG). In certain embodiments, the one or more separate ligands of such a conjugate are aminoethylmannose (AEM). In certain embodiments, the one or more separate ligands of such a conjugate are aminoethylbimannose (AEBM). In certain embodiments, the one or more separate ligands of such a conjugate are aminoethyltrimannose (AETM). In certain embodiments, the one or more separate ligands of such a conjugate are O-aminoethyl-N-acetylglucosamine (AEGA). In certain embodiments, the one or more separate ligands of such a conjugate are aminoethylfucose (AEF).

In certain embodiments, the insulin molecule is conjugated via the A1 amino acid residue. In certain embodiments, the insulin molecule is conjugated via the B1 amino acid residue. In certain embodiments, the insulin molecule is conjugated via the epsilon-amino group of Lys$^{B29}$. In certain embodiments, the insulin molecule is insulin glulisine conjugated via the epsilon-amino group of Lys.

A (Node)

In certain embodiments, each occurrence of A is independently an optionally substituted group selected from the group consisting of acyl, aliphatic, heteroaliphatic, aryl, heteroaryl, and heterocyclic. In some embodiments, each occurrence of A is the same. In some embodiments, the central A is different from all other occurrences of A. In certain embodiments, all occurrences of A are the same except for the central A.

In some embodiments, A is an optionally substituted aryl or heteroaryl group. In some embodiments, A is 6-membered aryl. In certain embodiments, A is phenyl.

In certain embodiments, A is a heteroatom selected from N, O, or S. In some embodiments, A is nitrogen atom. In some embodiments, A is an oxygen atom. In some embodiments, A is sulfur atom. In some embodiments, A is a carbon atom.

In certain embodiments, A is an aliphatic or heteroaliphatic group. In certain embodiments, A is aminomethylene.

T (Spacer)

In certain embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In certain embodiments, one, two, three, four, or five methylene units of T are optionally and independently replaced. In certain embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In certain embodiments, one or more methylene units of T is replaced by —C(O)—. In certain embodiments, one or more methylene units of T is replaced by —C(O)N(R)—. In certain embodiments, one or more methylene units of T is replaced by —O—.

In some embodiments, T is —C(O)(CH$_2$)$_n$—

In some embodiments, T is

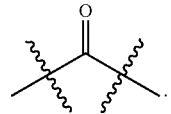 [SMILES: *C(*)=O]

In some embodiments, T is

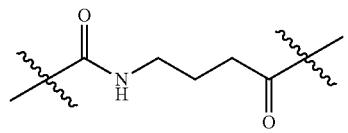

In some embodiments, T is

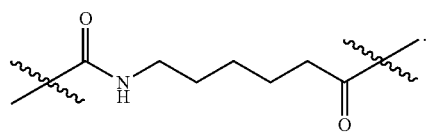 [SMILES: *C(=O)CCCCCNC(*)=O]

In some embodiments, T is

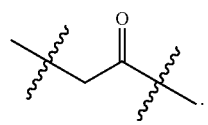 [SMILES: *CC(*)=O]

In some embodiments, T is

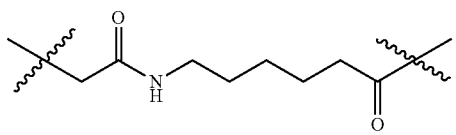

In some embodiments, T is

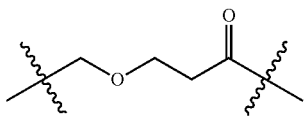

In some embodiments, T is

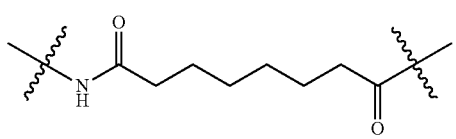

In some embodiments, T is

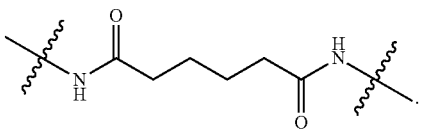 [SMILES: *NC(=O)CCCCC(=O)N*]

In certain embodiments, each occurrence of T is the same.
In certain embodiments, each occurrence of T is not the same.

$R^P$ (Fatty Spacer or Substituent)

In certain embodiments, $R^P$ is a bivalent, straight or branched, saturated or unsaturated, optionally substituted $C_{10-40}$ hydrocarbon chain wherein one or more methylene units of $R^P$ are optionally and independently replaced by one or more —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group, wherein the hydrocarbon chain comprises a $C_{8-30}$ fatty chain that is uninterrupted by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In certain embodiments, one or more methylene units of $R^P$ is replaced by —C(O)—. In certain embodiments, one or more methylene units of $R^P$ is replaced by —C(O)N(R)—. In certain embodiments, one or more methylene units of $R^P$ is replaced by —O—.

In certain embodiments, $R^P$ is

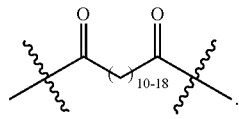

In some embodiments, $R^P$ is

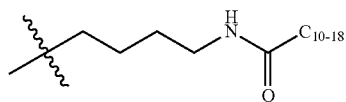

optionally and independently replaced by one or more —O—, —S—, —N(R)—, —C(O)—, —C(O)O—, —OC(O)—, —C(O)NHCH(CO$_2$H)(CH$_2$)$_n$C(O)—, —N(R)C(O)—, —C(O)N(R)—, —S(O)—, —S(O)$_2$—, —N(R)SO$_2$—, or —SO$_2$N(R)—. In some embodiments replacement is by one or more —C(O)—, —C(O)NHCH(CO$_2$H)(CH$_2$)$_n$C(O)—, —N(R)C(O)—, or —C(O)N(R)—.

In some embodiments, $R^P$ is

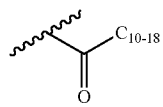

optionally and independently replaced by one or more —O—, —S—, —N(R)—, —C(O)—, —C(O)O—, —OC(O)—, —C(O)NHCH(CO$_2$H)(CH$_2$)$_n$C(O)—, —N(R)C(O)—, —C(O)N(R)—, —S(O)—, —S(O)$_2$—, —N(R)SO$_2$—, or —SO$_2$N(R)—. In some embodiments replacement is by one or more —C(O)—, —C(O)NHCH(CO$_2$H)(CH$_2$)$_n$C(O)—, —N(R)C(O)—, or —C(O)N(R)—.

In some embodiments, $R^P$ is

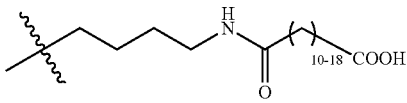

optionally and independently replaced by one or more —O—, —S—, —N(R)—, —C(O)—, —C(O)O—, —OC(O)—, —C(O)NHCH(CO$_2$H)(CH$_2$)$_n$C(O)—, —N(R)C(O)—, —C(O)N(R)—, —S(O)—, —S(O)$_2$—, —N(R)SO$_2$—, or —SO$_2$N(R)—. In some embodiments replacement is by one or more —C(O)—, —C(O)NHCH(CO$_2$H)(CH$_2$)$_n$C(O)—, —N(R)C(O)—, or —C(O)N(R)—.

In some embodiments, $R^P$ is

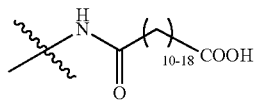

optionally and independently replaced by one or more —O—, —S—, —N(R)—, —C(O)—, —C(O)O—, —OC(O)—, —C(O)NHCH(CO$_2$H)(CH$_2$)$_n$C(O)—, —N(R)C(O)—, —C(O)N(R)—, —S(O)—, —S(O)$_2$—, —N(R)SO$_2$—, or —SO$_2$N(R)—. In some embodiments replacement is by one or more —C(O)—, —C(O)NHCH(CO$_2$H)(CH$_2$)$_n$C(O)—, —N(R)C(O)—, or —C(O)N(R)—.

B (Ligand)

In certain embodiments, —B is -T-$L^B$-X where X is a ligand and $L^B$ is a covalent bond or a group derived from the covalent conjugation of an X with a T. Exemplary ligands and their saccharide components are described above.

D (Insulin Molecule)

In certain embodiments, -D is -T-$L^D$-$W^I$ where $W^I$ is an insulin molecule and $L^D$ is a covalent bond or a group derived from the covalent conjugation of a $W^I$ with a T. Exemplary insulin molecules are described above.

$L^B$ and $L^D$ (Covalent Conjugation)

One of ordinary skill will appreciate that a variety of conjugation chemistries may be used to covalently conjugate an X with a T and/or a W with a T (generally "components"). Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between the conjugated element and the remainder of the conjugate framework). It is to be understood that components may be covalently bound to a conjugate framework through any number of chemical bonds, including but not limited to amide, amine, ester, ether, thioether, isourea, imine, etc. bonds. In certain embodiments, $L^B$ and/or $L^D$ (generally "L" for the purposes of this section) is a covalent bond. In some embodiments, L is an optionally substituted moiety derived from conjugating an optionally substituted carbonyl-reactive, thiol-reactive, amine-reactive, or hydroxyl-reactive moiety of T with a carboxyl, thiol, amine, or hydroxyl group of X or W. In some embodiments, L is an optionally substituted moiety derived from conjugating an optionally substituted carboxyl-reactive, thiol-reactive, amine-reactive, or hydroxyl-reactive moiety of X or W with a carboxyl, thiol, amine, or hydroxyl group of T. In some embodiments, L is

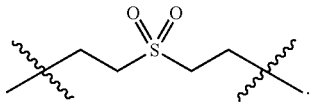 [SMILES: *CCS(=O)(=O)CC*]

In some embodiments, L is a succinimide moiety.

In various embodiments, components may be covalently bound to a conjugate framework using "click chemistry" reactions as is known in the art. These include, for example, cycloaddition reactions, nucleophilic ring-opening reactions, and additions to carbon-carbon multiple bonds (e.g., see Kolb and Sharpless, *Drug Discovery Today* 8:1128-1137, 2003 and references cited therein as well as Dondoni, *Chem. Asian J.* 2:700-708, 2007 and references cited therein). As discussed above, in various embodiments, the components may be bound to a conjugate framework via natural or chemically added pendant groups. In general, it will be appreciated that the first and second members of a pair of reactive groups (e.g., a carboxyl group and an amine group which react to produce an amide bond) can be present on either one of the component and framework (i.e., the relative location of the two members is irrelevant as long as they react to produce a conjugate). Exemplary linkages are discussed in more detail below.

In various embodiments, carboxyl (or reactive ester) bearing components can be conjugated to —OH bearing frameworks (OBFs) using the procedure outlined by Kim et al., Biomaterials 24:4843-4851 (2003). Briefly, the OBF is dissolved in DMSO along with the carboxyl bearing component and reacted by means of N',N'-dicyclohexylcarbodiimide (DCC) and 4-dimethylaminopyridine (DMAP) as catalysts under a dry atmosphere. Carboxyl bearing components can be conjugated to —NH$_2$ bearing frameworks (NBFs) using a carbodiimide (EDAC) coupling procedure. Using this procedure, the carboxyl bearing component is functionalized by reaction with EDAC in a pH 5 buffer followed by the addition of the NBF. In either of these cases (and in any of the following cases), the resulting products may be purified by any number of means available to those skilled in the art including, but not limited to, size exclusion chromatography, reversed phase chromatography, silica gel chromatography, ion exchange chromatography, ultrafiltration, and selective precipitation.

In various embodiments, amine bearing components can be coupled to —COOH bearing frameworks (CBFs). CBFs using activated ester moieties (e.g., see Hermanson in *Bioconjugate Techniques, 2$^{nd}$ edition*, Academic Press, 2008 and references cited therein). Briefly, a CBF with terminal activated esters such as —NHS, —SSC, —NPC, etc. is dissolved in an anhydrous organic solvent such as DMSO or DMF. The desired number of equivalents of amine bearing component are then added and mixed for several hours at room temperature. Amine bearing components can also be conjugated to CBFs to produce a stable amide bond as described by Baudys et al., *Bioconj. Chem.* 9:176-183, 1998. This reaction can be achieved by adding tributylamine (TBA) and isobutylchloroformate to a solution of the CBF and an amine bearing component in dimethylsulfoxide (DMSO) under anhydrous conditions. Amine bearing components can alternatively be coupled to OBFs through cyanalation using reagents including, but not limited to, cyanogen bromide (CNBr), N-cyanotriethylammonium tetrafluoroborate (CTEA), 1-Cyano-4-(Dimethylamino)-pyridinium tetrafluorborate (CDAP), and p-nitrophenylcyanate (pNPC). CNBr reactions can be carried out at mildly basic pH in aqueous solution. CDAP reactions are carried out in a mixture of DMSO and water at mildly basic pH using triethylamine (TEA) as a catalyst. In certain embodiments, amine bearing components can be conjugated to NBFs, e.g., through glutaraldehyde coupling in aqueous buffered solutions containing pyridine followed by quenching with glycine. In certain embodiments, amine bearing components can be conjugated to aldehyde bearing frameworks using a Schiff Base coupling procedure followed by reduction (e.g., see Hermanson in *Bioconjugate Techniques, 2$^{nd}$ edition*, Academic Press, 2008 and references cited therein as well as Mei et al. in *Pharm. Res.* 16: 1680-1686, 1999 and references cited therein). Briefly, a framework with terminal activated aldehydes (e.g., acetaldehyde, propionaldehyde, butyraldehyde, etc.) is dissolved in an aqueous buffer with the pH at or below neutral to prevent unwanted aldehyde hydrolysis. The desired number of equivalents of an amine bearing component are then added and mixed at room temperature followed by addition of an excess of suitable reducing agent (e.g., sodium borohydride, sodium cyanobrohydride, sodium triacetoxyborohydride pyridine borane, triethylamine borane, etc.).

In various embodiments, hydroxyl bearing components can be conjugated to OBFs according to the divinylsulfone (DVS) procedure. Using this procedure, the OBF is added to a pH 11.4 bicarbonate buffer and activated with DVS followed by addition of a hydroxyl bearing component after which glycine is added to neutralize and quench the reaction. Hydroxyl bearing components may also be coupled to OBFs using activated ester moieties as described above to produce ester bonds.

In various embodiments, sulfhydryl bearing components can be coupled to maleimide bearing frameworks (MBFs) using a relatively mild procedure to produce thioether bonds (e.g., see Hermanson in *Bioconjugate Techniques, 2$^{nd}$ edition*, Academic Press, 2008 and references cited therein). Because the maleimide group is much less susceptible to hydrolysis than activated esters, the reaction can be carried out under aqueous conditions. Briefly, an MBF is dissolved in a buffered aqueous solution at pH 6.5-7.5 followed by the desired number of equivalents of sulfhydryl bearing component. After mixing at room temperature for several hours, the thioether coupled conjugate may be purified. Sulfhydryl bearing components can also be conjugated to NBFs according to a method described by Thoma et al., *J. Am. Chem. Soc.* 121:5919-5929, 1999. This reaction involves suspending the NBF in anhydrous dimethylformamide (DMF) followed by the addition of 2,6-lutidine and acid anhydride and subsequent purification of the reactive intermediate. A sulfhydryl bearing component is then added to a solution of the intermediate in DMF with triethylamine.

In various embodiments, azide bearing components can be coupled to an alkyne bearing framework (ABF) using the copper(I)-catalyzed modern version of the Huisgen-type azide-alkyne cycloaddition to give a 1,4-disubstituted 1,2,3-triazole (e.g., see Dondoni, *Chem. Asian J.* 2:700-708, 2007 and references cited therein as well as Dedola et al., *Org. Biomol. Chem.* 5: 1006-1017, 2007). This reaction, commonly referred to as a "click" reaction, may be carried out for example in neat THE using N,N-diisopropylethylamine and Cu(PPh$_3$)$_3$Br as the catalyst system (e.g., see Wu et al., *Chem. Commun.* 5775-5777, 2005). The reaction may also be carried out in a 3:1 (THF:water) mixture using sodium ascorbate and CuSO$_4$·5H$_2$O as the catalyst system (e.g., see Wu et al., supra). In either case, the azide bearing component is added to the ABF at the desired number of equivalents followed by mixing for 12-48 hours at room temperature. Alternatively, alkyne bearing components may be conjugated to an azide bearing framework using exactly the same conditions described above.

Certain components may naturally possess more than one of the same chemically reactive moiety. In some examples, it is possible to choose the chemical reaction type and conditions to selectively react the component at only one of those sites. For example, in the case where insulin is conjugated through reactive amines, in certain embodiments, the N-terminal α-Phe-B1 is a preferred site of attachment over the N-terminal α-Gly-A1 and ε-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in certain embodiments it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., *Biochem. J* 109: 312-314, 1968; and Schuettler et al., *D. Brandenburg Hoppe Seyler's Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THE are added slowly and the solution allowed to mix for 30-60 minutes. After reaction, the crude solution is poured in an excess of acetone followed by dropwise addition of dilute HCl to precipitate the reacted insulin. The precipitated material is centrifuged, washed with acetone and dried completely under vacuum. The desired di-BOC protected product may be separated from unreacted insulin, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, rotovapped to remove acetonitrile, and lyophilized to obtain the pure product.

m, n, and v

Each occurrence of m is independently an integer from 1 to 5, inclusive. In certain embodiments, each occurrence of m is the same. In certain embodiments, m=1, 2 or 3. In certain embodiments, m=1.

n is an integer from 0 to 5, inclusive. In certain embodiments, each occurrence of n is the same. In certain embodiments, n=1, 2 or 3. In certain embodiments, n=0. In certain embodiments, n=1. In certain embodiments, n=2. In certain embodiments, n=3.

Each occurrence of v is independently an integer from 1 to 5, inclusive. In certain embodiments, each occurrence of v is the same. In certain embodiments, v=1, 2 or 3. In certain embodiments, v=1.

It is to be understood that while the preceding sections describe components of the conjugates (e.g., ligand, insulin molecule, framework) under separate headings, the present disclosure encompasses conjugates that are comprised of any and all of the disclosed ligands, insulin molecules and frameworks.

Exemplary Conjugates

In some embodiments, the present disclosure provides a conjugate of general formula I represented by formulas I-a through I-h:

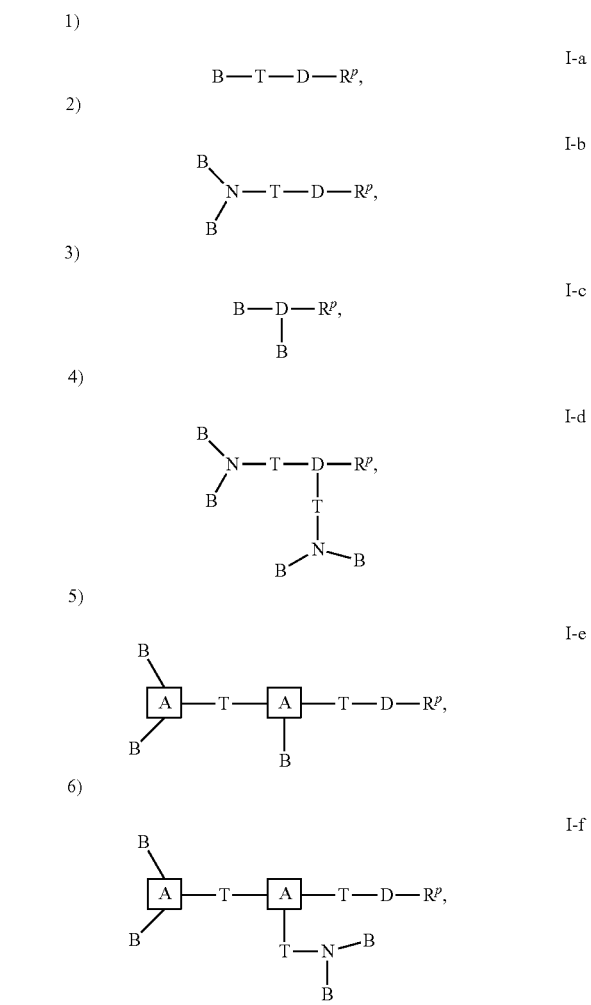

7)

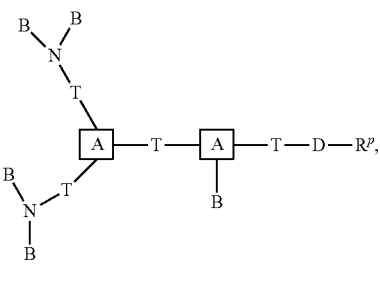

8)

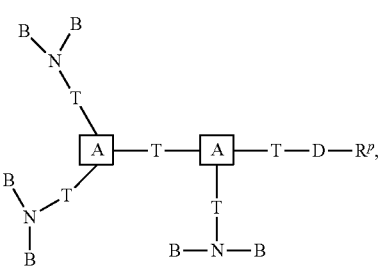

wherein B, T, D, and $R^p$ are as defined and described herein.

In an embodiment, the present disclosure provides a conjugate of formula I-a.

In an embodiment, the present disclosure provides a conjugate of formula I-b.

In an embodiment, the present disclosure provides a conjugate of formula I-c.

In an embodiment, the present disclosure provides a conjugate of formula I-d.

In an embodiment, the present disclosure provides a conjugate of formula I-e.

In an embodiment, the present disclosure provides a conjugate of formula I-f.

In an embodiment, the present disclosure provides a conjugate of formula I-g.

In an embodiment, the present disclosure provides a conjugate of formula I-h.

For example, in some embodiments, the present disclosure provides a conjugate of general formulas I-a through I-h selected from formulas I-1 through I-9:

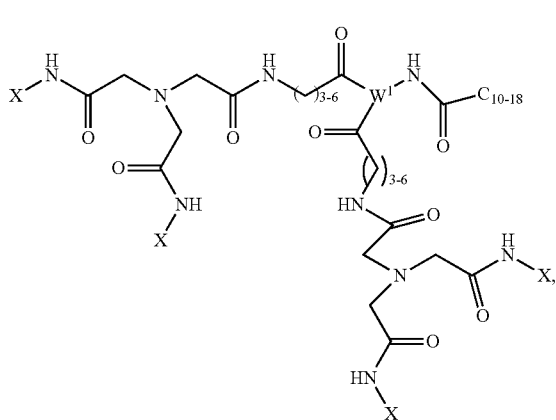

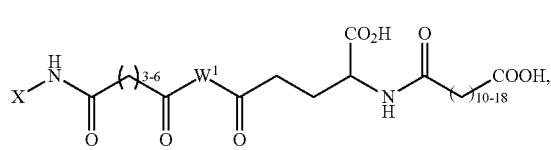

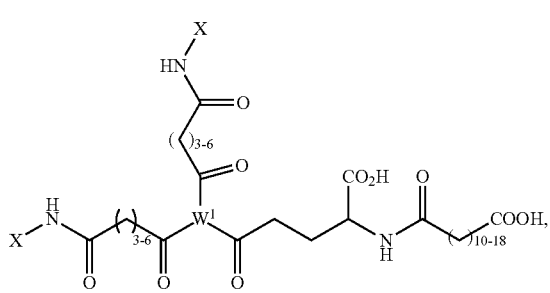

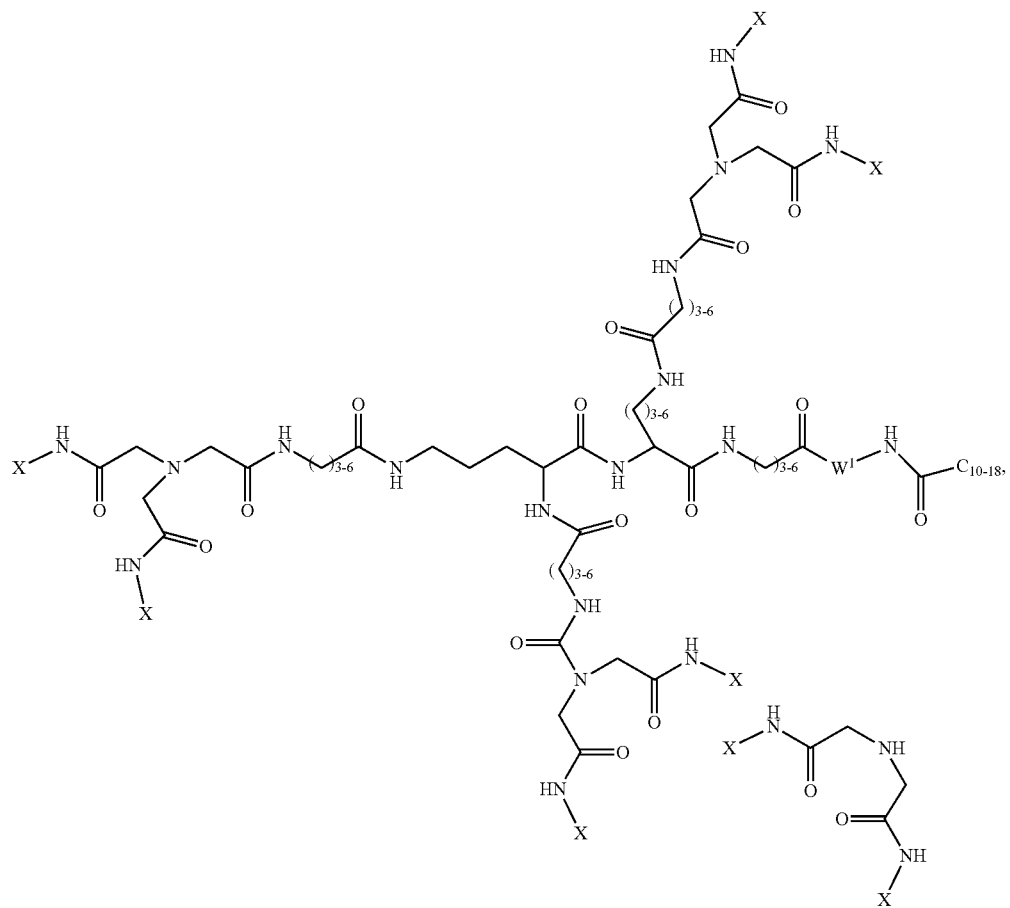
I-4
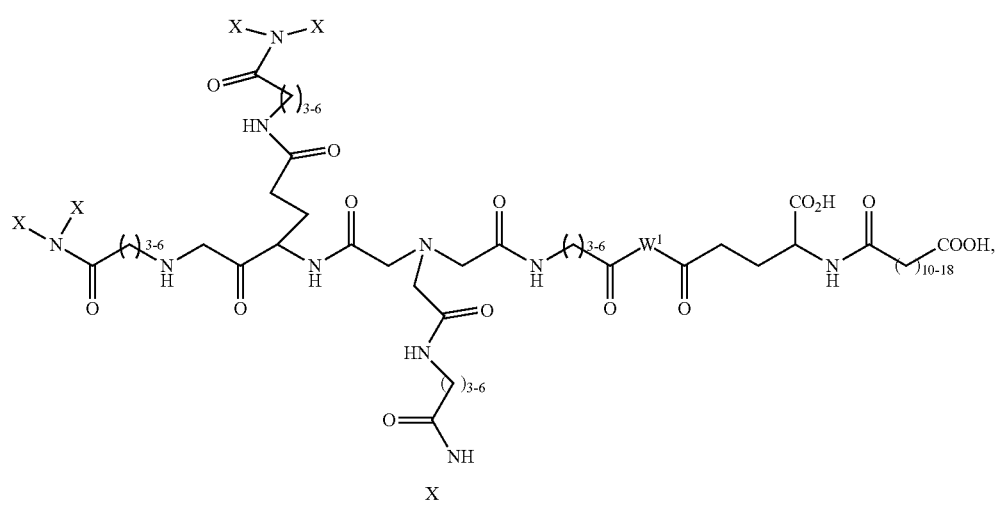
I-5

I-6
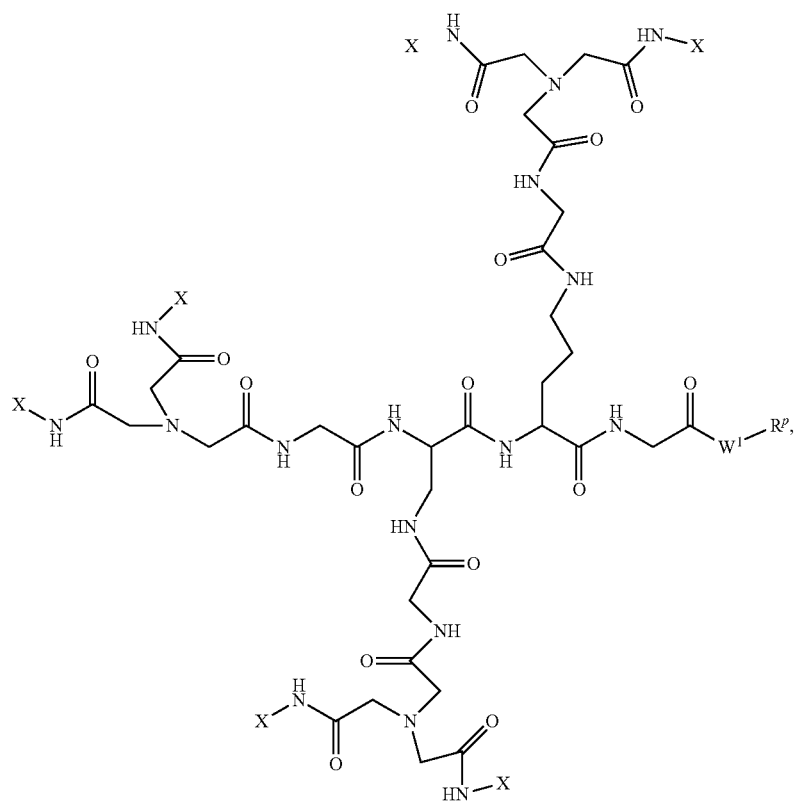
I-7
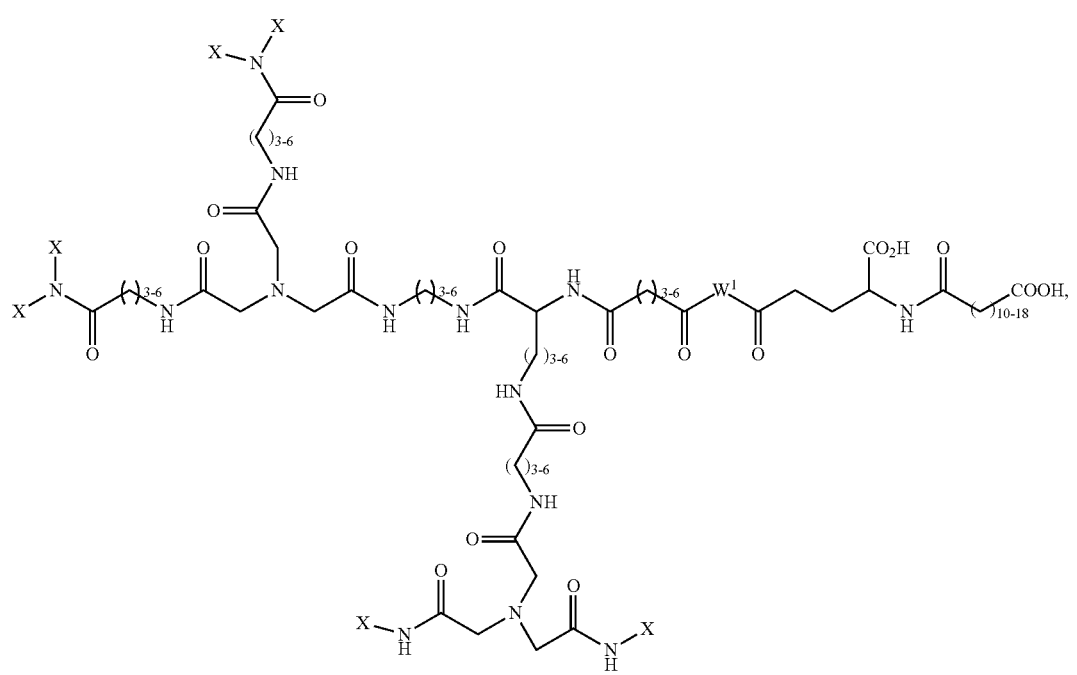

-continued
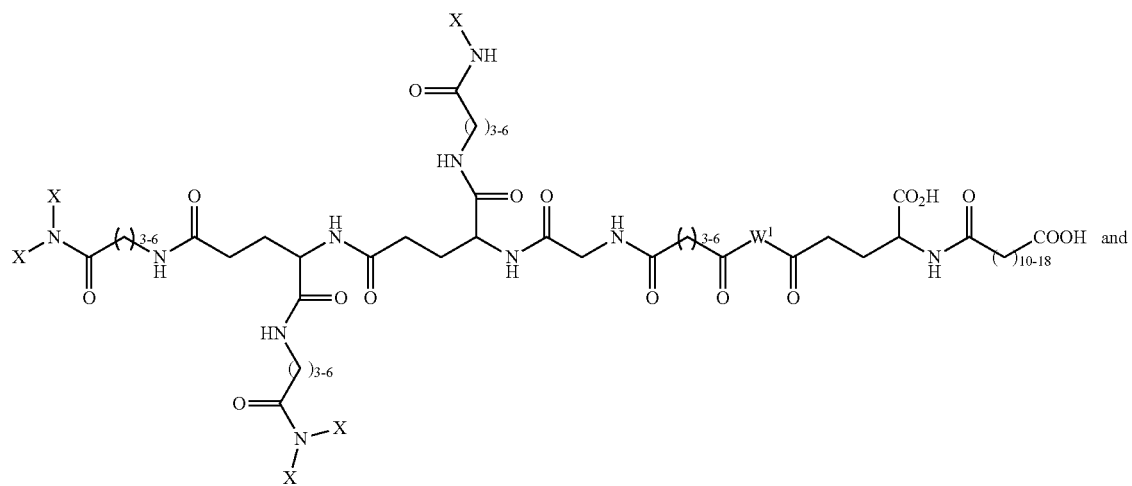
I-8
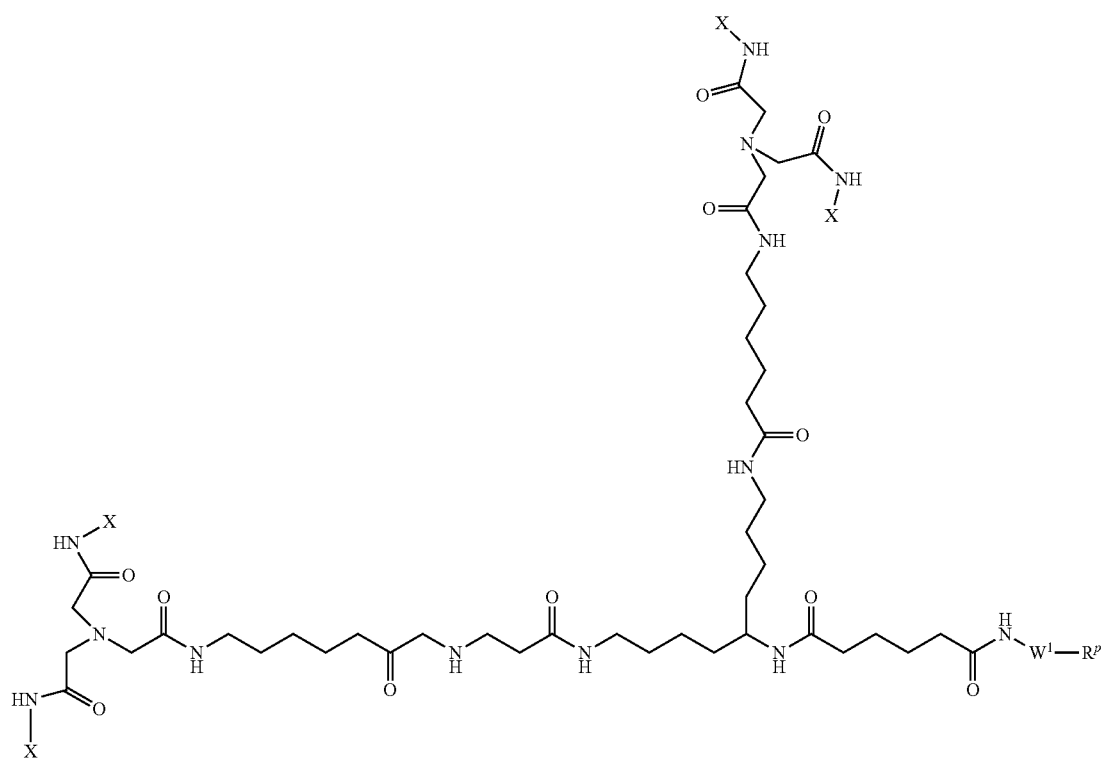
I-9
wherein X is a ligand selected from AEG, AEF, AEM, AETM, AEGA, AEBM, EG, EM, and $W^I$ and $R^p$ are as described and defined herein.

In an embodiment, the present disclosure provides a conjugate of formula I-1.

In an embodiment, the present disclosure provides a conjugate of formula I-2.

In an embodiment, the present disclosure provides a conjugate of formula I-3.

In an embodiment, the present disclosure provides a conjugate of formula I-4.

In an embodiment, the present disclosure provides a conjugate of formula I-5.

In an embodiment, the present disclosure provides a conjugate of formula I-6.

In an embodiment, the present disclosure provides a conjugate of formula I-7.

In an embodiment, the present disclosure provides a conjugate of formula I-8.

In an embodiment, the present disclosure provides a conjugate of formula I-9.

In some embodiments, the present disclosure provides a conjugate of general formula II represented by formulas II-a:

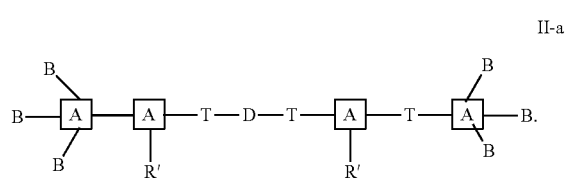

II-a

For example, in some embodiments, the present disclosure provides a conjugate of general formula IIa represented by formula II-1:

wherein J is 10, 11, 12, 13, 14, 15, 16, 17, or 18 and X is a ligand selected from AEG, AEF, AEM, AETM, AEGA, AEBM, EG, EM, and $W^I$ is as described and defined herein.

In some embodiments, the present disclosure provides a conjugate of general formula III represented by formulas III-a, III-b, and III-c:

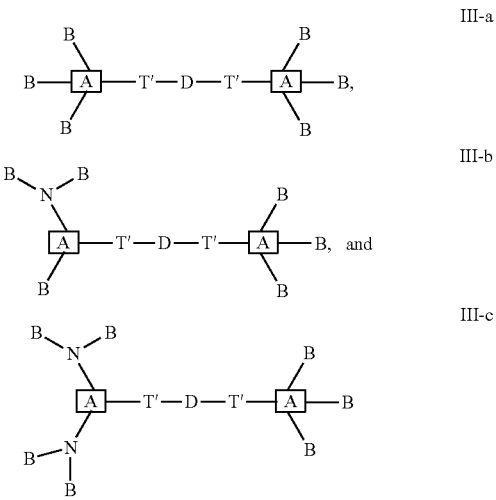

wherein A, B, T, and D are as defined and described herein, each T' is independently selected from a bond, T and $R^p$, and each R' is independently selected from a bond, hydrogen and $R^p$. A subembodiment of this aspect of the invention is realized when at least one of T' is $R^p$. A subembodiment of this aspect of the invention is realized when only one of T' is $R^p$. A subembodiment of this aspect of the invention is realized when at least one R' is $R^p$. A subembodiment of this aspect of the invention is realized when only one R' is $R^p$. A subembodiment of this aspect of the invention is realized when both R' are $R^p$.

In an embodiment, the present disclosure provides a conjugate of formula III-a.

In an embodiment, the present disclosure provides a conjugate of formula III-b.

In an embodiment, the present disclosure provides a conjugate of formula III-c.

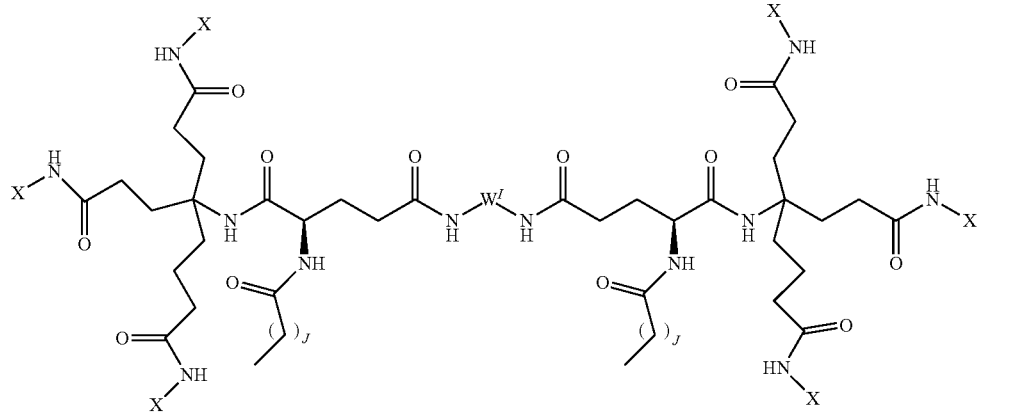

II-1

For example, in some embodiments, the present disclosure provides a conjugate of general formula III represented by formula III-1:

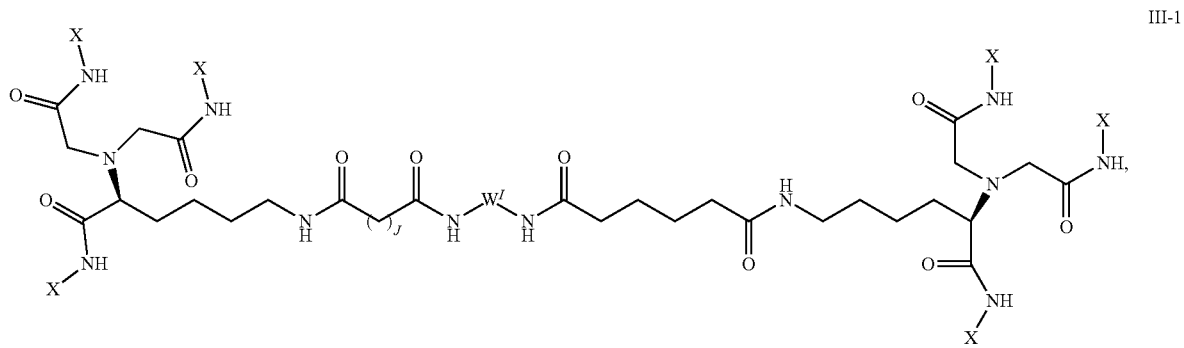

III-1 wherein J is 10, 11, 12, 13, 14, 15, 16, 17, or 18 and X is a ligand selected from AEG, AEF, AEM, AETM, AEGA, AEBM, EG, EM, and $W^I$ is as described and defined herein.

In some embodiments, the present disclosure provides a conjugate of general formula IV represented by formula IV:

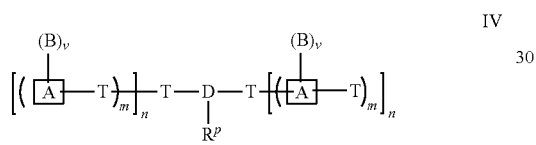

IV wherein B, T, D, and Rp are as defined and described herein.

In some embodiments, the present disclosure provides a conjugate of general formula IV represented by formula IV-a:

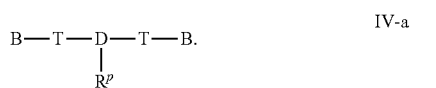

IV-a

For example, in some embodiments, the present disclosure provides a conjugate of general formula IV-a represented by formula IV-1:

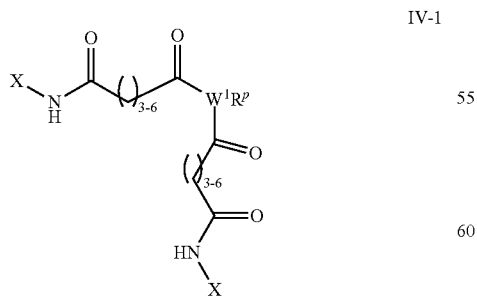

IV-1 wherein X is a ligand selected from AEG, AEF, AEM, AETM, AEGA, AEBM, EG, EM, and $R^p$ and $W^I$ is as described and defined herein.

Non-limiting examples of conjugates of the invention are:
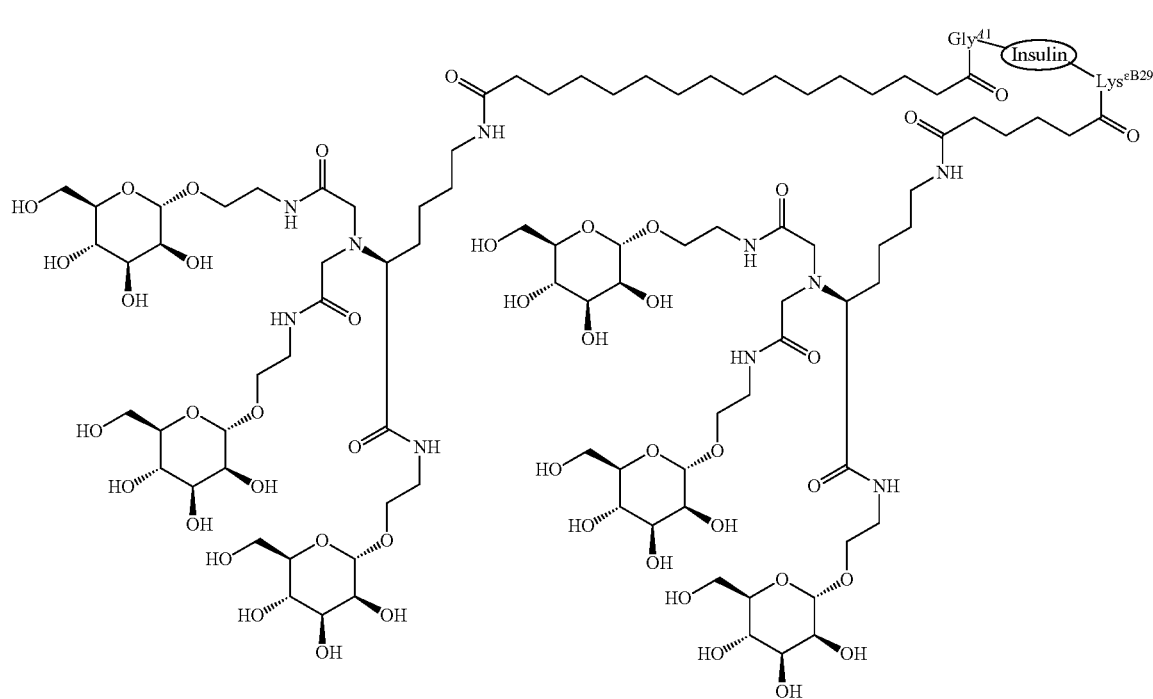
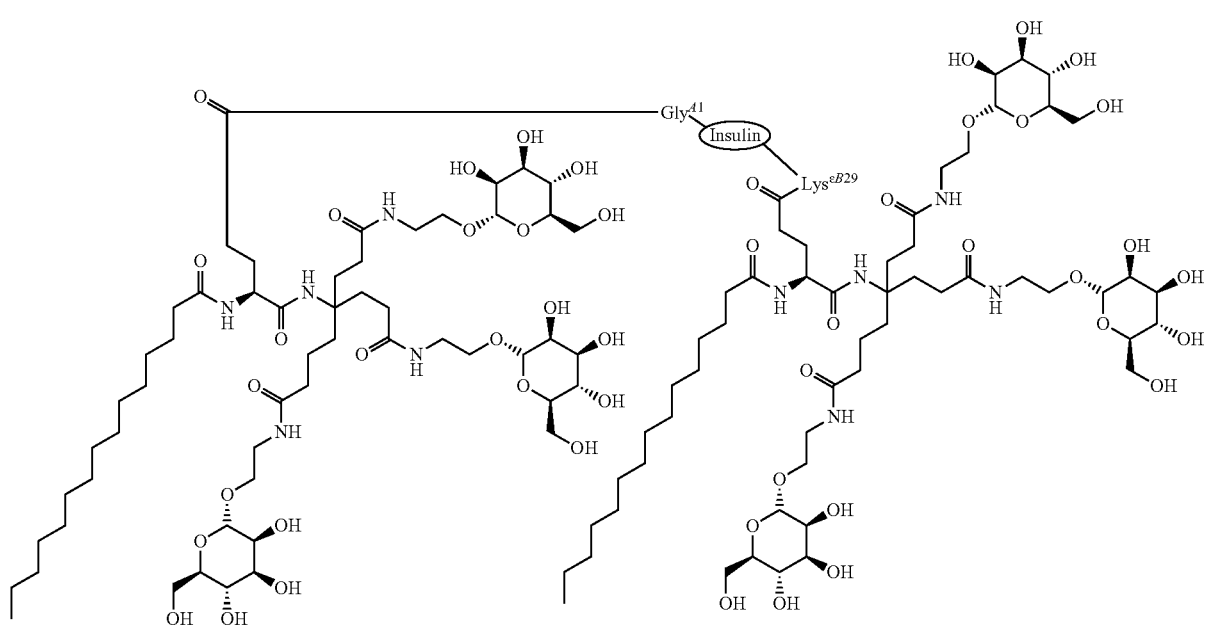

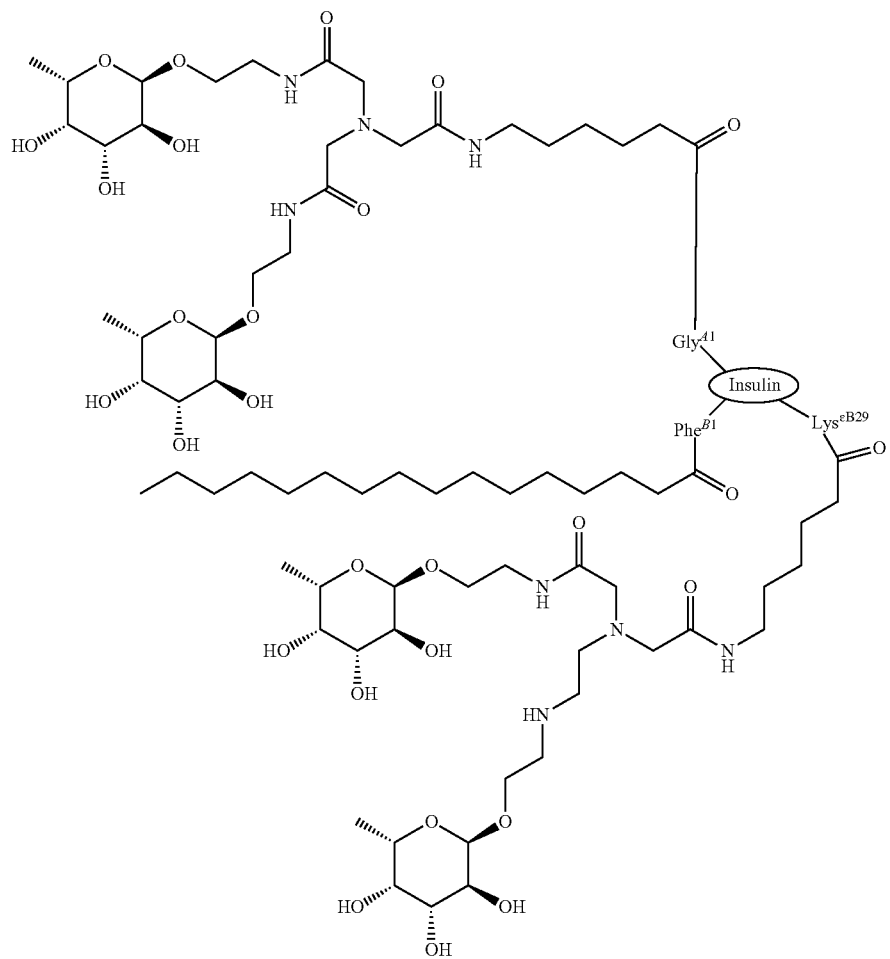

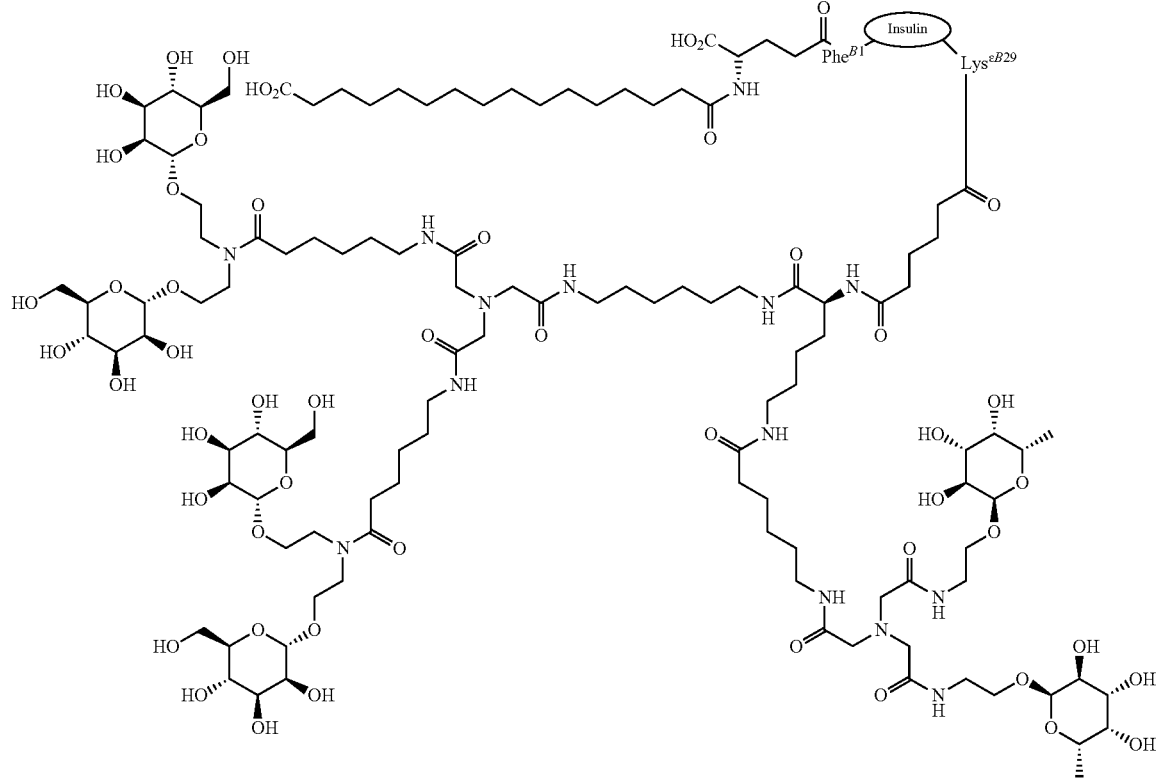
4
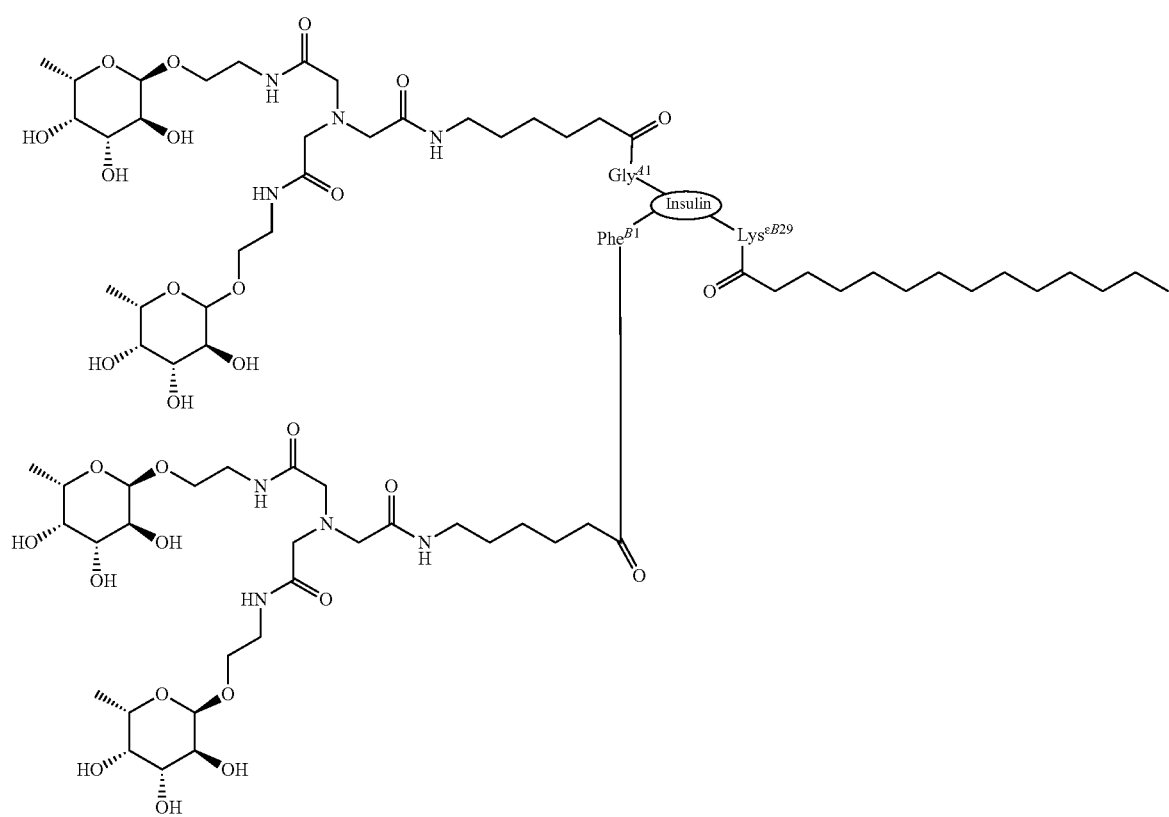
5

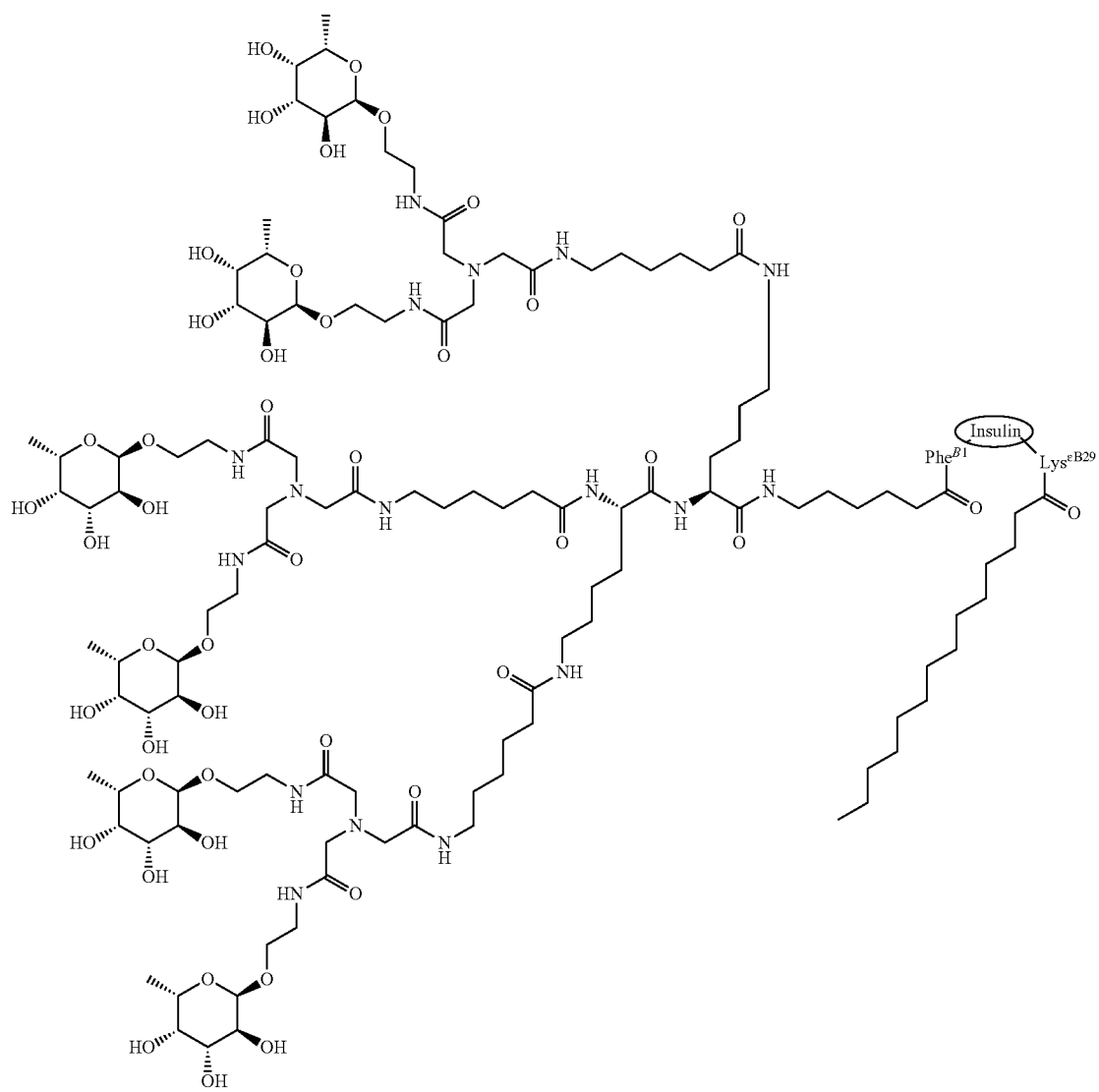

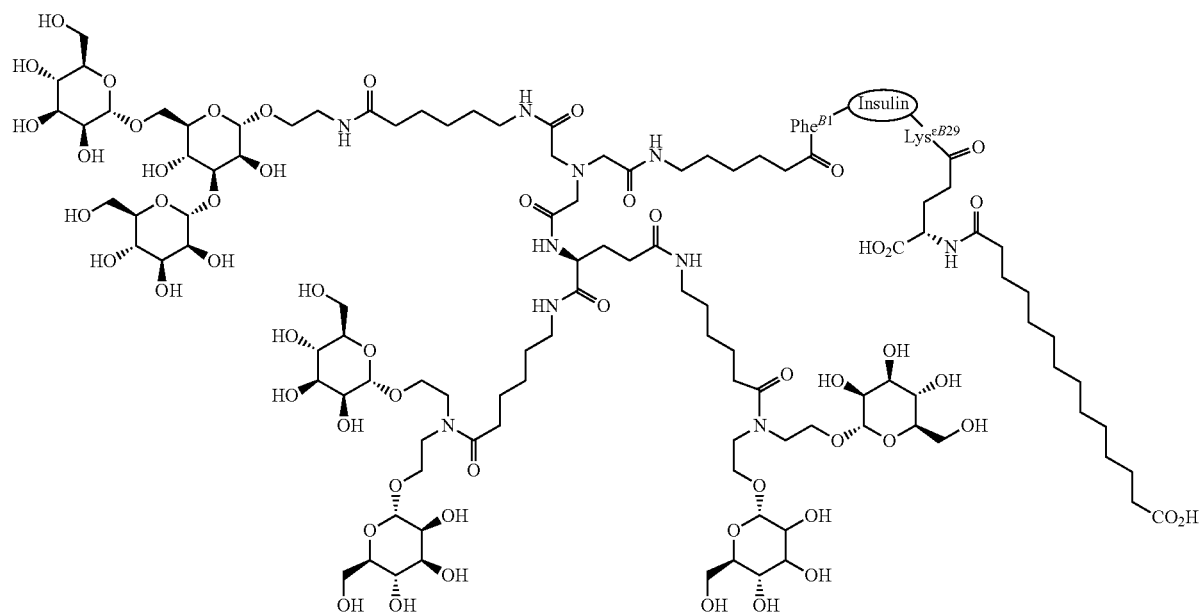
7
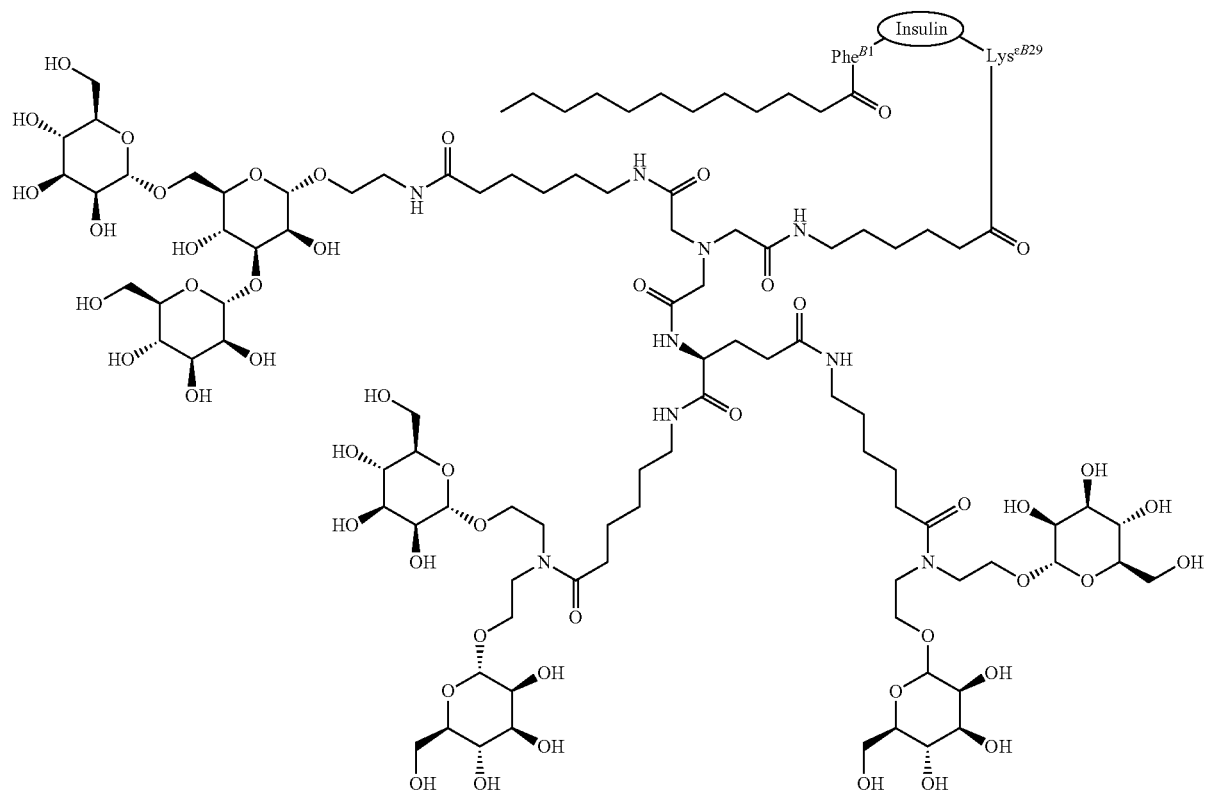
8

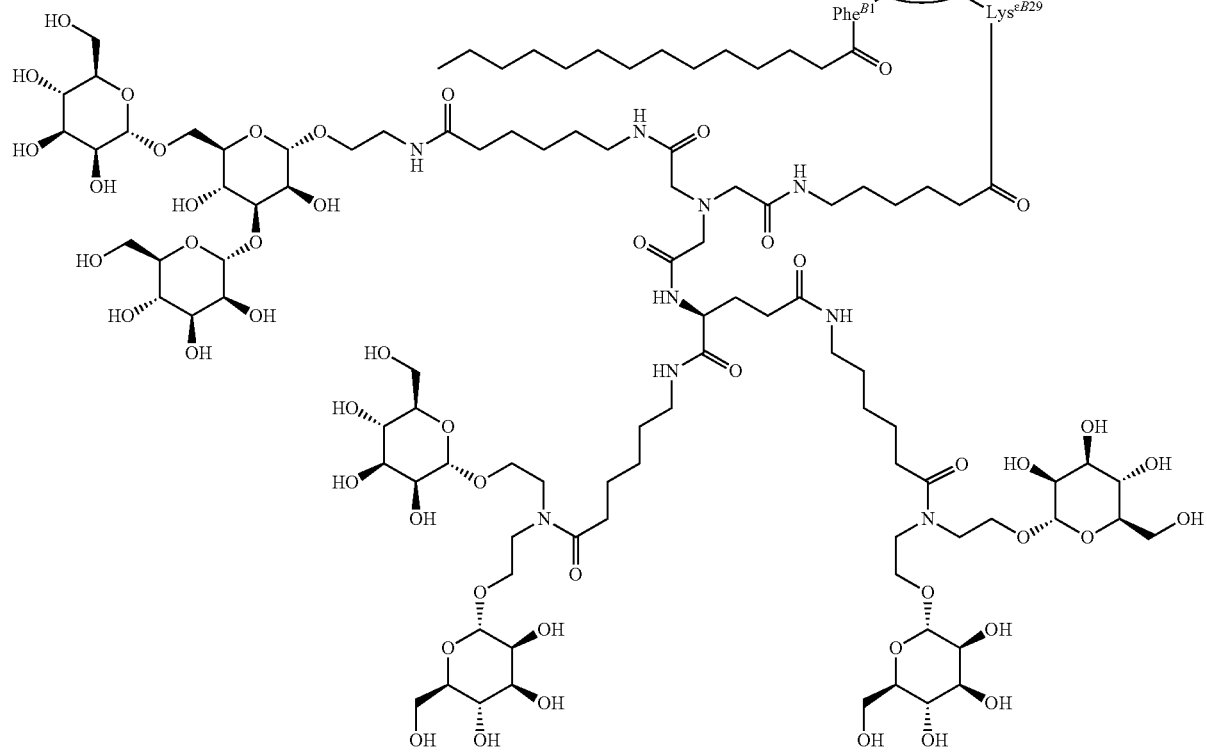
9
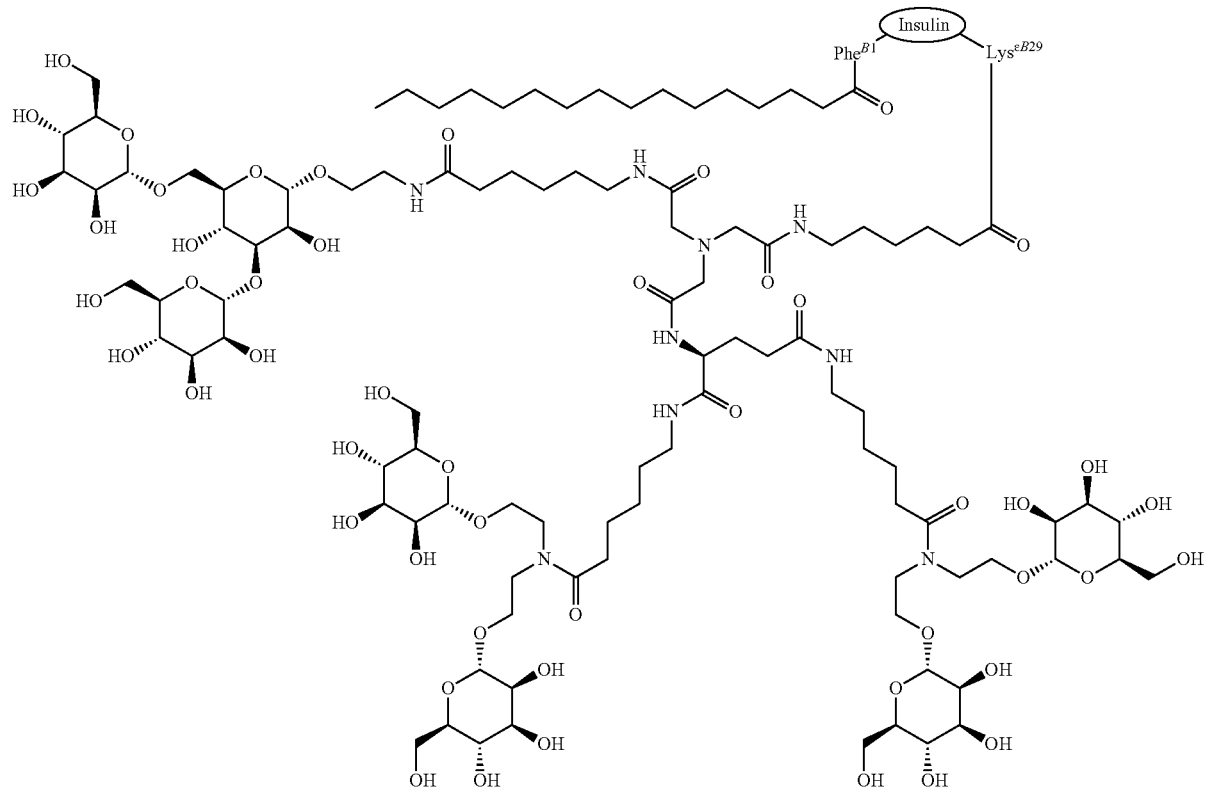
10

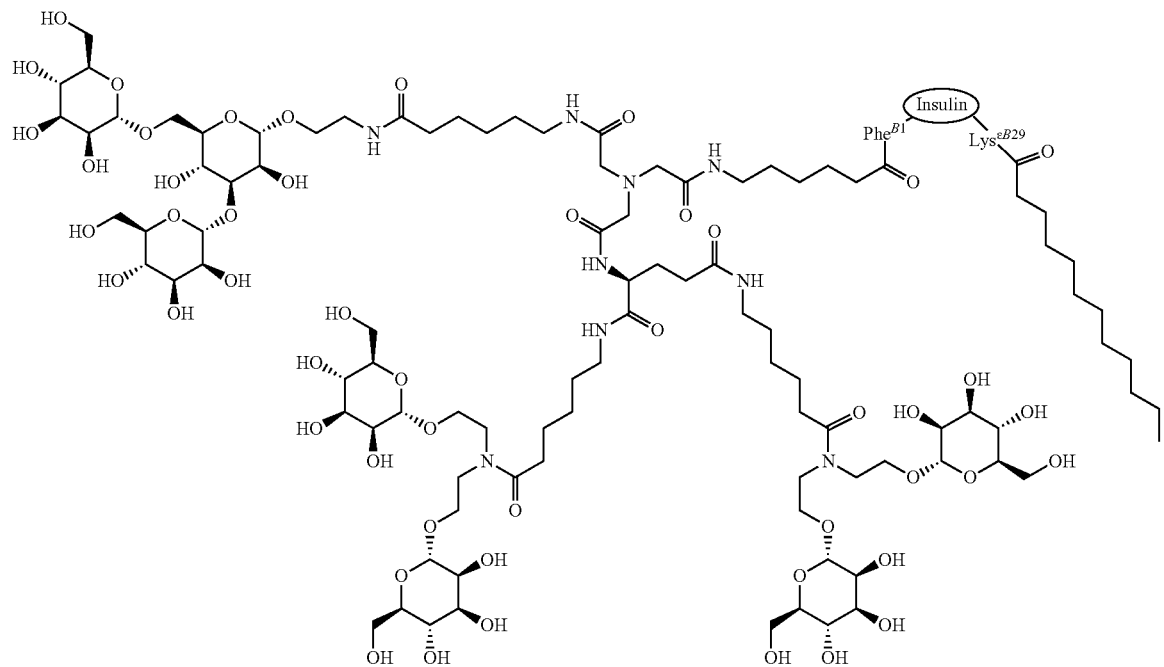
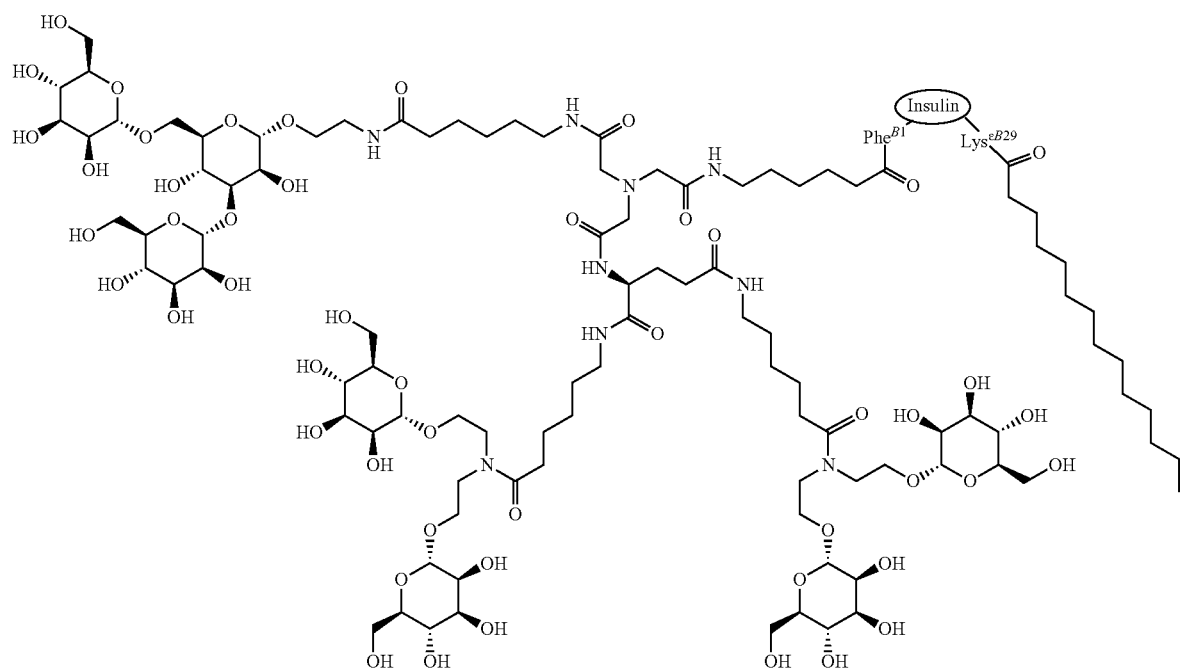

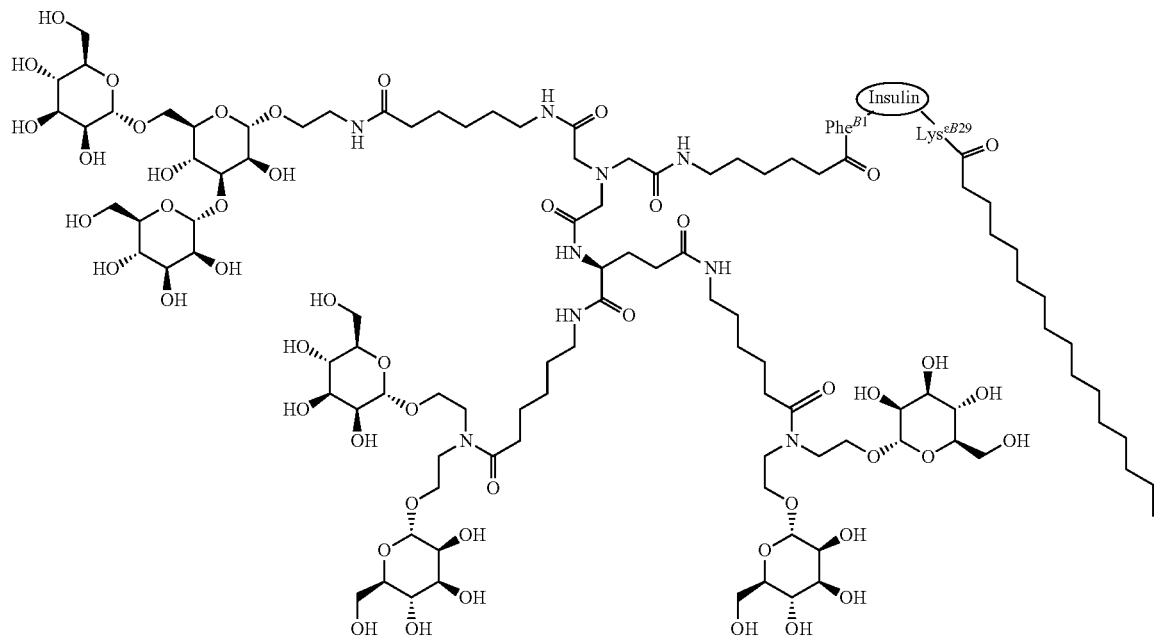
13
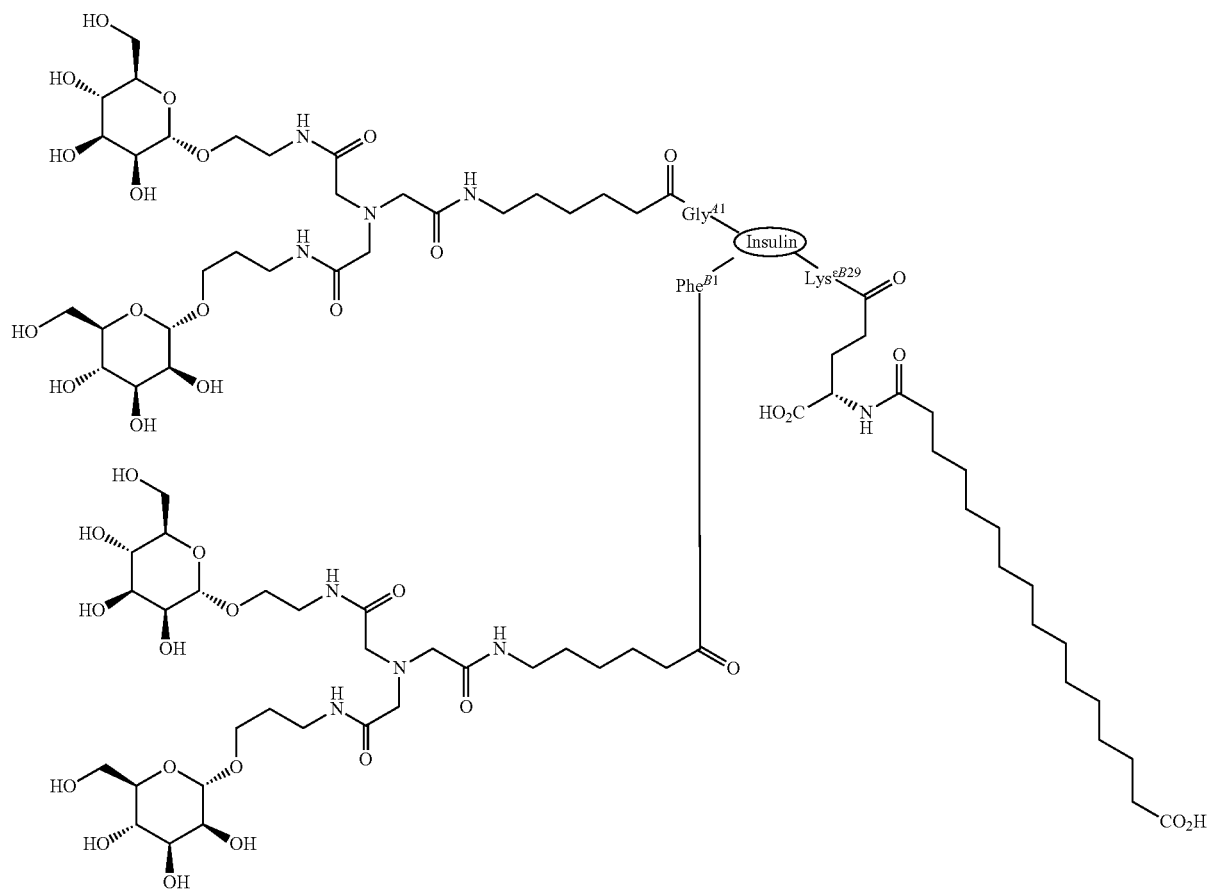
14

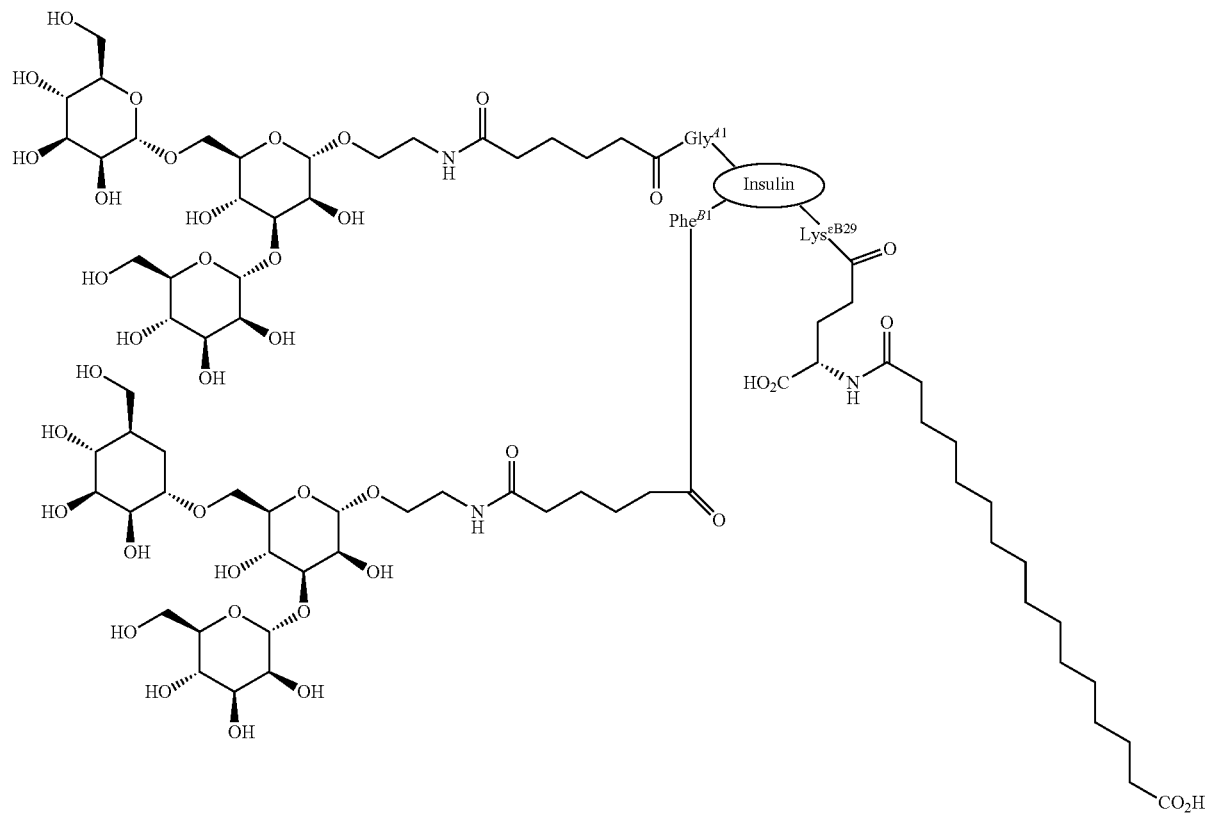
15
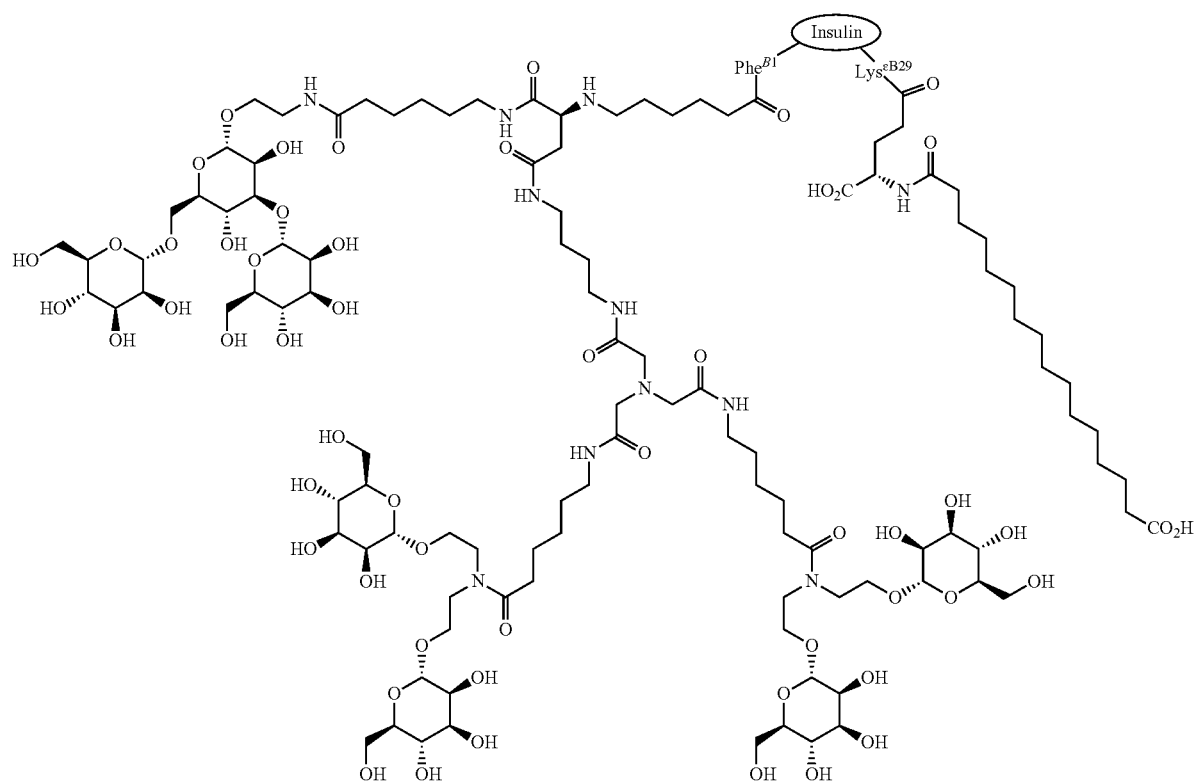
16

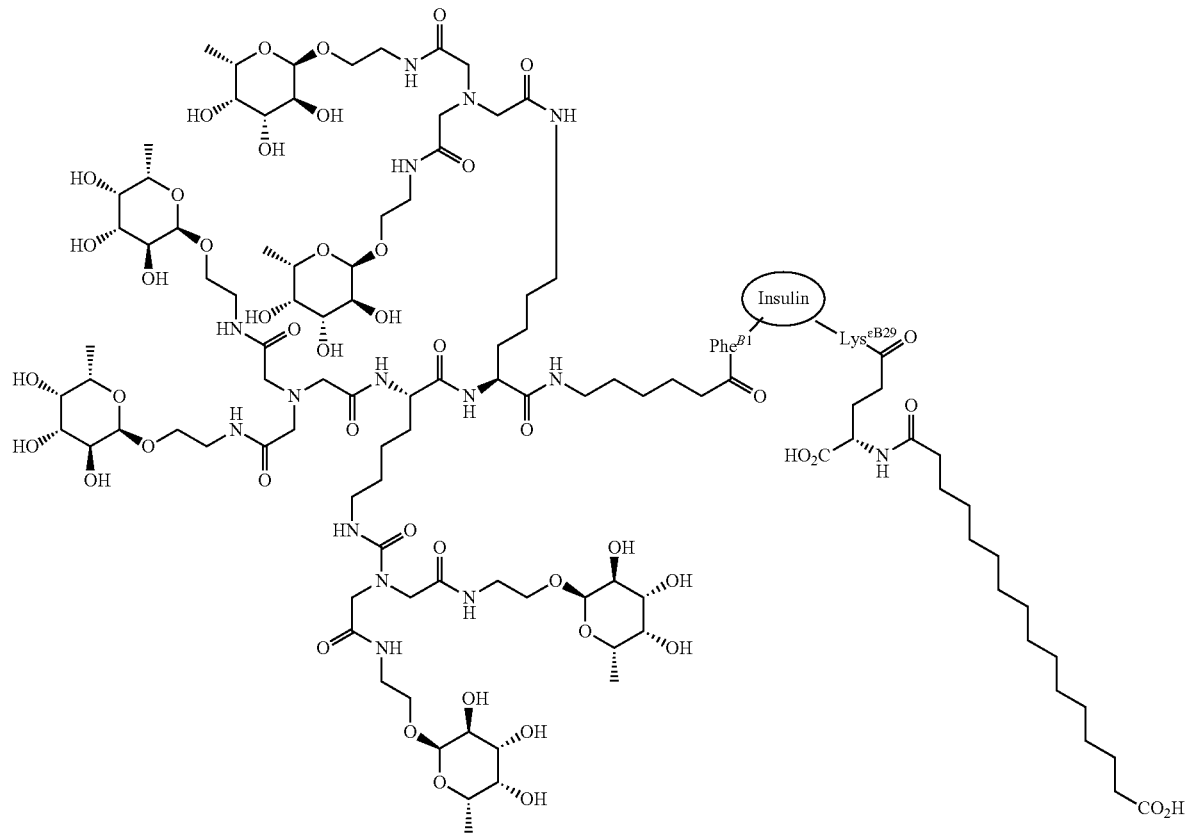
17
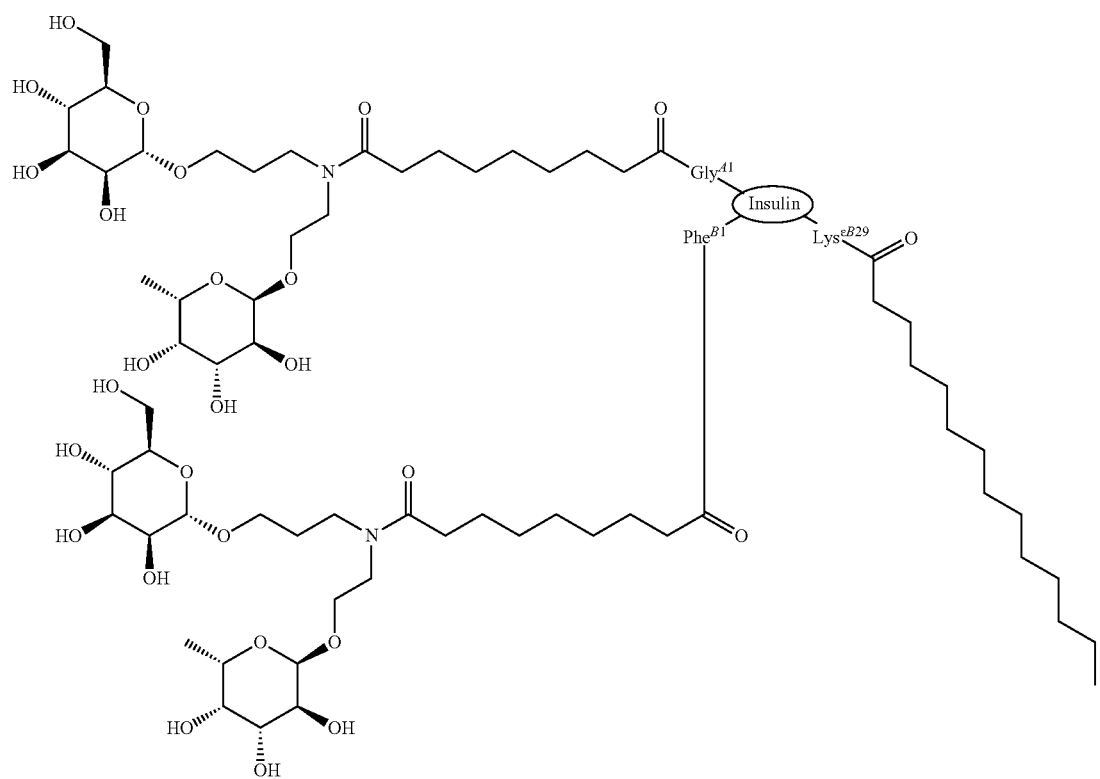
18

-continued
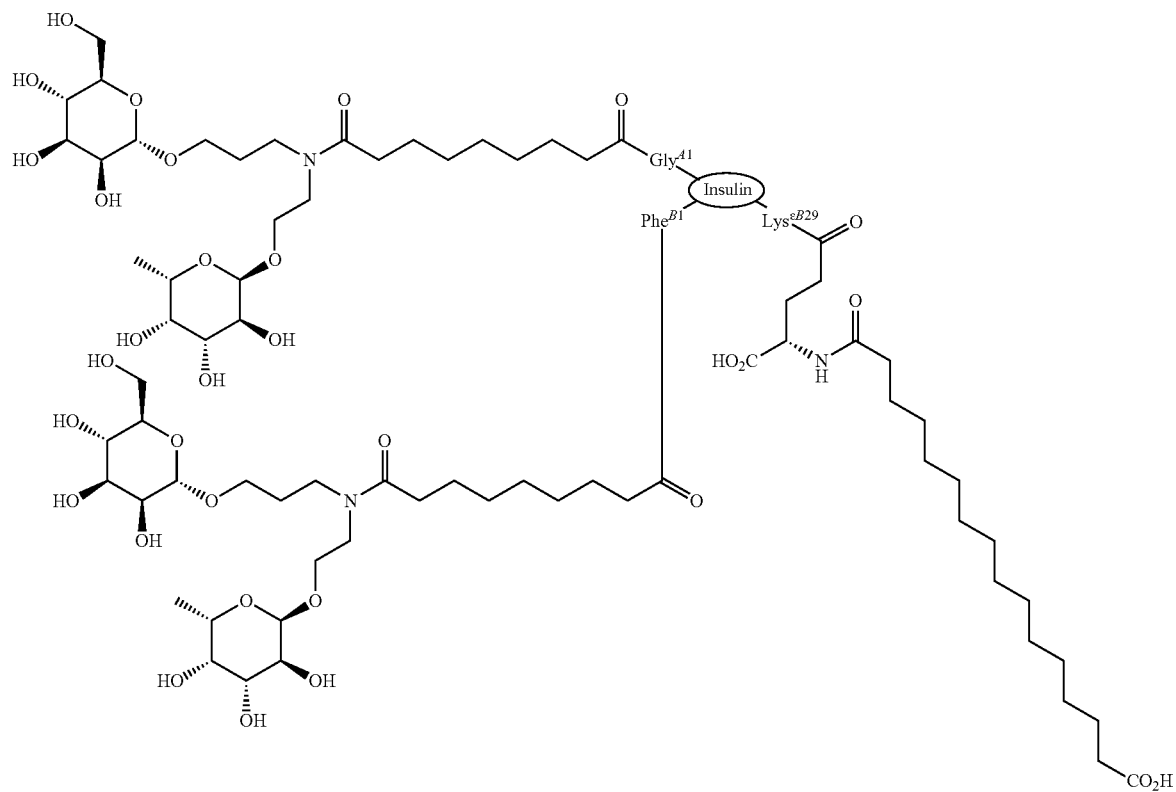
19
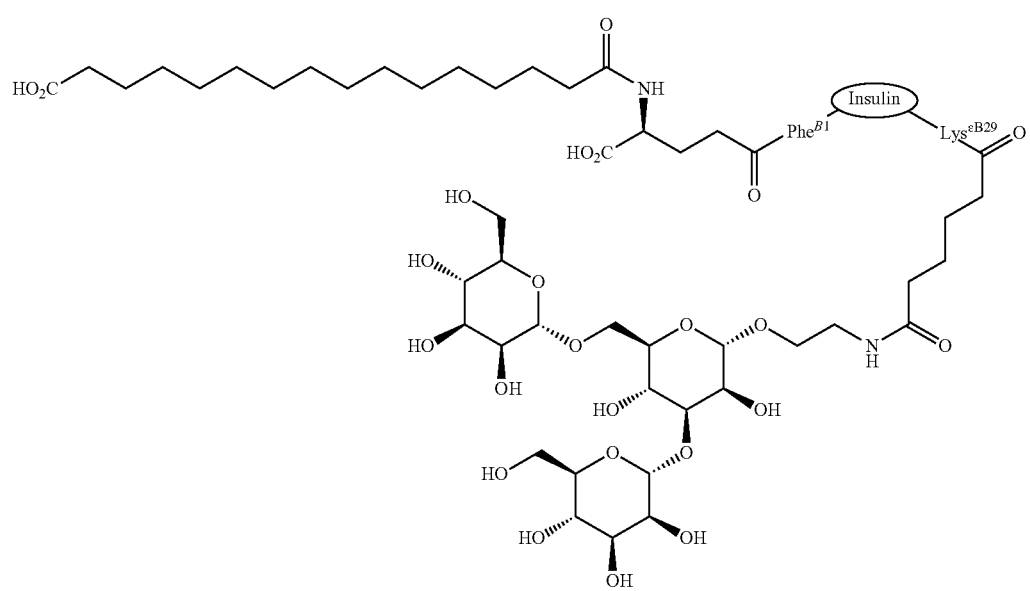
20

-continued
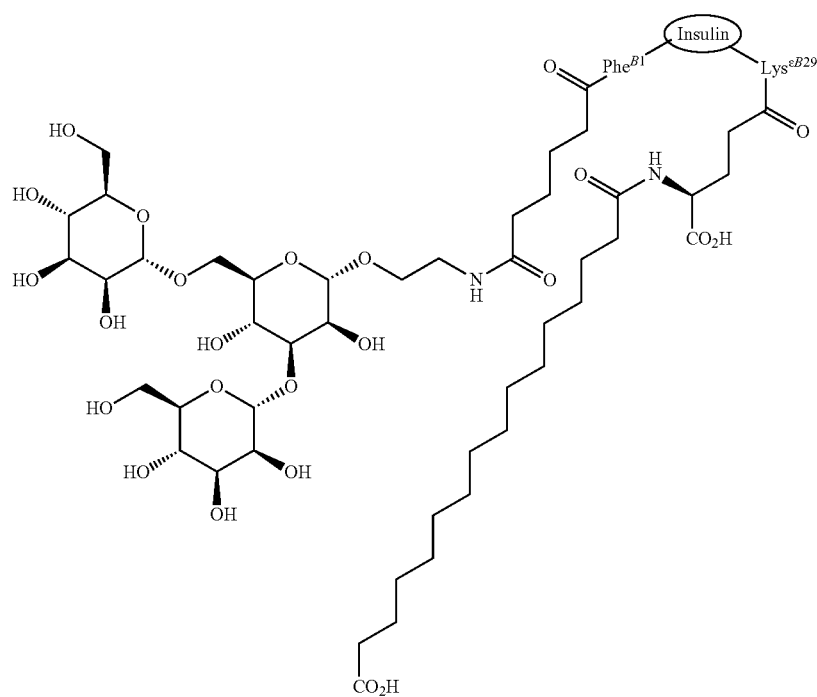
21
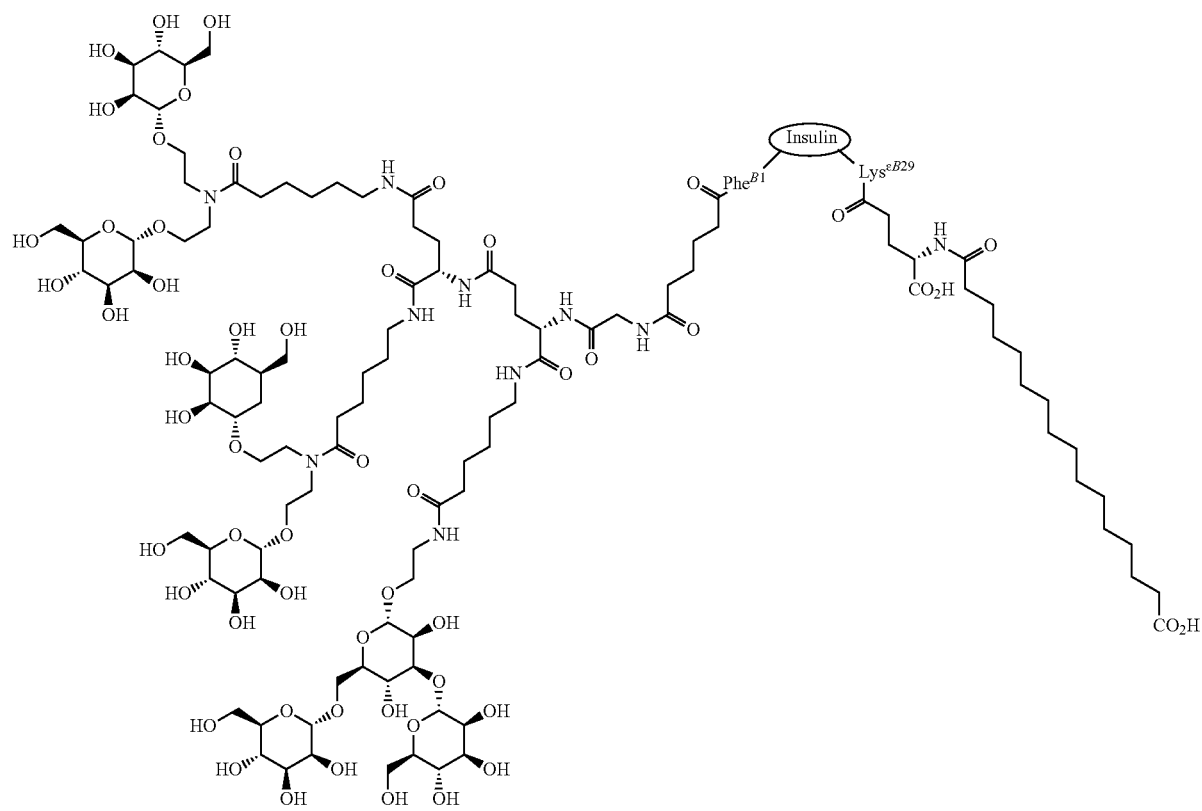
22

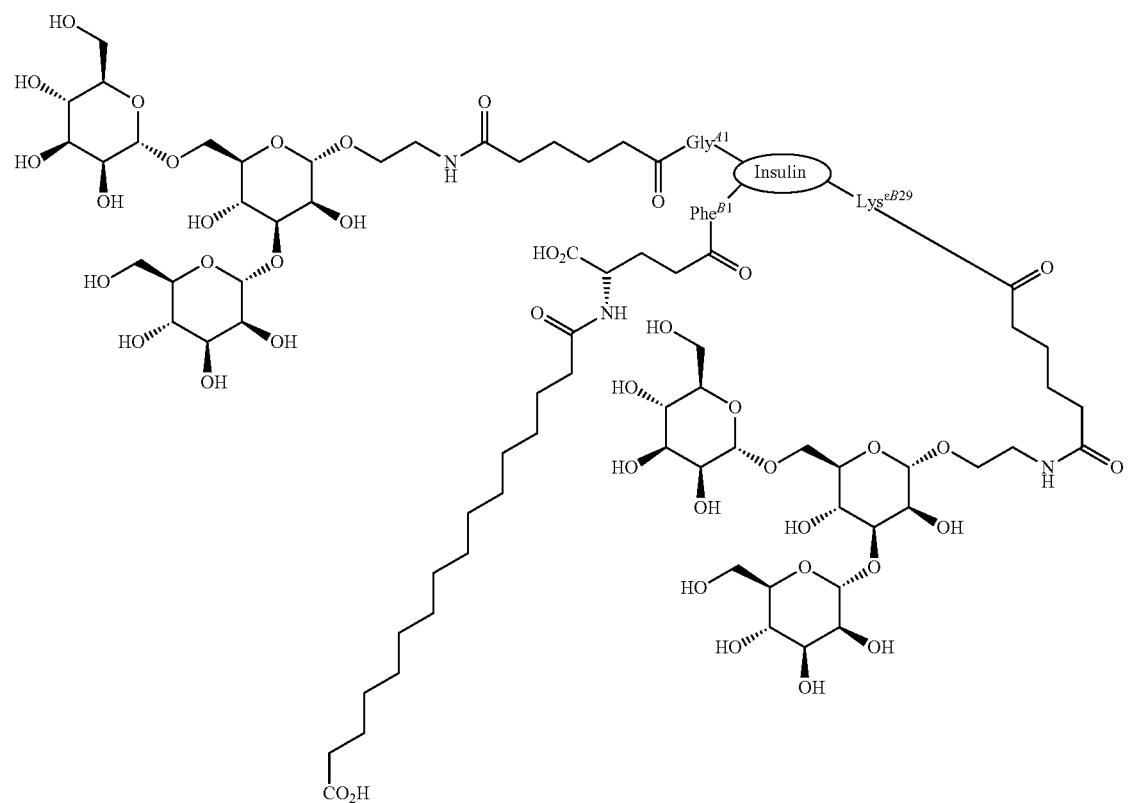

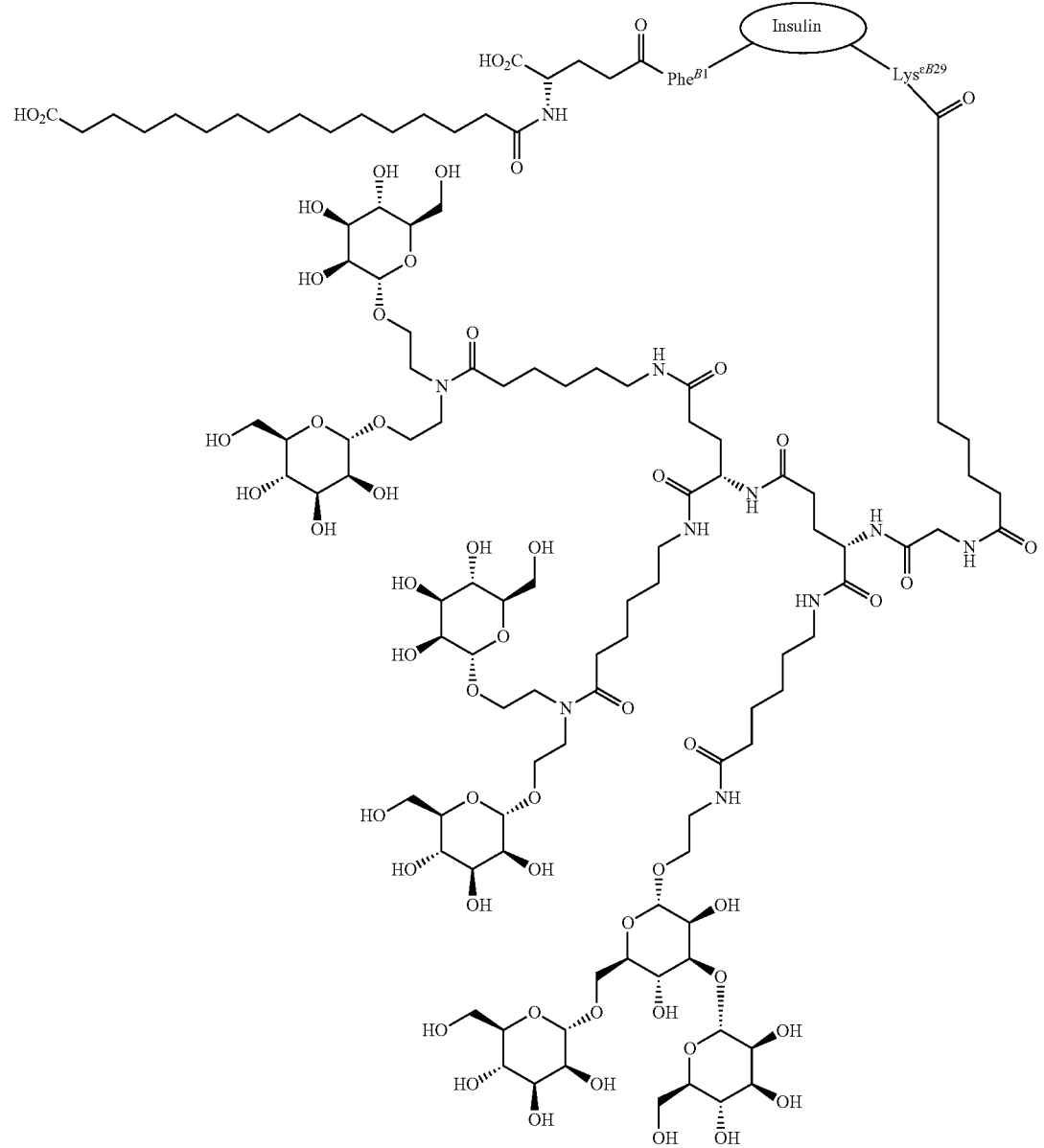

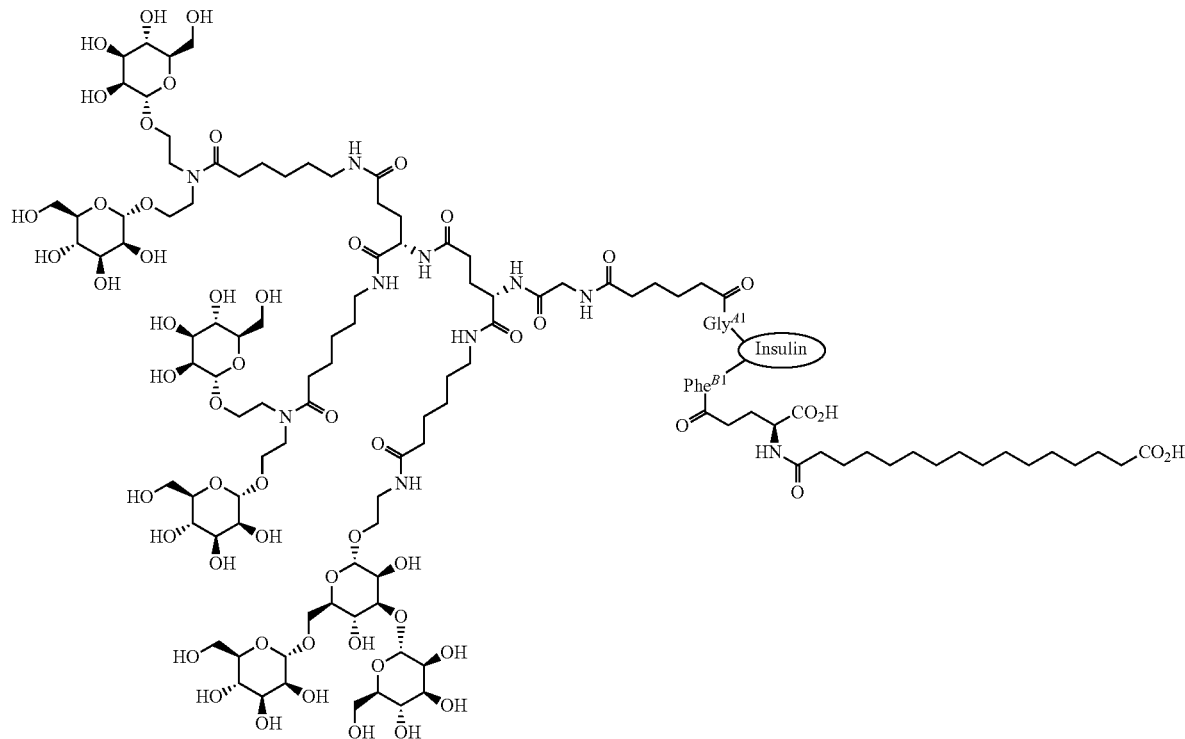

25

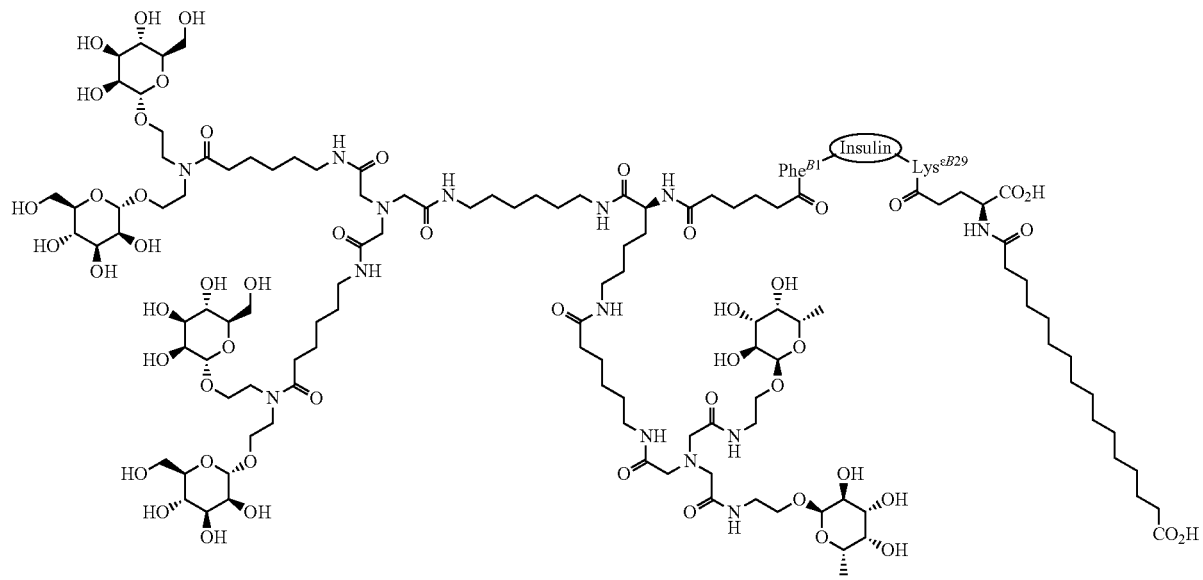

26 or a pharmaceutically acceptable salt thereof.

Intermediates for Preparing Conjugates

In one aspect, the present disclosure provides reagents for preparing conjugates. Thus, in various embodiments, a compound of general formula (I), (II), (III), and (IV), including subgroups thereof is provided wherein: each of $\boxed{A}$, T, T', $R^p$, R', B, q, n, m and v is defined as described above and herein; and -D is -T-$L^{D'}$; and each occurrence of $L^{D'}$ is an activated ester moiety. In certain embodiments, $L^{D'}$ is an N-hydroxysuccinimide (NHS) ester.

Methods for Preparing Conjugates

In various embodiments, an amine-bearing insulin molecule can be coupled to a prefunctionalized ligand framework (PLF) that contains a fatty chain and an activated ester moiety (e.g., see Hermanson in *Bioconjugate Techniques, 2nd edition*, Academic Press, 2008 and references cited therein) as described in the Examples. Briefly, a PLF having a terminal activated ester (e.g., —NHS, —SSC, —NPC, etc.) is dissolved in an anhydrous organic solvent such as DMSO or DMF. The desired number of equivalents of insulin molecule are then added and mixed for several hours at room temperature. An insulin molecule can also be conjugated to a free acid version of the prefunctionalized ligand framework to produce a stable amide bond as described by Baudys et al., *Bioconj. Chem.* 9:176-183, 1998. This reaction can be achieved by adding tributylamine (TBA) and isobutylchloroformate to a solution of the free acid prefunctionalized ligand framework and insulin molecule in dimethylsulfoxide (DMSO) under anhydrous conditions.

Certain insulin molecules may naturally possess more than one amino group. In some examples, it is possible to choose the chemical reaction type and conditions to selectively react the component at only one of those sites. For example, in the case where insulin is conjugated through reactive amines, in certain embodiments, the A1 and B29 amino groups of insulin are BOC-, Fmoc or trifluoracetate protected as described in the Examples so that each insulin can only react at the Phe-B1 α-amino group. In some embodiments, the B1 and B29 amino groups of insulin are BOC-protected as described in the Examples so that each insulin can only react at the Gly-A1 α-amino group. In certain embodiments, approximately one equivalent of BOC2-insulin as a solution in DMSO is added at room temperature to a solution of a prefunctionalized ligand framework in DMSO containing excess triethylamine and allowed to react for an appropriate amount of time. In certain embodiments, the reaction takes place in approximately one hour. In some embodiments, the resulting conjugate is purified via reverse phase HPLC (C8, acetonitrile/water mobile phase containing 0.1% TFA) to purify the desired product from unreacted BOC2-insulin. In certain embodiments, the desired elution peak is collected pooled and rotovapped to remove acetonitrile followed by lyophilization to obtain a dry powder. Finally, the BOC protecting groups are removed by dissolving the lyophilized powder in 90% TFA/10% anisole for one hour at 4 C followed by 1× superdilution in HEPES pH 8.2 buffer containing 0.150 M NaCl. The pH is adjusted to between 7.0 and 8.0 using NaOH solution after which the material is passed through a Biogel P2 column to remove anisole, BOC, and any other contaminating salts. The deprotected, purified aqueous conjugate solution is then concentrated to the desired level and stored at 4 C until needed.

In another aspect, reaction may take place at the B29 epsilon-amino group using unprotected insulin in carbonate buffer, since under those conditions the B29 amino group is the most reactive of the three amino groups present in wild-type insulin. In an exemplary synthesis, a PLF as described in the Examples is dissolved in anhydrous DMSO. The solution is stirred rapidly for a desired amount of time at room temperature. The unprotected insulin is then dissolved separately at 17.2 mM in sodium carbonate buffer (0.1 M, pH 11) and the pH subsequently adjusted to 10.8 with 1.0 N sodium hydroxide. Once dissolved, the PLF/DMSO solution is added dropwise to the insulin molecule/carbonate buffer solution. During the addition, the pH of the resulting mixture is adjusted periodically to 10.8 if necessary using dilute HCl or NaOH. The solution is allowed to stir for a desired amount of time after the dropwise addition to ensure complete reaction.

Conjugation Using N-Terminal Protecting Amino Acid Sequences

In certain embodiments, a recombinant insulin molecule that includes one or more N-terminal protecting amino acid sequences comprises an amino acid sequence of SEQ ID NO:3 (A-peptide) and an amino acid sequence of SEQ ID NO:4 (B-peptide) and three disulfide bridges as shown in formula $X^I$ herein, where Xaa at position A0 and B0 each include an N-terminal protecting amino acid sequence which may be the same or different.

It is to be understood that Xaa at positions A8, A9, A10, A18, A21, A22, B3, B28, B29, B30 and B31 of formula $X^I$ may be defined in accordance with any of the insulin molecules of formula $X^I$ that are described herein (including those set forth in Tables 1-3). In certain embodiments, A8, A9, A10, and B30 are selected from those shown in Table 3. In certain embodiments, A18 is Asn, Asp or Glu. In certain embodiments, A21 is Asn, Asp, Glu, Gly or Ala. In certain embodiments, A22, B30 and B31 are missing. In certain embodiments, B3 is Asn, Lys, Asp or Glu. In certain embodiments, B28 is Pro, Ala, Lys, Leu, Val, or Asp. In certain embodiments, B29 is Lys, Pro, or Glu. In certain embodiments, B29 is Lys.

In certain embodiments, A8, A9, A10, and B30 are selected from those shown in Table 3; A18 is Asn, Asp or Glu; A21 is Asn, Asp, Glu, Gly or Ala; A22, B30 and B31 are missing; B3 is Asn, Lys, Asp or Glu; B28 is Pro, Ala, Lys, Leu, Val, or Asp; and B29 is Lys.

In certain embodiments A22, B30 and B31 are missing and A8, A9, A10, A18, A21, B3, B28, and B29 are the same as in wild-type human insulin.

In certain embodiments, the N-terminal protecting amino acid sequence comprises the motif [Asp/Glu]-Xaa'''-Arg at the C-terminus where Xaa''' is missing or is a sequence of 1-10 codable amino acids with the proviso that Xaa''' does not include Arg.

In certain embodiments, Xaa''' does not include Cys or Lys.

In certain embodiments, Xaa''' includes 1-10 occurrences of Asp. In certain embodiments, Xaa''' includes 1-10 occurrences of Glu. In certain embodiments, Xaa''' includes 1-5 occurrences of Asp and 1-5 occurrences of Glu.

In certain embodiments, Xaa''' is Pro. In certain embodiments, Xaa''' includes Pro at the C-terminus. In certain embodiments, Xaa''' includes Pro at the C-terminus and 1-10 occurrences of Asp. In certain embodiments, Xaa''' includes Pro at the C-terminus and 1-10 occurrences of Glu. In certain embodiments, Xaa''' includes Pro at the C-terminus, 1-5 occurrences of Asp and 1-5 occurrences of Glu.

In certain embodiments, Xaa''' is Gly. In certain embodiments, Xaa''' includes Gly at the C-terminus. In certain embodiments, Xaa''' includes Gly at the C-terminus and 1-10 occurrences of Asp. In certain embodiments, Xaa''' includes Gly at the C-terminus and 1-10 occurrences of Glu. In certain embodiments, Xaa''' includes Gly at the C-terminus, 1-5 occurrences of Asp and 1-5 occurrences of Glu.

In certain embodiments, the N-terminal protecting amino acid sequence comprises the motif [Asp/Glu]-[Asp/Glu]-Arg at the C-terminus.

In certain embodiments, the N-terminal protecting amino acid sequence comprises the motif [Asp/Glu]-Asp-Arg at the C-terminus.

In certain embodiments, the N-terminal protecting amino acid sequence comprises the motif [Asp/Glu]-Glu-Arg at the C-terminus.

In certain embodiments, the N-terminal protecting amino acid sequence comprises the motif Asp-[Asp/Glu]-Arg at the C-terminus.

In certain embodiments, the N-terminal protecting amino acid sequence comprises the motif Glu-[Asp/Glu]-Arg at the C-terminus.

In certain embodiments, the N-terminal protecting amino acid sequence comprises the motif [Asp/Glu]-[Asp/Glu]-[Asp/Glu]-[Asp/Glu]-Pro-Arg at the C-terminus (SEQ ID NO:5).

In certain embodiments, the N-terminal protecting amino acid sequence comprises the motif [Asp/Glu]-[Asp/Glu]-Gly-[Asp/Glu]-Xaa'''-Arg at the C-terminus where Xaa''' is any codable amino acid (SEQ ID NO:6). In certain embodiments, Xaa''' is Gly. In certain embodiments, Xaa''' is Pro.

In certain embodiments, the N-terminal protecting amino acid sequence comprises the motif Asp-Asp-Gly-Asp-Pro-Arg at the C-terminus (SEQ ID NO:7).

In certain embodiments, the N-terminal protecting amino acid sequence comprises the motif Glu-Glu-Gly-Glu-Pro-Arg at the C-terminus (SEQ ID NO:8).

In certain embodiments, the N-terminal protecting amino acid sequence comprises the motif Asp-Asp-Gly-Asp-Gly-Arg at the C-terminus (SEQ ID NO:9).

In certain embodiments, the N-terminal protecting amino acid sequence comprises the motif Glu-Glu-Gly-Glu-Gly-Arg at the C-terminus (SEQ ID NO:10).

In certain embodiments, the N-terminal protecting amino acid sequence comprises the motif Asp-Glu-Arg at the C-terminus (SEQ ID NO:11).

In certain embodiments, the N-terminal protecting amino acid sequence consists of one of the aforementioned motifs. In certain embodiments, Xaa at position A0 consists of one of the aforementioned motifs. In certain embodiments, Xaa at position B0 consists of one of the aforementioned motifs. In certain embodiments, Xaa at position A0 and B0 both consist of one of the aforementioned motifs. In certain embodiments, Xaa at position A0 and B0 both consist of the same one of the aforementioned motifs.

In certain embodiments, the present disclosure provides a method comprising steps of: (a) performing an amide conjugation between a prefunctionalized ligand framework that includes a terminal activated ester and an insulin molecule that includes N-terminal protecting amino acid sequences to produce one or more conjugated insulin intermediates and (b) cleaving the N-terminal protecting amino acid sequences from the one or more conjugated insulin intermediates with a protease that cleaves on the C-terminal side of Arg. In some embodiments, the protease is trypsin. In some embodiments, the protease is a trypsin-like protease.

In certain embodiments, the insulin molecule is as shown in formula $X^I$ where Xaa at position B29 is Lys and the method produces an insulin molecule of formula $X^I$ where A0 and B0 are missing and a prefunctionalized ligand framework is conjugated at $Lys^{B29}$.

It will be appreciated that exemplary conjugation procedures described herein and in the Examples may be used to produce other conjugates with different ligands and insulin molecules, different conjugation chemistries, different separations between framework components, and/or different valencies by substituting these exemplary frameworks with a different framework.

Furthermore, ligands already containing a predetermined degree of multivalency may again be reacted according to the procedures described above to produce even higher orders of ligand multiplicity. For example, a divalent saccharide molecule containing a terminal reactive amine may be prepared by conjugating two of each ligand to a suitable framework to which a reactive amine is also conjugated. A trivalent saccharide molecule containing a terminal reactive amine may be prepared by conjugating three of each ligand to a suitable framework to which a reactive amine is also conjugated. The $NH_2$-divalent saccharides may be reacted with the same frameworks described above to produce insulin molecule conjugates with 4 and 6 ligands per insulin molecule. The $NH_2$-trivalent saccharides may be reacted with the same frameworks described above to produce insulin molecule conjugates with 6 and 9 ligands per insulin molecule.

In all cases, it should be recognized that a mixture of different ligands may be conjugated to the same insulin molecule via a multivalent framework by adjusting the framework chemistry, valency, and the ligand:framework stoichiometry.

PK and PD Properties

In certain embodiments, a conjugate of the present disclosure displays a protracted PK profile (e.g., a zero-order PK profile).

In certain embodiments, the pharmacokinetic and/or pharmacodynamic behavior of a conjugate (i.e., conjugated insulin molecule and/or insulin molecule which has been released from a conjugate by chemical or enzymatic degradation) may be modified by variations in the serum concentration of a saccharide. For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In certain embodiments, the serum concentration curve of a conjugate is substantially different when administered to the mammal under fasted and hyperglycemic conditions. As used herein, the term "substantially different" means that the two curves are statistically different as determined by a student t-test ($p<0.05$). As used herein, the term "fasted conditions" means that the serum concentration curve was obtained by combining data from five or more fasted non-diabetic individuals. In certain embodiments, a fasted non-diabetic individual is a randomly selected 18-30 year old human who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose $C_{max}$ at least 100 mg/dL above the mean glucose concentration observed under fasted conditions) were induced by concurrent administration of conjugate and glucose. Concurrent administration of conjugate and glucose simply requires that the glucose $C_{max}$ occur during the period when the conjugate is present at a detectable level in the serum. For example, a glucose injection (or ingestion) could be timed to occur shortly before, at the same time or shortly after the conjugate is administered. In certain embodiments, the conjugate and glucose are administered by different routes or at different locations. For example, in certain embodiments, the conjugate is administered subcutaneously while glucose is administered orally or intravenously.

In certain embodiments, the serum $C_{max}$ of the conjugate is higher under hyperglycemic conditions as compared to fasted conditions. Additionally or alternatively, in certain embodiments, the serum area under the curve (AUC) of the conjugate is higher under hyperglycemic conditions as compared to fasted conditions. In various embodiments, the serum elimination rate of the conjugate is slower under hyperglycemic conditions as compared to fasted conditions. As discussed in the Examples, we have found that in certain embodiments, the serum concentration curve of the conjugates can be fit using a two-compartment bi-exponential model with one short and one long half-life. The long half-life appears to be particularly sensitive to glucose concentration. Thus, in certain embodiments, the long half-life is longer under hyperglycemic conditions as compared to fasted conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$ in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/dl). Glucose concentrations below 60 mg/dL are considered hypoglycemic. Glucose concentrations above 200 mg/dL are considered hyperglycemic. In certain embodiments, the PK properties of the conjugate may be tested using a glucose clamp method (see Examples) and the serum concentration curve of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum T, serum $C_m$ax, mean serum residence time (MRT), mean serum absorption time (MAT) and/or serum half-life may be substantially different at the two glucose concentrations. As discussed below, in certain embodiments, 100 mg/dL and 300 mg/dL may be used as comparative glucose concentrations. It is to be understood however that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc.

Thus, in certain embodiments, the $C_{max}$ of the conjugate is higher when administered to the mammal at the higher of the two glucose concentrations (e.g., 300 vs. 100 mg/dL glucose). In certain embodiments, the $C_m$ax of the conjugate is at least 50% (e.g., at least 100%, at least 200% or at least 400%) higher when administered to the mammal at the higher of the two glucose concentrations (e.g., 300 vs. 100 mg/dL glucose).

In certain embodiments, the AUC of the conjugate is higher when administered to the mammal at the higher of the two glucose concentrations (e.g., 300 vs. 100 mg/dL glucose). In certain embodiments, the AUC of the conjugate is at least 50% (e.g., at least e.g., at least 100%, at least 200% or at least 400%) higher when administered to the mammal at the higher of the two glucose concentrations (e.g., 300 vs. 100 mg/dL glucose).

In certain embodiments, the serum elimination rate of the conjugate is slower when administered to the mammal at the higher of the two glucose concentrations (e.g., 300 vs. 100 mg/dL glucose). In certain embodiments, the serum elimination rate of the conjugate is at least 25% (e.g., at least 50%, at least 100%, at least 200%, or at least 400%) faster when administered to the mammal at the lower of the two glucose concentrations (e.g., 100 vs. 300 mg/dL glucose).

As discussed herein, we have found that in certain embodiments the serum concentration curve of conjugates such as those disclosed herein can be fit using a two-compartment bi-exponential model with one short and one long half-life. The long half-life appears to be particularly sensitive to glucose concentration. Thus, in certain embodiments, the long half-life is longer when administered to the mammal at the higher of the two glucose concentrations (e.g., 300 vs. 100 mg/dL glucose). In certain embodiments, the long half-life is at least 50% (e.g., at least 100%, at least 200% or at least 400%) longer when administered to the mammal at the higher of the two glucose concentrations (e.g., 300 vs. 100 mg/dL glucose).

In certain embodiments, the present disclosure provides a method in which the serum concentration curve of a conjugate is obtained at two different glucose concentrations (e.g., 300 vs. 100 mg/dL glucose); the two curves are fit using a two-compartment bi-exponential model with one short and one long half-life; and the long half-lives obtained under the two glucose concentrations are compared. In certain embodiments, this method may be used as an assay for testing or comparing the glucose sensitivity of one or more conjugates.

In certain embodiments, the present disclosure provides a method in which the serum concentration curves of a conjugated insulin molecule and the corresponding insulin molecule that lacks the ligand(s) are obtained under the same conditions (e.g., fasted conditions); the two curves are fit using a two-compartment bi-exponential model with one short and one long half-life; and the long half-lives obtained for the two insulin molecules are compared.

As used herein, the term "conjugated" generally refers to two or more things joined together.

As used herein the term "conjugate" refers to an insulin molecule attached to two or more groups selected from a fatty chain and one or more separate ligands which each include a saccharide, said ligand optionally containing a fatty chain.

As used herein, the term "corresponding insulin molecule that lacks the ligand(s)" refers to an insulin molecule that only includes the fatty chain component of the conjugate. For example, the "corresponding insulin molecule that lacks the ligand(s)" for the following conjugate:

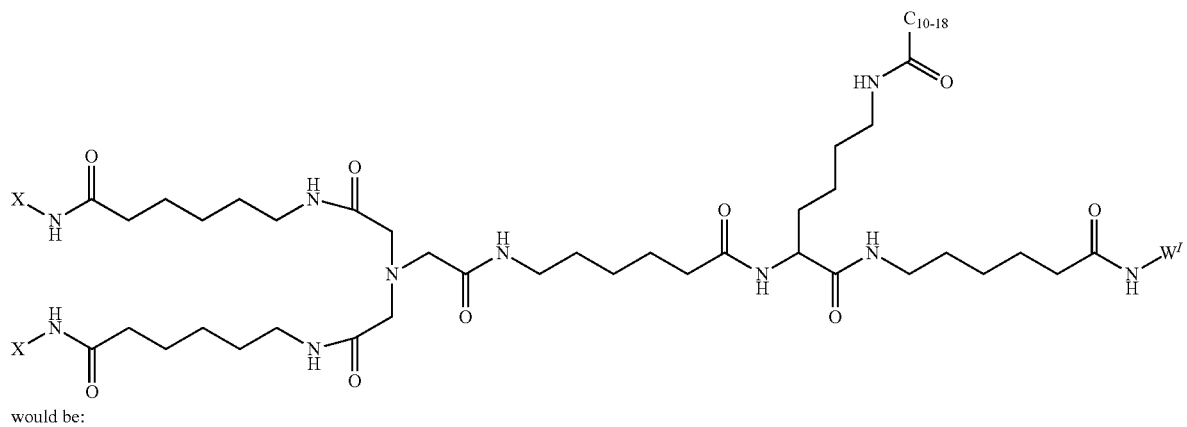

would be:

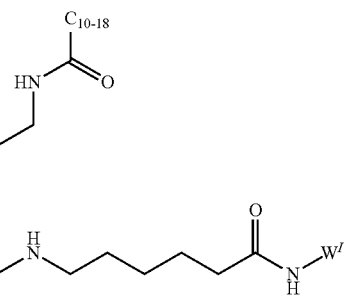

Similarly, the "corresponding insulin molecule that lacks the ligand(s)" for the following conjugate:

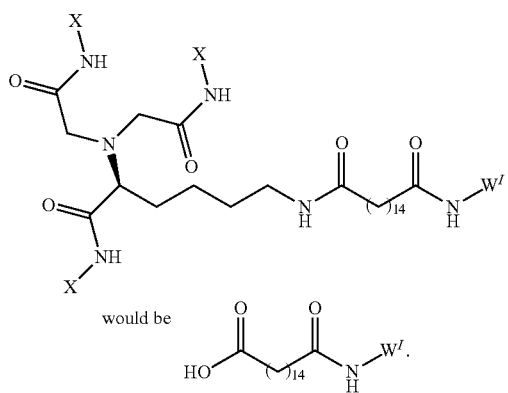

would be

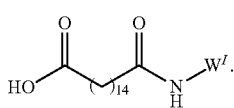

While the "corresponding insulin molecule that lacks the ligand(s)" for the following conjugate:

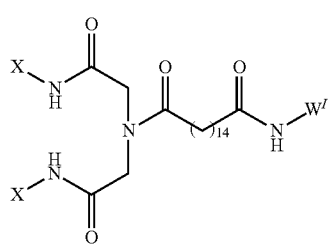

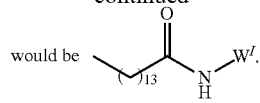

In certain embodiments, the serum concentration curve of a conjugate is substantially the same as the serum concentration curve of the corresponding insulin molecule that lacks the ligand(s) when administered to the mammal under hyperglycemic conditions. As used herein, the term "substantially the same" means that there is no statistical difference between the two curves as determined by a student t-test (p>0.05). In certain embodiments, the serum concentration curve of the conjugate is substantially different from the serum concentration curve of the corresponding insulin molecule that lacks the ligand(s) when administered under fasted conditions. In certain embodiments, the serum concentration curve of the conjugate is substantially the same as the serum concentration curve of the corresponding insulin molecule that lacks the ligand(s) when administered under hyperglycemic conditions and substantially different when administered under fasted conditions. In certain embodiments, the hyperglycemic conditions involve a glucose $C_{max}$, in excess of 200 mg/dL (e.g., 300 mg/dL, 400 mg/dL, 500 mg/dL, 600 mg/dL, etc.). In certain embodiments, the fasted conditions involve a glucose $C_{max}$, of less than 100 mg/dL (e.g., 80 mg/dL, 70 mg/dL, 60 mg/dL, 50 mg/dL, etc.). It will be appreciated that any of the aforementioned PK parameters such as serum $T_{max}$, serum $C_{max}$, AUC, mean serum residence time (MRT), mean serum absorption time (MAT) and/or serum half-life could be compared.

It is to be understood that in any of the foregoing embodiments, the serum concentration curve of a conjugate may alternatively be compared with the serum concentration curve for a specific long acting insulin molecule (e.g., insulin detemir or insulin degludec) instead of a corresponding insulin molecule that lacks the ligand(s).

From a pharmacodynamic (PD) perspective, the bioactivity of the conjugate may increase when the glucose concentration increases or when the glucose concentration crosses a threshold, e.g., is higher than normal glucose levels. In certain embodiments, the bioactivity of a conjugate is lower when administered under fasted conditions as compared to hyperglycemic conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$, in excess of 200 mg/dL (e.g., 300 mg/dL, 400 mg/dL, 500 mg/dL, 600 mg/dL, etc.).

In certain embodiments, the PD properties of the conjugate may be tested by measuring the glucose infusion rate (GIR) required to maintain a steady glucose concentration. According to such embodiments, the bioactivity of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in certain embodiments, the bioactivity of the conjugate is higher when administered to the mammal at the higher of the two glucose concentrations (e.g., 300 vs. 100 mg/dL glucose). In certain embodiments, the bioactivity of the conjugate is at least 25% (e.g., at least 50% or at least 100%) higher when administered to the mammal at the higher of the two glucose concentrations (e.g., 300 vs. 100 mg/dL glucose).

In certain embodiments, the PD behavior for insulin can be observed by comparing the time to reach minimum blood glucose concentration ($T_{nadir}$), the duration over which the blood glucose level remains below a certain percentage of the initial value (e.g., 70% of initial value or $T_{70\% BGL}$), etc.

In general, it will be appreciated that any of the PK and PD characteristics discussed in this section can be determined according to any of a variety of published pharmacokinetic and pharmacodynamic methods (e.g., see Baudys et al., *Bioconjugate Chem.* 9:176-183, 1998 for methods suitable for subcutaneous delivery). It is also to be understood that the PK and/or PD properties may be measured in any mammal (e.g., a human, a rat, a cat, a minipig, a dog, etc.). In certain embodiments, PK and/or PD properties are measured in a human. In certain embodiments, PK and/or PD properties are measured in a rat. In certain embodiments, PK and/or PD properties are measured in a minipig. In certain embodiments, PK and/or PD properties are measured in a dog.

It will also be appreciated that while the foregoing was described in the context of glucose-responsive conjugates, the same properties and assays apply to conjugates that are responsive to other saccharides including exogenous saccharides, e.g., mannose, L-fucose, N-acetyl glucosamine, alpha-methyl mannose, maltose and/or cellobiose, etc. As discussed in more detail below, instead of comparing PK and/or PD properties under fasted and hyperglycemic conditions, the PK and/or PD properties may be compared under fasted conditions with and without administration of the exogenous saccharide. It is to be understood that conjugates can be designed that respond to different $C_{max}$ values of a given exogenous saccharide.

Sustained Release Formulations

As discussed in the Examples, in certain embodiments it may be advantageous to administer a conjugate in a sustained release formulation. This will provide an even more sustained level of conjugate. In certain embodiments, the sustained release formulation may exhibit a zero-order release of the conjugate when administered to a mammal under non-hyperglycemic conditions (i.e., fasted conditions).

It will be appreciated that any formulation that provides a sustained absorption profile may be used. In certain embodiments this may be achieved by combining the conjugate with other ingredients that slow its release properties into systemic circulation.

For example, PZI (protamine zinc insulin) formulations may be used for this purpose. In certain embodiments the absorption profile and stability of PZI formulations prepared with conjugates of the present disclosure are sensitive to the absolute and relative amounts of protamine and zinc included in the formulation. For example, whereas commercial PZI and NPH (neutral protamine Hagedorn) insulin formulations require only about 0.05 to about 0.2 mg protamine/mg insulin, some PZI-conjugate preparations required about 1 to about 5 mg protamine/mg conjugate in order to effectively sustain the absorption profile. Furthermore, while commercial protamine insulin preparations contain about 0.006 mg zinc/mg insulin, increasing the zinc concentration along with the protamine concentration can, in certain embodiments, lead to more stable, easily dispersible formulations. In some embodiments, the zinc content is in the range of about 0.05 to about 0.5 mg zinc/mg conjugate.

In certain embodiments, a formulation of the present disclosure includes from about 0.05 to about 10 mg protamine/mg conjugate. For example, from about 0.2 to about 10 mg protamine/mg conjugate, e.g., about 1 to about 5 mg protamine/mg conjugate.

In certain embodiments, a formulation of the present disclosure includes from about 0.006 to about 0.5 mg zinc/mg conjugate. For example, from about 0.05 to about 0.5 mg zinc/mg conjugate, e.g., about 0.1 to about 0.25 mg zinc/mg conjugate.

In certain embodiments, a formulation of the present disclosure includes protamine and zinc in a ratio (w/w) in the range of about 100:1 to about 5:1, for example, from about 50:1 to about 5:1, e.g., about 40:1 to about 10:1. In certain embodiments, a PZI formulation of the present disclosure includes protamine and zinc in a ratio (w/w) in the range of about 20:1 to about 5:1, for example, about 20:1 to about 10:1, about 20:1 to about 15:1, about 15:1 to about 5:1, about 10:1 to about 5:1, about 10:1 to about 15:1.

In certain embodiments a formulation of the present disclosure includes an antimicrobial preservative (e.g., m-cresol, phenol, methylparaben, or propylparaben). In certain embodiments the antimicrobial preservative is m-cresol. For example, in certain embodiments, a formulation may include from about 0.1 to about 1.0% v/v m-cresol. For example, from about 0.1 to about 0.5% v/v m-cresol, e.g., about 0.15 to about 0.35% v/v m-cresol.

In certain embodiments a formulation of the present disclosure includes a polyol as isotonic agent (e.g., mannitol, propylene glycol or glycerol). In certain embodiments the isotonic agent is glycerol. In certain embodiments, the isotonic agent is a salt, e.g., NaCl. For example, a formulation may comprise from about 0.05 to about 0.5 M NaCl, e.g., from about 0.05 to about 0.25 M NaCl or from about 0.1 to about 0.2 M NaCl.

In certain embodiments a formulation of the present disclosure includes an amount of unconjugated insulin molecule. In certain embodiments, a formulation includes a molar ratio of conjugated insulin molecule to unconjugated insulin molecule in the range of about 100:1 to 1:1, e.g., about 50:1 to 2:1 or about 25:1 to 2:1.

The present disclosure also encompasses the use of standard sustained (also called extended) release formulations that are well known in the art of small molecule formulation (e.g., see *Remington's Pharmaceutical Sciences*, 19$^{th}$ ed., Mack Publishing Co., Easton, Pa., 1995). The present disclosure also encompasses the use of devices that rely on pumps or hindered diffusion to deliver a conjugate on a gradual basis.

Uses of Conjugates

In another aspect, the present disclosure provides methods of using conjugates. In general, the conjugates can be used to controllably provide a bioactive insulin molecule in response to a saccharide (e.g., glucose or an exogenous saccharide such as mannose, alpha-methyl mannose, L-fucose, etc. as described herein). The disclosure encompasses treating a disease or condition by administering a conjugate of the present disclosure. Although the conjugates can be used to treat any patient (e.g., dogs, cats, cows, horses, sheep, pigs, mice, etc.), they are most preferably used in the treatment of humans. A conjugate can be administered to a patient by any route. In general the most appropriate route of administration will depend upon a variety of factors including the nature of the disease or condition being treated, the nature of the insulin molecule, the condition of the patient, etc. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences*, 19$^{th}$ ed., Mack Publishing Co., Easton, Pa., 1995. In various embodiments, the conjugate may be administered subcutaneously, e.g., by injection. The conjugate can be dissolved in a carrier for ease of delivery. For example, the carrier can be an aqueous solution including, but not limited to, sterile water, saline or buffered saline.

In general, a therapeutically effective amount of an insulin molecule in the form of a conjugate will be administered. By a "therapeutically effective amount" of an insulin molecule is meant a sufficient amount of the insulin molecule to treat the disease or condition at a reasonable benefit/risk ratio, which involves a balancing of the efficacy and toxicity of the insulin molecule. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD^{50}$ (the dose that is lethal to 50% of treated subjects). The $ED_{50}/LD^{50}$ represents the therapeutic index of the insulin molecule. Ultimate selection of an appropriate range of doses for administration to humans is determined in the course of clinical trials.

In various embodiments, the average daily dose of an insulin molecule is in the range of 10 to 200 U, e.g., 25 to 100 U (where 1 Unit of insulin molecule is 0.04 mg). In certain embodiments, an amount of conjugate with these insulin doses is administered on a daily basis. In certain embodiments, an amount of conjugate with 5 to 10 times these insulin doses is administered on a weekly basis. In certain embodiments, an amount of conjugate with 10 to 20 times these insulin doses is administered on a bi-weekly basis. In certain embodiments, an amount of conjugate with 20 to 40 times these insulin doses is administered on a monthly basis.

In certain embodiments, a conjugate of the present disclosure may be used to treat hyperglycemia in a patient (e.g., a mammalian patient). In certain embodiments, the patient is diabetic. However, the present methods are not limited to treating diabetic patients. For example, in certain embodiments, a conjugate may be used to treat hyperglycemia in a patient with an infection associated with impaired glycemic control. In certain embodiments, a conjugate may be used to treat diabetes.

In certain embodiments, when a conjugate or formulation of the present disclosure is administered to a patient (e.g., a mammalian patient) it induces less hypoglycemia than an unconjugated version of the insulin molecule. In certain embodiments, a formulation of the present disclosure induces a lower HbA1c value in a patient (e.g., a mammalian patient) than a formulation comprising an unconjugated version of the insulin molecule. In certain embodiments, the formulation leads to an HbA1c value that is at least 10% lower (e.g., at least 20% lower, at least 30% lower, at least 40% lower, at least 50% lower) than a formulation comprising an unconjugated version of the insulin molecule. In certain embodiments, the formulation leads to an HbA1c value of less than 7%, e.g., in the range of about 4 to about 6%. In certain embodiments, a formulation comprising an unconjugated version of the insulin molecule leads to an HbA1c value in excess of 7%, e.g., about 8 to about 12%.

It will be understood that the total daily usage of a drug for any given patient will be decided by the attending physician within the scope of sound medical judgment. The specific therapeutically effective amount for any particular patient will depend upon a variety of factors including the disease or condition being treated; the activity of the specific insulin molecule employed; the specific composition employed; the age, body weight, general health, sex and diet of the patient; the time of administration, route of administration and rate of excretion of the specific insulin molecule employed; the duration of the treatment; drugs used in combination or coincidental with the specific insulin molecule employed; and like factors well known in the medical arts. In various embodiments, a conjugate of the present disclosure may be administered on more than one occasion. For example, the present disclosure specifically encompasses methods in which a conjugate is administered by subcutaneous injection to a patient on a continuous schedule (e.g., once a day, once every two days, once a week, once every two weeks, once a month, etc.).

In various embodiments, a conjugate of the present disclosure may be administered to a patient who is receiving at least one additional therapy. In various embodiments, the at least one additional therapy is intended to treat the same disease or disorder as the administered conjugate. In various embodiments, the at least one additional therapy is intended to treat a side-effect of the conjugate. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. In certain embodiments, an unconjugated secondary drug may be admixed with a conjugate of the present disclosure (i.e., a drug which is simply mixed with the conjugate formulation and not covalently bound to the conjugate). For example, in certain embodiments, any of these approaches may be used to administer more than one anti-diabetic drug to a subject.

Insulin sensitizers (e.g., biguanides such as metformin, glitazones) act by increasing a patient's response to a given amount of insulin. A patient receiving an insulin sensitizer will therefore require a lower dose of an insulin conjugate of the present disclosure than an otherwise identical patient would. Thus, in certain embodiments, an insulin conjugate may be administered to a patient who is also being treated with an insulin sensitizer. In various embodiments, the conjugate of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the conjugates of the present disclosure are only effective for this subclass of patients when they provide high levels of bioactive insulin in a suitable timeframe. In certain embodiments, the treatment of this subclass of patients may be facilitated by combining the two approaches. Thus in certain embodiments, a traditional insulin-based therapy is used to provide a baseline level of insulin and a conjugate of the present invention is administered to provide a controlled supplement of bioactive insulin when needed by the patient. Thus, in certain embodiments, insulin conjugates may be administered to a patient who is also being treated with insulin. In various embodiments, the insulin may be administered at up to 75% of the normal dose required in the absence of a conjugate of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

Exogenous Trigger

As mentioned previously, the methods, conjugates and compositions that are described herein are not limited to glucose responsive-conjugates. Several exemplary glucose-responsive conjugates are also responsive to exogenous saccharides such as mannose, L-fucose, N-acetyl glucosamine, alpha-methyl mannose, maltose and/or cellobiose. It will therefore be appreciated that in certain embodiments a conjugate may be triggered by exogenous administration of a saccharide other than glucose such as mannose, L-fucose, N-acetyl glucosamine, alpha-methyl mannose, maltose and/or cellobiose or any other saccharide that can alter the PK or PD properties of the conjugate.

Once a conjugate has been administered as described above, it can be triggered by administration of a suitable exogenous saccharide. In a certain embodiment, a triggering amount of the exogenous saccharide is administered. As used herein, a "triggering amount" of exogenous saccharide is an amount sufficient to cause a change in at least one PK and/or PD property of the conjugate (e.g., $C_{max}$, AUC, half-life, etc. as discussed previously). It is to be understood that any of the aforementioned methods of administration for the conjugate apply equally to the exogenous saccharide.

It is also be to be understood that the methods of administration for the conjugate and exogenous saccharide may be the same or different. In various embodiments, the methods of administration are different (e.g., for purposes of illustration the conjugate may be administered by subcutaneous injection on a weekly basis while the exogenous saccharide is administered orally on a daily basis). The oral administration of an exogenous saccharide is of particular value since it facilitates patient compliance. In general, it will be appreciated that the PK and PD properties of the conjugate will be related to the PK profile of the exogenous saccharide. Thus, the conjugate PK and PD properties can be tailored by controlling the PK profile of the exogenous saccharide. As is well known in the art, the PK profile of the exogenous saccharide can be tailored based on the dose, route, frequency and formulation used. For example, if a short and intense activation of the conjugate is desired then an oral immediate release formulation might be used. In contrast, if a longer less intense activation of conjugate is desired then an oral extended release formulation might be used instead. General considerations in the formulation and manufacture of immediate and extended release formulation may be found, for example, in *Remington's Pharmaceutical Sciences*, 19$^{th}$ ed., Mack Publishing Co., Easton, Pa., 1995.

It will also be appreciated that the relative frequency of administration of a conjugate of the present disclosure and an exogenous saccharide may be the same or different. In certain embodiments, the exogenous saccharide is administered more frequently than the conjugate. For example, in certain embodiment, the conjugate may be administered daily while the exogenous saccharide is administered more than once a day. In certain embodiment, the conjugate may be administered twice weekly, weekly, biweekly or monthly while the exogenous saccharide is administered daily. In certain embodiments, the conjugate is administered monthly and the exogenous saccharide is administered twice weekly, weekly, or biweekly. Other variations on these schemes will be recognized by those skilled in the art and will vary depending on the nature of the conjugate and formulation used.

The symbol "insulin" inside an oval as shown in the claims herein is intended to represent a wild-type human insulin (or des(B30) human insulin where indicated). The structure of wild-type human insulin is presented below. As discussed herein, it is to be understood that the present disclosure also encompasses inter alia versions of these and other conjugates that include an insulin molecule other than wild-type human insulin.

EXAMPLES

General Procedures

All chemicals were purchased from commercial sources, unless otherwise noted. Reactions sensitive to moisture or air were performed under nitrogen or argon using anhydrous solvents and reagents. The progress of reactions was monitored by analytical thin layer chromatography (TLC), high performance liquid chromatography-mass spectrometry (HPLC-MS), or ultra performance liquid chromatography-mass spectrometry (UPLC-MS). TLC was performed on E. Merck TLC plates precoated with silica gel 60F-254, layer thickness 0.25 mm. The plates were visualized using 254 nm UV and/or by exposure to cerium ammonium molybdate (CAM) or p-anisaldehyde staining solutions followed by charring. High performance liquid chromatography (HPLC) was conducted on an Agilent 1100 series HPLC using the following methods:

LC-MS Method A: Supelco Ascentis Express C18 2.7 μm 3.0×100 mm column with gradient 10:90-99:1 v/v $CH_3CN/H_2O$+v 0.05% TFA over 4.0 min then hold at 98:2 v/v $CH_3CN/H_2O$+v 0.05% TFA for 0.75 min; flow rate 1.0 mL/min, UV range 200-400 nm.

LC-MS Method B: Supelco Ascentis Express C18 2.7 μm 3.0×50 mm column with gradient 10:90-99:1 v/v $CH_3CN/H_2O$+v 0.05% TFA over 2.0 min then hold at 98:2 v/v $CH_3CN/H_2O$+v 0.05% TFA for 0.75 min; flow rate 1.0 mL/min, UV range 200-400 nm.

Mass analysis was performed on a Waters Micromass® ZQ™ with electrospray ionization in positive ion detection mode and the scan range of the mass-to-charge ratio was either 170-900 or 500-1500. Ultra performance liquid chromatography (UPLC) was performed on a Waters Acquity™ UPLC® system using the following methods:

UPLC-MS Method A: Waters Acquity™ UPLC® BEH C18 1.7 μm 2.1×100 mm column with 10:90-10:90 v/v $CH_3CN/H_2O$+v 0.1% TFA over 0.2 min, gradient 10:90-70:30 v/v $CH_3CN/H_2O$+v 0.1% TFA over 4.0 min and 70:30-95:5 v/v $CH_3CN/H_2O$+v 0.1% TFA over 40 sec; flow rate 0.3 mL/min, UV wavelength 200-300 nm.

UPLC-MS Method B: Waters Acquity™ UPLC® BEH C18 1.7 μm 2.1×100 mm column with 10:90-20:80 v/v $CH_3CN/H_2O$+v 0.1% TFA over 0.2 min, gradient 20:80-90:10 v/v $CH_3CN/H_2O$+v 0.1% TFA over 4.0 min and 100:0-95:5 v/v $CH_3CN/H_2O$+v 0.1% TFA over 40 sec; flow rate 0.3 mL/min, UV wavelength 200-300 nm.

UPLC-MS Method C: Waters Acquity™ UPLC® BEH C18 1.7 μm 2.1×100 mm column with 10:90-95:5 v/v $CH_3CN/H_2O$+v 0.1% TFA over 0.2 min, gradient 95:5-100:0 v/v $CH_3CN/H_2O$+v 0.1% TFA over 4.0 min and 100:0-95:5 v/v $CH_3CN/H_2O$+v 0.1% TFA over 40 sec; flow rate 0.3 mL/min, UV wavelength 200-300 nm.

UPLC-MS Method D: Waters Acquity™ UPLC® BEH C18 1.7 μm 2.1×100 mm column with 2:98-2:98 v/v $CH_3CN/H_2O$+v 0.1% TFA over 0.2 min, gradient 2:98-30:70 v/v $CH_3CN/H_2O$+v 0.1% TFA over 4.0 min and 30:70-95:5 v/v $CH_3CN/H_2O$+v 0.1% TFA over 0.05 min and hold at 95:5 v/v $CH_3CN/H_2O$+v 0.1% TFA for 0.65 min; flow rate 0.3 mL/min, UV wavelength 200-300 nm.

UPLC-MS Method E: Waters Acquity™ UPLC® BEH C18 1.7 μm 2.1×100 mm column with gradient 0:100-60:40 v/v $CH_3CN/H_2O$+v 0.1% TFA over 8.0 min and 60:40-90:10 v/v $CH_3CN/H_2O$+v 0.1% TFA over 3.0 min and hold at 100:0 v/v $CH_3CN/H_2O$+v 0.1% TFA for 2.0 min; flow rate 0.3 mL/min, UV wavelength 200-300 nm.

UPLC-MS Method F: Waters Acquity™ UPLC® BEH C8 1.7 μm 2.1×100 mm column with 10:90-10:90 v/v $CH_3CN/H_2O$+v 0.1% TFA over 0.2 min, gradient 10:90-55:45 v/v $CH_3CN/H_2O$+v 0.1% TFA over 4.0 min and 100:0-95:5 v/v $CH_3CN/H_2O$+v 0.1% TFA over 0.4 min; flow rate 0.3 mL/min, UV wavelength 200-300 nm.

UPLC-MS Method G: Waters Acquity™ UPLC® BEH C8 1.7 μm 2.1×100 mm column with 10:90-20:80 v/v $CH_3CN/H_2O$+v 0.1% TFA over 0.2 min, gradient 20:80-90:10 v/v $CH_3CN/H_2O$+v 0.1% TFA over 4.0 min and 90:10-95:5 v/v $CH_3CN/H_2O$+v 0.1% TFA over 0.4 min; flow rate 0.3 mL/min, UV wavelength 200-300 nm.

UPLC-MS Method H: Waters Acquity™ UPLC® BEH300 C4 1.7 μm 2.1×100 mm column with 10:90-10:90 v/v $CH_3CN/H_2O$+v 0.1% TFA over 0.2 min, gradient 10:90-90:10 v/v $CH_3CN/H_2O$+v 0.1% TFA over 4.0 min and 90:10-95:5 v/v $CH_3CN/H_2O$+v 0.1% TFA over 0.5 min; flow rate 0.3 mL/min, UV wavelength 200-300 nm.

UPLC-MS Method I: Waters Acquity™ UPLC® BEH300 C4 1.7 μm 2.1×100 mm column with 10:90-10:90 v/v $CH_3CN/H_2O$+v 0.1% TFA over 0.2 min, gradient 10:90-50:50 v/v $CH3CN/H2O$+v 0.1% TFA over 4.0 min and 50:50-70:30 v/v $CH3CN/H2O$+v 0.1% TFA over 0.5 min; flow rate 0.3 mL/min, UV wavelength 200-300 nm.

Mass analysis was performed on a Waters Micromass® LCT Premier™ XE with electrospray ionization in positive ion detection mode and the scan range of the mass-to-charge ratio was 300-2000. The identification of the produced insulin conjugates was confirmed by comparing the theoretical molecular weight to the experimental value that was measured using UPLC-MS. For the determination of the position of sugar modification(s), specifically, insulin conjugates were subjected to DTT treatment (for a/b chain) or Glu-C digestion (with reduction and alkylation), and then the resulting peptides were analyzed by LC-MS. Based on the measured masses, the sugar positions were deduced.

Flash chromatography was performed using either a Biotage Flash Chromatography apparatus (Dyax Corp.) or a CombiFlash®Rf instrument (Teledyne Isco). Normal-phase chromatography was carried out on silica gel (20-70 μm, 60 Å pore size) in pre-packed cartridges of the size noted. Reverse-phase chromatography was carried out on C18-bonded silica gel (20-60 μm, 60-100 Å pore size) in pre-packed cartridges of the size noted. Preparative scale HPLC was performed on Gilson 333-334 binary system using Waters Delta Pak C4 15 μm, 300 Å, 50×250 mm column or Kromasil® C8 10 μm, 100 Å, 50×250 mm column, flow rate 85 mL/min, with gradient noted. Concentration of solutions was carried out on a rotary evaporator under reduced pressure or freeze-dried on a VirTis Freezemobile Freeze Dryer (SP Scientific).

$^1$H NMR spectra were acquired at 500 MHz (or otherwise specified) spectrometers in deuterated solvents noted. Chemical shifts were reported in parts per million (ppm). Tetramethylsilane (TMS) or residual proton peak of deutrated solvents was used as an internal reference. Coupling constant (J) were reported in hertz (Hz).

Abbreviations: acetic acid (AcOH), acetonitrile (AcCN), aqueous (aq), O-(7-azabenzotriazol-1-yl)-N,N,N',N'-tetramethyluronium hexafluorophosphate) (HATU), column volume (CV), dichloromethane (DCM), diethyl ether (ether or $Et_2O$), N,N-diisopropylethylamine or Hünig's base (DIPEA), N,N-dimethylacetamide (DMA), (4-dimethylamino)pyridine (DMAP), N,N-dimethylformamide (DMF), ethyl acetate (EtOAc), disuccinimidyl suberate (DSS), N-(3-dimethylaminopropyl)-N'-ethylcarbodiimide hydrochloride (EDC), gram(s) (g), 1-hydroxybenzotriazole hydrate (HOBt), hour(s) (h or hr), mass spectrum (ms or MS), N-methylmorpholine (NMM), microliter(s) (L), milligram(s) (mg), milliliter(s) (mL), millimole (mmol), minute(s) (min), pentafluorphenol-tetramethyluronium hexafluorophosphate (PFTU), petroleum ether (PE), retention time ($t_R$), room temperature (rt), saturated (sat. or sat'd), saturated aq sodium chloride solution (brine), triethylamine (TEA), trifluoroacetic acid (TFA), trifluoroacetic anhydride (TFAA), tetrahydrofuran (THF), and N,N,N',N'-tetramethyl-O—(N-succinimidyl)uronium tetrafluoroborate (TSTU).

The following preparative examples are non-limiting examples of oligosaccharide linkers useful in the instant invention.

Preparative Example 1

The synthesis of oligosaccharide linker 2,5-dioxopyrrolidin-1-yl 6-[(2-{[α-D-mannopyranosyl-(1→3)-[α-D-mannopyranosyl-(1→6)]-α-D-mannopyranosyl]oxy}ethyl)amino]-6-oxohexanoate (ML-1) having the following structure is described.

ML-1

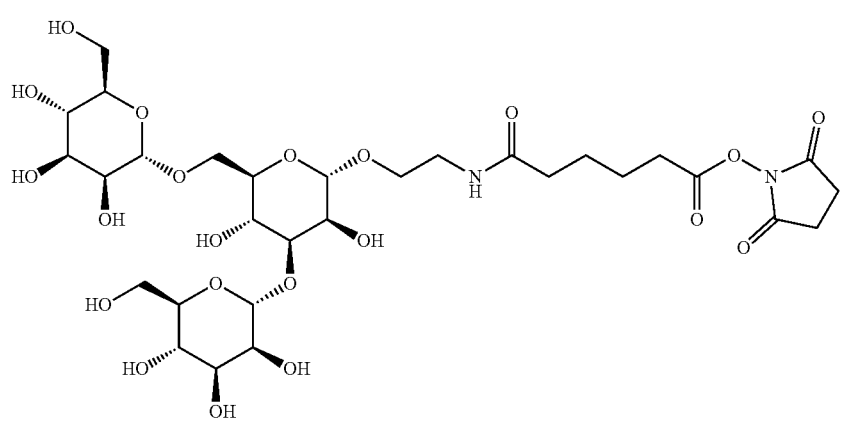

Step A. benzyl 6-[(2,5-dioxopyrrolidin-1-yl)oxy]-6-oxohexanoate

To a solution of 6-(benzyloxy)-6-oxohexanoic acid (3.3 g, 13.97 mmol) in DMF (50 mL) at 0° C. was added TSTU (4.3 g, 14.28 mmol) and DIPEA (2.5 mL, 14.31 mmol). After stirring at 0° C. for 1 hr, the reaction mixture was partitioned between Et$_2$O and water. The organic layer was separated and the aqueous layer was further extracted with ether (2×150 mL). The combined organic phase was washed with brine, dried over Na$_2$SO$_4$, filtered and concentrated to afford the title compound. UPLC-MS Method B: calculated for C$_{17}$H$_{19}$NO$_6$ 333.12, observed m/z: 334.10 (z=1); t$_R$=3.75 min. $^1$H NMR (CDCl$_3$) δ 7.40-7.30 (5H, m), 5.10 (2H, s), 2.80 (4H, s), 2.62-2.58 (2H, m), 2.41-2.37 (2H, m), 1.80-1.72 (4H, m).

Step B. benzyl 6-({2-[(α-D-mannopyranosyl-(1→3)-[α-D-mannopyranosyl-(1→6)]-α-D-mannopyranosyl)oxy]ethyl}amino)-6-oxohexanoate To a solution of 2-aminoethyl α-D-mannopyranosyl-(1→3)-[α-D-mannopyranosyl-(1→6)]-α-D-mannopyranoside (1.23 g, 2.247 mmol, WO 2010/088294 A1) in DMF (20 mL) at 0° C. was added benzyl 6-[(2,5-dioxopyrrolidin-1-yl)oxy]-6-oxohexanoate (1.02 g, 3.06 mmol) and TEA (0.5 mL, 3.59 mmol). After stirring at 0° C. for 1 hr, the reaction mixture was concentrated and the residue was purified by flash chromatography on C18 reverse phase silica gel column (275 g), eluting with 0-40% AcCN in H$_2$O, to give the title compound. UPLC-MS Method A: calculated for C$_{33}$H$_{51}$NO$_{19}$ 765.31, observed m/z=766.26 (z=1); t$_R$=4.04 min. $^1$H NMR (D$_2$O) δ 7.43-7.37 (5H, m), 5.14 (2H, s), 5.07-5.06 (1H, m), 4.82-4.81 (1H, m), 4.77-4.76 (1H, m), 4.06-4.01 (2H, m), 3.96-3.92 (2H, m), 3.87-3.81 (5H, m), 3.79-3.77 (1H, m), 3.74-3.67 (5H, m), 3.65-3.60 (4H, m), 3.53-3.49 (1H, m), 3.37-3.35 (2H, m), 2.43-2.40 (2H, m), 2.22-2.19 (2H, m), 1.62-1.52 (4H, m).

Step C. 6-({2-[(α-D-mannopyranosyl-(1→3)-[α-D-mannopyranosyl-(1→6)]-α-D-mannopyranosyl)oxy]ethyl}amino)-6-oxohexanoic acid A mixture of benzyl 6-({2-[(α-D-mannopyranosyl-(1→3)-[α-D-mannopyranosyl-(1→6)]-α-D-mannopyranosyl)oxy]ethyl}amino)-6-oxohexanoate (1.15 g, 1.502 mmol) and Pd/C (80 mg, 0.075 mmol) in water (10 mL) was degassed and allowed to stir under a balloon of H$_2$ at rt for 16 hr. The catalyst was filtered off and washed with H$_2$O (3×10 mL). The filtrate was freeze-dried to give the title compound. UPLC-MS Method A: calculated for C$_{26}$H$_{45}$NO$_{19}$ 675.26, observed m/z: 676.21 (z=1); t$_R$=3.50 min.

Step D. 2,5-dioxopyrrolidin-1-yl 6-[(2-{[α-D-mannopyranosyl-(1→3)-[α-D-mannopyranosyl-(1→6)]-α-D-mannopyranosyl]oxy}ethyl)amino]-6-oxohexanoate To a solution of 6-({2-[(α-D-mannopyranosyl-(1→3)-[α-D-mannopyranosyl-(1→6)]-α-D-mannopyranosyl)oxy]ethyl}amino)-6-oxohexanoic acid (1.55 g, 2.294 mmol) in DMF (22 mL) at 0° C. was added TSTU (760 mg, 2.52 mmol) and DIPEA (0.52 mL, 2.98 mmol). After stirring at 0° C. for 1 hr, the reaction was quenched by the addition of TFA (371 μL, 4.82 mmol) and the resulting mixture was concentrated down to about 3 mL. The residue was transferred dropwise, via autopipette, to a tube containing anhydrous AcCN (45 mL). The precipitate was collected through centrifugation (3000 rpm, 15 min, at 4° C.), washed with AcCN (1 mL) and dried to yield the title compound. UPLC-MS Method A: calculated for C$_{30}$H$_{48}$N$_2$O$_{21}$ 772.27, observed m/z: 773.23 (z=1); t$_R$=3.65 min. $^1$H NMR (D$_2$O) δ 5.07-5.06 (1H, m), 4.84-4.83 (1H, m), 4.79-4.78 (1H, m), 4.06-4.01 (2H, m), 3.96-3.93 (2H, m), 3.87-3.83 (5H, m), 3.80-3.78 (1H, m), 3.75-3.69 (5H, m), 3.67-3.61 (4H, m), 3.57-3.52 (1H, m), 3.41-3.38 (2H, m), 2.91 (4H, s), 2.75-2.71 (2H, m), 2.29-2.25 (2H, m), 1.75-1.58 (4H, m).

Preparative Example 2

The synthesis of oligosaccharide linker 2,2'-{[2-({6-[(2,5-dioxopyrrolidin-1-yl)oxy]-6-oxohexyl}amino)-2-oxoethyl]imino}bis(N-{2-[(α-L-fucopyranosyl)oxy]ethyl}acetamide) (ML-4) having the following structure is described.

ML-4

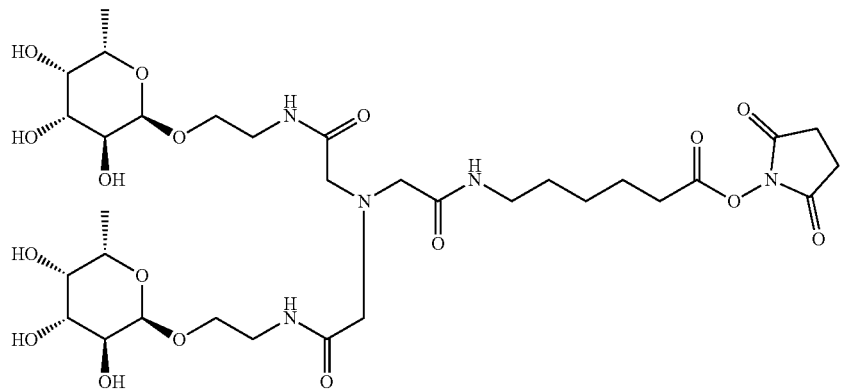

Step A. 2,2'-[(2-{[6-(benzyloxy)-6-oxohexyl]amino}-2-oxoethyl)imino]diacetic acid To a solution of 6-(benzyloxy)-6-oxohexan-1-aminium 4-methylbenzenesulfonate (2.0 g, 5.08 mmol) in DMF (10 mL) at 0° C. was added $K_2CO_3$ (738 mg, 5.34 mmol). After stirring at 0° C. for 2 hr, the supernatant of the reaction mixture was added to a solution of 3-(2,6-dioxomorpholin-4-yl)propanoic acid (1.10 g, 6.35 mmol) in DMF (10 mL) at 0° C. After stirring at 0° C. for 30 min, the reaction mixture was allowed to stir at rt for 1 hr and then cooled down to 0° C. followed by the addition of water (10 mL). The resulting mixture was concentrated and the residue was suspended in water (10 mL). After stirring at 0° C. for 16 hr, the solid was collected through filtration and dried to yield the title compound. $^1H$ NMR ($CD_3OD$) δ 7.36-7.30 (m, 5H), 5.11 (s, 2H), 3.56 (s, 4H), 3.43 (s, 2H), 3.23 (t, J=6.7, 2H), 2.39 (t, J=7.3, 2H), 1.68-1.62 (m, 2H), 1.57-1.51 (m, 2H), 1.40-1.35 (m, 2H).

Step B. benzyl 6-[({bis[2-({2-[(α-L-fucopyranosyl)oxy]ethyl}amino)-2-oxoethyl]amino}acetyl)amino]hexanoate To a solution of 2-aminoethyl α-L-fucopyranoside (7.88 g, 38.04 mmol) and 2,2'-[(2-{[6-(benzyloxy)-6-oxohexyl]amino}-2-oxoethyl)imino]diacetic acid (2.5 g, 19.02 mmol) in DMF (10 mL) was added HOBt (2.43 g, 15.85 mmol) and EDC (3.04 g, 15.85 mmol). After stirring at rt for 16 hr, the reaction mixture was concentrated and the residue was purified by flash chromatography on C18 reverse phase silica gel (120 g), eluting with 0-50% AcCN in water, to give the title compound. UPLC-MS Method B: $t_R$=3.74 min; m/z=773.292 (z=1).

Step C. 2,2'-{[2-({6-[(2,5-dioxopyrrolidin-1-yl)oxy]-6-oxohexyl}amino)-2-oxoethyl]imino}bis(N-{2-[(α-L-fucopyranosyl)oxy]ethyl}acetamide)

The title compound was prepared using procedures analogous to those described for Step C and D in Preparative Example 1 (ML-1) substituting benzyl 6-[({bis[2-({2-[(α-L-fucopyranosyl)oxy]ethyl}amino)-2-oxoethyl]amino}acetyl)amino]hexanoate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C. UPLC-MS Method B: $t_R$=2.39 min; m/z=780.265 (z=1).

Preparative Example 3

The synthesis of oligosaccharide linker 2,2'-{[2-({6-[(2,5-dioxopyrrolidin-1-yl)oxy]-6-oxohexyl}amino)-2-oxoethyl]imino}bis(N-{2-[(α-D-mannopyranosyl)oxy]ethyl}acetamide) (ML-5) having the following structure is described.

ML-5

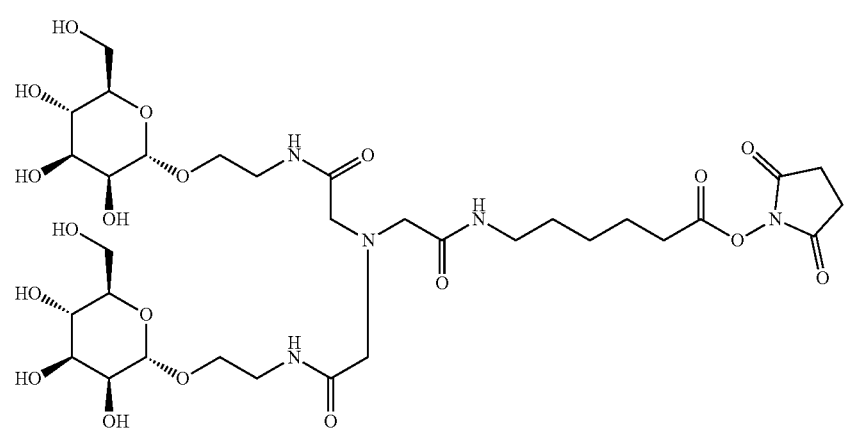

The title compound was prepared using procedure analogous to those described for Preparative Example 2 (ML-4) substituting 2-aminoethyl α-D-mannopyranoside (Bilstein J. Org. Chem. 2010, 6, 699-703) for 2-aminoethyl α-L-fucopyranoside in Step B. UPLC-MS Method A: $t_R$=4.27 min; m/z=812.38 (z=1).

Preparative Example 4

The synthesis of oligosaccharide linker 2,5-dioxopyrrolidin-1-yl 9-({3-[(α-D-mannopyranosyl)oxy]propyl}{2-[(α-L-fucopyranosyl)oxy]ethyl}amino)-9-oxononanoate (ML-8) having the following structure is described.

mixture was concentrated to give {2-[(α-L-fucopyranosyl)oxy]ethyl}-N-{3-[(α-D-mannopyranosyl)oxy]}propan-1-amine as an intermediate (LC-MS Method B: $t_R$=1.10 min, m/z=428.2252 (z=1)), which was used without further purification.

To a solution of aforementioned intermediate (250 mg, 0.585 mmol) in DMF at 0° C. was added benzyl (2,5-dioxopyrrolidin-1-yl) adipate (195 mg, 0.585 mmol) and TEA (82 μL, 0.585 mmol). After stirring at rt for 18 hr, the reaction mixture was concentrated and the residue was purified by C18 reverse phase chromatography, eluting with

ML-8

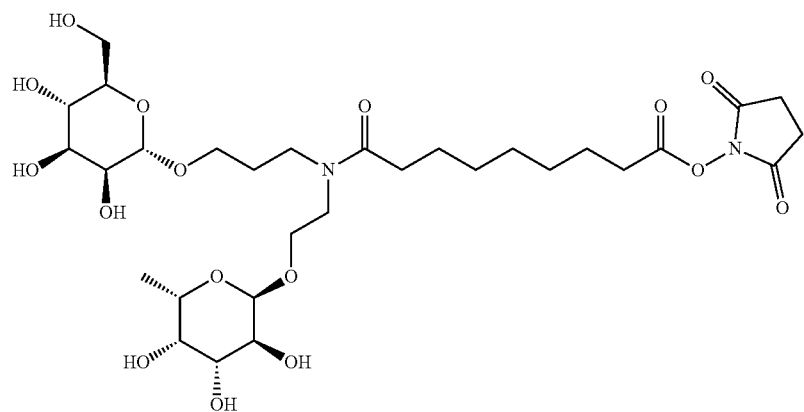

Step A. 3-iodopropyl α-D-mannopyranoside

To a solution of D-mannose (1.0 g, 5.55 mmol) and TEA (4.02 ml, 28.9 mmol) in DMF (25 mL) at 0° C. was added TMS-Cl (3.69 mL, 28.9 mmol). After stirring at rt for 4 hr, the mixture was poured into a mixture of ice and hexane (v/v=1/1, 100 mL). The aqueous layer was separated and extracted with hexane. The organic layers were combined and dried over MgSO$_4$ and filtered. The filtrate was concentrated to give the per-silayted mannose intermediate, which was dissolved in DCM (25 mL) and treated with iodotrimethylsilane (1.43 mL, 10.48 mmol) at 0° C. After stirring at rt for 1 hr, the reaction mixture was concentrated and the residue was dissolved in DCM (10 mL) and treated with oxetane (488 μL, 7.49 mmol) at 0° C. After stirring at rt for 5 hr, the reaction mixture was concentrated. To the resulting residue was added MeOH and Dowex H+ resin. After stirring for 1 hr, the reaction mixture was filtered through a pad of Celite, and the filtrate was concentrated and the residue was purified by HPLC (C8, eluting with 5-25% AcCN/water in 25 min) to give the two stereoisomers: LC-MS Method B: $t_R$=0.46 min (for 3-isomer), m/z=696.96 (z=0.5). $^1$H NMR (CD$_3$OD): 4.55 (1H, H$_1$), 3.4-4.0 (10H), 2.1 (2H); $t_R$=0.50 min (for α-isomer), m/z=696.96 (z=0.5). $^1$H NMR (CD$_3$OD): 4.78 (1H, H$_1$), 3.3-3.9 (10H), 2.1 (2H).

Step B. benzyl 6-({3-[(α-D-mannopyranosyl)oxy]propyl}{2-[(α-L-fucopyranosyl)oxy]ethyl}amino)-6-oxohexanoate To a solution of 3-iodopropyl α-D-mannopyranoside (220 mg, 0.632 mmol) in DMF (5 mL) was added 2-aminoethyl α-L-fucopyranoside (131 mg, 0.632 mmol) and LiOH (15.13 mg, 0.632 mmol). After stirring at rt for 24 hr, the 0-40% AcCN/H$_2$O in 16 CV, to give the title compound. UPLC-MS Method A: $t_R$=3.05 min, m/z=688.4191 (z=1).

Step C. 6-({3-[(α-D-mannopyranosyl)oxy]propyl}{2-[(α-L-fucopyranosyl)oxy]ethyl}amino)-6-oxohexanoic acid To a solution of benzyl 6-({3-[(α-D-mannopyranosyl)oxy]propyl}{2-[(α-L-fucopyranosyl)oxy]ethyl}amino)-6-oxohexanoate (115 mg, 0.178 mmol) in water (5 mL) was added Pd/C (62.2 mg, 0.058 mmol). The mixture was degassed and stirred under a balloon of H$_2$ for 18 hr. The catalyst was filtered off through a pad of Celite, and washed with water/MeOH (5 mL). The filtrate was concentrated and freeze-dried to give the title compound. UPLC-MS Method A: $t_R$=2.11 min, m/z=598.3737 (z=1).

Step D. 2,5-dioxopyrrolidin-1-yl 9-({3-[(α-D-mannopyranosyl)oxy]propyl}{2-[(α-L-fucopyranosyl)oxy]ethyl}amino)-9-oxononanoate To a solution of 6-({3-[(α-D-mannopyranosyl)oxy]propyl}{2-[(α-L-fucopyranosyl)oxy]ethyl}amino)-6-oxohexanoic acid (280 mg, 0.469 mmol) in DMF (1 mL) at 0° C. was added TSTU (197 mg, 0.656 mmol) and TEA (104 μL, 0.750 mmol). After stirring at rt for 1 hr, the mixture was concentrated and the residue was purified by C18 reverse phase chromatograph, eluting with 0-30% AcCN/H$_2$O in 16 CV, to give the title compound. LC-MS Method B: $t_R$=0.60 min, m/z=695.55 (z=1).

Preparative Example 5

The synthesis of oligosaccharide linker 2,5-dioxopyrrolidin-1-yl 6-(2-{[2-({2-[(α-L-fucopyranosyl)oxy]ethyl}amino)-2-oxoethyl](2-oxo-2-{[2-({α-D-mannopyranosyl-(1→3)-[α-D-mannopyranosyl-(1→6)]-2-deoxy-2-palmitamido-α-D-glucopyranosyl}oxy)ethyl]amino}ethyl)amino}acetamido)hexanoate (ML-10) having the following structure is described.

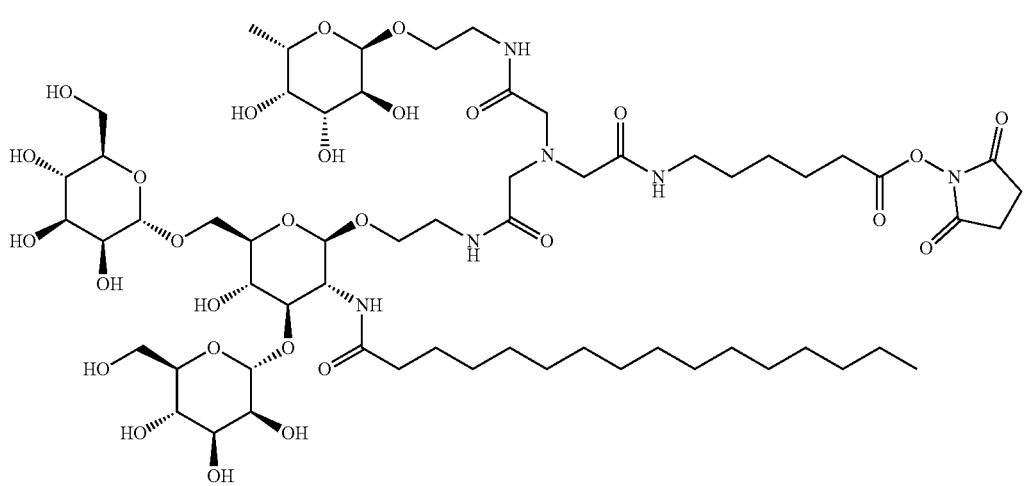

ML-10

Step A. 5-(tert-butyl)-2-methylphenyl 4-O-benzyl-2-deoxy-2-(1,3-dioxoisoindolin-2-yl)-1-thio-β-D-glucopyranoside To a solution of 5-(tert-butyl)-2-methylphenyl 4,6-O-benzylidene-2-deoxy-2-(1,3-dioxoisoindolin-2-yl)-1-thio-β-D-glucopyranoside (9.85 g, 17.60 mmol, Tetrahedron 2008, 64, 1523-1535) and borane tetrahydrofuran complex (100 mL, 100.0 mmol, 1.0 M in THF) at 0° C. was added a solution of trimethylsilyl trifluoromethanesulfonate (0.5 mL, 2.77 mmol). After stirring at rt for 16 hr., TEA (0.8 mL) was added to the reaction mixture and followed by careful addition of $CH_3OH$ until the evolution of $H_2$ had ceased. The reaction mixture was concentrated and the residue was purified by flash chromatography on silica gel (330 g), eluting with 0-100% EtOAc in hexanes to give the title compound. TLC: silica gel, hexanes/EtOAc: 55/45, $R_f$=0.5. 1H NMR ($CDCl_3$): δ 7.86 (d; J=36.88 Hz; 2H); 7.74 (dd; J=5.80; 2.78 Hz; 2H); 7.44 (d; J=2.11 Hz; 1H); 7.33-7.34 (m; 5H); 7.18 (dd; J=7.95; 2.11 Hz; 1H); 7.05 (d; J=7.98 Hz; 1H); 5.54 (d; J=10.52 Hz; 1H); 4.74-4.82 (m; 2H); 4.52 (ddd; J=10.38; 8.24; 4.39 Hz; 1H); 4.28 (t; J=10.44 Hz; 1H); 3.96 (ddd; J=12.11; 5.54; 2.31 Hz; 1H); 3.81 (ddd; J=12.08; 8.21; 3.97 Hz; 1H); 3.53-3.61 (m; 2H); 2.16 (s; 3H); 2.10 (d; J=4.40 Hz; 1H); 1.95 (dd; J=8.20; 5.51 Hz; 1H); 1.26 (s; 9H).

Step B. 2-chloroethyl 4-O-benzyl-2-deoxy-2-(1,3-dioxoisoindolin-2-yl)-[(2,3,4,6-tetra-O-benzoyl-α-D-mannopyranosyl)-(1→3)]-[2,3,4,6-tetra-O-benzoyl-α-D-mannopyranosyl-(1→6)]-β-D-glucopyranoside To a mixture of 5-(tert-butyl)-2-methylphenyl 2-deoxy-2-(1,3-dioxoisoindolin-2-yl)-1-thio-β-D-glucopyranoside (6.72 g, 11.96 mmol), 2,3,4,6-tetra-O-benzoyl-D-mannopyranosyl trichloroacetimidate (18.6 g, 25.1 mmol, Organic Letters 2003, 5, 4041) and 4 Å molecular sieves in DCM (120 mL) at −40° C. was added trimethylsilyl trifluoromethanesulfonate (216 μL, 1.196 mmol). After stirring at −40° C. for 2 hr, NIS (4.0 g, 17.78 mmol) and 2-chloroethanol (2 mL, 29.8 mmol) were added and the resulting mixture was stirred at −10° C. for additional 1 hr. Upon completion, the reaction was quenched with TEA (0.4 mL, 2.87 mmol), filtered and concentrated. The residue was purified by flash chromatography on silica gel (330 g), eluting with 0-100% EtOAc in hexanes to give the title compound. UPLC-MS Method B: calculated for $C_9H_{76}ClNO_{25}$, 1617.44, observed m/z=1618.50 (z=1), $t_R$=2.16 min.

Step C. 2-chloroethyl 4-O-benzyl-2-deoxy-2-(1,3-dioxoisoindolin-2-yl)-[(α-D-mannopyranosyl)-(1→3)]-[α-D-mannopyranosyl-(1→6)]-β-D-glucopyranoside To a solution of 2-chloroethyl 4-O-benzyl-2-deoxy-2-(1,3-dioxoisoindolin-2-yl)-[(2,3,4,6-tetra-O-benzoyl-α-D-mannopyranosyl)-(1→3)]-[2,3,4,6-tetra-O-benzoyl-α-D-mannopyranosyl-(1→6)]-β-D-glucopyranoside (14.54 g, 8.98 mmol) in $CH_3OH$/DCM (v/v=7:3, 50 mL) was added $NaOCH_3$ (3.6 mL, 1.8 mmol, 0.5 M in $CH_3OH$). After stirring at rt for 24 hr, Amberlite IR 120 (H) ion exchange resin (pre-washed with $CH_3OH$ 3×30 mL) was added to the reaction mixture. The resulting mixture was allowed to stir for additional 15 min. The resin was filtered off and washed with $CH_3OH$ (3×15 mL). The filtrate was concentrated to give the title compound. UPLC-MS Method A: calculated for $C_{35}H_{44}ClNO_{17}$, 785.23, observed m/z=786.30 (z=1), $t_R$=2.66 min.

Step D. 2-azidoethyl 4-O-benzyl-2-deoxy-2-(1,3-dioxoisoindolin-2-yl)-[(α-D-mannopyranosyl)-(1→3)]-[α-D-mannopyranosyl-(1→6)]-β-D-glucopyranoside To a solution of 2-chloroethyl 4-O-benzyl-2-deoxy-2-(1,3-dioxoisoindolin-2-yl)-[(α-D-mannopyranosyl)-(1→3)]-[α-D-mannopyranosyl-(1→6)]-β-D-glucopyranoside (6.14 g, 7.81 mmol) in DMF (40 mL) at rt was added sodium azide (600 mg, 9.23 mmol). After stirring at 80° C. for 16 hr, the reaction mixture was cooled down to rt and concentrated. The residue was purified by reverse phase C18 chromatograph (280 g), eluting with 5-70% AcCN in $H_2O$, to give the

Step E. 2-azidoethyl 4-O-benzyl-2-amino-2-deoxy-[(α-D-mannopyranosyl)-(1→3)]-[α-D-mannopyranosyl-(1→6)]-β-D-glucopyranoside To a solution of 2-azidoethyl 4-O-benzyl-2-deoxy-2-(1,3-dioxoisoindolin-2-yl)-[(α-D-mannopyranosyl)-(1→3)]-[α-D-mannopyranosyl-(1→6)]-β-D-glucopyranoside (0.75 g, 0.946 mmol) in H$_2$O/Ethanol (v/v=2/1, 9 mL) at rt was added hydrazine (424 µL, 4.73 mmol). After stirring at reflux for 16 hr, the reaction mixture was cooled down to rt and reduced to half volume. The residue was purified by C18 reverse phase chromatography (280 g), eluting with 5-60% AcCN in H$_2$O, to give the title compound. UPLC-MS Method B: calculated for C$_{27}$H$_{42}$N$_4$O$_{15}$ 662.15, observed m/z=663.33 (z=1), t$_R$=1.30 min.

Step F. 2-azidoethyl 4-O-benzyl-2-deoxy-2-palmitamido-[(α-D-mannopyranosyl)-(1→3)]-[α-D-mannopyranosyl-(1→6)]-β-D-glucopyranoside To a solution of 2-azidoethyl 4-O-benzyl-2-amino-2-deoxy-[(α-D-mannopyranosyl)-(1→3)]-[α-D-mannopyranosyl-(1→6)]-β-D-glucopyranoside (147 mg, 0.222 mmol) in DMF (4 mL) at rt was added 2,5-dioxopyrrolidin-1-yl palmitate (128.2 mg, 0.363 mmol) and DIPEA (58 µl, 0.332 mmol). The resulting mixture was heated to 70° C. and stirred for 2 hr. The reaction mixture was cooled down to rt and concentrated. The residue was purified by C18 reverse phase chromatography (50 g), eluting with 5-80% AcCN in H$_2$O, to give the title compound. UPLC-MS Method B: calculated for C$_{43}$H$_{72}$N$_4$O$_{16}$ 900.49, observed m/z=901.57 (z=1), t$_R$=2.61 min.

Step G. 2-aminoethyl 2-deoxy-2-palmitamido-[(α-D-mannopyranosyl)-(1→3)]-[α-D-mannopyranosyl-(1→6)]-β-D-glucopyranoside A mixture of 2-azidoethyl 4-O-benzyl-2-palmitamido-2-deoxy-[(α-D-mannopyranosyl)-(1→3)]-[α-D-mannopyranosyl-(1→6)]-β-D-glucopyranoside (73 mg, 0.081 mmol) and Pearlman's catalyst (2.84 mg, 4.05 µmol) in ethanol:H$_2$O (v/v=5/1, 6 mL) was allowed to stir under a balloon of H$_2$ at rt for 16 hr. The catalyst was filtered off and washed with H$_2$O (3×3 mL). The filtrate was concentrated to give the title compound. UPLC-MS Method B: calculated for C$_{36}$H$_{68}$N$_2$O$_{16}$ 784.46, observed m/z=785.53 (z=1), t$_R$=1.53 min.

Step H. benzyl 6-(2-{[2-oxo-2-({2-[(2-deoxy-2-palmitamido-D-glucopyranosyl)oxy]ethyl}amino)ethyl][2-oxo-2-({2-[(α-L-fucopyranosyl)oxy]ethyl}amino)ethyl]amino}acetamido)hexanoate To a solution of N-(2-{[6-(benzyloxy)-6-oxohexyl]amino}-2-oxoethyl)-N-[2-oxo-2-({2-[(α-L-fucopyranosyl)oxy]ethyl}amino)ethyl]glycine (45.7 mg, 0.078 mmol, WO 2015051052 A2 20150409), and 2-aminoethyl 2-deoxy-2-palmitamido-[(α-D-mannopyranosyl)-(1→3)]-[α-D-mannopyranosyl-(1→6)]-β-D-glucopyranoside (58.6 mg, 0.075 mmol) in DMF (2 mL) was added HOBt (17.6 mg, 0.115 mmol), and EDC (33.2 mg, 0.173 mmol). After stirring for 16 hr at rt, the reaction mixture was concentrated and the residue was purified by flash chromatography on C18 reverse phase silica gel (50 g), eluting with 10-60% AcCN in water, to give the title compound. UPLC-MS Method A: calculated for C$_{63}$H$_{107}$N$_5$O$_{26}$ 1349.72, observed m/z=1350.80 (z=1), t$_R$=2.00 min.

Step I. 6-(2-{[2-oxo-2-({2-[(2-deoxy-2-palmitamido-D-glucopyranosyl)oxy]ethyl}amino)ethyl][2-oxo-2-({2-[(α-L-fucopyranosyl)oxy]ethyl}amino)ethyl]amino}acetamido)hexanoic acid A mixture of benzyl 6-(2-{[2-oxo-2-({2-[(2-deoxy-2-palmitamido-D-glucopyranosyl)oxy]ethyl}amino)ethyl][2-oxo-2-({2-[(α-L-fucopyranosyl)oxy]ethyl}amino)ethyl]amino}acetamido)hexanoate (66 mg, 0.049 mmol) and Pearlman's catalyst (2 mg, 2.85 µmol) in H$_2$O (2 mL) was degassed and allowed to stir under a balloon of H$_2$ at rt for 16 hr. The catalyst was filtered off and washed with H$_2$O (3×2 mL). The filtrate was concentrated to give the title compound. UPLC-MS Method A: calculated for C$_{56}$H$_{101}$N$_5$O$_{26}$ 1259.67, observed m/z=1260.75 (z=1), t$_R$=1.48 min.

Step J. 2,5-dioxopyrrolidin-1-yl 6-(2-{[2-oxo-2-({2-[(2-deoxy-2-palmitamido-D-glucopyranosyl)oxy]ethyl}amino)ethyl][2-oxo-2-({2-[(α-L-fucopyranosyl)oxy]ethyl}amino)ethyl]amino}acetamido)hexanoate To a stirred solution of 6-(2-{[2-oxo-2-({2-[(2-deoxy-2-palmitamido-D-glucopyranosyl)oxy]ethyl}amino)ethyl][2-oxo-2-({2-[(α-L-fucopyranosyl)oxy]ethyl}amino)ethyl]amino}acetamido)hexanoic acid (60 mg, 0.048 mmol) in DMF (1.0 mL) at 0° C. was added TSTU (28 mg, 0.093 mmol), and DIPEA (11 µL, 0.063 mmol). After stirring for 1 hr at 0° C., the reaction was quenched with TFA (7 µL, 0.091 mmol). The resulting mixture was added dropwise to EtOAc (45 mL). The white precipitate was collected through centrifugation (30 min, 3500 rpm, 4° C.), which was re-dissolved in H$_2$O and freeze-dried to give the title product. UPLC-MS Method A: calculated for C$_{60}$H$_{104}$N$_6$O$_{28}$ 1356.69, observed m/z=1357.78 (z=1), t$_R$=1.56 min.

Preparative Example 6

The synthesis of oligosaccharide linker 2,5-dioxopyrrolidin-1-yl (S)-16-{[5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-16-oxohexadecanoate (ML-11) having the following structure is described.

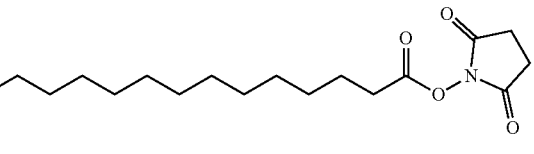

ML-11

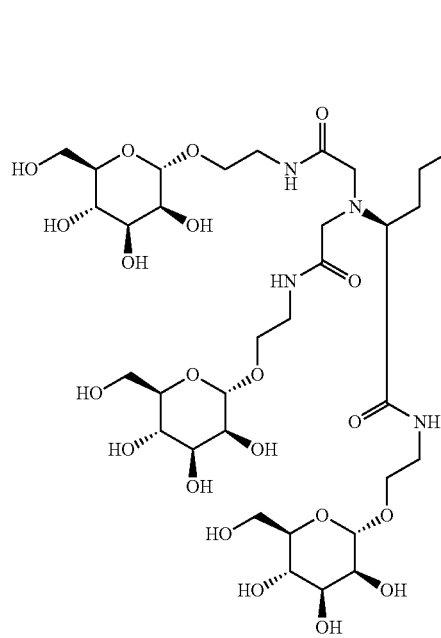

Step A. benzyl (S)-[5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]carbamate To a solution of $N^6$-[(benzyloxy)carbonyl]-$N^2$,$N^2$-bis(carboxymethyl)-L-lysine (1.0 g, 2.52 mmol) in DMF (15 mL) at rt was added a solution of 2-aminoethyl α-D-mannopyranoside (2.48 g, 11.10 mmol) in $H_2O$ (2 mL) and HOBt (1.78 g, 11.60 mmol). The mixture was cooled to 0° C., to which EDC (2.23 g, 11.60 mmol) was added. After stirring at 0° C. for 1.5 hr, the resulting solution was allowed to stir at rt for 48 hr. The mixture was concentrated and the residue was purified by flash chromatography on C18 silica gel (120 g), eluting with 0-30% AcCN in water. The desired fractions were combined and freeze-dried to afford the title compound. UPLC-MS Method A: $t_R$=3.78 min; m/z=1012.32 (z=1).

Step B. 2,2'-{[(2S)-6-amino-1-({2-[(α-D-mannopyranosyl)oxy]ethyl}amino)-1-oxohexan-2-yl]azanediyl}bis(N-{2-[(α-D-mannopyranosyl)oxy]ethyl}acetamide)

To a solution of benzyl (S)-[5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]carbamate (700 mg, 0.69 mmol) in water (15 mL) was added Pd/C (150 mg, 0.14 mmol). The mixture was degassed and allowed to stir under a balloon of $H_2$ at rt for 16 hr. The catalyst was filtered off through a Celite pad, and the filtrate was freeze-dried to afford the title product. UPLC Method A: $t_R$=3.64 min; m/z=878.28 (z=1).

Step C. benzyl 16-((2,5-dioxopyrrolidin-1-yl)oxy)-16-oxohexadecanoate

To a solution of 16-(benzyloxy)-16-oxohexadecanoic acid (300 mg, 0.797 mmol) in DMF (10 mL) at 0° C. was added TSTU (252 mg, 0.837 mmol) and followed by DIPEA (146 μL, 0.837 mmol). After stirring at 0° C. for 1 hr, the reaction mixture was partitioned between $Et_2O$ and water. The organic layer was separated, washed with brine, dried over $MgSO_4$, and concentrated to give the title compound. $^1H$ NMR ($CDCl_3$) δ 7.37 (m, 5H), 5.13 (s, 2H), 2.84 (m, 4H), 2.62 (m, 2H), 2.37 (m, 2H), 1.76 (m, 2H), 1.74 (m, 2H), 1.45-1.20 (m, 20H).

Step D. benzyl 16-{[(5S)-5-[bis(2-{[2-(α-D-mannopyranosyloxy)ethyl]amino}-2-oxoethyl)amino]-6-{[2-(α-D-mannopyranosyloxy)ethyl]amino}-6-oxohexyl]amino}-16-oxohexadecanoate To a solution of benzyl 16-[(2,5-dioxopyrrolidin-1-yl)oxy]-16-oxohexadecanoate (170 mg, 0.359 mmol) in DMF (5 mL) at 0° C. was added 2,2'-{[(2S)-6-amino-1-({2-[(α-D-mannopyranosyl)oxy]ethyl}amino)-1-oxohexan-2-yl]azanediyl}bis(N-{2-[(α-D-mannopyranosyl)oxy]ethyl}acetamide) (300 mg, 0.342 mmol) and followed by TEA (50 μL, 0.359 mmol). After stirring at 0° C. for 30 min, the reaction mixture was allowed to gradually warm up to rt. After 2 hr, the reaction mixture was concentrated and the residue was purified by flash chromatography on C18 silica gel (120 g), eluting with 0-50% AcCN in water. The desired fractions were combined and freeze-dried to afford the title compound. $^1H$ NMR ($CDCl_3$) δ 7.98 (s, 2H), 7.35 (m, 5H), 5.13 (s, 2H), 4.80 (m, 2H), 3.88-3.15 (m, 56H), 2.35 (m, 2H), 2.18 (m, 2H), 1.70-1.22 (m, 26H). LC-MS Method A: $t_R$=2.10 min; m/z=1237.40 (z=1).

Step E. 2,5-dioxopyrrolidin-1-yl (S)-16-[(5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl)amino]-16-oxohexadecanoate The title compound was prepared using procedure analogous to those described for Step C and Step D in Preparative Example 1 (ML-1) substituting benzyl 16-{[(5S)-5-[bis(2-{[2-(α-D-mannopyranosyloxy)ethyl]amino}-2-oxoethyl)amino]-6-{[2-(α-D-mannopyranosyloxy)ethyl]amino}-6-oxohexyl]amino}-16-oxohexadecanoate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C.

Preparative Example 7

The synthesis of oligosaccharide linker 2,5-dioxopyrrolidin-1-yl (S)-6-{[5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoate (ML-12) having the following structure is described.

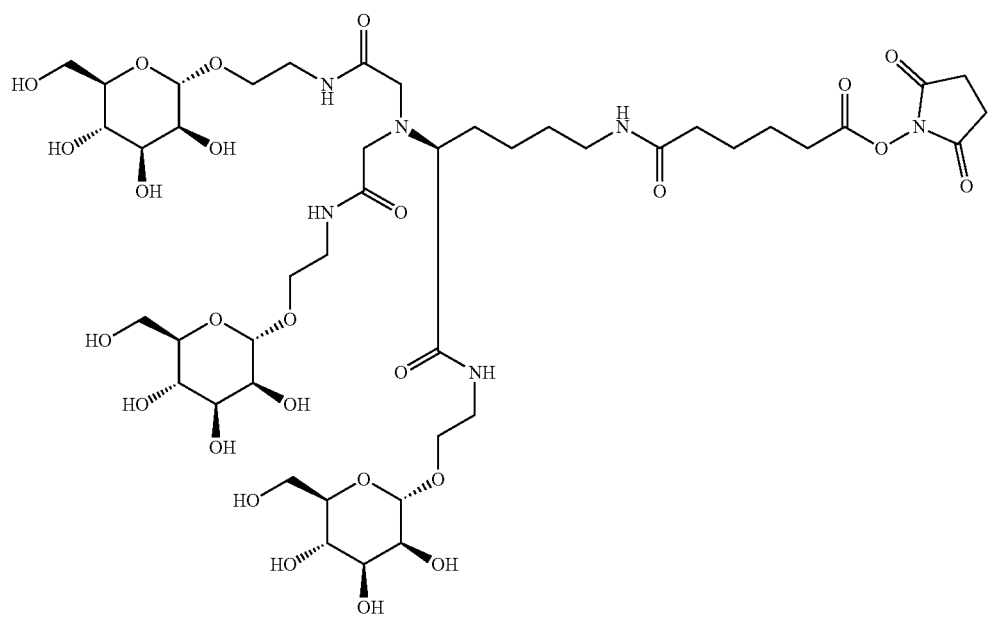

ML-12

Step A. benzyl 6-[(2,5-dioxo-1-pyrrolidinyl)oxy]-6-oxohexanoate

To a solution of benzyl (2,5-dioxopyrrolidin-1-yl) adipate (7.0 g, 29.6 mmol) in DMF (15 mL) at 0° C. was added TSTU (9.37 g, 31.1 mmol) and DIPEA (5.43 mL, 31.1 mmol). After stirring at 0° C. for 1 hr, the reaction mixture was partitioned between Et$_2$O and water. The ether layer was separated, washed with brine, dried over MgSO$_4$, and concentrated to give the title compound. $^1$H NMR (CDCl$_3$) δ 7.33 (m, 5H), 5.09 (m, 2H), 2.74 (m, 4H), 2.59 (m, 2H), 2.38 (m, 2H), 1.23 (m, 4H).

Step B. benzyl 6-{[(5S)-5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoate To a solution of 2,2'-{[(2S)-6-amino-1-({2-[(α-D-mannopyranosyl)oxy]ethyl}amino)-1-oxohexan-2-yl]azanediyl}bis(N-{2-[(α-D-mannopyranosyl)oxy]ethyl}acetamide) (108 mg, 0.323 mmol) in DMF (5 mL) at 0° C. was added benzyl 6-[(2,5-dioxo-1-pyrrolidinyl)oxy]-6-oxohexanoate (270 mg, 0.308 mmol) and TEA (45 μL, 0.323 mmol). After stirring at 0° C. for 30 min, the reaction mixture was allowed to gradually warm up to rt. After stirring at rt for 2 hr, the reaction mixture was concentrated and the residue was purified by flash chromatography on C18 silica gel (120 g), eluting with 0-50% AcCN in water, to afford the title product. $^1$H NMR (DMSO-d$_6$) δ 3.64-2.97 (m, 63H), 2.41 (m, 2H), 2.20 (m, 2H), 1.60 (m, 4H). LC-MS Method A: t$_R$=1.26 min; m/z=1096.77 (z=1).

Step C. 6-{[(5S)-5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoic acid To a solution of benzyl 6-{[(5S)-5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoate (520 mg, 0.474 mmol) in H$_2$O (5 mL) was added Pd/C (136 mg, 0.119 mmol). The mixture was degassed and allowed to stir under a balloon of H$_2$ at rt for 16 hr. The catalyst was filtered off through a pad of Celite and the filtrate was freeze-dried to afford the title product. $^1$H NMR (DMSO-d$_6$) δ 7.35 (m, 5H), 5.12 (s, 2H), 5.13 (s, 2H), 3.88-3.15 (m, 62H), 2.41 (m, 2H), 2.20 (m, 2H), 1.60 (m, 4H).

Step D. 2,5-dioxopyrrolidin-1-yl (S)-6-{[5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoate To a solution of 6-{[(5S)-5-{bis[2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-6-oxohexanoic acid (477 mg, 0.474 mmol) in DMF (35 mL) at 0° C. was added TSTU (150 mg, 0.498 mmol) and DIPEA (91 μL, 0.522 mmol). After stirring at 0° C. for 1 hr, the reaction mixture was concentrated and the residue was purified by flash chromatography on C18 silica gel (120 g), eluting with 0-50% AcCN in water, to afford the title product. ¹H NMR (DMSO-d6) δ 3.64-2.97 (m, 62H), 2.68 (m, 4H) 2.41 (m, 2H), 2.20 (m, 2H), 1.60 (m, 4H). LC-MS Method A: $t_R$=0.17 min; m/z=1103.79 (z=1).

Preparative Example 8

The synthesis of oligosaccharide 2,5-dioxopyrrolidin-1-yl (S)-5-({1,7-bis({2-[(α-D-mannopyranosyl)oxy]ethyl}amino)-4-[3-({2-[(α-D-mannopyranosyl)oxy]ethyl}amino)-3-oxopropyl]-1,7-dioxoheptan-4-yl}amino)-5-oxo-4-pentadecanamidopentanoate (ML-18) having the following structure is described.

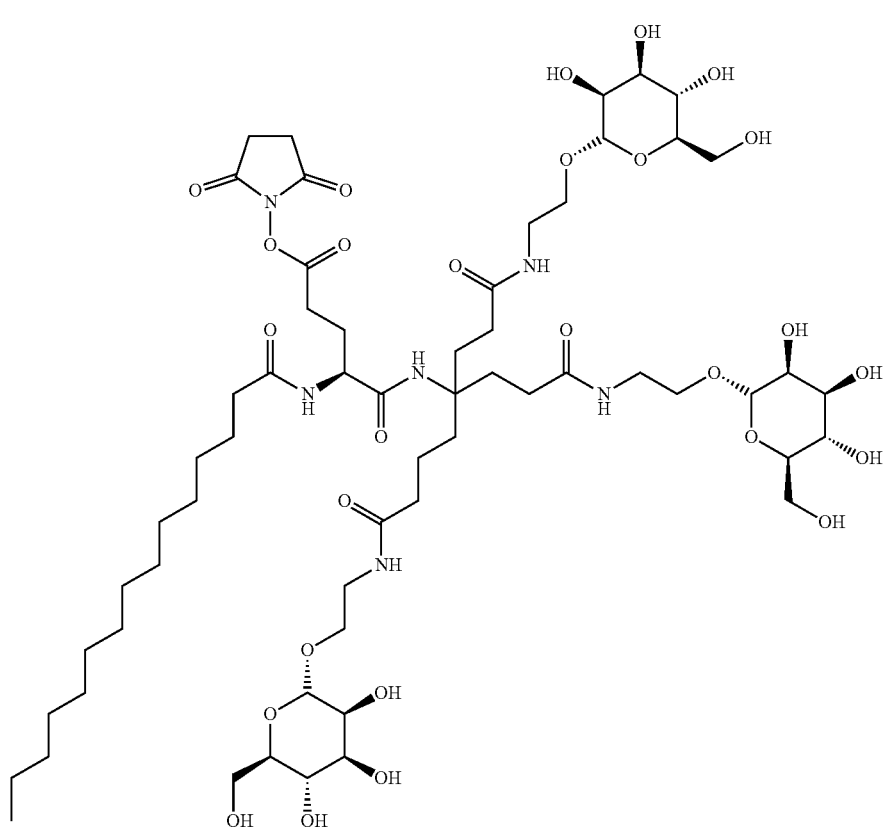

ML-18

Step A. di-tert-butyl (S)-4-[5-(benzyloxy)-5-oxo-2-pentadecanamidopentanamido]-4-[3-(tert-butoxy)-3-oxopropyl]heptanedioate To a solution of di-tert-butyl 4-amino-4-[3-(tert-butoxy)-3-oxopropyl]heptanedioate (1.0 g, 2.406 mmol), (S)-5-(benzoyloxy)-5-oxo-2-pentadecanamidopentanoic acid (1.11 g, 2.406 mmol) and HATU (1.0 g, 2.63 mmol) in DMF (24 mL) at rt was added DIPEA (1.0 mL, 5.73 mmol). After stirring at rt for 24 hr, the reaction mixture was concentrated and the residue was partitioned between water and CH₂Cl₂. The aq layer was separated and extracted twice with CH₂Cl₂. The combined organic layers were washed twice with 1.0 N HCl, sat'd NaHCO₃, and brine, dried over Na₂SO₄, and concentrated. The residue was purified by flash chromatography on silica gel (120 g), eluting with 15% EtOAc in hexanes to give the title compound. ¹H NMR (CDCl3): δ 7.30 (m, 5H), 6.60 (s, 1H), 6.30 (d, 1H), 5.10 (d, 2H), 4.30 (q, 1H), 2.60-2.55 (m, 1H), 2.40-2.35 (m, 1H), 2.10-2.20 (m, 9H), 1.85-1.95 (m, 7H), 1.55-1.60 (m, 2H), 1.40 (s, 27H), 1.20-1.30 (m, 22H), 0.85 (t, 3H).

Step B. (S)-4-[5-(benzyloxy)-5-oxo-2-pentadecanamidopentanamido]-4-(2-carboxyethyl)heptanedioic acid A solution of di-tert-butyl (S)-4-[5-(benzyloxy)-5-oxo-2-pentadecanamidopentanamido]-4-[3-(tert-butoxy)-3-oxopropyl]heptanedioate (1.3 g, 1.513 mmol) in formic acid (40 mL) at rt was allowed to stir for 24 hr. The reaction mixture was concentrated to afford the title compound. ¹H NMR (CD₃OD): δ 7.30-7.40 (m, 5H), 5.10 (s, 2H), 4.30 (q, 1H), 2.45 (t, 2H), 2.20-2.30 (m, 8H), 1.90-2.10 (m, 8H), 1.60 (m, 2H), 1.20-1.40 (m, 22H), 0.90 (t, 3H).

Step C. benzyl (4S)-5-((1,7-bis((2-(α-D-mannopyranosyloxy)ethyl)amino)-4-(3-((2-(α-D-mannopyranosyloxy)ethyl)amino)-3-oxopropyl)-1,7-dioxoheptan-4-yl)amino)-5-oxo-4-pentadecanamidopentanoate To a solution of (S)-4-[5-(benzyloxy)-5-oxo-2-pentadecanamidopentanamido]-4-(2-carboxyethyl)heptanedioic acid (101.8 mg, 0147 mmol), 2-aminoethyl α-D-mannopyranoside (132 mg, 0.589 mmol), EDC (200 mg, 1.043 mmol), and HOBt (142 mg, 0.927 mmol) in DMF (6.0 mL) at rt was added DIPEA (0.15 ml, 0.589 mmol). After stirring at rt for 48 hr, the reaction mixture was concentrated and the residue was purified by flash chromatography on silica gel (40 g), eluting with EtOAc/MeOH/AcCN/H₂O (v/v/v/v=6/

1/1/1) in 10 CV, to give the title product. UPLC-MS Method D: calculated for $C_{61}H_{103}N_5O_{25}$ 1305.69 observed m/z=1306.54 (z=1); $t_R$=4.81 min. H NMR (CD$_3$OD): δ 7.40-7.30 (m, 5H), 5.15 (s, 2H), 4.75 (s, 3H), 4.20 (m, 1H), 3.85-3.80 (m, 6H), 3.75-3.65 (m, 9H), 3.60 (t, 3H), 3.55-3.50 (m, 3H), 3.45-3.35 (m, 7H), 3.20 (q, 2H), 2.50 (t, 2H), 2.25-2.05 (m, 9H), 2.00-1.95 (m, 7H), 1.60 (m, 2H), 1.40-1.20 (m, 22H), 0.90 (t, 3H).

Step D. (S)-5-({1,7-bis({2-[(α-D-mannopyranosyl)oxy]ethyl}amino)-4-[3-({2-[(α-D-mannopyranosyl)oxy]ethyl}amino)-3-oxopropyl]-1,7-dioxoheptan-4-yl}amino)-5-oxo-4-pentadecanamidopentanoic acid To a solution of benzyl (4S)-5-({1,7-bis({2-[(α-D-mannopyranosyl)oxy]ethyl}amino)-4-[3-({2-[(α-D-mannopyranosyl)oxy]ethyl}amino)-3-oxopropyl]-1,7-dioxoheptan-4-yl}amino)-5-oxo-4-pentadecanamidopentanoate (140 mg, 0.107 mmol) and CH$_3$OH (0.2 mL) and water (2.3 mL) was added 10% Pd/C (11 mg, 10.34 µmol). The resulting suspension was degassed and stirred under a balloon of H$_2$ for 24 h. The catalyst was filtered off through a cake of Celite and rinsed with methanol. The filtrate was concentrated to afford the title compound. $^1$H NMR (CD$_3$OD): δ 4.75 (s, 3H), 4.20-4.15 (m, 1H), 3.85-3.80 (m, 6H), 3.75-3.65 (m, 9H), 3.60 (t, 3H), 3.55-3.50 (m, 3H), 3.45-3.35 (m, 7H), 3.20 (q, 2H), 2.40 (t, 2H), 2.25-2.15 (m, 7H), 2.05-1.95 (m, 9H), 1.60 (m, 2H), 1.40-1.20 (m, 22H), 0.90 (t, 3H).

Step E. 2,5-dioxopyrrolidin-1-yl (S)-5-({1,7-bis({2-[(α-D-mannopyranosyl)oxy]ethyl}amino)-4-[3-({2-[(α-D-mannopyranosyl)oxy]ethyl}amino)-3-oxopropyl]-1,7-dioxoheptan-4-yl}amino)-5-oxo-4-pentadecanamidopentanoate To a solution of (S)-5-({1,7-bis({2-[(α-D-mannopyranosyl)oxy]ethyl}amino)-4-[3-({2-[(α-D-mannopyranosyl)oxy]ethyl}amino)-3-oxopropyl]-1,7-dioxoheptan-4-yl}amino)-5-oxo-4-pentadecanamidopentanoic acid (120 mg, 0.099 mmol) in DMF (2.0 mL) at 0° C. was added TSTU (33 mg, 0.110 mmol) and DIPEA (22 µL, 0.128 mmol). The reaction mixture was stirred at 0° C. for 1 hr. The reaction was quenched with addition of TFA (15 µL, 0.197 mmol), then concentrated down to half volume (~1 mL). The resulting solution was transferred dropwise, via pipette, to a centrifuge tube containing anhydrous AcCN (40 mL). The resulting white suspension was collected by centrifugation (3000 rpm, 15 min, 4° C.), briefly rinsed with AcCN (1.0 mL), and dried to yield the title compound. UPLC-MS Method D: calculated for $C_{58}H_{100}N_6O_{27}$ 1312.66 observed m/z=1313.57 (z=1); $t_R$=3.95 min.

Preparative Example 9

The synthesis of oligosaccharide linker 2,5-dioxopyrrolidin-1-yl (7S,26S)-1-[(α-L-fucopyranosyl)oxy]-6-[2-({2-[(α-L-fucopyranosyl)oxy]ethyl}amino)-2-oxoethyl]-7-({2-[(α-L-fucopyranosyl)oxy]ethyl}carbamoyl)-26-heptadecanamido-4,13,17,25-tetraoxo-15-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,6,12,15,18,24-hexaazanonacosan-29-oate (ML-19) having the following structure is described.

ML-19

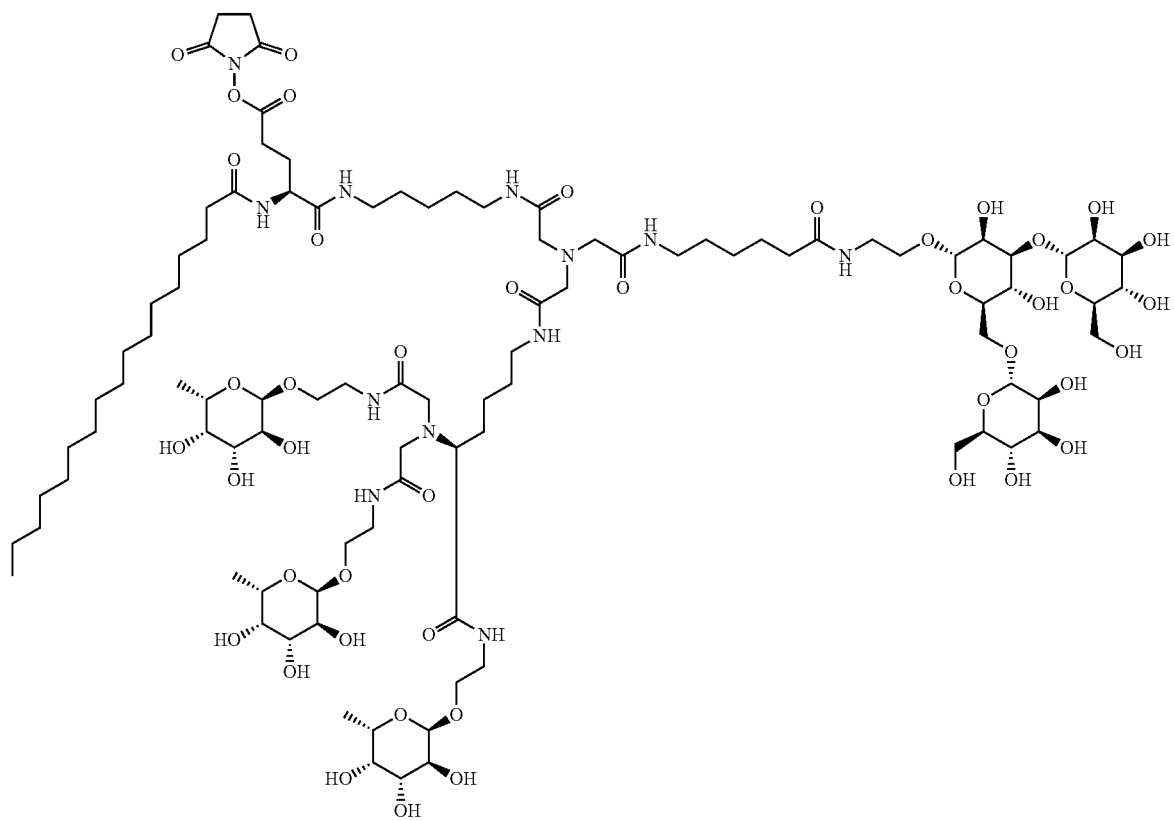

Step A. benzyl (6-{[2-({α-D-mannopyranosyl-(1→3)-[α-D-mannopyranosyl-(1→6)]-α-D-mannopyranosyl}oxy)ethyl]amino}-6-oxohexyl)carbamate To a solution of 2-aminoethyl α-D-mannopyranosyl-(1→3)-[α-D-mannopyranosyl-(1→6)]-α-D-mannopyranoside (1.80 g, 3.29 mmol) in DMF (50 mL) at 0° C. was added 2,5-dioxopyrrolidin-1-yl 6-{[(benzyloxy)carbonyl]amino}hexanoate (1.79 g, 4.93 mmol). After stirring at 0° C. for 30 min, TEA (1.15 mL, 8.22 mmol) was added. The reaction mixture was allowed to gradually warm up to rt and to stir for 16 hr. The reaction mixture was concentrated and the residue was purified by flash chromatography on C18 silica gel (240 g), eluting with 5-40% AcCN/H$_2$O over 15 CV. Fractions containing product were combined and freeze-dried to yield the title product. $^1$H NMR (CD$_3$OD): δ 1.35 (br s, 2H), 1.52 (br s, 2H), 1.63 (br s, 2H), 2.21 (s, 2H), 3.12 (s, 2H), 3.37 (s, 1H), 3.51-3.37 (br m, 5H), 3.81-3.69 (br m, 14H), 3.98 (s, 1H), 4.06 (s, 1H), 4.72 (s, 1H), 4.81 (s, 2H), 5.07 (s, 2H), 7.35 (s, 5H). UPLC-MS Method A: $t_R$=2.49 min; m/z=795.30 (z=1).

Step B. 6-amino-N-[2-({α-D-mannopyranosyl-(1→3)-[α-D-mannopyranosyl-(1→6)]-α-D-mannopyranosyl}oxy)ethyl]hexanamide To a solution of benzyl (6-{[2-({α-D-mannopyranosyl-(1→3)-[α-D-mannopyranosyl-(1→6)]-α-D-mannopyranosyl}oxy)ethyl]amino}-6-oxohexyl)carbamate (1.51 g, 1.91 mmol) in H$_2$O (20 mL) was added Pd/C (61 mg, 0.57 mmol). The resulting suspension was degassed (3×) with H$_2$ and allowed to stir under a balloon of H$_2$ at rt. After 1 hr, the reaction was determined to be complete and the catalyst was filtered off through a cake of Celite and washed with H$_2$O. The filtrate was freeze-dried to give the title compound. $^1$H NMR (CD$_3$OD): δ 1.40 (2H, d, J=7.97), 1.63 (4H, d, J=12.78), 2.23 (2H, t, J=7.37), 2.82 (2H, q, J=8.46), 3.44-3.37 (2H, m), 3.53-3.46 (1H, m), 3.63-3.61 (4H, m), 3.72-3.70 (6H, m), 3.80 (5H, dd, J=9.96, 4.52), 3.83 (2H, s), 3.90 (1H, dd, J=11.05, 5.87), 3.97 (1H, s), 4.03 (1H, s), 4.72 (1H, s), 4.81 (1H, s), 5.06 (1H, s). UPLC-MS Method A: $t_R$=3.89 min; m/z=661.35 (z=1).

Step C. 13-(carboxymethyl)-3,11-dioxo-1-phenyl-2-oxa-4,10,13-triazapentadecan-15-oic acid To a solution of benzyl (5-aminopentyl)carbamate hydrochloride (5.0 g, 18.33 mmol) in DMF (22 mL) at 0° C. was added K$_2$CO$_3$ (2.53 g, 18.33 mmol). After stirring at 0° C. for 2 hr, the resulting suspension was filtered through a cake of Celite and the filtrate was added to a solution of 2-(2,6-dioxomorpholino)acetic acid (3.17 g, 18.33 mmol) in DMF (22 mL) at 0° C. After stirring at 0° C. for 30 min, the mixture was allowed to gradually warm to rt and stirred overnight. The reaction mixture was evaporated. The residue was suspended in H$_2$O (20 mL) and stirred at rt for 30 min. A white precipitate forms which is collected by filtration, washed with a small amount of H$_2$O, and dried to give the title compound. UPLC-MS Method A: $t_R$=3.64 min; m/z=410.12 (z=1).

Step D. 13-{2-[(6-{[2-({α-D-mannopyranosyl-(1→3)-[α-D-mannopyranosyl-(1→6)]-α-D-mannopyranosyl}oxy)ethyl]amino}-6-oxoethyl)amino]-2-oxoethyl}-3,11-dioxo-1-phenyl-2-oxa-4,10,13-triazapentadecan-15-oic acid To a suspension of 13-(carboxymethyl)-3,11-dioxo-1-phenyl-2-oxa-4,10,13-triazapentadecan-15-oic acid in CH$_2$Cl$_2$ (7 mL) at 0° C. was added TFAA (194 μL, 1.374 mmol). After stirring at 0° C. for 3 hr, the reaction mixture was cooled to −30° C. and a solution of TEA (368 μL, 2.64 mmol) in DMF (7 mL) was added dropwise over 30 min. After stirring at −30° C. for additional 30 min, to the reaction mixture was added a mixture of 6-amino-N-[2-({α-D-mannopyranosyl-(1→3)-[α-D-mannopyranosyl-(1→6)]-α-D-mannopyranosyl}oxy)ethyl]hexanamide (670 mg, 1.014 mmol, Step B) in DMF (7 mL). The resulting mixture was allowed to stir at rt for 16 hr and then concentrated. Residue was purified by flash chromatography on C18 silica gel (130 g), eluting with 5-40% AcCN/H$_2$O over 20 CV. Fractions containing product were combined and freeze-dried to give the title product. $^1$H NMR (CD$_3$OD): δ 1.25 (t, 4H), 1.43 (dt, 6H), 1.53 (t, 2H), 2.11 (t, 2H), 3.01 (t, 2H), 3.12 (t, 4H), 3.22-3.19 (m, 4H), 3.38 (s, 4H), 3.60-3.55 (m, 9H), 3.73-3.71 (m, 9H), 3.87 (t, 1H), 3.95 (s, 1H), 4.62 (s, 1H), 4.71 (s, 1H), 4.97 (d, 2H), 7.24 (d, 2H). UPLC-MS Method A: $t_R$=2.75 min; m/z=1052.51 (z=1).

Step E. (S)-2,2'-{[6-amino-1-({2-[(α-L-fucopyranosyl)oxy]ethyl}amino)-1-oxohexan-2-yl]azanediyl}bis(N-{2-[(α-L-fucopyranosyl)oxy]ethyl}acetamide)

The title compound was prepared using procedure analogous to those described for Step A-B in Preparative Example 6 (ML-11) 12 substituting 2-aminoethyl α-L-fucopyranoside for 2-aminoethyl α-D-mannopyranoside in Step A. UPLC Method A: $t_R$=3.68 min; m/z=830.29 (z=1).

Step F. N$^6$—(N-{2-[(5-{[(benzyloxy)carbonyl]amino}pentyl)amino]-2-oxoethyl}-N-{2[(6-{[2-({α-D-mannopyranosyl-(1→3)-[α-D-mannopyranosyl-(1→6)]-α-D-mannopyranosyl}oxy)ethyl]amino}-6-oxohexyl)amino]-2-oxoethyl}glycyl)-N-{2-[(α-L-fucopyranosyl)oxy]ethyl}-N$^2$,N$^2$-bis[2-({2-[(α-L-fucopyranosyl)oxy]ethyl}amino)-2-oxoethyl]-L-lysinamide To a solution of 13-{2-[(6-{[2-({α-D-mannopyranosyl-(1→3)-[α-D-mannopyranosyl-(1→6)]-α-D-mannopyranosyl} oxy)ethyl]amino}-6-oxoethyl)amino]-2-oxoethyl}-3,11-dioxo-1-phenyl-2-oxa-4,10,13-triazapentadecan-15-oic acid (100 mg, 0.095 mmol) in DMF (2 mL) was added EDC (27.3 mg, 0.143 mmol), HOBt (17.5 mg, 0.114 mmol), TEA (33 μL, 0.238 mmol), and (S)-2,2'-{[6-amino-1-({2-[(α-L-fucopyranosyl)oxy]ethyl}amino)-1-oxohexan-2-yl]azanediyl}bis(N-{2-[(α-L-fucopyranosyl)oxy]ethyl}acetamide) (118 mg, 0.143 mmol). After stirring at rt for 16 hr, the reaction mixture was concentrated and the residue was purified by flash chromatography on C18 silica gel (86 g), eluting with 10-40% AcCN/H$_2$O over 20 CV, to yield the title product. UPLC-MS Method A: $t_R$=4.18 min; m/z=1864.45 (z=1).

Step G. N$^6$—(N-{2-[(5-aminopentyl)amino]-2-oxoethyl}-N-{2-[(6-{[2-({α-D-mannopyranosyl-(1→3)-[α-D-mannopyranosyl-(1→6)]-α-D-mannopyranosyl}oxy)ethyl]amino}-6-oxohexyl)amino]-2-oxoethyl}glycyl)-N-{2-[(α-L-fucopyranosyl)oxy]ethyl}-N$^2$,N$^2$-bis[2-({2-[(α-L-fucopyranosyl)oxy]ethyl}amino)-2-oxoethyl]-L-lysinamide To a solution of N$^6$—(N-{2-[(5-{[(benzyloxy)carbonyl]amino}pentyl)amino]-2-oxoethyl}-N-{2[(6-{[2-({α-D- mannopyranosyl-(1→3)-[α-D-mannopyranosyl-(1→6)]-α-D-mannopyranosyl}oxy)ethyl]amino}-6-oxohexyl)amino]-2-oxoethyl}glycyl)-N-{2-[(α-L-fucopyranosyl)oxy]ethyl}-N2,N2-bis[2-({2-[(α-L-fucopyranosyl)oxy]ethyl}amino)-2-oxoethyl]-L-lysinamide (124.7 mg, 0.067 mmol) in H$_2$O (2 mL) was added Pd/C (0.21 mg, 2.007 μmol). The reaction mixture was degassed (3×) with H$_2$. After stirring under a balloon of H$_2$ for 1 hr, the catalyst was filtered off through a cake of Celite and washed with H$_2$O. The filtrate was freeze-dried to give the title compound. UPLC-MS Method A: $t_R$=4.20 min; m/z=1730.37 (z=1).

Step H. benzyl (7S,25S)-1-[(α-L-fucopyranosyl)oxy]-6-[2-({2-[(α-L-fucopyranosyl)oxy]ethyl}amino)-2-oxoethyl]-7-({2-[(α-L-fucopyranosyl)oxy]ethyl}carbamoyl)-25-heptadecanamido-5-{3-[(6-{[2-({α-D-mannopyranosyl-(1→3)-[α-D-mannopyranosyl-(1→6)]-α-D-mannopyranosyl}oxy)ethyl]amino}-6-oxohexyl)amino]-3-oxopropyl}-4,13,17,24-tetraoxo-3,6,12,15,18,23-hexaazaoctacosan-28-oate To a solution of N$^6$—(N-{2-[(5-aminopentyl)amino]-2-oxoethyl}-N-{2-[(6-{[2-({α-D-mannopyranosyl-(1→3)-[α-D-mannopyranosyl-(1→6)]-α-D-mannopyranosyl}oxy)ethyl]amino}-6-oxohexyl)amino]-2-oxoethyl}glycyl)-N-{2-[(α-L-fucopyranosyl)oxy]ethyl}-N$^2$,N$^2$-bis[2-({2-[(α-L-fucopyranosyl)oxy]ethyl}amino)-2-oxoethyl]-L-lysinamide (98.6 mg, 0.057 mmol) in DMF (2 mL) was added DIPEA (25 μL, 0.143 mmol), EDC (13.11 mg, 0.068 mmol), HOBt (8.73 mg, 0.057 mmol) and (S)-5-(benzyloxy)-2-heptadecanamido-5-oxopentanoic acid (27.9 mg, 0.057 mmol). After stirring for 16 hr, the reaction mixture was concentrated and the resulting oil was purified on HPLC (BEH C18, 300×19 mm, gradient 10-50% AcCN in H$_2$O with 0.05% TFA). The desired fractions were combined and freeze-dried to produce the title compound. UPLC Method B: $t_R$=4.78 min; m/z=1101.67 (z=2).

Step I. 2,5-dioxopyrrolidin-1-yl (7S,26S)-1-[(α-L-fucopyranosyl)oxy]-6-[2-({2-[(α-L-fucopyranosyl)oxy]ethyl}amino)-2-oxoethyl]-7-({2-[(α-L-fucopyranosyl)oxy]ethyl}carbamoyl)-26-heptadecanamido-4,13,17,25-tetraoxo-15-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,6,12,15,18,24-hexaazanonacosan-29-oate The title compound was prepared using procedure analogous to those described for Step C-D in Preparative Example 1 (ML-1) substituting benzyl (7S,25S)-1-[(α-L-fucopyranosyl)oxy]-6-[2-({2-[(α-L-fucopyranosyl)oxy]ethyl}amino)-2-oxoethyl]-7-({2-[(α-L-fucopyranosyl)oxy]ethyl}carbamoyl)-25-heptadecanamido-15-{3-[(6-{[2-({α-D-mannopyranosyl-(1→3)-[α-D-mannopyranosyl-(1→6)]-α-D-mannopyranosyl}oxy)ethyl]amino}-6-oxohexyl)amino]-3-oxopropyl}-4,13,17,24-tetraoxo-3,6,12,15,18,23-hexaazaoctacosan-28-oate for benzyl 6-({2-[(α-D-mannopyranosyl-(1→3)-[α-D-mannopyranosyl-(1→6)]-α-D-mannopyranosyl)oxy]ethyl}amino)-6-oxohexanoate in Step C. UPLC-MS Method B: $t_R$=4.41 min; m/z=1105.15 (z=2).

Preparative Example 10

The synthesis of oligosaccharide 2,5-dioxopyrrolidin-1-yl (S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,10,15,18,21-pentaazaheptacosan-27-oate (ML-21) having the following structure is described.

ML-21

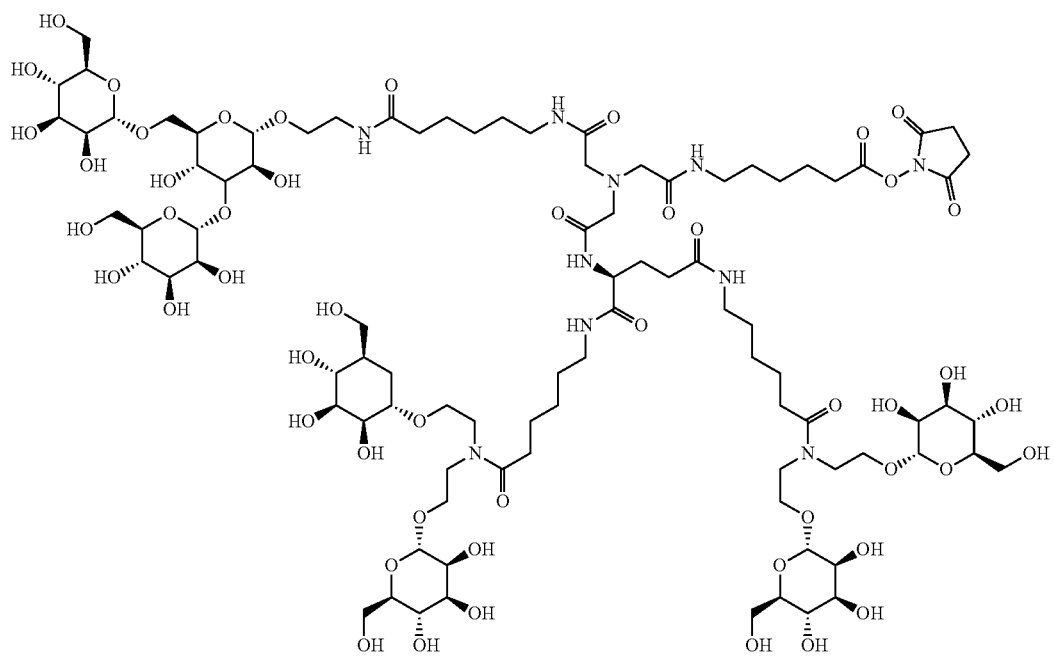

Step A. allyl 2,3,4,6-tetra-O-acetyl-α-D-mannopyranoside

To a mixture of α-D-mannose pentaacetate (5.0 g, 12.81 mmol) and allyl alcohol (1.12 g, 19.21 mmol) in AcCN (32.0 mL) at 0° C. was added dropwise boron trifluoride etherate (8.12 mL, 64.0 mmol). The mixture was stirred for 1 hr at 0° C. and then at rt overnight. The reaction mixture was partitioned between EtOAc (100 mL) and $H_2O$ (100 mL). The organic phase was separated, washed with sat'd $NaHCO_3$ and brine, dried over $Na_2SO_4$ and concentrated. The residue was purified by flash chromatography on silica gel (120 g), eluting with 0-30% EtOAc/Hex over 30 min (flow rate 100 mL/min) followed by hold column, to give the title compound. LC-MS Method A: $t_R$=1.82 min; m/z=410.91 (M+Na, z=1).

Step B. 2,3-dihydroxy-propyl 2,3,4,6-tetra-O-acetyl-α-D-mannopyranoside

To a solution of allyl 2,3,4,6-tetra-O-acetyl-α-D-mannopyranoside (2.10 g, 5.41 mmol) in a mixture of acetone (43.3 mL) and $H_2O$ (10.8 mL) was added NMO (1.27 g, 10.81 mmol) as solid and followed by $OsO_4$ (1.72 g, 0.270 mmol, 4 wt % $OsO_4$ in $H_2O$). After stirring for 3 hr, the reaction mixture was diluted with EtOAc (100 mL) and washed with $H_2O$ (100 mL). The aqueous layer was separated and extracted with EtOAc (3×70 mL). The organic layers were combined and washed with brine, dried over $Na_2SO_4$, and concentrated. The residue was purified by flash chromatography on silica gel (120 g), eluting with 0-100% EtOA/Hexanes over 30 min (flow rate=80 mL/min) followed by hold, to give the title compound. LC-MS Method A: $t_R$=1.20 min, m/z=440 (M+$H_2O$, z=1).

Step C. 2-oxoethyl 2,3,4,6-tetra-O-acetyl-α-D-mannopyranoside

To a solution of 2,3-dihydroxy-propyl 2,3,4,6-tetra-1-acetyl-α-D-mannopyranoside (2.01 g, 4.76 mmol) in AcCN (74.4 mL) was added a solution of $NaIO_4$ (2.04 g, 9.52 mmol) in $H_2O$ (44.6 mL). After stirring at rt overnight, the reaction mixture was partitioned between EtOAc (100 mL) and $H_2O$ (100 mL). The aqueous layer was separated and extracted with EtOAc (3×50 mL). The organic layers were combined, washed with brine, dried over $Na_2SO_4$ and concentrated. The residue was purified by flash chromatography on silica gel (40 g), eluting with 0-80% EtOAc/Hex over 20 min (flow rate 40 mL/min) followed by hold, to give the title compound.

Step D. N-benzyl-2-[(2,3,4,6-tetra-O-acetyl-α-D-mannopyranosyl)oxy]-N-{2-[(2,3,4,6-tetra-O-acetyl-α-D-mannopyranoside)oxy]ethyl}ethan-1-amine To a solution of 2-oxoethyl 2,3,4,6-tetra-O-acetyl-α-D-mannopyranoside (1.82 g, 4.67 mmol) and benzylamine (200 mg, 1.866 mmol) in DCM (18.7 mL) was added HOAc (32 µL, 0.560 mmol) followed by addition of $NaBH(OAc)_3$ (1.19 g, 5.60 mmol). After stirring at rt overnight, the reaction mixture was partitioned carefully between DCM (100 mL) and sat'd $NaHCO_3$ (100 mL). After formation of bubbles ceased (~20 min), the aqueous layer was separated and extracted DCM (2×50 mL). The organic layers were combined, dried over $Na_2SO_4$ and concentrated. The residue was purified by flash chromatography on silica gel (120 g), eluting with 0-50% EtOAc/Hex followed by hold, to give the title compound. LC-MS Method A: $t_R$=1.66 min; m/z=856.41 (z=1).

Step E. bis{2-[(2,3,4,6-tetra-O-acetyl-α-D-mannopyranosyl)oxy]ethyl}amine

A mixture of Pearlman's catalyst (433 mg, 0.617 mmol) and N-benzyl-2-[(2,3,4,6-tetra-O-acetyl-α-D-mannopyranosyl)oxy]-N-{2-[(2,3,4,6-tetra-O-acetyl-α-D-mannopyranoside)oxy]ethyl}ethan-1-amine (1.32 g, 1.542 mmol) in MeOH (15.42 mL) was shaken on a Parr shaker under 50 psi of $H_2$ over the weekend. The catalyst was filtered off through a cake of Celite and the filtrate was concentrated to give the title product. LC-MS Method A: $t_R$=1.52 min; m/z=766.26 (z=1).

Step F. benzyl [6-(bis{2-[(2,3,4,6-tetra-O-acetyl-α-D-mannopyranosyl)oxy]ethyl}amino)-6-oxohexyl]carbamate To a solution of bis{2-[(2,3,4,6-tetra-O-acetyl-α-D-mannopyranosyl)oxy]ethyl}amine (4.0 g, 5.22 mmol) was in DMF (16 mL) at 0° C. was added 2,5-dioxopyrrolidin-1-yl 6-{[(benzyloxy)carbonyl]amino}hexanoate (2.29 g, 6.32 mmol) in DMF (8 mL) portionwise over a period of 15 min and then TEA (1.10 mL, 7.89 mmol) was added dropwise over a period of 10 min. After stirring at rt overnight, the reaction mixture was concentrated. The residue was purified by flash chromatography on C18 reverse phase silica gel (240 g), eluting with 30-60% AcCN/$H_2O$ in 15 CV, to give the title compound. UPLC-MS Method B: $t_R$=4.5 min; m/z=1013.46 (z=1).

Step G. benzyl [6-(bis{2-[(α-D-mannopyranosyl)oxy]ethyl}amino)-6-oxohexyl]carbamate To a suspension of benzyl [6-(bis{2-[(2,3,4,6-tetra-O-acetyl-α-D-mannopyranosyl)oxy]ethyl}amino)-6-oxohexyl]carbamate (2.96 g, 2.92 mmol) in MeOH (75 mL) was added $NaOCH_3$ (501 µL, 2.192 mmol, 4.37M in MeOH). After stirring at rt for 20 hr, the reaction mixture was clear and concentrated. The residue was taken into EtOAc (75 mL) and stirred for 3 hr. The precipitate was collected by filtration, washed with EtOAc (2×20 mL) and dried to give the title compound. UPLC-MS Method A: $t_R$=3.96 min; m/z=677.36 (z=1).

Step H. 6-amino-N,N-bis{2-[(α-D-mannopyranosyl)oxy]ethyl}hexanamide

To a solution of benzyl [6-(bis{2-[(α-D-mannopyranosyl)oxy]ethyl}amino)-6-oxohexyl]carbamate (1.96 g, 2.89 mmol) in H$_2$O (35 mL) was added Pd/C (308 mg, 0.289 mmol). The resulting mixture was degassed and stirred under a balloon of H$_2$ at rt for 6 hr. The catalyst was filtered off through a cake of Celite and washed with H$_2$O. The filtrate was freeze-dried to afford the title compound. UPLC-MS Method A: t$_R$=1.29 min; m/z=543.28 (z=1).

Step I. benzyl (S)-(1,25-bis[(α-D-mannopyranosyl)oxy]-3,23-bis{2-[(α-D-mannopyranosyl)oxy]ethyl}-4,11,15,22-tetraoxo-3,10,16,23-tetraazapentacosan-12-yl)carbamate To a mixture of 6-amino-N,N-bis{2-[(α-D-mannopyranosyl)oxy]ethyl}hexanamide (2.3 g, 4.27 mmol) and Z-Glu-OH (500 mg, 1.78 mmol) in DMF (15 mL) was added EDC (1.02 g, 5.33 mmol) and HOBt (681 mg, 2.5 mmol). After stirring at rt overnight, the reaction mixture was added dropwise to stirred AcCN (200 mL). The resulting white precipitate collected by filtration and purified by flash chromatography on C18 silica gel (270 g), eluting with 5-60% AcCN/H$_2$O, to give the title compound. UPLC-MS Method A: t$_R$=3.30 min; m/z=1330.75 (z=1).

Step J. (S)-2-amino-N,N-bis[6-(bis{2-[(α-D-mannopyranosyl)oxy]ethyl}amino)-6-oxohexyl]pentanediamide A mixture of benzyl (S)-(1,25-bis[(α-D-mannopyranosyl)oxy]-3,23-bis{2-[(α-D-mannopyranosyl)oxy]ethyl}-4,11,15,22-tetraoxo-3,10,16,23-tetraazapentacosan-12-yl)carbamate (2.0 g, 1.5 mmol) in H$_2$O (50 mL) and 10% Pd/C (160 mg, 0.150 mmol) was degassed and stirred under a balloon of H$_2$ over the weekend. The catalyst was filtered off through a cake of Celite and the filtrate was freeze-dried to give the title compound. UPLC-MS Method A: t$_R$=3.43 min; m/z=1196.69 (z=1).

Step K. N-(2-{[6-(benzyloxy)-6-oxohexyl]amino}-2-oxoethyl)-N-{2-[(6-{[2-({α-D-mannopyranosyl-(1→3)-[α-D-mannopyranosyl-(1→6)]-α-D-mannopyranosyl}oxy)ethyl]amino}-6-oxohexyl)amino]-2-oxoethyl}glycine The title compound was prepared using procedure analogous to those described for Step A-D in Preparative Example 9 (ML-19) substituting benzyl 6-aminohexanoate for benzyl (5-aminopentyl)carbamate hydrochloride in Step C. UPLC-MS Method A: t$_R$=2.91 min; m/z=1037.52 (z=1).

Step L. benzyl (S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-8-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,10,15,18,21-pentaazaheptacosan-27-oate To a mixture of N-(2-{[6-(benzyloxy)-6-oxohexyl]amino}-2-oxoethyl)-N-{2-[(6-{[2-({α-D-mannopyranosyl-(1→3)-[α-D-mannopyranosyl-(1→6)]-α-D-mannopyranosyl}oxy)ethyl]amino}-6-oxohexyl)amino]-2-oxoethyl}glycine (900 mg, 0.868 mmol) and (S)-2-amino-N$^1$,N$^5$-bis[6-(bis{2-[(α-D-mannopyranosyl)oxy]ethyl}amino)-6-oxohexyl]pentanediamide (1.04 g, 0.868 mmol) in DMF (10 mL) was added EDC (333 mg, 1.74 mmol) and HOBt (199 mg, 1.3 mmol). After stirring at rt for 3 hr, the reaction mixture was added dropwise to stirred AcCN (200 mL). The resulting white precipitate was collected by filtration, and purified by flash chromatography on C18 reverse phase silica gel (270 g), eluting with 5-40% AcCN in H$_2$O, to give the title compound. UPLC-MS Method A: t$_R$=3.40 min; m/z=1108.60 (z=2).

Step M 2,5-dioxopyrrolidin-1-yl (S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,10,15,18,21-pentaazaheptacosan-27-oate The title compound was prepared using procedure analogous to those described for Step C and D in Preparative Example 1 (ML-1) substituting benzyl (S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,10,15,18,21-pentaazaheptacosan-27-oate for benzyl 6-{[2-({α-D-mannopyranosyl-(1→3)-[α-D-mannopyranosyl-(1→6)]-α-D-mannopyranosyl}oxy)ethyl]amino}-6-oxohexanoate in Step C. UPLC-MS Method A: t$_R$=2.37 min; m/z=1112.02 (z=2).

Preparative Example 11

The synthesis of oligosaccharide 2,5-dioxopyrrolidin-1-yl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,23-tetraoxo-25-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-3,10,13,16,22,26-hexaazadotriacontan-32-oate (ML-26) having the following structure is described.

ML-26

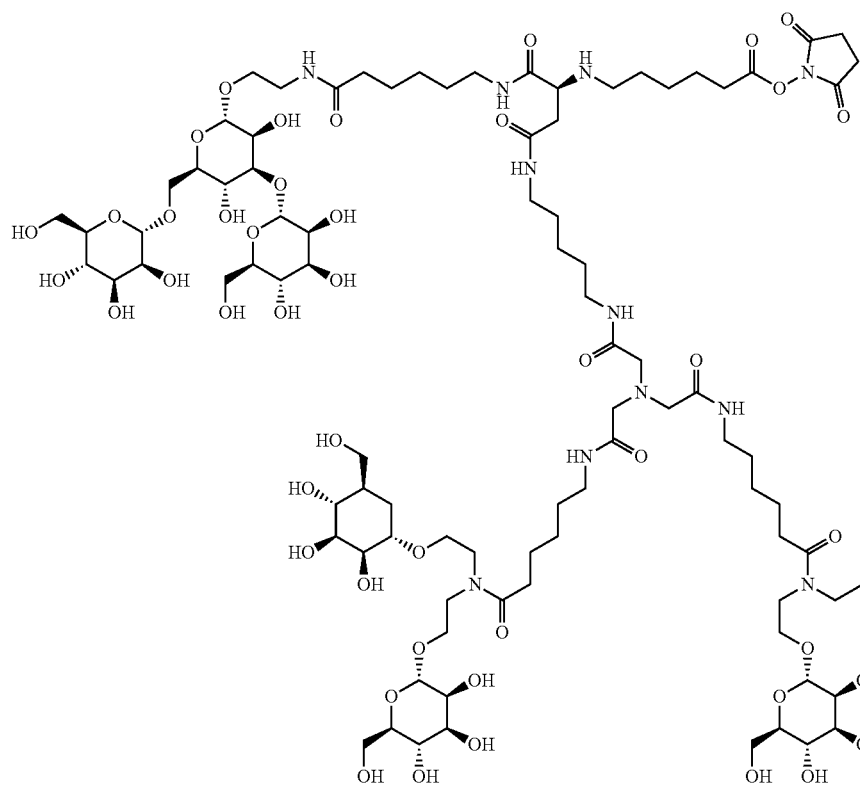

Step A. benzyl (S)-3-(benzylamino)-4-oxo-4-[(6-oxo-6-{[2-({α-D-mannopyranosyl-(1→3)-[α-D-mannopyranosyl-(1→6)]-α-D-mannopyranosyl}oxy)ethyl]amino}hexy)amino]butanoate To a solution of 6-amino-N-[2-({α-D-mannopyranosyl-(1→3)-[α-D-mannopyranosyl-(1→6)]-α-D-mannopyranosyl}oxy)ethyl]hexanamide (818 mg, 1.238 mmol) in DMF (3 mL) at rt was added Z-ASP(OBZL)-OH (465 mg, 1.300 mmol), followed by EDC (249 mg, 1.300 mmol) and HOBt (199 mg, 1.300 mmol). After stirring at rt overnight, the reaction mixture was concentrated and the residue was purified by flash chromatography on C18 silica gel (120 g), eluting with 0-35% AcCN in water in 20CV, to give the title compound. UPLC-MS Method A: $t_R$=4.13 min; m/z=1000.49 (z=1).

Step B. (S)-3-amino-4-oxo-4-[(6-oxo-6-{[2-({α-D-mannopyranosyl-(1→3)-[α-D-mannopyranosyl-(1→6)]-α-D-mannopyranosyl}oxy)ethyl]amino}hexyl)amino]butanoic acid A mixture of benzyl (S)-3-(benzylamino)-4-oxo-4-[(6-oxo-6-{[2-({α-D-mannopyranosyl-(1→3)-[α-D-mannopyranosyl-(1→6)]-α-D-mannopyranosyl}oxy)ethyl]amino}hexyl)amino]butanoate (1.0 g, 1.000 mmol) and Pd/C (106 mg, 1.000 mmol) in $H_2O$ (20 mL) was degassed and stirred under a balloon of $H_2$ overnight. The catalyst was filtered off through a cake of Celite and the filtrate was freeze-dried to afford the title compound.

Step C. (S)-3-{[6-(benzyloxy)-6-oxohexyl]amino}-4-oxo-4-[(6-oxo-6-{[2-({α-D-mannopyranosyl-(1→3)-[α-D-mannopyranosyl-(1→6)]-α-D-mannopyranosyl}oxy)ethyl]amino}hexyl)amino]butanoic acid To a solution of (S)-3-amino-4-oxo-4-[(6-oxo-6-{[2-({α-D-mannopyranosyl-(1→3)-[α-D-mannopyranosyl-(1→6)]-α-D-mannopyranosyl}oxy)ethyl]amino}hexyl)amino]butanoic acid (760 mg, 0.980 mmol) in DMF (3 mL) was added benzyl (2,5-dioxopyrrolidin-1-yl) adipate (408 mg, 1.225 mmol), followed by DIPEA (214 μL, 1.225 mmol). After stirring at rt for 4 hr, the reaction mixture was concentrated and the residue was purified by flash chromatography on C18 silica gel (120 g), eluting with 0-20% AcCN in water in 20 CV, to give the title compound. UPLC-MS Method A: $t_R$=3.94 min; m/z=994.51 (z=1).

Step D. benzyl [13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15-trioxo-3,10,13,16-tetraazahenicosan-21-yl]carbamate To a solution of 13-(carboxymethyl)-3,11-dioxo-1-phenyl-2-oxa-4,10,13-triazapentadecan-15-oic acid (400 mg, 0.977 mmol) in DMF (5 mL) was added 6-amino-N,N-bis{2-[(α-D-mannopyranosyl)oxy]ethyl}hexanamide (1.060 g, 1.954 mmol), EDC (468 mg, 2.442 mmol) and HOBt (15 mg, 0.098 mmol). After stirring at rt overnight, the reaction mixture was concentrated and the residue was purified by flash chromatography on C18 silica gel (120 g), eluting with 0-20% AcCN in water in 20 CV, to give the title compound. UPLC-MS Method A: $t_R$=2.89 min; m/z=1459.80 (z=1).

Step E. 6,6'-{[2,2'-({2-[(5-aminopentyl)amino]-2-oxoethyl}azanediyl)bis(acetyl)]bis(azanediyl)}bis(N,N-bis{2-[(α-D-mannopyranosyl)oxy]ethyl}hexanamide)

A suspension of benzyl [13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15-trioxo-3,10,13,16-tetraazahenicosan-21-yl]carbamate (880 mg, 0.603 mmol) and Pd/C (3 mg, 0.030 mmol) in H$_2$O (30 mL) was degassed and stirred under a balloon of H$_2$ at rt overnight. After overnight, the catalyst was filtered off through a cake of Celite and the filtrate was freeze-dried to give the title product. UPLC-MS Method A: $t_R$=3.19 min; m/z=1324.73 (z=1).

Step F. benzyl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,23-tetraoxo-25-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-3,10,13,16,22,26-hexaazadotriacontan-32-oate To a solution of (S)-3-{[6-(benzyloxy)-6-oxohexyl]amino}-4-oxo-4-[(6-oxo-6-{[2-({α-D-mannopyranosyl-(1→3)-[α-D-mannopyranosyl-(1→6)]-α-D-mannopyranosyl}oxy)ethyl]amino}hexyl)amino]butanoic acid (500 mg, 0.503 mmol) in DMF (5 mL) was added 6,6'-{[2,2'-({2-[(5-aminopentyl)amino]-2-oxoethyl}azanediyl)bis(acetyl)]bis(azanediyl)}bis(N,N-bis{2-[(α-D-mannopyranosyl)oxy]ethyl}hexanamide) (666 mg, 0.503 mmol), HOBt (96 mg, 0.629 mmol) and EDC (121 mg, 0.629 mmol). After stirring at rt overnight, the reaction mixture was concentrated and the residue was purified by flash chromatography on C18 silica gel (120 g), eluting with 0-20% AcCN in water in 20 CV, to give the title compound. UPLC-MS Method A: $t_R$=2.27 min; m/z=1151.19 (z=2).

Step G. 2,5-dioxopyrrolidin-1-yl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,23-tetraoxo-25-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-3,10,13,16,22,26-hexaazadotriacontan-32-oate The title compound was prepared using procedure analogous to those described for Step C and D in Preparative Example 1 (ML-1) substituting benzyl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,23-tetraoxo-25-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-3,10,13,16,22,26-hexaazadotriacontan-32-oate for benzyl 6-{[2-({α-D-mannopyranosyl-(1→3)-[α-D-mannopyranosyl-(1→6)]-α-D-mannopyranosyl}oxy)ethyl]amino}-6-oxohexanoate in Step C. UPLC-MS Method A: $t_R$=1.72 min; m/z=1154.61 (z=2).

Preparative Example 12

The synthesis of oligosaccharide 2,5-dioxopyrrolidin-1-yl (14S,19S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,21,24-pentaoxo-19-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-3,10,15,20,23-pentaazanonacosan-29-oate (ML-27) having the following structure is described.

ML-27

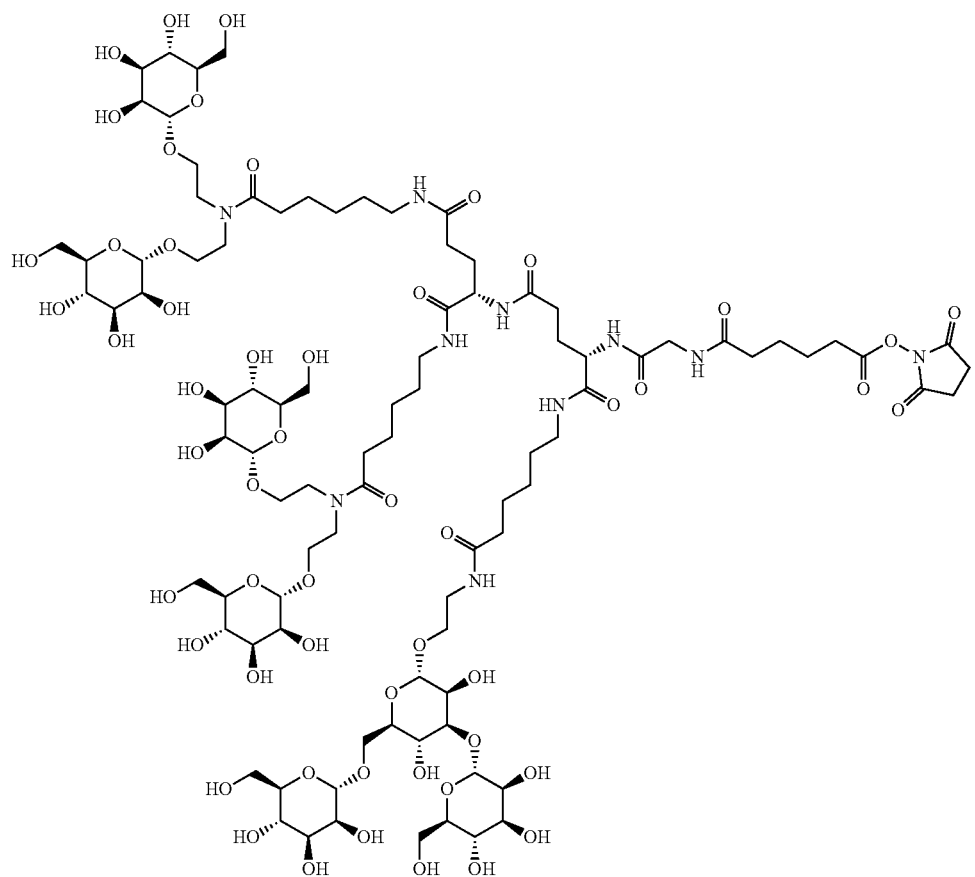

Step A. [(S)-4-{2-[6-(benzyloxy)-6-oxohexanamido]acetamido}-5-(tert-butoxy)-5-oxopentanoyl]-L-glutamic acid To a solution of Gly-γGlu(OtBu)-Glu (1.487 g, 3.82 mmol) in DMF (20 mL) at 0° C. was added 6-(benzyloxy)-6-oxohexanoic acid (1.337 g, 4.01 mmol) in DMF (4 mL) portionwise over a period of 15 min and then TEA (1.064 mL, 7.64 mmol) dropwise over a period of 10 min. After stirring at rt overnight, the reaction mixture was concentrated. The residue was purified by flash chromatography on C18 reverse phase silica gel (150 g), eluting with 5-60% AcCN/H₂O 24 CV, to give the title compound. UPLC-MS Method B: $t_R$=4.71 min; m/z=608.33 (z=1).

Step B. benzyl (14S,19S)-14-{[6-(bis{2-[(α-D-mannopyranosyl)oxy]ethyl}amino)-6-oxohexyl]carbamoyl}-19-(tert-butoxycarbonyl)-1-[(α-D-mannopyranosyl)oxy]-3-{2-[(α-D-mannopyranosyl)oxy]ethyl}-4,11,16,21,24-pentaoxo-3,10,15,20,23-pentaazanonacosan-29-oate To a solution of [(S)-4-{2-[6-(benzyloxy)-6-oxohexanamido]acetamido}-5-(tert-butoxy)-5-oxopentanoyl]-L-glutamic acid (1.0 g, 1.646 mmol) in dry DMF (40.0 mL) at 0° C. was added EDC (946 mg, 4.94 mmol) and HOBt (252 mg, 1.646 mmol). After stirring at 0° C. for 30 min, to resulting mixture was added 6-amino-N,N-bis{2-[(α-D-mannopyranosyl)oxy]ethyl}hexanamide (2.05 g, 3.79 mmol). After stirring at rt overnight, the reaction mixture was concentrated. The residue was purified by flash chromatography on C18 reverse phase silica gel (150 g), eluting with 0-50% AcCN/H₂O in 20 CV, to give the title compound. UPLC-MS Method B: $t_R$=4.6 min; m/z=829.01 (z=2).

Step C. N²-{[6-(benzyloxy)-6-oxohexanoyl]glycyl}-N⁵—[(S)-1,25-bis[(α-D-mannopyranosyl)oxy]-3,23-bis{2-[(α-D-mannopyranosyl)oxy]ethyl}-4,11,15,22-tetraoxo-3,10,16,23-tetraazapentacosan-12-yl]-L-glutamine (14S,19S)-14-{[6-(Bis{2-[(α-D-mannopyranosyl)oxy]ethyl}amino)-6-oxohexyl]carbamoyl}-19-(tert-butoxycarbonyl)-1-[(α-D-mannopyranosyl)oxy]-3-{2-[(α-D-mannopyranosyl)oxy]ethyl}-4,11,16,21,24-pentaoxo-3,10,15,20,23-pentaazanonacosan-29-oate (1.967 g, 1.187 mmol) was dissolved in TFA (14 mL, 182 mmol) at 0° C. After stirring at 0° C. for 2 hr, the reaction mixture was concentrated and the residue was purified by flash chromatography on C18 reverse phase silica gel (100 g), eluting with 0-55% AcCN/H₂O, to give the title compound. UPLC-MS Method B: $t_R$=4.08 min; m/z=1601.84 (z=1).

Step D. benzyl (14S,19S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,21,24-pentaoxo-9-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl-3,10,15,20,23-pentaazanonacosan-29-oate To a solution of N²-{[6-(benzyloxy)-6-oxohexanoyl]glycyl}-N⁵—[(S)-1,25-bis[(α-D-mannopyranosyl)oxy]-3, 23-bis{2-[(α-D-mannopyranosyl)oxy]ethyl}-4,11,15,22-tetraoxo-3,10,16,23-tetraazapentacosan-12-yl]-L-glutamine (700 mg, 0.437 mmol) in dry DMF (20 mL) at 0° C. was added EDC (168 mg, 0.875 mmol) and HOBt (34 mg, 0.219 mmol). The mixture was allowed to stir at 0° C. for 30 min. To the resulting mixture was added 6-amino-N-[2-({α-D-mannopyranosyl-(1→3)-[α-D-mannopyranosyl-(1→6)]-α-D-mannopyranosyl}oxy)ethyl]hexanamide (373 mg, 0.565 mmol). After stirring at rt overnight, the reaction mixture was concentrated and the residue was purified by flash chromatography on C18 reverse phase silica gel (100 g), eluting with 0-50% AcCN/H$_2$O in 20 CV, to give the title compound. UPLC-MS Method A: $t_R$=2.70 min; m/z=1122.67 (z=2).

Step E. 2,5-dioxopyrrolidin-1-yl (14S,19S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,21,24-pentaoxo-19-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-3,10,15,20,23-pentaazanonacosan-29-oate The title compound was prepared using procedure analogous to those described for Step C and D in Preparative Example 1 (ML-1) substituting benzyl (14S,19S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,21,24-pentaoxo-19-[(6-oxo-6-{[2-({α-D-mannopyranosyl-(1→3)-[α-D-mannopyranosyl-(1→6)]-α-D-mannopyranosyl}oxy)ethyl]amino}hexyl)carbamoyl]-3,10,15,20,23-pentaazanonacosan-29-oate for benzyl 6-{[2-({α-D-mannopyranosyl-(1→3)-[α-D-mannopyranosyl-(1→6)]-α-D-mannopyranosyl}oxy)ethyl]amino}-6-oxohexanoate in Step C. UPLC-MS Method A: $t_R$=1.63 min; m/z=1125.6691 (z=2).

Preparative Example 13

The synthesis of oligosaccharide 2,5-dioxopyrrolidin-1-yl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,24,27-pentaoxo-25-{4,8,15-trioxo-6-[2-oxo-2-({2-[(α-L-fucopyranosyl)oxy]ethyl}amino)ethyl]-1-[(α-L-fucopyranosyl)oxy]-3,6,9,16-tetraazaicosan-20-yl}-3,10,13,16,23,26-hexaazadotriacontan-32-oate (ML-28) having the following structure is described.

ML-28

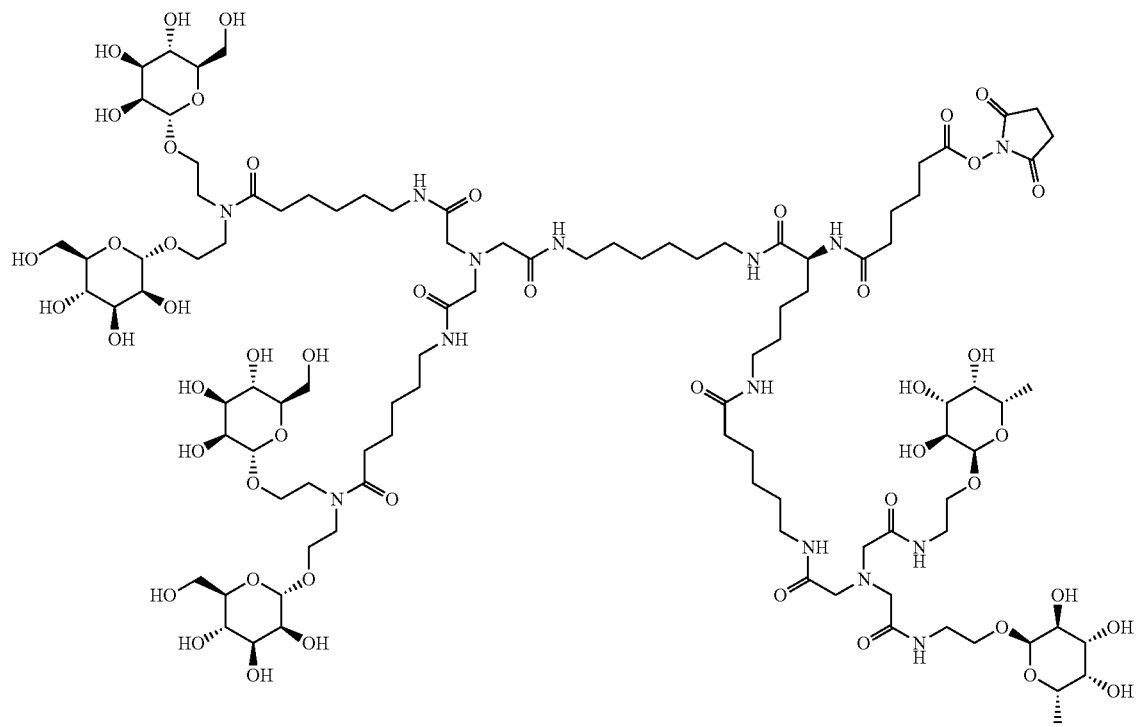

Step A. (S)-21-{[(benzyloxy)carbonyl]amino}-1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazadocosan-22-oic acid To a solution of Z-lysine (500 mg, 1.783 mmol) in DMF (10 mL) was added 2,2'-{[2-({6-[(2,5-dioxopyrrolidin-1l-yl)oxy]-6-oxohexyl}amino)-2-oxoethyl]imino}bis(N-{2-[(α-L-fucopyranosyl)oxy]ethyl}acetamide) (1.39 g, 1.783 mmol, ML-4) and TEA (298 µL, 2.139 mmol). After stirring at 25° C. for 8 hr, the reaction mixture was concentrated and the residue was purified by flash chromatograph on C18 reverse phase silica gel (43 g), eluting with 0-30% AcCN/H$_2$O in 15 CV, to give the title compound. UPLC-MS Method B: $t_R$=2.68 min; m/z=945.35 (z=1).

Step B. (S)-21-amino-1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazadocosan-22-oic acid A mixture of (S)-21-{[(benzyloxy)carbonyl]amino}-1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazadocosan-22-oic acid (1.783 mmol) and Pd/C (95 mg, 0.089 mmol in H$_2$O (5 mL) was degassed and stirred under a balloon of H$_2$ for 18 hr. The catalyst was filtered off through a cake of Celite and the filtrate was freeze-dried to give the title compound. UPLC-MS Method B: $t_R$=1.51 min; m/z=811.48 (z=1).

Step C. (S)-21-[6-(benzyloxy)-6-oxohexanamido]-1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazadocosan-22-oic acid In a solution of (S)-21-amino-1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazadocosan-22-oic acid (1.10 g, 1.353 mmol) in DMF (2 mL) at 0° C. was added benzyl (2,5-dioxopyrrolidin-1-yl) adipate (496 mg, 1.488 mmol) and DIPEA (284 µL, 1.623 mmol). After stirring at rt for 18 hr, the reaction mixture was concentrated and the residue was purified by flash chromatography on C18 reverse phase silica gel (43 g), eluting with 0-40% AcCN/H$_2$O in 15 CV, to give the title compound. UPLC-MS Method A: $t_R$=3.28 min; m/z=1029.37 (z=1).

Step D. 14-(carboxymethyl)-3,12-dioxo-1-phenyl-2-oxa-4,11,14-triazahexadecan-16-oic acid The title compound was prepared using procedure analogous to that described for Step C in Preparative Example 9 (ML-19) substituting benzyl (6-aminohexyl)carbamate hydrochloride for benzyl (5-aminopentyl)carbamate hydrochloride. UPLC-MS Method A: $t_R$=3.56 min; m/z=424.21 (z=1).

Step E. 6,6'-{[2,2'-({2-[(6-aminohexyl)amino]-2-oxoethyl}azanediyl)bis(acetyl)]bis(azanediyl)}bis(N,N-bis{2-[(α-D-mannopyranosyl)oxy]ethyl}hexanamide)

The title compound was prepared using procedure analogous to those described for Step D-E in Preparative Example 11 (ML-26) substituting 14-(carboxymethyl)-3,12-dioxo-1-phenyl-2-oxa-4,11,14-triazahexadecan-16-oic acid for 13-(carboxymethyl)-3,11-dioxo-1-phenyl-2-oxa-4,10,13-triazapentadecan-15-oic acid in Step D. UPLC-MS Method A: $t_R$=1.46 min; m/z=1339.74 (z=1).

Step F. benzyl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,24,27-pentaoxo-25-{4,8,15-trioxo-6-[2-oxo-2-({2-[(α-L-fucopyranosyl)oxy]ethyl}amino)ethyl]-1-[(α-L-fucopyranosyl)oxy]-3,6,9,16-tetraazaicosan-20-yl}-3,10,13,16,23,26-hexaazadotriacontan-32-oate In a solution of (S)-21-[6-(benzyloxy)-6-oxohexanamido]-1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazadocosan-22-oic acid (1.05 g, 1.020 mmol) in DMF (2 mL) was added TSTU (369 mg, 1.224 mmol)) and DIPEA (267 µL, 1.530 mmol). After stirring at 25° C. for 2 hr, the reaction mixture was added to a solution of 6,6'-{[2,2'-({2-[(6-aminohexyl)amino]-2-oxoethyl}azanediyl)bis(acetyl)]bis(azanediyl)}bis(N,N-bis{2-[(α-D-mannopyranosyl)oxy]ethyl}hexanamide) (1.37 g, 1.020 mmol) and DIPEA (267 µL, 1.530 mmol). After stirring at rt for 18 hr, the reaction mixture was concentrated and the residue was purified by HPLC (C8, gradient with 5-50% AcCN/water with 0.05% TFA over 30 min) to give the title compound. UPLC-MS Method A: $t_R$=2.41 min; m/z=1175.4 (z=1).

Step G. 2,5-dioxopyrrolidin-1-yl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,24,27-pentaoxo-25-{4,8,15-trioxo-6-[2-oxo-2-({2-[(α-L-fucopyranosyl)oxy]ethyl}amino)ethyl]-1-[(α-L-fucopyranosyl)oxy]-3,6,9,16-tetraazaicosan-20-yl}-3,10,13,16,23,26-hexaazadotriacontan-32-oate The title compound was prepared using procedure analogous to those described for Step C-D in Preparative Example 1 (ML-1) substituting benzyl (S)-13-(2-{[6-(bis{2-[(α-D-mannopyranosyl)oxy]ethyl}amino)-6-oxohexyl]amino}-2-oxoethyl)-1-[(α-D-mannopyranosyl)oxy]-3-{2-[(α-D-mannopyranosyl)oxy]ethyl}-4,11,15,24,27-pentaoxo-25-{4,8,15-trioxo-6-[2-oxo-2-({2-[(α-L-fucopyranosyl)oxy]ethyl}amino)ethyl]-1-[(α-L-fucopyranosyl)oxy]-3,6,9,16-tetraazaicosan-20-yl}-3,10,13,16,23,26-hexaazadotriacontan-32-oate for benzyl 6-{[2-({α-D-mannopyranosyl-(1→3)-[α-D-mannopyranosyl-(1→6)]-α-D-mannopyranosyl}oxy)ethyl]amino}-6-oxohexanoate in Step C. UPLC-MS Method A: $t_R$=1.93 min; m/z=1178.9 (z=2)

Preparative Example 14

The synthesis of oligosaccharide linker 2,5-dioxopyrrolidin-1-yl (21S,24S)-21-[6-(2-{bis[2-({2-[(α-L-fucopyranosyl)oxy]ethyl}amino)-2-oxoethyl]amino}acetamido)hexanamido]-1-[(α-L-fucopyranosyl)oxy]-24-{1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazaicosan-20-yl}-6-2-({2-[(α-L-fucopyranosyl)oxy]ethyl}amino)-2-oxoethyl]-4,8,15,22,25-pentaoxo-3,6,9,16,23,26-hexaazadotriacontan-32-oate (ML-29) having the following structure is described.

ML-29

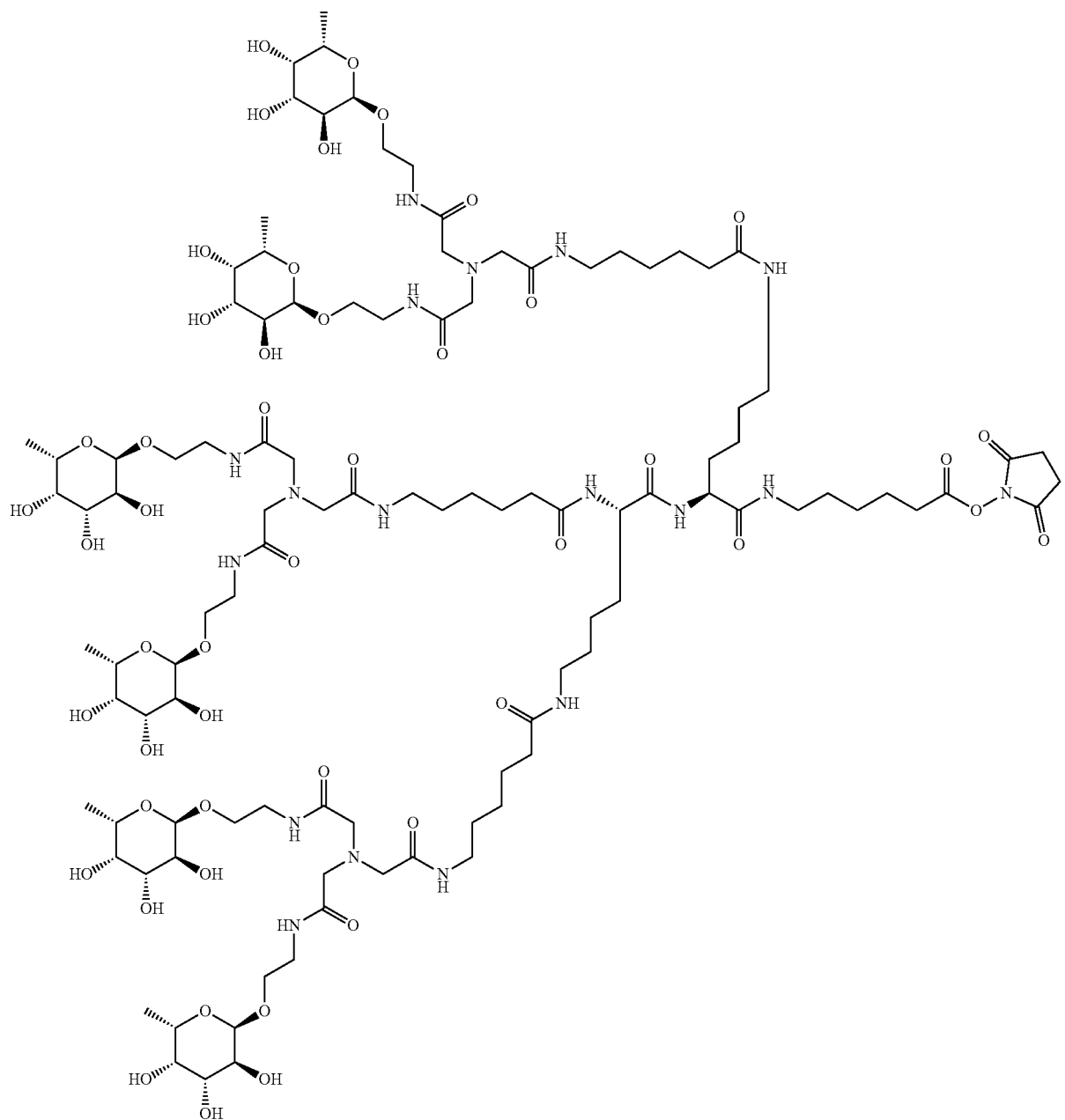

Step A. $N^6$-[(benzyloxy)carbonyl]-$N^2$—{$N^2,N^6$-bis[(benzyloxy)carbonyl]-L-lysyl}-L-lysine To a solution of L-lysyl-L-lysine (1.0 g, 2.88 mmol) in a mixture of 1,4-dioxane (19.20 mL) and NaOH (8.64 ml, 8.64 mmol, 1.0 M) was added benzyl 4-nitrophenyl carbonate (787 mg, 2.88 mmol). After stirring at rt for 1 hr, to the reaction mixture was added additional amounts of benzyl 4-nitrophenyl carbonate (787 mg, 2.88 mmol) and NaOH (2.88 ml, 2.88 mmol, 1.0 M). After stirring overnight, the reaction mixture was diluted with DCM (100 mL) and acidified until pH ~2 with 1.0 M HCl (~50 mL). The aqueous phase was separated and extracted DCM (50 mL). The organic phases were combined, dried over $Na_2SO_4$, and concentrated. The residue was purified by flash chromatography on silica gel (80 g), eluting with 0-100% Solvent B in Solvent A (Solvent A=hexanes and Solvent B=EtOAc with 5% AcOH), to give the title compound. UPLC-MS Method C: $t_R$=3.32 min; m/z=677.36 (z=1).

Step B. methyl (9S,12S)-9-{[(benzyloxy)carbonyl]amino}-12-(4-{[(benzyloxy)carbonyl]amino}butyl)-3,10,13-trioxo-1-phenyl-2-oxa-4,11,14-triazaicosan-20-oate To a solution of $N^6$-[(benzyloxy)carbonyl]-$N^2$—{$N^2,N^6$-bis[(benzyloxy)carbonyl]-L-lysyl}-L-lysine (1.68 g, 2.482 mmol) and methyl 6-aminohexanoate hydrochloride (902 mg, 4.96 mmol) in DMF (12 mL) at rt was EDC (714 mg, 3.72 mmol), DIPEA (1.73 mL, 993 mmol) and HOBt (570 mg, 3.72 mmol). After stirring at rt overnight, the reaction mixture was partitioned between EtOAc and 1.0 M HCl. The organic phase was separated and washed with sat'd NaHCO$_3$ and brine, dried over Na$_2$SO$_4$ and concentrated. The residue was purified by flash chromatography on silica gel, eluting with 0-50% Solvent B in Solvent A (Solvent A=EtOAc and Solvent B=EtOAc with 25% EtOH), to give the title compound. UPLC-MS Method C: $t_R$=3.47 min; m/z=804.45 (z=1).

Step C. methyl 6-{(S)-6-amino-2-[(S)-2,6-diaminohexanamido]hexanamido}hexanoate

A mixture of methyl (9S,12S)-9-{[(benzyloxy)carbonyl]amino}-12-(4-{[(benzyloxy)carbonyl]amino}butyl)-3,10,13-trioxo-1-phenyl-2-oxa-4,11,14-triazaicosan-20-oate (775 mg, 1.930 mmol) and Pearlman's catalyst (124 mg, 0.177 mmol) in EtOH (159 mL) and 1,4-dioxane (18 mL) was shaken on a Parr shaker at 50 psi of H$_2$ for 48 hr. The catalyst was filtered off through a cake of Celite and the filtrate was freeze-dried to give the title compound. UPLC-MS Method C: $t_R$=2.19 min; m/z=402.35 (z=1).

Step D. methyl (21S,24S)-21-[6-(2-{bis[2-({2-[(α-L-fucopyranosyl)oxy]ethyl}amino)-2-oxoethyl]amino}acetamido)hexanamido]-1-[(α-L-fucopyranosyl)oxy]-24-{1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazaicosan-20-yl}-6-[2-({2-[(α-L-fucopyranosyl)oxy]ethyl}amino)-2-oxoethyl]-4,8,15,22,25-pentaoxo-3,6,9,16,23,26-hexaazadotriacontan-32-oate To a solution of methyl 6-{(S)-6-amino-2-[(S)-2,6-diaminohexanamido]hexanamido}hexanoate (75 mg, 0.187 mmol) in a mixture of DMSO (1 mL) and H$_2$O (250 µL) was added 2,2'-{[2-({6-[(2,5-dioxopyrrolidin-1-yl)oxy]-6-oxohexyl}amino)-2-oxoethyl]imino}bis(N-{2-[(α-L-fucopyranosyl)oxy]ethyl}acetamide) (0.15M/DMF) (5.0 mL, 0.747 mmol). After stirring at rt for overnight, the reaction mixture was directly purified by HPLC (C8, 10 µm, 100 Å, size 250×50 mm; flow rate=85 mL/min, gradient 0-50% AcCN in water with 0.05% TFA over 30 min) to give the title compound. UPLC-MS Method A: $t_R$=4.41 min; m/z=1198.71 (z=2).

Step E. (21S,24S)-21-[6-(2-{bis[2-({2-[(α-L-fucopyranosyl)oxy]ethyl}amino)-2-oxoethyl]amino}acetamido)hexanamido]-1-[(α-L-fucopyranosyl)oxy]-24-{-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazaicosan-20-yl}-6-[2-({2-[(α-L-fucopyranosyl)oxy]ethyl}amino)-2-oxoethyl]-4,8,15,22,25-pentaoxo-3,6,9,16,23,26-hexaazadotriacontan-32-oic acid To a solution of methyl (21S,24S)-21-[6-(2-{bis[2-({2-[(α-L-fucopyranosyl)oxy]ethyl}amino)-2-oxoethyl]amino}acetamido)hexanamido]-1-[(α-L-fucopyranosyl)oxy]-24-{1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazaicosan-20-yl}-6-[2-({2-[(α-L-fucopyranosyl)oxy]ethyl}amino)-2-oxoethyl]-4,8,15,22,25-pentaoxo-3,6,9,16,23,26-hexaazadotriacontan-32-oate (183 mg, 0.076 mmol) in H$_2$O (764 µL) and added NaOH (306 µL, 0.306 mmol, 1.0 M). After stirring at rt for 1 hr, the reaction mixture was diluted with H$_2$O (10 mL), the pH value was adjusted to 7.0, and added 10% of AcCN. The resulting mixture was freeze-dried to give the title compound. UPLC-MS Method A: $t_R$=1.53 min; m/z=1191.75 (z=2).

Step F. 2,5-dioxopyrrolidin-1-yl (21S,24S)-21-[6-(2-{bis[2-({2-[(α-L-fucopyranosyl)oxy]ethyl}amino)-2-oxoethyl]amino}acetamido)hexanamido]-1-[(α-L-fucopyranosyl)oxy]-24-{-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazaicosan-20-yl}-6-[2-({2-[(α-L-fucopyranosyl)oxy]ethyl}amino)-2-oxoethyl]-4,8,15,22,25-pentaoxo-3,6,9,16,23,26-hexaazadotriacontan-32-oate The title compound was prepared using procedure analogous to that described for Step D in Preparative Example 1 (ML-1) substituting (21S,24S)-21-[6-(2-{bis[2-({2-[(α-L-fucopyranosyl)oxy]ethyl}amino)-2-oxoethyl]amino}acetamido)hexanamido]-1-[(α-L-fucopyranosyl)oxy]-24-{1-[(α-L-fucopyranosyl)oxy]-6-[2-({2-[(α-L-fucopyranosyl)oxy]ethyl}amino)-2-oxoethyl]-4,8,15-trioxo-3,6,9,16-tetraazaicosan-20-yl}-6-[2-({2-[(α-L-fucopyranosyl)oxy]ethyl}amino)-2-oxoethyl]-4,8,15,22,25-pentaoxo-3,6,9,16,23,26-hexaazadotriacontan-32-oic acid for 6-{[2-({α-D-mannopyranosyl-(1→3)-[α-D-mannopyranosyl-(1→6)]-α-D-mannopyranosyl}oxy)ethyl]amino}-6-oxohexanoic acid in Step D. UPLC-MS Method A: $t_R$=4.00 min; m/z=1240.28 (z=2).

Preparative Example 15

The synthesis of oligosaccharide 2,5-dioxopyrrolidin-1-yl (13S,16S)-13-(2-{bis[2-({2-[(α-L-fucopyranosyl)oxy]ethyl}amino)-2-oxoethyl]amino}acetamido)-16-[4-(2-{bis[2-({2-[(α-L-fucopyranosyl)oxy]ethyl}amino)-2-oxoethyl]amino}acetamido)butyl]-1-[(α-L-fucopyranosyl)oxy]-6-[2-({2-[(α-L-fucopyranosyl)oxy]ethyl}amino)-2-oxoethyl]-4,7,14,17-tetraoxo-3,6,8,15,18-pentaazatetracosan-24-oate (ML-30) having the following structure is described.

ML-30

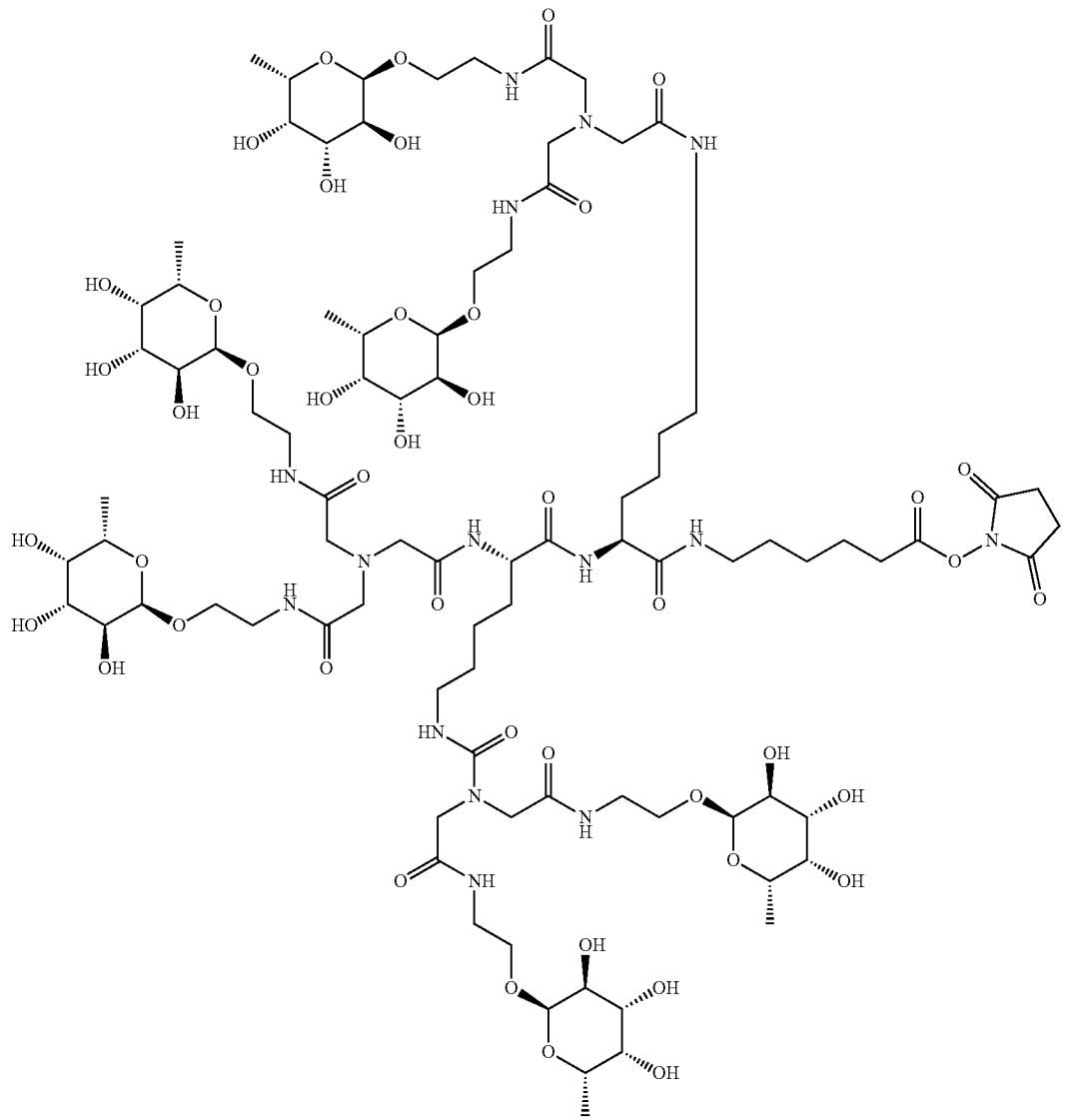

Step A. bis[2-({2-[(α-L-fucopyranosyl)oxy]ethyl}amino)-2-oxoethyl]glycine

To a solution of 2-(2,6-dioxomorpholino)acetic acid (1.0 g, 5.78 mmol) and TSTU (1.74 g, 5.78 mmol) in DMF (29 mL) at 0° C. was added DIPEA (1.01 mL, 5.78 mmol). After stirring for 45 min, to the reaction mixture was added 2-aminoethyl α-L-fucopyranoside hydrobromide (3.33 g, 11.55 mmol) and DIPEA (6.05 mL, 34.7 mmol). After stirring overnight, the reaction mixture was concentrated and the residue was purified by HPLC (C8 10 μm 100 Å, flow rate=85 mL/min, gradient 0-20% AcCN in water with 0.05% TFA over 30 min) to give the title compound. UPLC-MS Method D: $t_R$=2.41 min; m/z=570.28 (z=1).

Step B. 2,5-dioxopyrrolidin-1-yl bis[2-({2-[(α-L-fucopyranosyl)oxy]ethyl}amino)-2-oxoethyl]glycinate To a solution of bis[2-({2-[(α-L-fucopyranosyl)oxy]ethyl}amino)-2-oxoethyl]glycine (1.94 g, 3.41 mmol) in DMF (17.03 ml) at rt was added TSTU (1.23 g, 4.09 mmol). The resulting mixture was cooled to 0° C., to which TEA (712 μL, 5.11 mmol) was added. After stirring for 45 min at 0° C., the reaction mixture was poured into 20× volume of acetone/ether mixture (v/v=1/1). The precipitate was isolated by centrifugation and washed with acetone/ether (v/v=1/1, 20 mL). The solid was redissolved in H₂O/AcCN (v/v=5/1, 6 mL) and freeze-dried to give the title compound. UPLC-MS Method A: $t_R$=1.88 min; m/z=667.30 (z=1).

Step C. $N^2$—($N^6$-{bis[2-({2-[(α-L-fucopyranosyl)oxy]ethyl}amino)-2-oxoethyl]carbamoyl}-$N^2$-{bis[2-({2-[(α-L-fucopyranosyl)oxy]ethyl}amino)-2-oxoethyl]glycyl}-L-lysyl)-N-{bis[2-({2-[(α-L-fucopyranosyl)oxy]ethyl}amino)-2-oxoethyl]glycyl}-L-lysine To a solution of H-Lys-Lys-OH hydrochloride (50 mg, 0.161 mmol) in a mixture of DMSO (1.4 mL) and H₂O (0.2 mL) was added TEA (224 μL, 1.609 mmol) followed by 2,5-dioxopyrrolidin-1-yl bis[2-({2-[(α-L-fucopyranosyl)

oxy]ethyl}amino)-2-oxoethyl]glycinate (429 mg, 0.643 mmol). After stirring at rt overnight, the reaction mixture was concentrated and the residue was purified by HPLC (C8, gradient 0-30% AcCN in water with 0.05% TFA over 30 min) to give the title compound. UPLC-MS Method D: $t_R$=2.98 min; m/z=1928.97 (z=1).

Step D. benzyl (13S,16S)-13-(2-{bis[2-({2-[(α-L-fucopyranosyl)oxy]ethyl}amino)-2-oxoethyl] amino}acetamido)-16-[4-(2-{bis[2-({2-[(α-L-fucopyranosyl)oxy]ethyl}amino)-2-oxoethyl] amino}acetamido)butyl]-1-[(α-L-fucopyranosyl) oxy]-6-[2-({2-[(α-L-fucopyranosyl)oxy] ethyl}amino)-2-oxoethyl]-4,7,14,17-tetraoxo-3,6,8, 15,18-pentaazatetracosan-24-oate To a solution of $N^2$—($N^6$-{bis[2-({2-[(α-L-fucopyranosyl)oxy]ethyl}amino)-2-oxoethyl]carbamoyl}-$N^2$-{bis[2-({2-[(α-L-fucopyranosyl)oxy]ethyl}amino)-2-oxoethyl] glycyl}-L-lysyl)-$N^6$-{bis[2-({2-[(α-L-fucopyranosyl)oxy] ethyl}amino)-2-oxoethyl]glycyl}-L-lysine (205 mg, 0.106 mmol) in DMF (2.125 mL) was added TSTU (35 mg, 0.117 mmol) followed by TEA (59 µL, 0.425 mmol). After stirring for 30 min, to the resulting mixture was added 6-(benzyloxy)-6-oxohexan-1-aminium 4-methylbenzenesulfonate (63 mg, 0.159 mmol) and additional TEA (29.6 mL, 0.213 mmol). After stirring overnight, the reaction mixture was poured into acetone (20 mL) and the precipitate was isolated by centrifugation, which was further purified by HPLC (C8, gradient 0-30% AcCN in water with 0.05% TFA over 30 min) to give the title compound. UPLC-MS Method A: $t_R$=2.26 min; m/z=1066.63 (z=2).

Step E. 2,5-dioxopyrrolidin-1-yl (13S,16S)-13-(2-{bis[2-({2-[(α-L-fucopyranosyl)oxy]ethyl}amino)-2-oxoethyl]amino}acetamido)-16-[4-(2-{bis[2-({2-[(α-L-fucopyranosyl)oxy]ethyl}amino)-2-oxoethyl] amino}acetamido)butyl]-1-[(α-L-fucopyranosyl) oxy]-6-[2-({2-[(α-L-fucopyranosyl)oxy] ethyl}amino)-2-oxoethyl]-4,7,14,17-tetraoxo-3,6,8, 15,18-pentaazatetracosan-24-oate The title compound was prepared using procedure analogous to those described for Step C-D in Preparative Example 1 (ML-1) substituting benzyl (13S,16S)-13-(2-{bis[2-({2-[(α-L-fucopyranosyl)oxy]ethyl}amino)-2-oxoethyl] amino}acetamido)-16-[4-(2-{bis[2-({2-[(α-L-fucopyranosyl)oxy]ethyl}amino)-2-oxoethyl]amino}acetamido)butyl]-1-[(α-L-fucopyranosyl)oxy]-6-[2-({2-[(α-L-fucopyranosyl) oxy]ethyl}amino)-2-oxoethyl]-4,7,14,17-tetraoxo-3,6,8,15, 18-pentaazatetracosan-24-oate for benzyl 6-{[2-({α-D-mannopyranosyl-(1→3)-[α-D-mannopyranosyl-(1→6)]-α-D-mannopyranosyl}oxy)ethyl]amino}-6-oxohexanoate in Step C. UPLC-MS Method A: $t_R$=1.93 min; m/z=1070.56 (z=2).

Preparative Example 16

Synthesis of Conjugates with Functional Group on $N^{A1}$ of Insulin

In an appropriate sized container, insulin is suspended at rt in an organic solvent, e.g., DMSO, in the presence of a base, e.g., TEA. The mixture is allowed to stir gently until insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that most of the unmodified insulin has reacted and that a substantial portion of the reaction mixture has converted into A1-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing A1-conjugate with desired purity are combined and concentrated using TFF system or Amicon Ultra-15. The resulting solution is then further purified by reverse phase IPLC (Waters C4 250×50 mm column, 10 µm, 1000 Å column or Kromasil C8 250×50 mm, 10 µm, 100 column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Preparative Example 17

Synthesis of Conjugates with Functional Group on $N^{B1}$ of Insulin $N^{B1}$ insulin conjugate may be prepared according to Example 29. Or it may be prepared using protected insulin as substrate:

In an appropriate sized container, protected insulin, e.g., $N^{A1}$,$N^{\varepsilon B29}$-bis[(9H-fluoren-9-ylmethoxy)carbonyl]- or $N^{A1}$, $N^{\varepsilon B29}$-bis(trifluoroacetyl) human insulin is suspended at rt in an organic solvent, e.g., DMSO, in the presence of a base, e.g., TEA. The mixture is allowed to stir gently until protected insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified insulin has reacted and that a substantial portion of the reaction mixture has converted into B1-conjugated protected insulin. The reaction is quenched at low temperature by the addition of excess amount of an amine nucleophile, e.g., 2-aminoethanol or ammonia. The reaction solution is stirred at low temperature until UPLC chromatogram indicated complete removal of the protecting group. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B1-conjugate with desired purity are combined and concentrated using TFF system or Amicon Ultra-15. The resulting solution is then further purified by reverse phase IPLC (Waters C4 250×50 mm column, 10 µm, 1000 Å column or Kromasil C8 250×50 mm, 10 µm, 100 column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Preparative Example 18

Synthesis of Conjugates with Functional Group on $N^{\varepsilon B29}$ of Insulin In an appropriate sized container, insulin is dissolved, with gentle stirring, at rt in a mixed solvent: 2:3 v/v 0.1 M $Na_2CO_3$:AcCN. After the mixture cleared, the pH is adjusted to the value of 10.5-10.8 using alkaline solution, e.g., 0.1 N NaOH. In a separate vial, an activated ester intermediate is dissolved in an organic solvent, e.g., DMSO, at rt. Aliquots of the solution of the activated ester is added over a period of time to the solution containing insulin until UPLC chromatogram shows that most of the unmodified insulin has reacted and that a substantial portion of the reaction mixture has converted into B29-conjugated insulin. The reaction is quenched by the addition of an amine nucleophile, e.g., 2-aminoethanol. The reaction solution is stirred at rt for 30 min. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B29-conjugate with desired purity are combined and concentrated using TFF system or Amicon Ultra-15. The resulting solution is then further purified by reverse phase IPLC (Waters C4 250×50 mm column, 10 µm, 1000 Å column or Kromasil C8 250×50 mm, 10 µm, 100 Å column; Buffer A: 0.05-0.1% TFA in water; Buffer B: 0.05-0.1% TFA in AcCN). Fractions containing the title conjugate are combined and freeze-dried or buffer exchanged using TFF system and/or Amicon Ultra-15 to give the title product.

Preparative Example 19

Synthesis of Conjugates with Different Functional Groups on $N^{41}$ and $N^{\varepsilon B29}$ of Insulin (or Same Functional Groups on $N^{41}, N^{B1}$ but Different Functional Group on $N^{\varepsilon 29}$ of Insulin)

In an appropriate sized container, B29-conjugated insulin is suspended at rt in an organic solvent, e.g., DMSO, in the presence of a base, e.g., TEA. The mixture is allowed to stir gently until B29-conjugated insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified protected insulin has reacted and that a substantial portion of the reaction mixture has converted into A1,B29-conjugated insulin. The reaction is quenched at low temperature by the addition of excess amount of an amine nucleophile, e.g., 2-aminoethanol or ammonia. The reaction solution is stirred at low temperature until UPLC chromatogram indicated complete removal of the protecting group. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing A1,B29-conjugate with desired purity are combined and concentrated using TFF system or Amicon Ultra-15. The resulting solution is then further purified by reverse phase HPLC (Waters C4 250×50 mm column, 10 µm, 1000 Å column or Kromasil C8 250×50 mm, 10 µm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Examples for making conjugates of the instant invention, including conjugates 1-30 are described herein. Also disclosed are one or more linkers, and for making the same, that are used to make the conjugates. By way of example only, linker ML-1 was used to make conjugates 15, 20, 21 and 23; linkers ML-1 and ML-12 were used to make conjugate 1; linker ML-4 was used to make conjugates 3 and 5; linker ML-5 was used to make conjugate 14; linker ML-8 was used to make conjugates 18 and 19; linker ML-18 was used to make conjugate 2; linker ML-21 was used to make conjugates 7 through 13; linker ML-26 was used to make conjugate 16; linker ML-27 was used to make conjugates 22, 24 and 25; linker ML-28 was used to make conjugate 4 and 26; linker ML-29 was used to make conjugate 6; and ML-30 was used to make conjugate 17.

Example 1

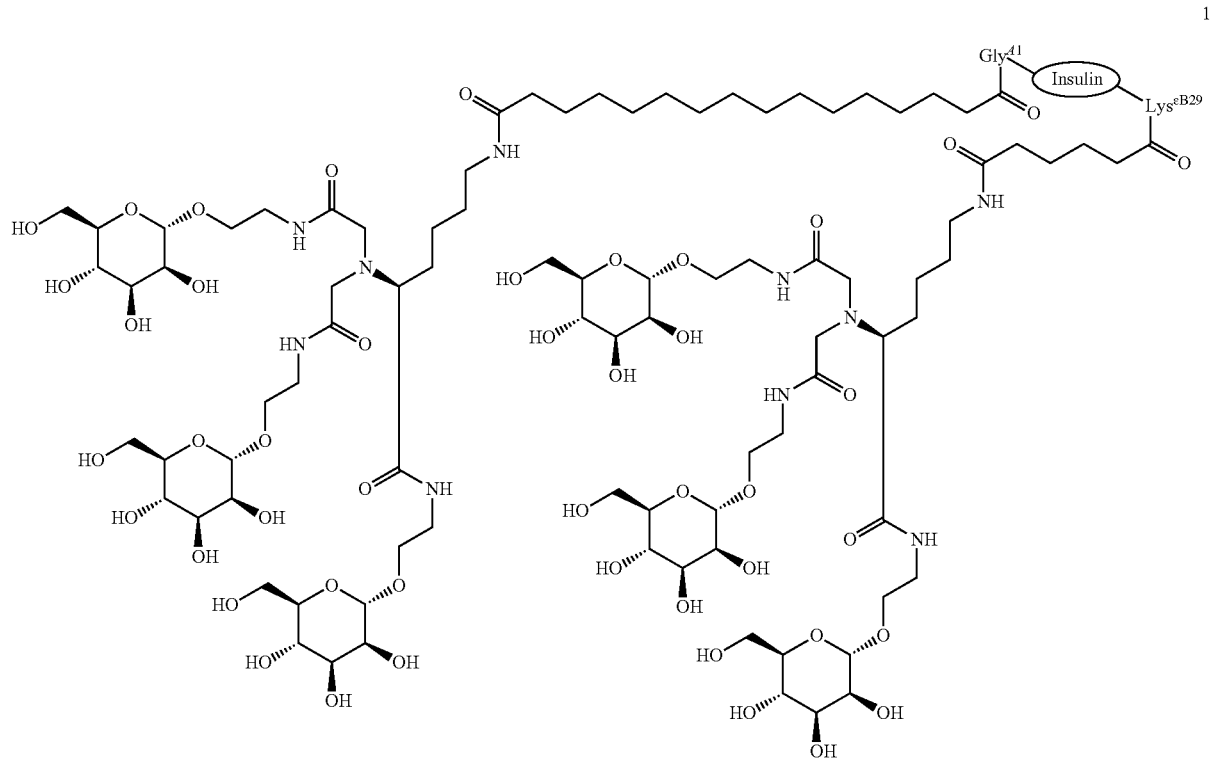

Synthesis of conjugate 1, human insulin conjugated at A1 and B29 to different activated esters ML-11 and ML-12, respectively, exemplified synthesis of insulin analogs having two different sugar linker groups.

To a solution of $N^{\epsilon B29}$-16-(((5S)-5-(bis(2-((2-(α-D-mannopyranosyloxy)ethyl)amino)-2-oxoethyl)amino)-6-((2-(α-D-mannopyranosyloxy)ethyl)amino)-6-oxohexyl)amino)-16-oxohexanoyl human insulin (100 mg, 0.015 mmol) and TEA (29.8 mg, 0.29 mmol) in DMSO (1.25 mL) at rt was added a solution of 2,5-dioxopyrrolidin-1-yl (S)-16-{[5-{bis [2-({2-[(α-D-mannopyranosyl)oxy]ethyl}amino)-2-oxoethyl]amino}-6-({2-[(α-D-mannopyranosyl)oxy]ethyl}amino)-6-oxohexyl]amino}-16-oxohexadecanoate (36.6 mg, 0.029 mmol, ML-11) in DMSO (1.0 mL) in portions over 3 hr. The reaction was quenched by adding ethanolamine (27.0 mg, 0.44 mmol). After stirring at rt for 15 min, the resulting mixture was diluted with $H_2O$ (15 mL) and its pH was adjusted to 2.5 using 1.0 N HCl. The mixture was purified on HPLC (C4, flow rate at 90 mL/min, gradient of 25-29% AcCN in $H_2O$ with 0.1% TFA over 30 min). The desired fractions were collected and freeze-dried to give the title compound. UPLC Method F: $t_R$=3.85 min; m/z=1981.52 (z=4).

Example 2

Synthesis of Conjugates with Same Functional Groups on $N^{B1}$ and $N^{\epsilon B29}$ of Insulin In an appropriate sized container, protected insulin, e.g., $N^{A1}$-(9H-fluoren-9-ylmethoxy)carbonyl- or $N^{A1}$-(trifluoroacetyl) human insulin is suspended at rt in an organic solvent, e.g., DMSO, in the presence of a base, e.g., TEA. The mixture is allowed to stir gently until protected insulin completely dissolved. In a separate vial, an activated ester intermediate is dissolved in an organic solvent, e.g., DMSO, at rt. Aliquots of the solution of the activated ester is added over a period of time to the solution containing insulin until UPLC chromatogram shows that all of the unmodified protected insulin has reacted and that a substantial portion of the reaction mixture has converted into B1,B29-conjugated protected insulin. The reaction is quenched at low temperature by the addition of excess amount of an amine nucleophile, e.g., 2-aminoethanol or ammonia. The reaction solution is stirred at low temperature until UPLC chromatogram indicated complete removal of the protecting group. The resulting solution is carefully diluted with cold $H_2O$ (20×) at 0° C. and its pH is adjusted to a final pH of 2.5 using 1 N HCl (and 0.1 N NaOH if needed). The solution is first concentrated by ultrafiltration, either through a tangential flow filtration (TFF) system or using Amicon Ultra-15 Centrifugal Units, with 1K, 3K or 10K MWCO membrane. The concentrated solution is usually first subjected to ion exchange chromatography (PolySULFOETHYL A column, PolyLC Inc., 250×21 mm, 5 µm, 1000 Å; Buffer A: 0.1% (v/v) $H_3PO_4$/25% AcCN; Buffer B: 0.1% (v/v) $H_3PO_4$/25% AcCN/0.5 M NaCl). Fractions containing B1,B29-conjugate with desired purity are combined and concentrated using TFF system or Amicon Ultra-15. The resulting solution is then further purified by reverse phase HPLC (Waters C4 250×50 mm column, 10 µm, 1000 Å column or Kromasil C8 250×50 mm, 10 µm, 100 Å column; Buffer A: 0.05-0.1% TFA in deionized water; Buffer B: 0.05-0.1% TFA in AcCN). Fractions containing the title conjugate are combined and freeze-dried or buffer exchanged using TFF system and/or Amicon Ultra-15 to give the title product.

Example 3

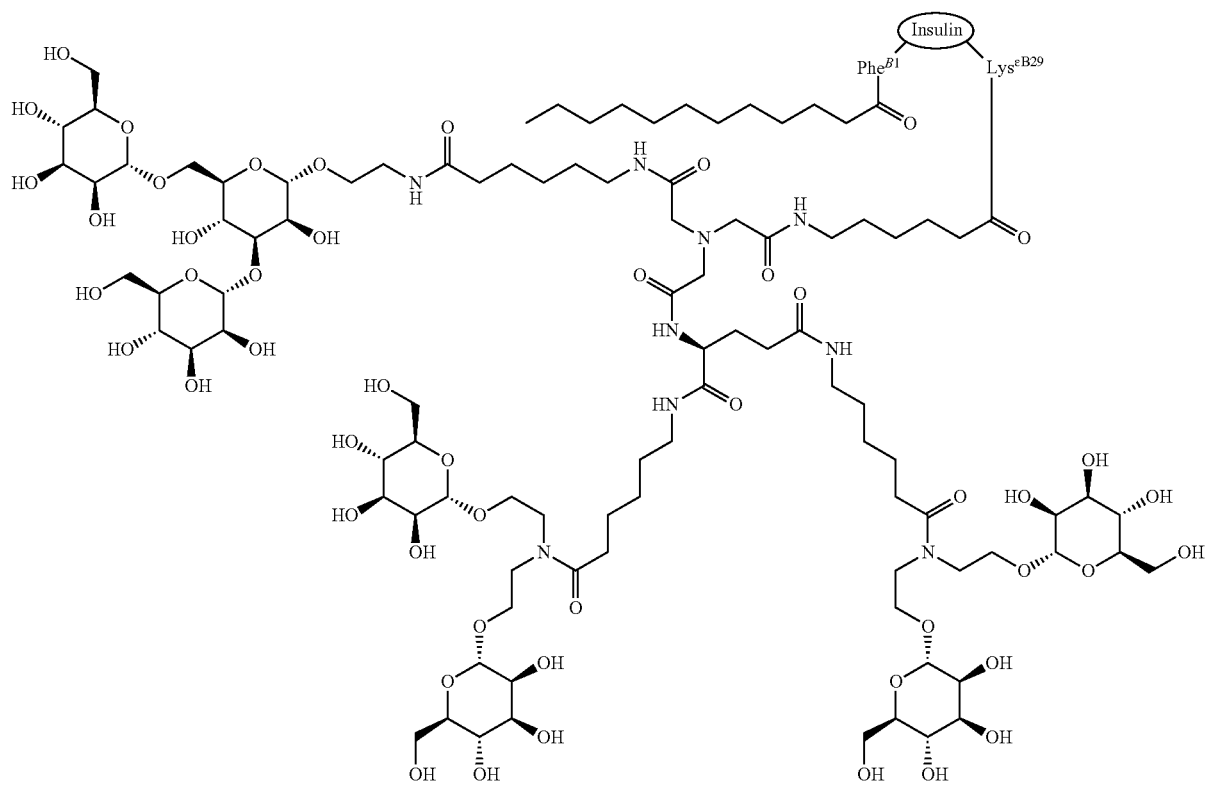

Synthesis of conjugate 10, human insulin conjugated at B1 and B29 to different activated esters, exemplified the synthesis of insulins with two different functional groups on B1 and B29 positions, exemplified synthesis of insulin analogs having two different type of sugar linker groups that requires protected insulin as starting point.

Step A: $N^{\varepsilon B29}$—(S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-18-{2-oxo-2-[(6-oxo-6-{[2-({α-D-mannopyranosyl-(1→3)-[α-D-mannopyranosyl-(I-6)]-α-D-mannopyranosyl}oxy)ethyl]amino}hexyl)amino]ethyl}-3,10,15,18,21-pentaazaheptacosan-27-oyl-$N^1$-trifluoroacetyl insulin To a solution of $N^{A1}$-trifluoroacetyl insulin (350 mg, 0.059 mmol, WO 2015051052 A2) in 0.1M aq. NaHCO$_3$ (2 mL, 0.208 mmol) and AcCN (1 mL) with pH adjusted to 10.5 by the addition of 1N NaOH was added a solution of 2,5-dioxopyrrolidin-1-yl (S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,10,15,18,21-pentaazaheptacosan-27-oate (132 mg, 0.059 mmol) in DMSO (0.8 mL) portionwise over 2 hr. The reaction mixture was diluted with ice cold water (35 mL) and pH adjusted to 2.5 by the addition of 1N HCl.

The resulting solution was purified by reverse phase prep HPLC (C-8 column, 50×250 cm, 85 µm/min, gradient from 27% to 37% in 20 min) to give the title compound. UPLC Method F: $t_R$=3.50 min; m/z=1602.95 (z=5).

Step Be: $N^{\varepsilon B29}$—(S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-8-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,10,15,18,21-pentaazaheptacosan-27-oyl-$N^{B1}$-dodecanoyl insulin To a solution of $N^{\varepsilon B29}$—(S)-14-{[6-(bis{2-[(α-D-mannopyranosyl)oxy]ethyl}amino)-6-oxohexyl]carbamoyl}-1-[(α-D-mannopyranosyl)oxy]-3-{2-[(α-D-mannopyranosyl)oxy]ethyl}-4,11,16,20-tetraoxo-18-{2-oxo-2-[(6-oxo-6-{[2-({α-D-mannopyranosyl-(1→3)-[α-D-mannopyranosyl-(1→6)]-α-D-mannopyranosyl}oxy)ethyl]amino}hexyl)amino]ethyl}-3,10,15,8,21-pentaazaheptacosan-27-oyl-$N^{A1}$-trifluoroacetyl insulin (45 mg, 0.0056 mmol) and TEA (11.7 µL, 0.084 mmol) in DMSO was added 2,5-dioxopyrrolidin-1-yl dodecanoate (3.4 mg, 0.011 mmol). After stirring at rt for 2 hr, UPLC-MS analysis showed incomplete conversion and more 2,5-dioxopyrrolidin-1-yl dodecanoate (3.4 mg, 0.011 mmol) was added. After another 2 hr, UPLC-MS analysis showed almost complete conversion. The reaction mixture was diluted with ice-cold H$_2$O (10 mL), to which ammonium hydroxide solution (3 mL) was added. The resulting mixture was left standing in the refrigerator. After overnight, UPLC-MS showed complete removal of the TFA protecting group. The resulting mixture was diafiltrated in a Amicon tube with 3K MWCO to against H$_2$O (50 mL). The retentee solution was acidified by addition of 1N HCl to a pH of ~2.5 and was purified by reverse phase prep HPLC (C8 column, 50×250 cm, 85 μm/min, gradient from 30% to 45% in 30 min) to give the title compound. UPLC Method F: t$_R$=4.22 min; m/z=1620.11 (z=5).

Insulin Receptor Ectodomain Binding Assays were performed as follows:

Human insulin receptor antibody (R&D Systems #MAB15441) was diluted 100-fold in Superblock (Thermo #37516) blocking buffer and 0.1 ml volume added to each well of a 96-well IgG coated plate (R&D Systems #CP001) for a 2 hr incubation at room temperature. The plate was washed three times with 0.2 ml binding buffer containing 100 mM HEPES, 100 mM NaCl, 10 mM MgCl2, 0.02% Triton X-100, pH 8.0. His tagged human insulin receptor ectodomain purified protein (R&D Systems #1544 IR/CF) was diluted to 2 μg/ml in binding buffer and 0.1 ml was added to each well and incubated for 2 hrs at room temperature. The plate was washed three times with 0.2 ml of binding buffer. Titrated compounds (final 1 μM, 1:3 dilution) in binding buffer (0.05 ml) were added to each well followed by 0.05 ml of [125I]-insulin (Perkin Elmer #NEX42 0050UC, specific activity 2200 Ci/mmol) diluted in binding buffer for a final concentration of 0.1 nM. The plate was incubated overnight at 4° C. The plate was washed three times with 0.1 ml of binding buffer followed by addition of 0.05 ml of Microscint-40 and counting on PerkinElmer Topcount instrument.

Assays

The following table lists conjugates that were prepared using appropriate intermediates following one of the General Methods described above. These conjugates were characterized using UPLC-MS Method F, UPLC-MS Method G (†), UPLC-MS Method H (T), or UPLC-MS Method I ($) exhibiting either four charged, i.e. z=4, (or five charged, i.e. z=5, noted by an asterisk) species of parent compound at certain retention time (t$_R$). Their in vitro biological activities towards insulin receptor (IR) were measured by either ligand competition assays or functional phosphorylation assays, as described above, labeled as following: Method A: IR binding assay method A; Method B: IR binding assay method B; Method C: IR phosphorylation assay based on 96-well; Method D: IR phosphorylation assay based on 384-well.

TABLE 4

| Conjugate No. | t$_R$ (min) | m/z | sIR Binding IC$_{50}$ (nM) |
| --- | --- | --- | --- |
| 1 | 3.87 | 1981.05 | 23.5 |
| 2 | 4.74$ | 1641.43* | 27.5 |
| 3 | 3.36 | 1844.91 | 186 |
| 4 | 3.99 | 1689.50* | 45.5 |
| 5 | 3.17 | 1837.55 | 87.9 |
| 6 | 3.86† | 1677.32* | 28.6 |
| 7 | 4.00 | 1663.38* | 16.4 |
| 8 | 4.22 | 1620.11* | 15.5 |
| 9 | 4.44 | 1626.08* | 21.5 |
| 10 | 4.64 | 1631.33* | 26.7 |
| 11 | 4.43 | 1620.22* | 17.9 |
| 12 | 4.60 | 1626.00* | 24.2 |
| 13 | 3.51† | 1631.37* | 29.8 |
| 14 | 4.12 | 1859.12 | 38.7 |
| 15 | 3.73 | 1880.67 | 37.3 |
| 16 | 3.71 | 1680.43* | 16.7 |

TABLE 4-continued

| Conjugate No. | t$_R$ (min) | m/z | sIR Binding IC$_{50}$ (nM) |
| --- | --- | --- | --- |
| 17 | 2.25† | 1626.47* | 25.5 |
| 18 | 3.00† | 1795.27 | 44.4 |
| 19 | 2.32† | 1841.61 | 117.8 |
| 20 | 3.80 | 1716.21 | 6.70 |
| 21 | 3.80 | 1716.19 | 20.4 |
| 22 | 4.01 | 1668.59* | 31.8 |
| 23 | 2.64 | 1880.64 | 63.1 |
| 24 | 3.95 | 1669.17* | 34.9 |
| 25 | 4.11 | 1668.79* | 66.1 |
| 26 | 4.00 | 1689.9* | 37.1 |

Effect of Methyl α-D-Mannopyranoside (αMM) on PK and PD of various IOCs in Non-Diabetic Minipigs was evaluated.

Male Yucatan miniature pigs, non-diabetic, instrumented with two Jugular vein vascular access ports (VAP), are used in these studies. Animals are fasted overnight prior to the study. On the day of the study, animals are restrained in slings, and VAPs accessed for infusion and sampling. At t=-60 minutes, a constant infusion of PBS (n=3) or 21.2% α-methyl mannose (αMM) (n=3) is started, at a rate of 2.67 mL/kg/hr. This infusion will be maintained for the duration of the study. At t=0 min, and after collecting a baseline blood sample for plasma glucose measurement, animals are administered IOC as a single bolus IV. Sampling continues for 180 minutes, with final readouts of plasma glucose and compound levels.

IOCs are formulated at 69 nmol/mL in sodium chloride (87 mM), phenol (21 mM), dibasic sodium phosphate (26.5 mM), Osmolality=275 mOsm, pH=7.4; QS with Water for Injection.

Time points for sample collection: -60 min, 0 min, 1 min, 2 min, 4 min, 6 min, 8 min, 10 min, 15 min, 20 min, 25 min, 30 min, 35 min, 45 min, 60 min, 90 min, 120 min, 150 min and 180 min or -60 min, 0 min, 8 min, 15 min, 30 min, 45 min, 60 min, 75 min, 90 min, 105 min, 120 min, 135 min, 150 min and 180 min.

Blood is collected in K3-EDTA tubes, supplemented with 10 μg/ml Aprotinin, and kept on an ice bath until processing, within 30 minutes of collection. After centrifugation at 3000 rpm, 4° C., for 8 minutes, plasma is collected and aliquoted for glucose measurement using a Beckman Coulter AU480 Chemistry analyzer and for compound levels measurement by LC-MS.

Effect of Various IOCs on Plasma Glucose after Subcutaneous Administration

Male Yucatan miniature pigs, type 1 diabetic, instrumented with two Jugular vein vascular access ports (VAP), are used in these studies. Animals are fasted overnight prior to the study. On the day of the study, animals are restrained in slings, and VAPs accessed for sampling. At t=0 min, and after collecting a baseline blood sample for plasma glucose measurement, animals are administered IOC as a single bolus SC. Sampling continues for 18 hours (IOC) or 8 hours (RHI), with final readouts of plasma glucose and compound levels.

IOCs are formulated at 600 nmol/ml in glycerol 19.6 mg/mL, phenol 1.50 mg/mL, metacresol 1.72 mg/mL, zinc 32.7 mcg/mL, pH 7.6; QS with Water for Injection.

Time points for sample collection: 0 min, 8 min, 15 min, 30 min, 60 min, 90 min, 120 min, 150 min, 180 min, 210 min, 4 hours, 5 hours, 6 hours, 7 hours, 8 hours, 9 hours, 10 hours, 11 hours, 12 hours, 14 hours, 16 hours, 18 hours (IOC) or 0 min, 8 min, 15 min, 30 min, 60 min, 90 min, 120 min, 150 min, 180 min, 210 min, 4 hours, 4.5 hos, 5 hours, 6 hours, 7 hours, 8 hours (RHI).

Blood is collected in K3-EDTA tubes, supplemented with 10 µg/ml Aprotinin, and kept on an ice bath until processing, within 30 minutes of collection. After centrifugation at 3000 rpm, 4° C., for 8 minutes, plasma is collected and aliquoted for glucose measurement using a Beckman Coulter AU480 Chemistry analyzer and for compound levels measurement by LC-MS.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:
1. A conjugate which is:
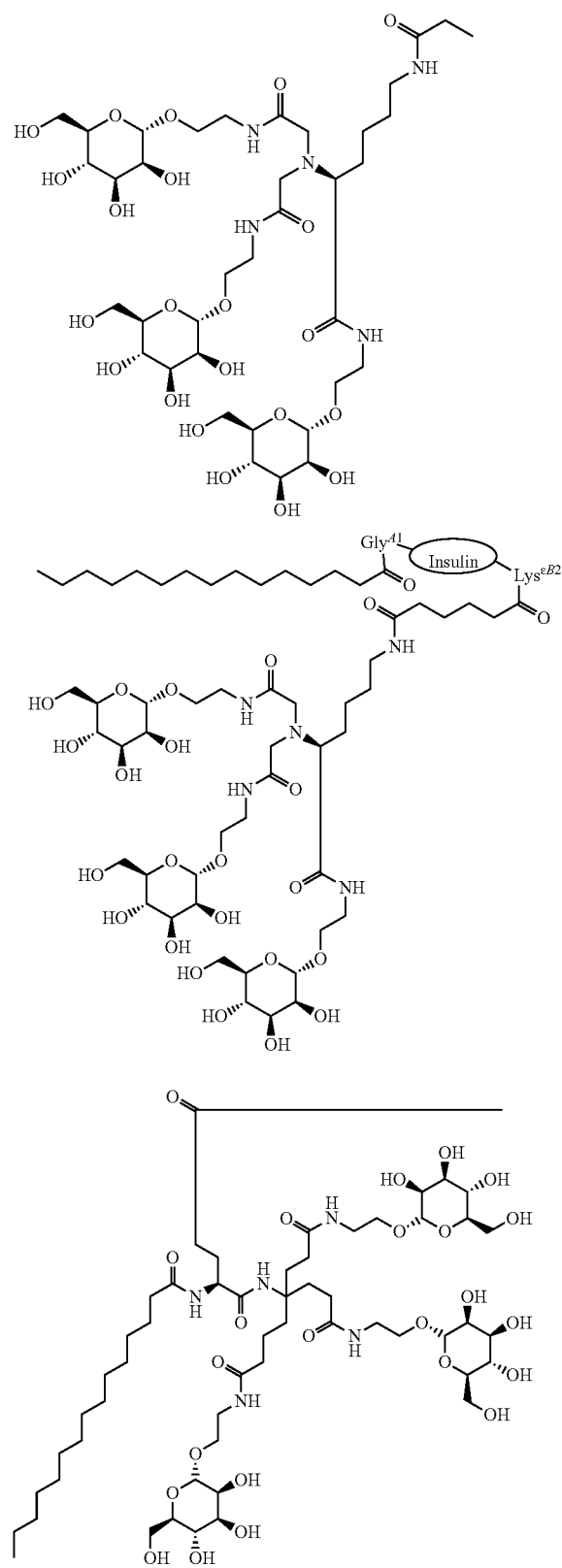
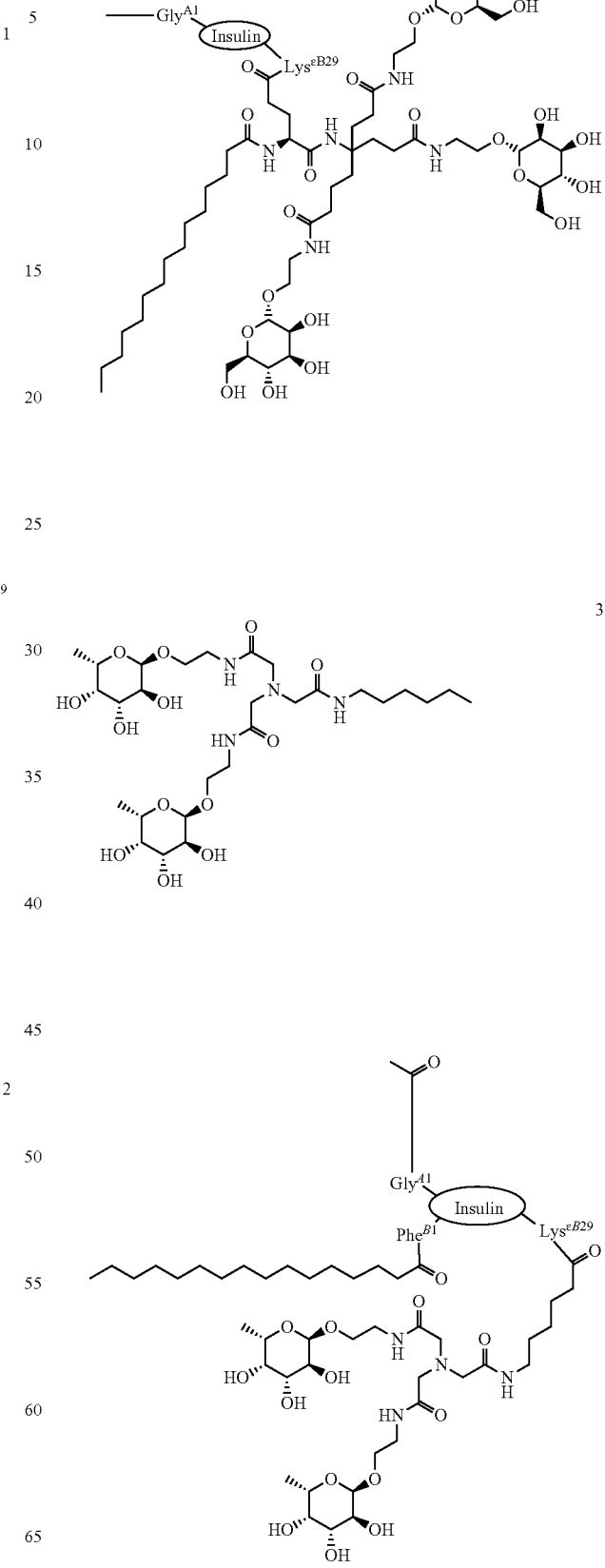

151
-continued
4
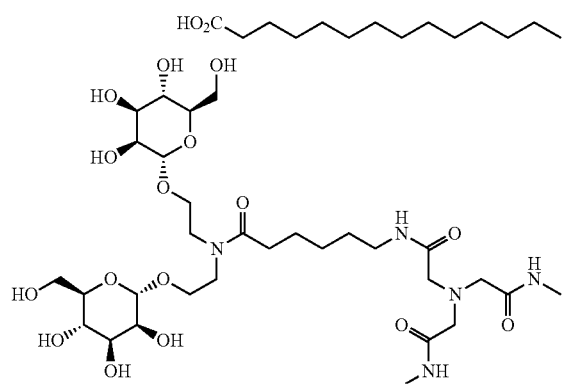
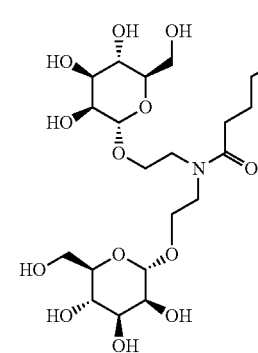
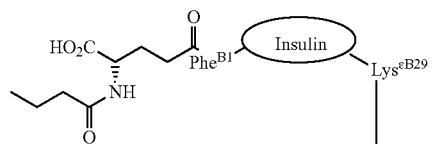
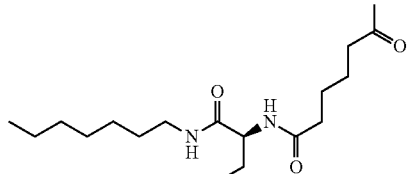
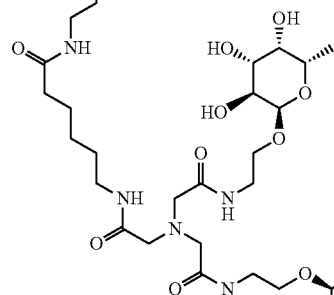
152
-continued
5
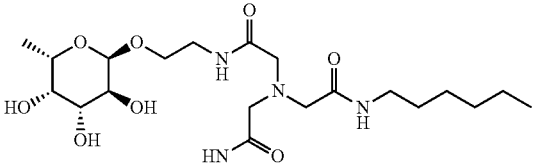
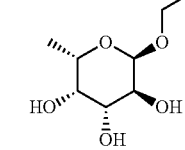
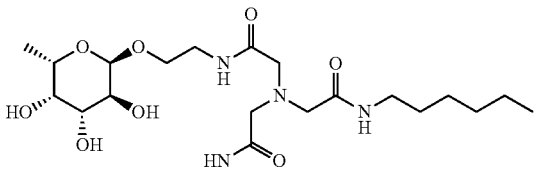
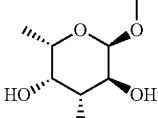
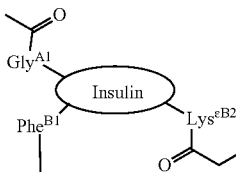
6
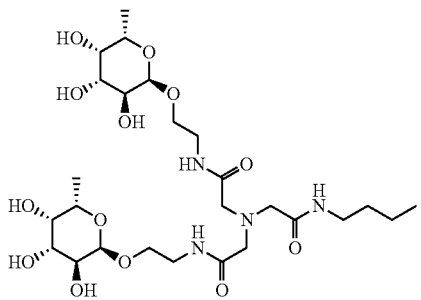

153
-continued
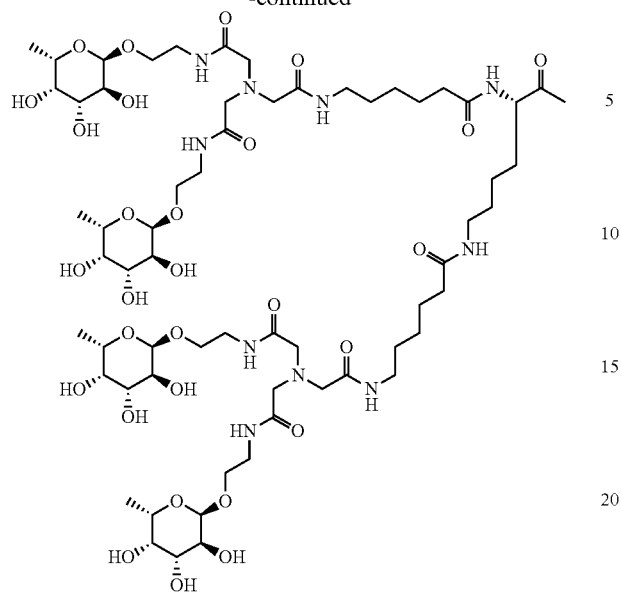
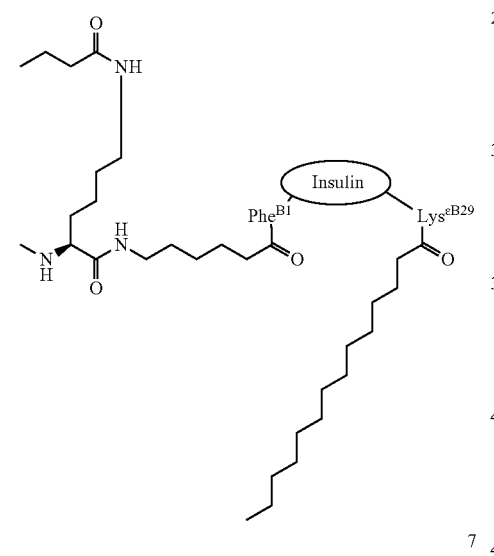
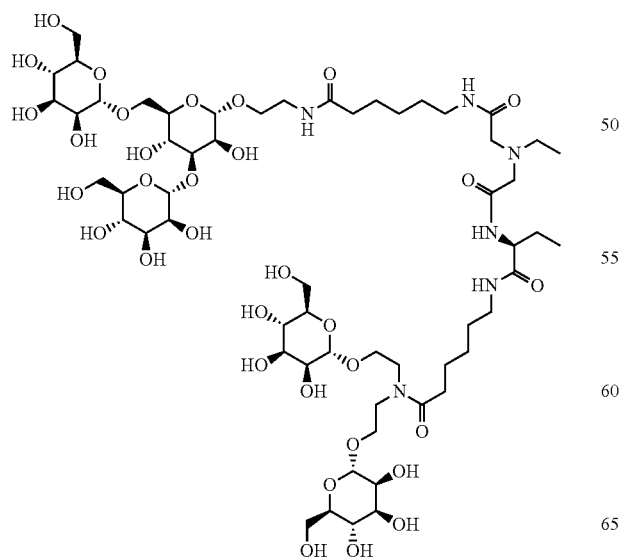
154
-continued
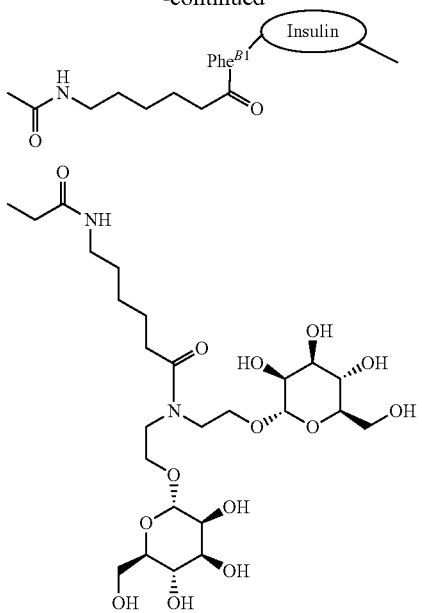
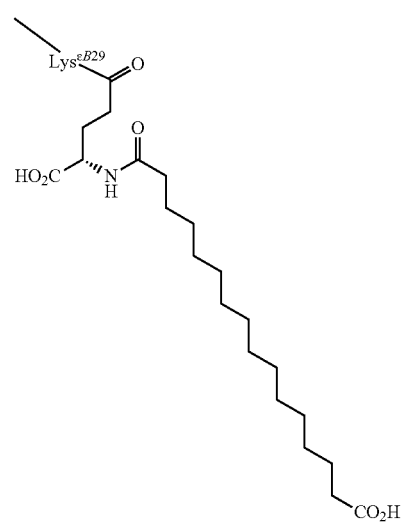

155 156
-continued -continued
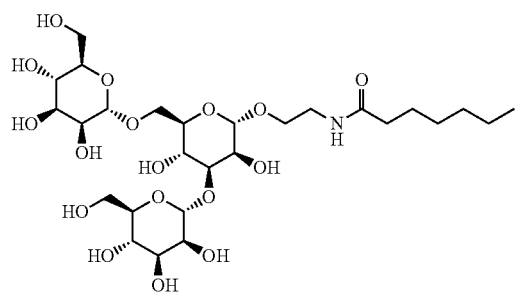
8
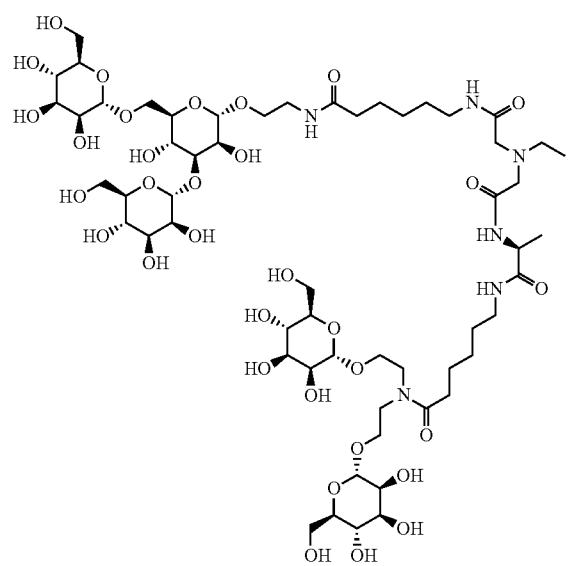
9
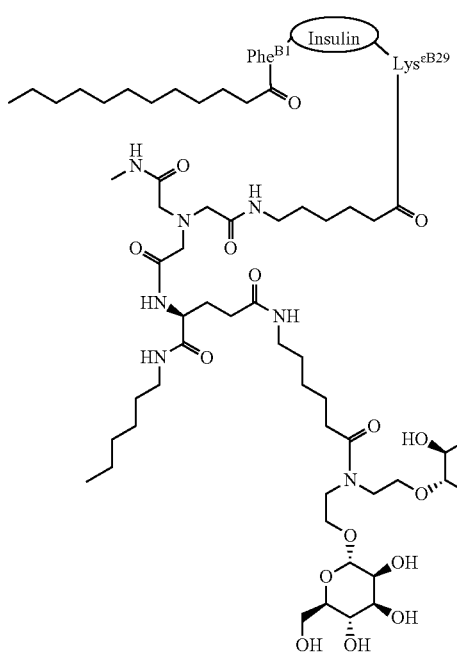
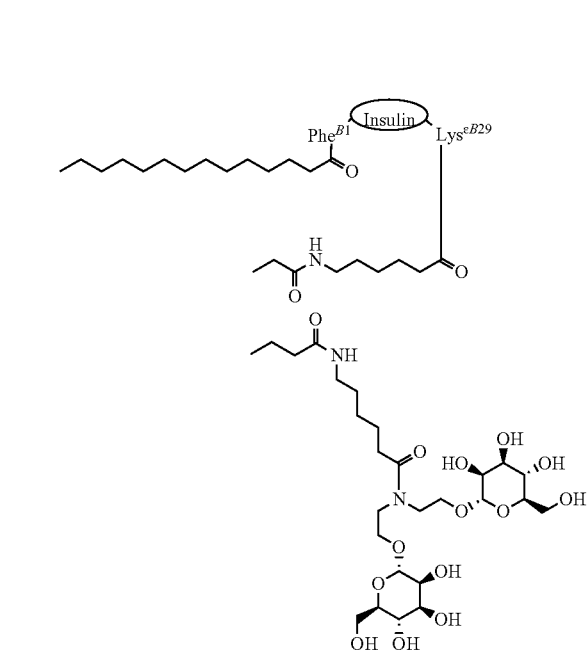

157
-continued
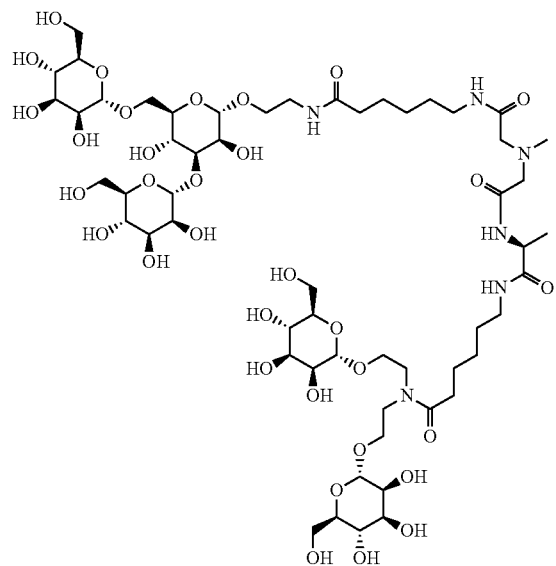
158
-continued
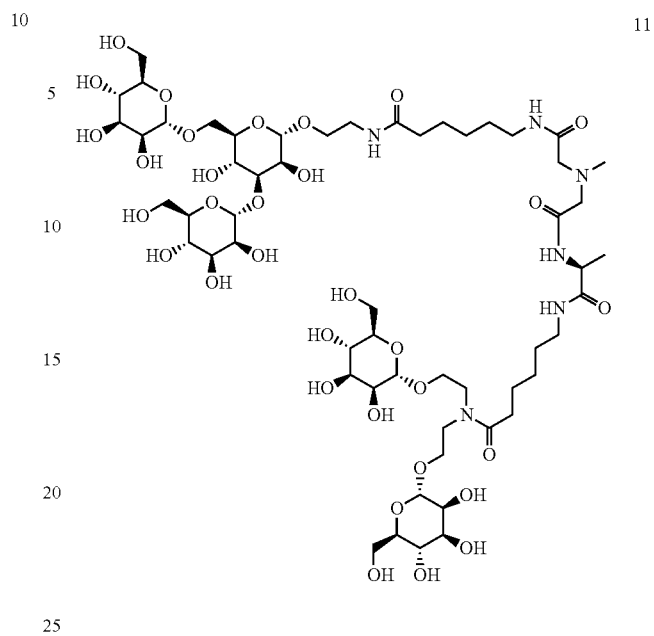
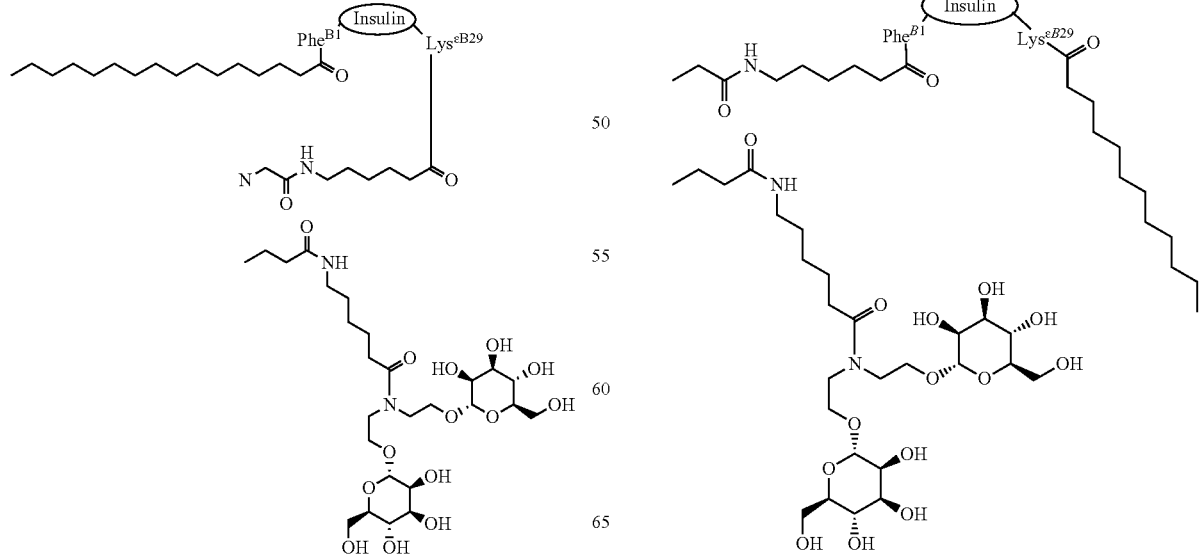

159
-continued
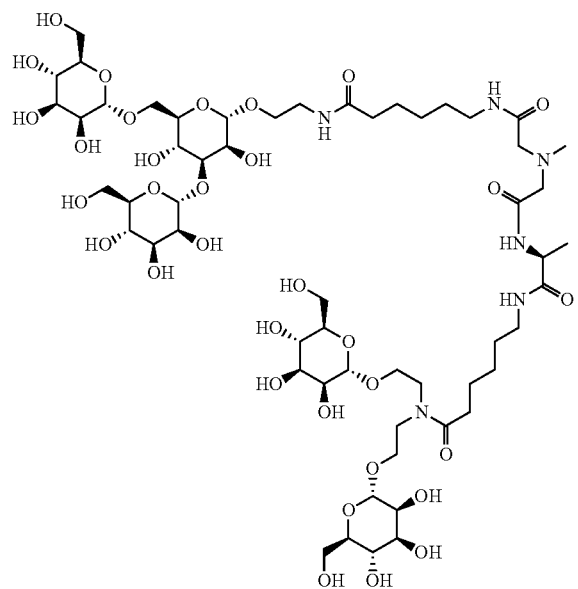
12
160
-continued
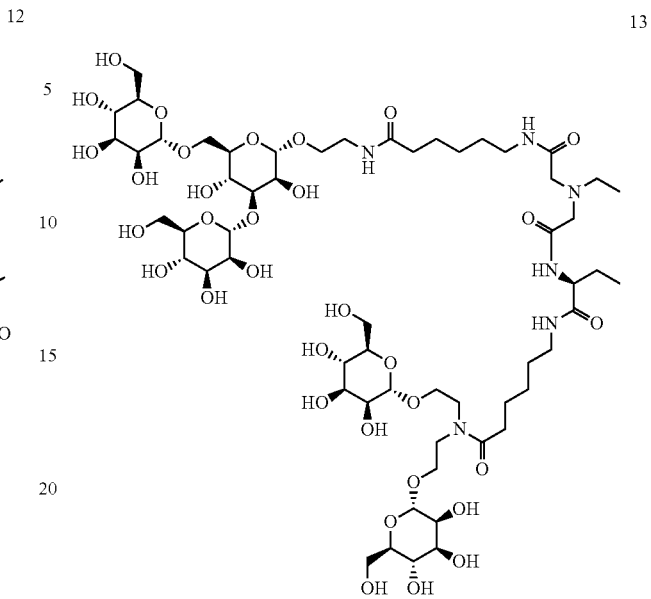
13
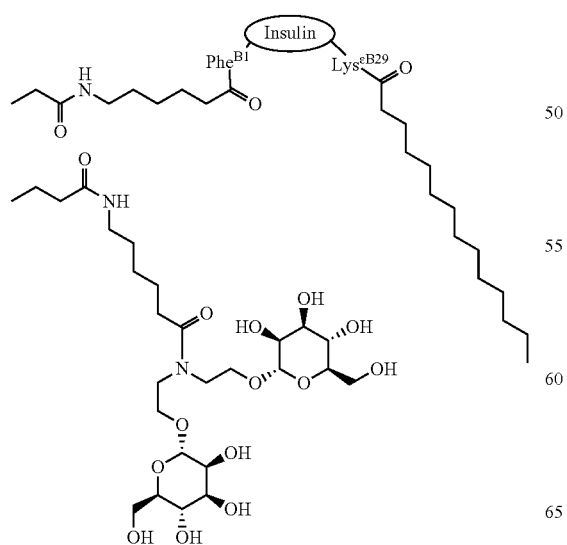
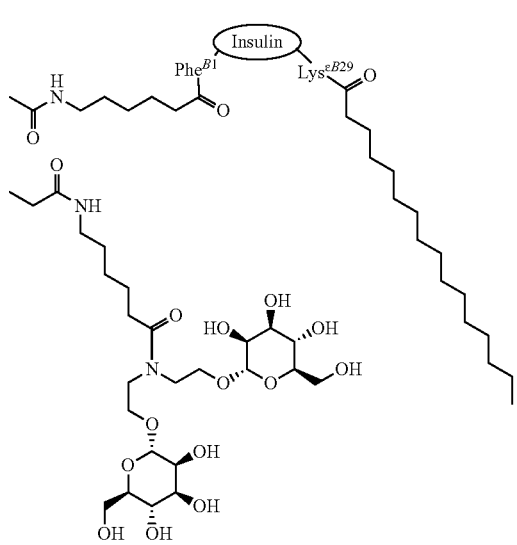

161
-continued
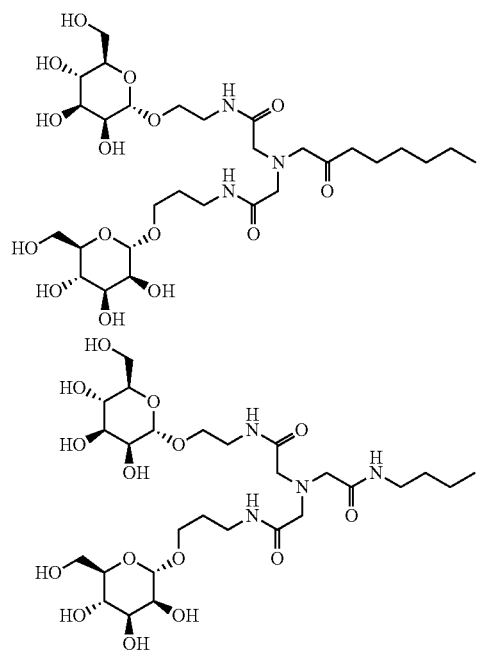
162
-continued
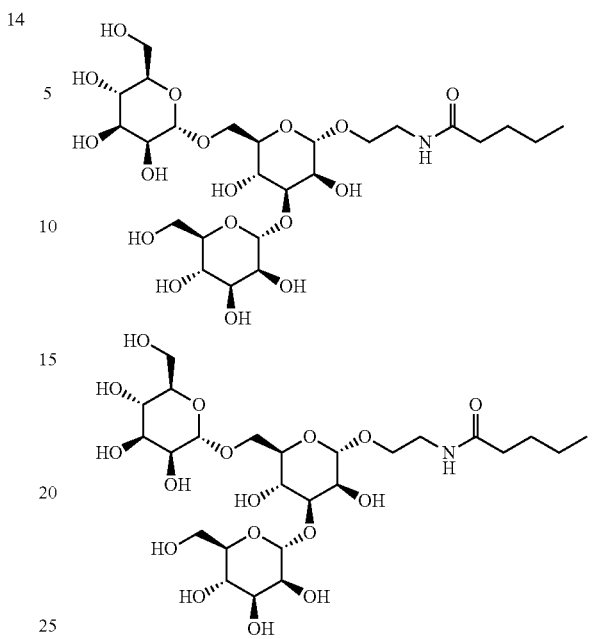
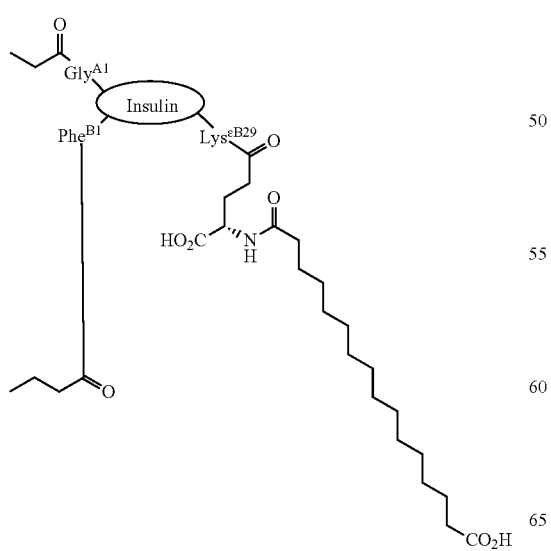
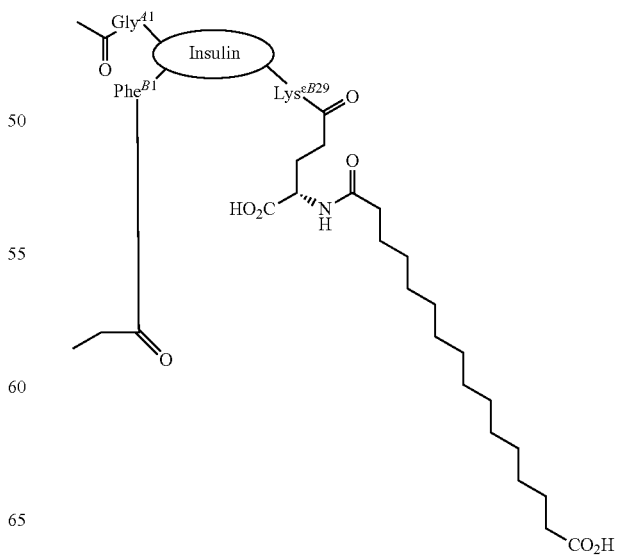

163
-continued
16
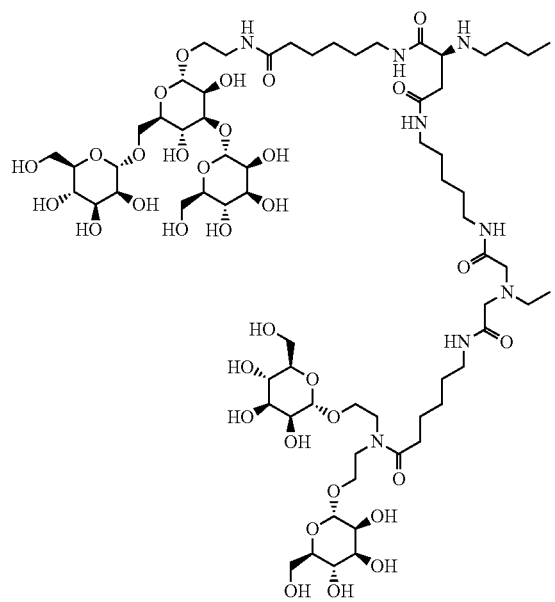
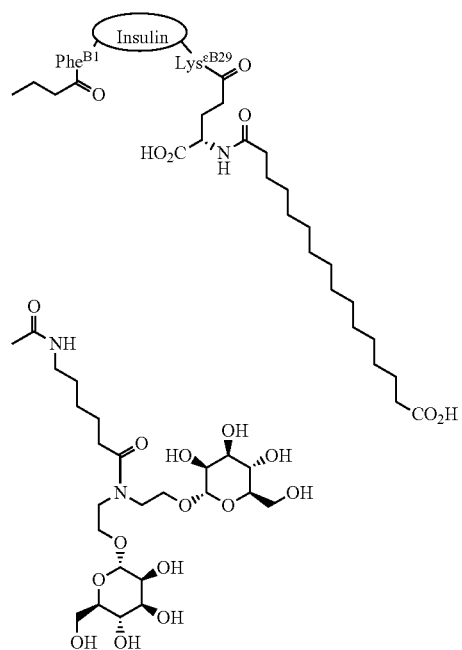
164
-continued
17
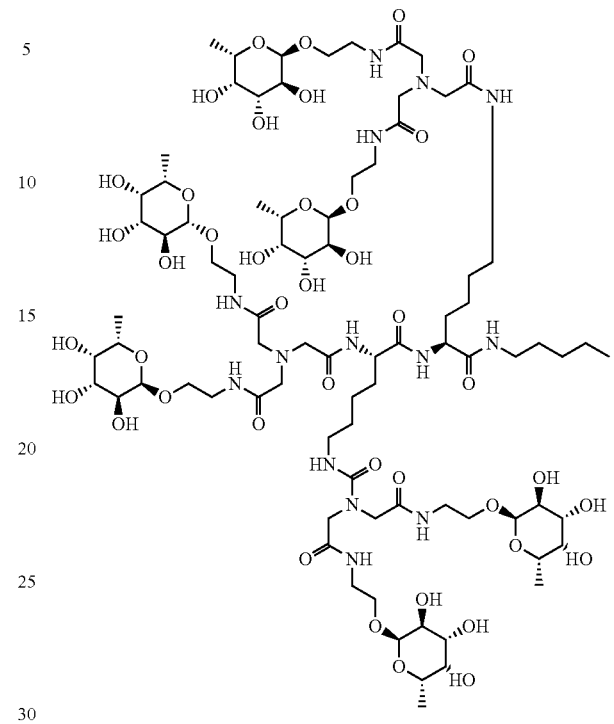
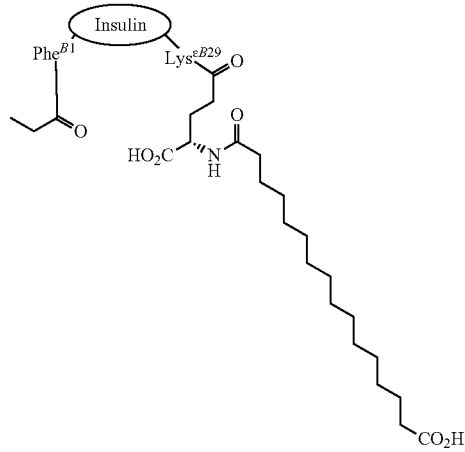

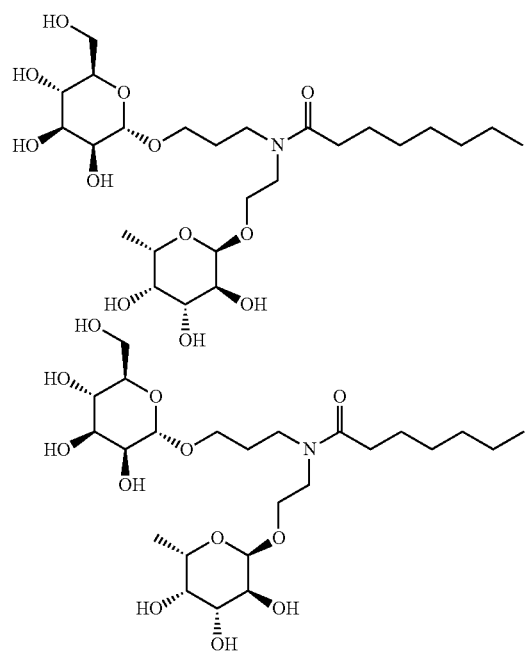
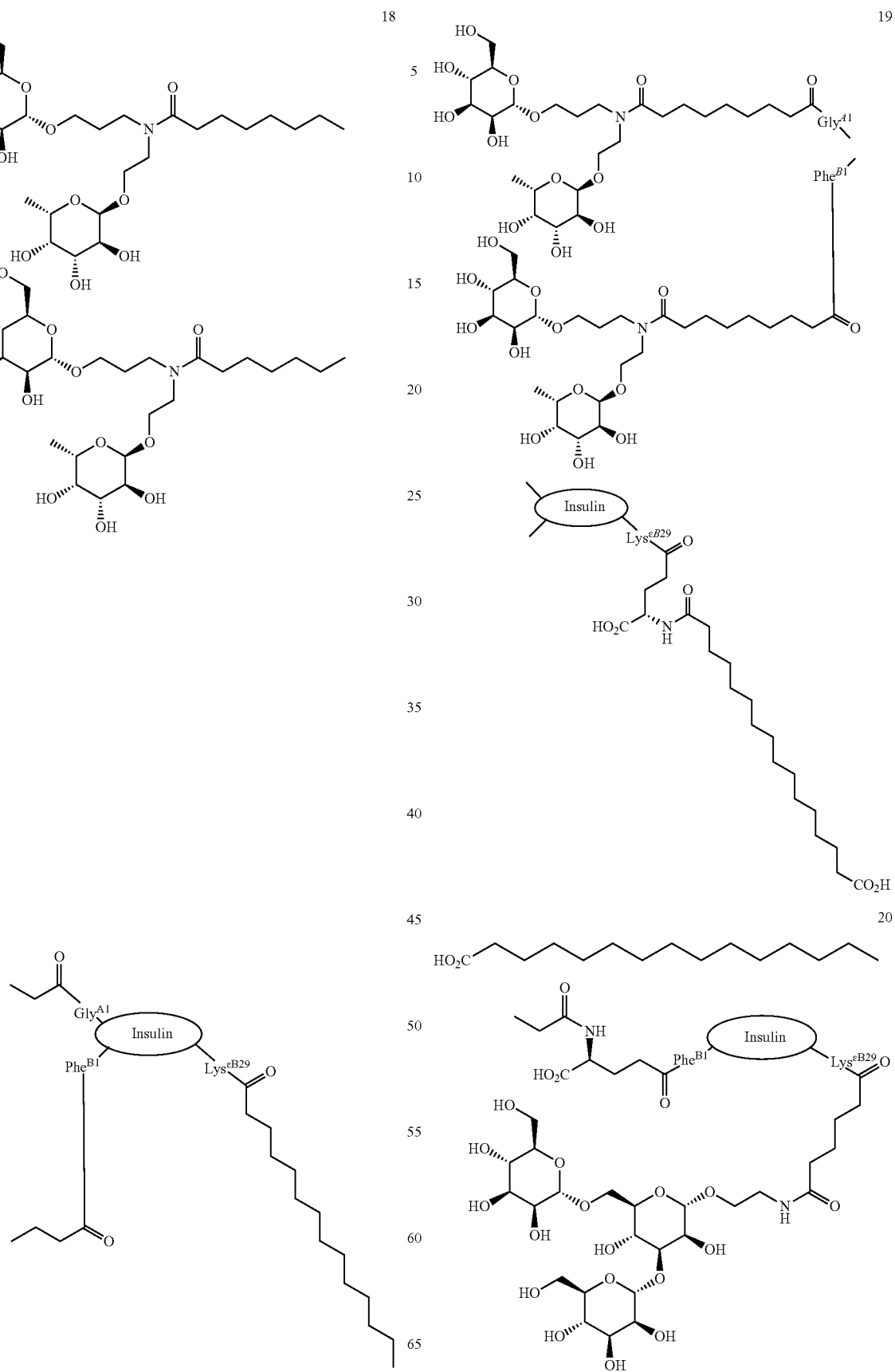

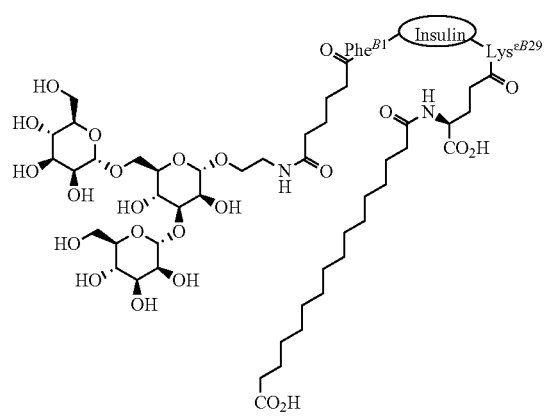
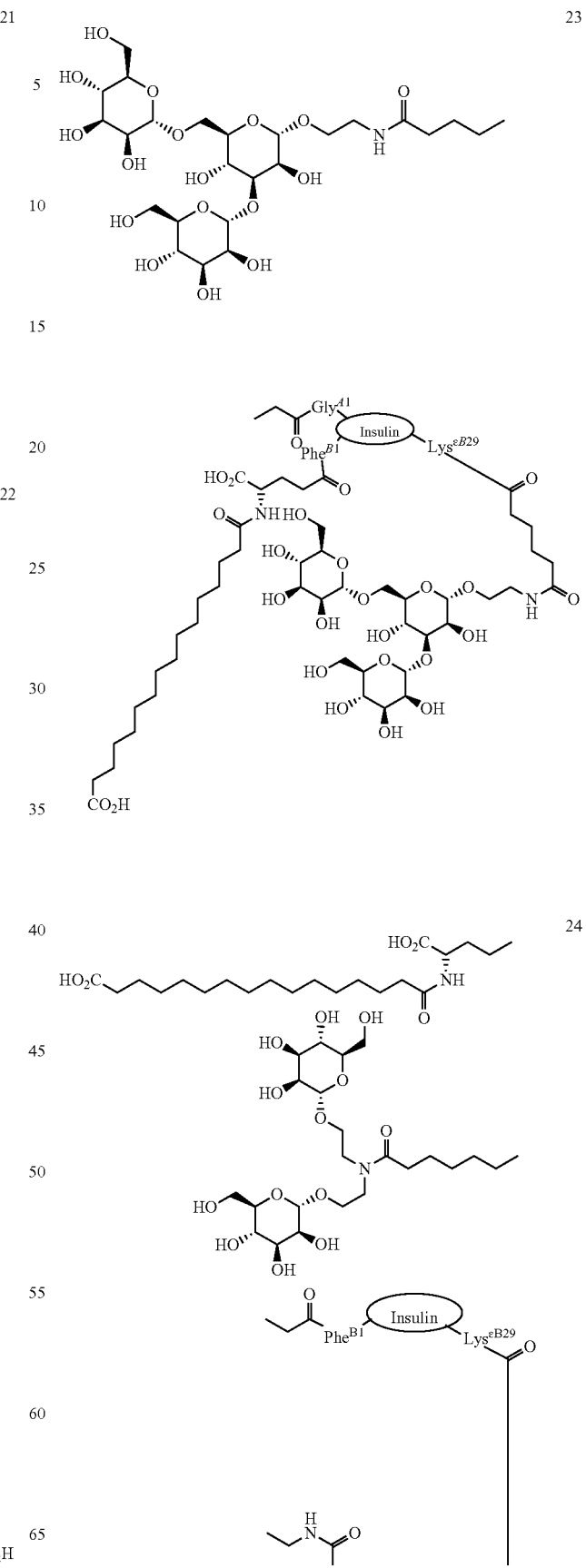

169
-continued

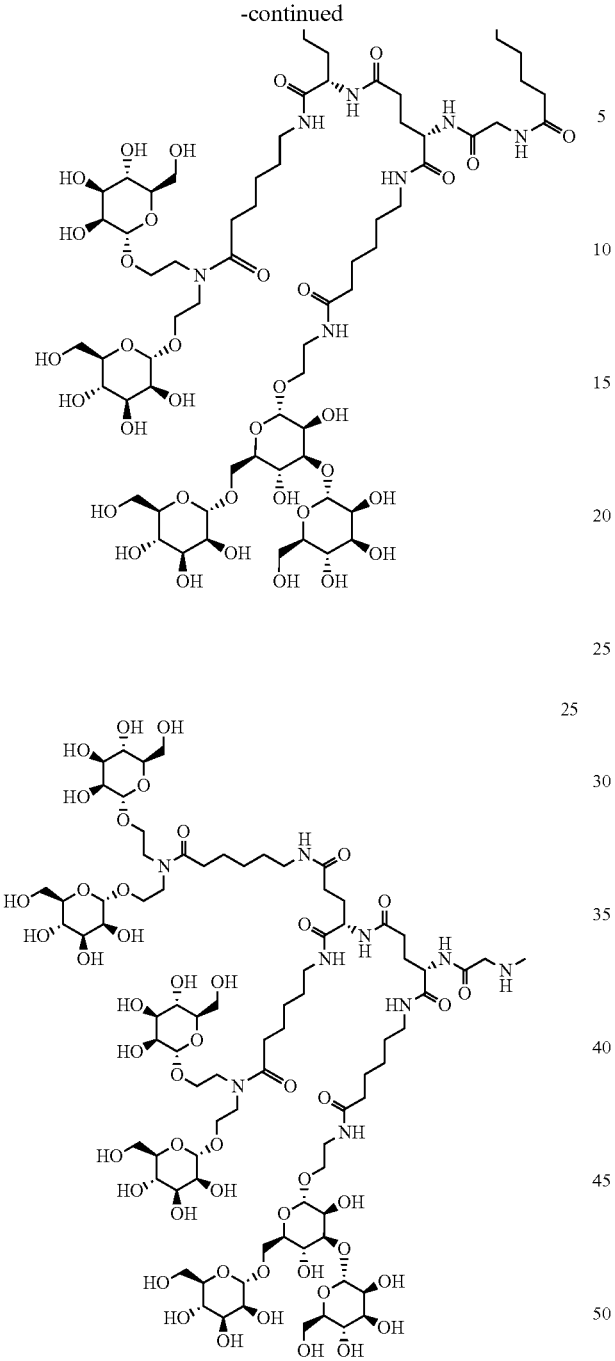

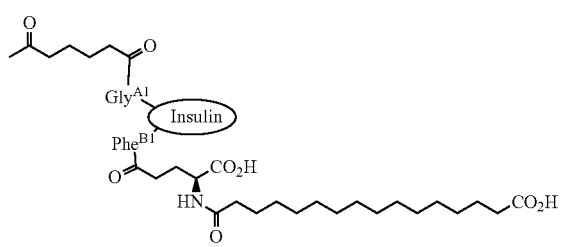

170
-continued

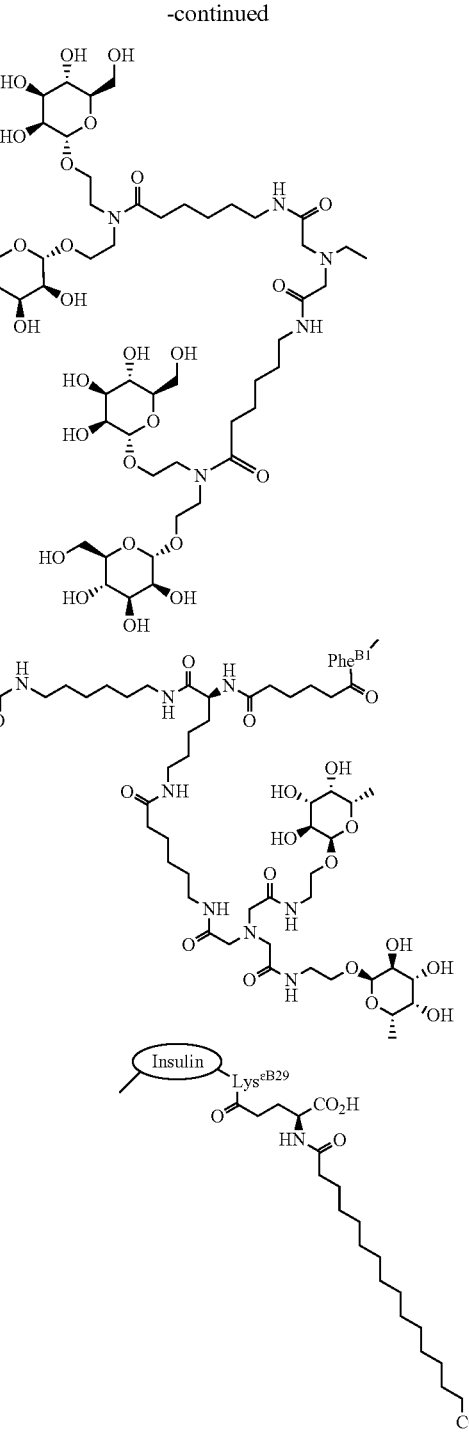

or a pharmaceutically acceptable salt thereof.

2. A method of treating hyperglycemia comprising administering a conjugate of claim 1, or a pharmaceutically acceptable salt thereof, to a mammalian patient in need thereof.

3. A pharmaceutical composition which comprises a pharmaceutically acceptable carrier and a conjugate of claim 1, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 11,820,805 B2 |
| APPLICATION NO. | : 16/771818 |
| DATED | : November 21, 2023 |
| INVENTOR(S) | : Lin Yan et al. |

It is certified that error appears in the above-identified patent and that said Letters Patent is hereby corrected as shown below:

On the Title Page

Item (71) following the heading Applicant:
Delete "Merck Sharp & Dohme Corp., Rahway, NJ (US)" and insert -- Merck Sharp & Dohme LLC, Rahway, NJ (US); --

Signed and Sealed this
Twentieth Day of August, 2024

Katherine Kelly Vidal
*Director of the United States Patent and Trademark Office*

SEQUENCE LISTING

```
<160> NUMBER OF SEQ ID NOS: 11

<210> SEQ ID NO 1
<211> LENGTH: 22
<212> TYPE: PRT
<213> ORGANISM: Homo sapiens

<400> SEQUENCE: 1

Ala Gly Ile Val Glu Gln Cys Cys Thr Ser Ile Cys Ser Leu Tyr Gln
1               5                   10                  15

Leu Glu Asn Tyr Cys Asn
            20

<210> SEQ ID NO 2
<211> LENGTH: 32
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (30)..(32)
<223> OTHER INFORMATION: Xaa can be any naturally occurring amino acid

<400> SEQUENCE: 2

Xaa Phe Val Ala Xaa Gln His Leu Cys Gly Ser His Leu Val Glu Ala
1               5                   10                  15

Leu Tyr Leu Val Cys Gly Glu Arg Gly Phe Phe Tyr Thr Xaa Xaa Xaa
            20                  25                  30

<210> SEQ ID NO 3
<211> LENGTH: 23
<212> TYPE: PRT
<213> ORGANISM: Artificial Sequence
<220> FEATURE:
<223> OTHER INFORMATION: A - PEPTIDE  and amino acid sequence
<220> FEATURE:
<221> NAME/KEY: MISC_FEATURE
<222> LOCATION: (0)..(0)
<223> OTHER INFORMATION: Xaa=Any codable amino acid, dequence of codable
      amino acids, or missing
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa=TYR or ALA
<220> FEATURE:
<221> NAME/KEY: MISC_FEATURE
<222> LOCATION: (9)..(9)
<223> OTHER INFORMATION: Xaa=SER or GLY
<220> FEATURE:
```

```
<221> NAME/KEY: MISC_FEATURE
<222> LOCATION: (10)..(10)
<223> OTHER INFORMATION: Xaa=Ile or Val
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa=ASN, ASP or GLU
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa= ASN ASP GlU GLY or Ala
<220> FEATURE:
<221> NAME/KEY: MISC_FEATURE
<222> LOCATION: (22)..(22)
<223> OTHER INFORMATION: Xaa= Any codable amino acids sequence of
      codable amino acids or missing
<220> FEATURE:
<221> NAME/KEY: misc_feature
<222> LOCATION: (23)..(23)
<223> OTHER INFORMATION: Xaa can be any naturally occurring amino acid

<400> SEQUENCE: 3

Xaa Gly Ile Val Glu Gln Cys Cys Xaa Xaa Xaa Cys Ser Leu Tyr Gln
1               5                   10                  15

Leu Glu Xaa Tyr Cys Xaa Xaa
            20

<210> SEQ ID NO 4
<211> LENGTH: 32
<212> TYPE: PRT
<213> ORGANISM: Artificial Sequence
<220> FEATURE:
<223> OTHER INFORMATION: B - Peptide and three Disulfide bridges as
      shown in formula X
<220> FEATURE:
<221> NAME/KEY: MISC_FEATURE
<222> LOCATION: (0)..(0)
<223> OTHER INFORMATION: Xaa=any codablle amino acid, sequence of
      codable amino acids, or missing
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa=ASN, LYS, ASP or Glu , or missing
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa=Pro, Ala , Lys Leu, Val or Asp or missing
<220> FEATURE:
<221> NAME/KEY: MISC_FEATURE
<222> LOCATION: (29)..(29)
<223> OTHER INFORMATION: Xaa=LYS, Pro, or Glu or missing
<220> FEATURE:
<221> NAME/KEY: MISC_FEATURE
<222> LOCATION: (30)..(30)
<223> OTHER INFORMATION: Xaa=Thr Ala Lys Glu Ser aor Arg or Missing
<220> FEATURE:
<221> NAME/KEY: MISC_FEATURE
<222> LOCATION: (31)..(31)
<223> OTHER INFORMATION: Xaa=any codable amino acid dequence of codable
      amino acids, Arg-Arg or missing
```

```
<220> FEATURE:
<221> NAME/KEY: misc_feature
<222> LOCATION: (32)..(32)
<223> OTHER INFORMATION: Xaa can be any naturally occurring amino acid

<400> SEQUENCE: 4

Xaa Phe Val Ala Xaa Gln His Leu Cys Gly Ser His Leu Val Glu Ala
1               5                  10                  15

Leu Tyr Leu Val Cys Gly Glu Arg Gly Phe Phe Tyr Thr Xaa Xaa Xaa
            20                  25                  30

<210> SEQ ID NO 5
<211> LENGTH: 6
<212> TYPE: PRT
<213> ORGANISM: ARTIFICIAL SEQUENCE
<220> FEATURE:
<223> OTHER INFORMATION: N-Terminal Protecting Amino Acid
<220> FEATURE:
<221> NAME/KEY: VARIANT
<222> LOCATION: (1)..(1)
<223> OTHER INFORMATION: xaa is Asp or Glu
<220> FEATURE:
<221> NAME/KEY: VARIANT
<222> LOCATION: (2)..(2)
<223> OTHER INFORMATION: xaa is Asp or Glu
<220> FEATURE:
<221> NAME/KEY: VARIANT
<222> LOCATION: (3)..(3)
<223> OTHER INFORMATION: xaa is Asp or Glu
<220> FEATURE:
<221> NAME/KEY: VARIANT
<222> LOCATION: (4)..(4)
<223> OTHER INFORMATION: xaa is Asp or Glu

<400> SEQUENCE: 5

Xaa Xaa Xaa Xaa Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: N-TERMINAL PROTECTING AMINO ACID SEQUENCE
<220> FEATURE:
<221> NAME/KEY: VARIANT
<222> LOCATION: (1)..(1)
<223> OTHER INFORMATION: Xaa= asp or glu
<220> FEATURE:
<221> NAME/KEY: VARIANT
<222> LOCATION: (2)..(2)
<223> OTHER INFORMATION: Xaa= asp or glu
<220> FEATURE:
<221> NAME/KEY: VARIANT
<222> LOCATION: (4)..(4)
<223> OTHER INFORMATION: Xaa= asp or glu
<220> FEATURE:
<221> NAME/KEY: VARIANT
<222> LOCATION: (5)..(5)
<223> OTHER INFORMATION: Xaa= is any codeble aminio acid
```

```
<400> SEQUENCE: 6

Xaa Xaa Gly Xaa Xaa Arg
1               5

<210> SEQ ID NO 7
<211> LENGTH: 6
<212> TYPE: PRT
<213> ORGANISM: Artificial Sequence
<220> FEATURE:
<223> OTHER INFORMATION: N-terminal protecting amino acid sequence

<400> SEQUENCE: 7

Asp Asp Gly Asp Pro Arg
1               5

<210> SEQ ID NO 8
<211> LENGTH: 6
<212> TYPE: PRT
<213> ORGANISM: Artificial Sequence
<220> FEATURE:
<223> OTHER INFORMATION: the N-terminal protecting amino acid sequence
      comprises

<400> SEQUENCE: 8

Glu Glu Gly Glu Pro Arg
1               5

<210> SEQ ID NO 9
<211> LENGTH: 6
<212> TYPE: PRT
<213> ORGANISM: Artificial Sequence
<220> FEATURE:
<223> OTHER INFORMATION: the N-terminal protecting amino acid

<400> SEQUENCE: 9

Asp Asp Gly Asp Gly Arg
1               5

<210> SEQ ID NO 10
<211> LENGTH: 6
<212> TYPE: PRT
<213> ORGANISM: Artificial Sequence
<220> FEATURE:
<223> OTHER INFORMATION: N-terminal protecting amino

<400> SEQUENCE: 10

Glu Glu Gly Glu Gly Arg
1               5

<210> SEQ ID NO 11
<211> LENGTH: 3
<212> TYPE: PRT
<213> ORGANISM: Artificial Sequence
<220> FEATURE:
<223> OTHER INFORMATION: N-terminal protecting amino acid

<400> SEQUENCE: 11

Asp Glu Arg
1
```